United States Patent
Yu

(10) Patent No.: US 10,696,635 B2
(45) Date of Patent: Jun. 30, 2020

(54) VERSATILE LIGAND FOR PALLADIUM-CATALYZED META-C—H FUNCTIONALIZATIONS OF AROMATIC SUBSTRATES

(71) Applicant: The Scripps Research Institute, La Jolla, CA (US)

(72) Inventor: Jin-Quan Yu, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 16/094,707

(22) PCT Filed: Apr. 18, 2017

(86) PCT No.: PCT/US2017/028116
§ 371 (c)(1),
(2) Date: Oct. 18, 2018

(87) PCT Pub. No.: WO2017/184589
PCT Pub. Date: Oct. 26, 2017

(65) Prior Publication Data
US 2019/0119212 A1    Apr. 25, 2019

Related U.S. Application Data

(60) Provisional application No. 62/324,087, filed on Apr. 18, 2016.

(51) Int. Cl.
| | |
|---|---|
| *C07C 6/02* | (2006.01) |
| *C07D 213/68* | (2006.01) |
| *C07D 401/14* | (2006.01) |
| *C07D 405/14* | (2006.01) |
| *C07D 231/12* | (2006.01) |
| *C07D 231/56* | (2006.01) |
| *C07D 401/12* | (2006.01) |
| *C07D 405/12* | (2006.01) |
| *C07D 239/42* | (2006.01) |
| *C07D 409/12* | (2006.01) |
| *C07D 409/14* | (2006.01) |
| *C07D 241/12* | (2006.01) |
| *C07D 413/12* | (2006.01) |
| *C07D 217/12* | (2006.01) |
| *C07D 213/36* | (2006.01) |
| *C07D 213/26* | (2006.01) |
| *B01J 23/44* | (2006.01) |
| *C07D 213/30* | (2006.01) |
| *C07D 213/40* | (2006.01) |
| *C07D 213/55* | (2006.01) |

(Continued)

(52) U.S. Cl.
CPC ............ *C07D 213/68* (2013.01); *B01J 23/44* (2013.01); *C07D 213/26* (2013.01); *C07D 213/30* (2013.01); *C07D 213/36* (2013.01); *C07D 213/40* (2013.01); *C07D 213/55* (2013.01); *C07D 213/72* (2013.01); *C07D 215/38* (2013.01); *C07D 217/12* (2013.01); *C07D 217/18* (2013.01); *C07D 217/24* (2013.01); *C07D 231/12* (2013.01); *C07D 231/56* (2013.01); *C07D 239/26* (2013.01); *C07D 239/42* (2013.01); *C07D 241/12* (2013.01); *C07D 401/12* (2013.01); *C07D 401/14* (2013.01); *C07D 405/12* (2013.01); *C07D 405/14* (2013.01); *C07D 409/12* (2013.01); *C07D 409/14* (2013.01); *C07D 413/12* (2013.01)

(58) Field of Classification Search
CPC ...................................................... C07C 6/02
USPC ........................................................ 585/419
See application file for complete search history.

(56) References Cited

FOREIGN PATENT DOCUMENTS

WO    WO-2017184589 A1    10/2017

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*

(Continued)

*Primary Examiner* — Douglas M Willis
(74) *Attorney, Agent, or Firm* — Schwegman Lundberg & Woessner, P.A.

(57) ABSTRACT

A class of mono-protected 3-amino-2-hydroxypyridine (MPAHP) ligands that enable the meta-C—H arylation of anilines, phenols, phenylacetic acids, and biologically relevant heterocyclic compounds using norbornene as a transient mediator is disclosed, such as in the formation of a reaction product of Formula IA:

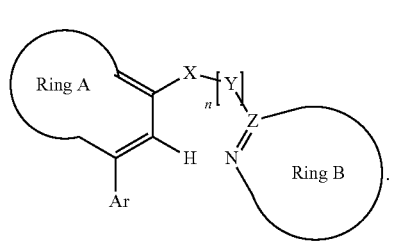

The applicability of this meta-arylation methodology in the pharmaceutical industry is illustrated for heteroaryl substrates and heteroaryl iodide coupling partners, a feat made possible by using the MPAHP ligand. The enabling nature of MPAHP ligands to achieve other meta-C—H functionalization processes is also illustrated by the development of a meta-C—H amination reaction and a meta-C—H alkynylation reaction.

18 Claims, No Drawings

(51) Int. Cl.
*C07D 213/72* (2006.01)
*C07D 215/38* (2006.01)
*C07D 217/18* (2006.01)
*C07D 217/24* (2006.01)
*C07D 239/26* (2006.01)

(56) References Cited

OTHER PUBLICATIONS

"International Application Serial No. PCT/US2017/028116, International Preliminary Report on Patentability dated Nov. 1, 2018", 10 pgs.
"International Application Serial No, PCT/US2017/028116, International Search Report dated Jul. 28, 2017", 4 pgs.
"International Application Serial No. PCT/US2017/028116, Written Opinion dated Jul. 28, 2017", 8 pgs.
Leow, Dasheng, et al., "Activation of Remote Meta-C-H Bonds Assisted by an end-on Template", Nature, vol. 486, (Jun. 28, 2012), 518-522.
Li, Shangda, et al., "Pd(II)-Catalysed Meta-C-H Functionalizations of Benzoic Acid Derivatives", Nature Communications, vol. 7, Article No. 10443, (Jan. 27, 2016), 8 pgs.
Piotrowski, Holger, et al., "Self-Assembled Organometallic [12]metallacrown-3 Complexes", Chemistry: A European Journal, vol. 7, No. 15, (2001), 3196-3208.
Song, Bingrui, "Palladium-Catalyzed C-C Bond Formations Vla Activation of Carboxylic Acids and their Derivatives", Doctoral Thesis of Technische Universitat Kaiserslautern, (2013), 1-293.
Wang, Peng, et al., "Ligand-Promoted Meta-C-H Arylation of Ani Lines, Phenols, and Heterocycles", HHS Public Access: Author Manuscript, Published in final edited form as: Journal of the American Chemical Society, vol. 138, No. 29, (2016), 16 pgs.
Wang, Xiao-Chen, et al,, "Ligand-Enabled Meta-C-H Activation Using a Transient Mediator", Nature, vol. 519, No. 7543, (Mar. 19, 2015), 334-338.

* cited by examiner

VERSATILE LIGAND FOR PALLADIUM-CATALYZED META-C—H FUNCTIONALIZATIONS OF AROMATIC SUBSTRATES

GOVERNMENTAL SUPPORT

This invention was made with governmental support under NIGMS 1R01 GM102265 awarded by the National Institutes of Health. The government has certain rights in the invention.

TECHNICAL FIELD

The present invention contemplates a method for forming a carbon-to-carbon (C—C) bond between a reactive substrate and an aromatic or heteroaromatic iodide, and the reagents that facilitate that electrophilic bond-formation reaction. More particularly, the new C—C bond is formed on an aromatic or heteroaromatic substrate molecule that would normally direct electrophilic substitutions to ortho or para positions instead to a position meta to a substituent already present on the substrate through the use of a palladium catalyst, a directing group bonded as part of the substrate, a directing ligand that is dissolved or dispersed in the reaction mixture.

BACKGROUND ART

Cyclopalladation reactions have been extensively studied since 1965.[3] Recently, Pd(II)-catalyzed C—H activation reactions have been shown to be compatible with a wide range of carbon-carbon and carbon-heteroatom bond-forming reactions through Pd(II)/Pd(0), Pd(II)/Pd(IV) and Pd(II)/Pd(II) catalytic cycles.[4-6] However, versatile ligands that can promote both C—H cleavage and the subsequent functionalization steps remain scarce and are largely limited to mono-protected amino acids (MPAAs) and pyridine/quinoline based ligands.[7]

As effective C—H functionalization often requires a synergistic relationship between ligand and substrate coordinated to the metal center, it is essential to develop ligands that match with a variety of directing groups so that the assembled complexes are reactive in cleaving C—H bonds of a number of substrate classes.[7] This fact is exemplified in recent efforts towards developing broadly useful norbornene-mediated meta-selective C—H functionalizations, where previously developed ligand scaffolds have proven insufficient at promoting reactivity with two important classes of substrates: anilines and phenols. A general pathway for meta-arylation using norbornene as a mediator is shown schematically below, where "DG" is a directing group, $L_n$ is a ligand, and Ar—I is an aryl iodide coupling partner.

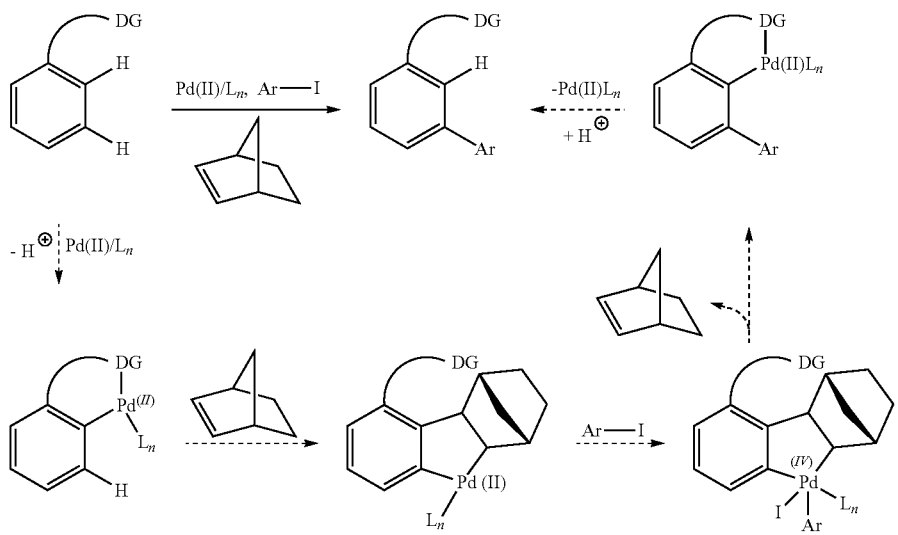

The norbornene insertion step from the Catellani reaction[8,9] has previously been successfully combined with palladium catalyzed C—H activation to achieve selective C—H functionalization of indoles.[10,11] Recently, this key step was combined with ortho-directed C—H activation to achieve a net meta-functionalization via a relay process.[12-14] Further development of this newly emerging meta-C—H functionalization strategy remains a significant, yet important challenge as it is complementary to other approaches for the direct meta-functionalization of arenes.[15-23]

BRIEF SUMMARY OF THE INVENTION

The present invention contemplates method of forming a reaction product containing carbon-to-carbon (C—C) bond to an aryl or heteroaryl substituent at a position meta to a substituent previously present on the ring of an aromatic reactive substrate compound, and particularly a substituted 3-amino-2-hydroxy-pyridine ligand useful in that reaction. A contemplated method comprises the steps of heating a reaction mixture to a temperature of about 70° to about 120° C. The reaction mixture contains i) an aromatic reactive substrate compound of Formula I dissolved or dispersed in a non-aqueous solvent having a boiling point at 1 atmosphere of about 40° to about 200° C., that further contains dissolved or dispersed therein ii) a catalytic amount of a Pd(II) catalyst, iii) a substituted 3-amino-2-hydroxy-pyridine ligand of Formula III is present at about 10 to about 50 mole percent based on the moles of reactive substrate, iv) an ethylenically unsaturated bicyclic compound of Formula II as a transient mediator present in excess over the amount of reactive substrate, v) about 1.5 to about 5 equivalents of an oxidant based on the amount of said reactive substrate, and vi) about 1.1 to about 10 equivalents of a iodo-substituted aryl or heteroaryl coupling agent (Ar—I). The temperature is maintained for a time period sufficient to carry out the C—C bond formation at a position meta to the substituent and form a reaction product whose structural formula is shown in Formula IA

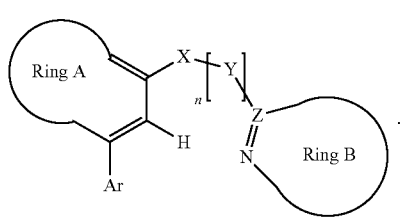

IA

In that reaction mixture, the iodo-substituted aryl or heteroaryl coupling agent can additionally be unsubstituted. Alternatively, the iodo-substituted aryl coupling agent can be further substituted a) at the meta and para positions with one or two substituents independently selected from the group consisting of halogen (fluoro, chloro, bromo or iodo), $C_1$-$C_7$-hydrocarbyl that is straight, branched or cyclic, $C_1$-$C_7$-hydrocarbyloxy ($C_1$-$C_7$—O—), $C_1$-$C_7$-hydrocarbylthioxy ($C_1$-$C_7$—S—), cyano, nitro, perfluoro-$C_1$-$C_3$-hydrocarbyl, carboxy $C_1$-$C_7$-hydrocarbyl, $C_1$-$C_7$-hydrocarboyl (acyl), protected hydroxyl, protected hydroxyl-substituted $C_1$-$C_7$-hydrocarbyl that is straight, branched or cyclic, di-($C_1$-$C_7$-hydrocarbyl) $C_1$-$C_7$-hydrocarbylphosphonate, protected amino wherein the protecting group(s) contains up to 10 carbon atoms and the amine nitrogen has no reactive hydrogen, and a fused ring that includes 3 or 4 added ring atoms, and b) substituted at the ortho position by a carboxy $C_1$-$C_7$-hydrocarbyl or NH—$C_1$-$C_7$-hydrocarboyl group.

An iodo-substituted heteroaryl coupling agent can be further substituted with one or two substituents independently selected from the group consisting of halogen other than iodo, $C_1$-$C_7$-hydrocarbyl that is straight, branched or cyclic, $C_1$-$C_7$-hydrocarbyloxy ($C_1$-$C_7$—O—), $C_1$-$C_7$-hydrocarbylthioxy ($C_1$-$C_7$—S—), perfluoro-$C_1$-$C_3$-hydrocarbyl, carboxy $C_1$-$C_7$-hydrocarbyl, $C_1$-$C_7$-hydrocarboyl (acyl), a fused ring that includes 3 or 4 added ring atoms and in which any nitrogen atom present is free of reactive hydrogens.

The aromatic reactive substrate compound has a structural formula shown in Formula I, below:

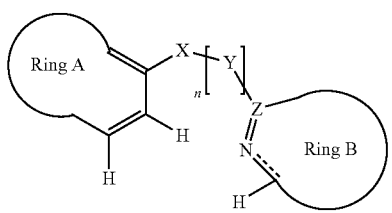

I wherein, Ring A is a heteroaromatic or carbocyclic aromatic ring structure in which the bond shown to X is at the 1-position of the ring and the substituent bonded at the 1-position constitutes the substituent previously present on the ring. The ring position rotated clock-wise from the 1-position is the ortho-position at which a hydrogen (H) is bonded, and the next position clock-wise from the ortho-position at which another hydrogen (H) is bonded is the meta-position and is the position at which the new C—C bond is formed.

The Ring A contains a single ring or two fused rings having a total of 5 to 10 ring atoms and in which the ring bonded to X is aromatic and any other ring fused to that aromatic ring is independently aromatic or aliphatic. A heteroaromatic ring structure that is all or a part of Ring A contains one, two or three heteroatoms that can independently be nitrogen, oxygen or sulfur atoms.

The Ring A optionally further contains 1, 2 or 3 substituents other than hydrido (H) bonded to the ring atoms. Those optional substituents when present are selected from the group consisting of halo other than iodo (fluoro, chloro or bromo), $C_1$-$C_7$-hydrocarbyl that is straight, branched or includes a 4- to 6-membered ring bonded to a straight or branched chain, $C_1$-$C_7$-hydrocarbyloxy ($C_1$-$C_7$—O—), $C_1$-$C_7$-hydrocarbylthioxy ($C_1$-$C_7$—S—), $C_1$-$C_2$-hydrocarbyldioxy, cyano, nitro, perfluoro-$C_1$-$C_3$-hydrocarbyl, carboxy $C_1$-$C_7$-hydrocarbyl, $C_1$-$C_7$-hydrocarboyl (acyl), protected amino wherein the protecting group(s) contains up to 10 carbon atoms, and a fused ring.

In structural Formula I, n is zero (0) or one, such that the methylene group Y within the brackets is absent when n is zero, and present when n is one.

X is O (oxygen) or NPG (a nitrogen bonded to a protecting group) when n is 1, and NPG or $CH_2$ (methylene) when n is zero.

Ring B is a heteroaromatic single 6-membered ring or a fused 6,6- or 5,6-membered ring system containing the depicted nitrogen atom and 1 or 2 other nitrogen ring atoms. Z is carbon when n is zero or 1. Z is nitrogen (a) when n is zero, and (b) the double bond depicted is absent and replaced by a double bond at the position of the dashed line.

Ring B optionally further contains 1, 2 or 3 substituents other than hydrido (H) bonded to the ring atoms. Those optional substituents when present are selected from the group consisting of $C_1$-$C_7$-hydrocarbyl that is straight, branched or includes a 4- to 6-membered ring bonded to a straight or branched chain $C_1$-$C_3$-substituent, $C_1$-$C_7$-hydrocarbyloxy, trifluoromethyl-$C_1$-$C_3$-hydrocarbyl, trifluoromethyl-$C_1$-$C_3$-hydrocarbyloxy, and a fused ring.

The reaction mixture also contains a transient mediator that is an ethylenically unsaturated bicyclic compound of Formula II

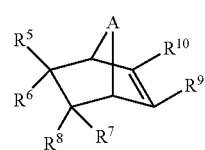

II wherein
A is $CH_2$, C=O or O,
each of $R^5$, $R^6$, $R^7$, $R^8$, $R^9$, and $R^{10}$ is independently H, $C_1$-$C_6$-hydrocarbyl, $C_1$-$C_6$-hydrocarbyloxy, $C_1$-$C_6$-hydrocarbyl carboxylate, $C_1$-$C_6$-hydrocarboyl, one or both of $R^5$ plus $R^6$ and $R^7$ plus $R^8$ together with the carbon atom to which they are bonded form one or two carbonyl groups, or one each of $R^5$ and $R^6$, or $R^7$ and $R^8$ together with the atoms to which they are bonded form a further 4- to 6-membered aliphatic or aromatic ring that itself can be independently substituted with one or two substituent groups selected from the group consisting of a $C_1$-$C_6$-hydrocarbyl, a $C_1$-$C_6$-hydrocarbyloxy, a $C_1$-$C_6$-hydrocarbyl carboxylate and a nitro group.

The substituted 3-amino-2-hydroxypyridine ligand present in the reaction mixture has the structure of Formula III

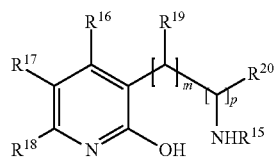

III wherein $R^{15}$ is an acyl group containing 2 to about 12 carbon atoms or a perfluorinated acyl group containing 2 to about 6 carbon atoms, $R^{16}$ is hydrido or $C_1$-$C_6$-hydrocarbyl, $R^{17}$ is hydrido, $C_1$-$C_6$-hydrocarbyl or trifluoromethyl, $R^{18}$ is hydrido or $C_1$-$C_6$-hydrocarbyl, or $R^{16}$ and $R^{17}$ or $R^{17}$ and $R^{18}$ together with the carbon atoms to which they are bonded form a 6-membered ring with the depicted pyridine ring, m and p are the same and are zero or 1 such that m and p are zero, the bracketed carbon atoms are absent and the $NHR^{15}$ group is bonde directly to the depicted pyridine ring, and when m and p are both one, $R^{19}$ and $R^{20}$ together with the carbons to which they are bonded form a phenyl ring. When $R^{16}$ and $R^{17}$ form a 6-membered ring with the depicted pyridine ring, it is preferred that $R^{18}$ be hydrido.

In preferred embodiments, at least one of $R^{16}$ and $R^{17}$ is other than hydrido. In one aspect of a preferred embodiment, $R^{17}$ is trifluoromethyl. More preferably, $R^{15}$ is acetyl, 1-adamantoyl or trifluoroacetyl and $R^{16}$ is hydrido. In another preferred aspect, one of $R^{16}$ and $R^{17}$ is $C_1$-$C_6$-hydrocarbyl and the other is hydrido. In this aspect, $R^{15}$ is more preferably acetyl.

In some embodiments, m and p are both zero. In some preferred aspects of this embodiment, $R^{16}$, $R^{17}$, $R^{17}$ and $R^{18}$ are independently hydrido, $C_1$-$C_6$-hydrocarbyl or trifluoromethyl as defined above so that the ligand is a 2-hydroxypyridine derivative as is shown in Formula IIIa, below. In other preferred

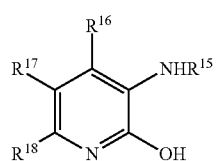

IIIa aspects of this embodiment, $R^{16}$ and $R^{17}$, or $R^{17}$ and $R^{18}$ together with their bonded carbons form a 6-membered aromatic ring so that the ligand is a derivative of a quinoline or isoquinoline, as are shown in Formulas IIIb and IIIc, respectively, below.

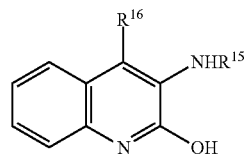

IIIb

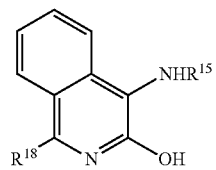

IIIc

In a still further embodiment, m and p are both one and $R^{19}$ and $R^{20}$ together with the carbons to which they are bonded form a phenyl ring. In this case, the ligand is a 3-(ortho-aminophenyl)-2-hydroxypyridine derivative as is shown in Formula IIId, below.

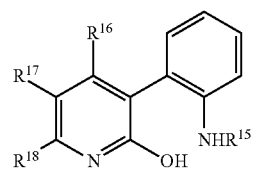

IIId

The present invention has several benefits and advantages.

One benefit is that it provides a new route to the preparation of meta-substituted aromatics that are either not possible to readily synthesize by other means or can be synthesized but require the presence of a chemically bonded directing ligand.

An advantage of the invention is that one can prepare meta-substituted aromatic compounds using aromatic reactive substrates whose substituent group(s) would usually direct a new C—C bond to an ortho position.

Another benefit of the invention is that the meta-directing ligand not being bonded to the aromatic substrate need not be removed by a separate reaction as compared to removal by physical separation.

Another advantage of the invention is that the desired products can often be prepared in yields that are greater than about 50%.

Still further benefits and advantages of the invention will be apparent to the skilled worker from the discussion that follows.

Definitions

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

The words "ortho", "meta" and "para" are used in their usual manner to describe benzenoid compounds that are substituted "1-2", "1-3" and "1-4", respectively. Those same words are also used herein as a convenience to describe those same substitution patterns in aliphatic compounds.

The word "hydrocarbyl" is used herein as a short hand term for a non-aromatic group that includes straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter.

Where a specific aliphatic hydrocarbyl substituent group is intended, that group is recited; i.e., $C_1$-$C_4$ alkyl, methyl or hexenyl. Exemplary hydrocarbyl groups contain a chain of 1 to about 7 carbon atoms, and preferably 1 to about 4 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, iso-amyl, hexyl, octyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of alkynyl radicals include ethynyl, 2-propynyl, 3-propynyl, decynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, n-propoxy, isopropoxy, allyloxy, n-butoxy, iso-butoxy, sec-butoxy, tert-butoxy, cyclohexenyloxy groups and the like. On the other hand, a hydrocarbyl group containing a —C(O)O— functionality is referred to as a hydrocarboyl (acyl) group inasmuch as there is no ambiguity in using that suffix. Exemplary hydrocarboyl and hydrocarboyloxy groups include acyl and acyloxy groups, respectively, such as acetyl and acetoxy, acryloyl and acryloyloxy.

As a skilled worker will understand, a substituent that cannot exist such as a $C_1$ alkenyl group is not intended to be encompassed by the word "hydrocarbyl", although such substituents with two or more carbon atoms are intended.

A "carboxyl" substituent is a —C(O)OH group. A $C_1$-$C_6$ hydrocarbyl carboxylate is a $C_1$-$C_6$ hydrocarbyl ester of a carboxyl group [—C(=O)—O—$C_1$-$C_6$ hydrocarbyl].

The term "aryl", alone or in combination, means a phenyl or naphthyl or other aromatic radical. An aryl group can be carbocyclic, containing only carbon atoms in the ring(s) or heterocyclic as a heteroaryl group discussed hereinafter. A "heteroaryl" group is an aromatic heterocyclic ring substituent that preferably contains one, or two, up to three or four, atoms in the ring other than carbon. Those heteroatoms can be nitrogen, sulfur or oxygen. A heteroaryl group can contain a single 5- or 6-membered ring or a fused ring system having two 6-membered rings or a 5- and a 6-membered ring. Exemplary heteroaryl groups include 6-membered ring substituents such as pyridyl, pyrazyl, pyrimidinyl, and pyridazinyl; 5-membered ring substituents such as 1,3, 5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2, 5-, or 1,3,4-oxadiazolyl and isothiazolyl groups; 6-/5-membered fused ring substituents such as benzothiofuranyl, isobenzothiofuranyl, benzisoxazolyl, benzoxazolyl, purinyl and anthranilyl groups; and 6-/6-membered fused rings such as 1,2-, 1,4-, 2,3- and 2,1-benzopyronyl, quinolinyl, isoquinolinyl, cinnolinyl, quinazolinyl, and 1,4-benzoxazinyl groups.

The term "halogen" means fluorine, chlorine or bromine. The term perfluorohydrocarbyl means a hydrocarbyl group wherein each hydrogen is replaced by a fluorine atom. Examples of such perfluorohydrocarbyl groups, in addition to trifluoromethyl, which is preferred, are perfluorobutyl, perfluoroisopropyl, perfluorododecyl and perfluorodecyl.

The terms "amino-protecting group" and "amine-protecting group" as used herein refer to one or more selectively removable substituents on the amino group commonly employed to block or protect the amino functionality. Examples of such amine-protecting groups include the formyl ("For") group, the trityl group ("Trt"), the phthalimido group ("Phth"), the trichloroacetyl group, the chloroacetyl, bromoacetyl, and iodoacetyl groups. Urethane blocking groups, such as t-butoxy-carbonyl ("Boc"), 2-(4-biphenylyl)propyl-(2)oxycarbonyl ("Bpoc"), 2-phenylpropyl(2)oxycarbonyl ("Poc"), 2-(4xenyl)-isopropoxycarbonyl, 1,1-diphenyl-ethyl(l)oxycarbonyl, 1,1-diphenylpropyl(1)-oxycarbonyl, 2-(3,5-dimethoxyphenyl) propyl(2)oxycarbonyl ("Ddz"), 2-(p-5-toluyl)-propyl(2) oxycarbonyl, cyclopentanyl-oxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methyl-sulfonyl)-ethoxycarbonyl, 2-(triphenylphosphino)-ethoxy-carbonyl, 9-fluoroenylmethoxycarbonyl ("Fmoc"), 2-(trimethyl-silyl)ethoxycarbonyl, allyloxycarbonyl, 1-(trimethyl-silylmethyl)prop-l-enyloxycarbonyl, 5-benzisoxalyl-methoxycarbonyl, 4-acetoxybenzyloxycarbonyl, 2,2,2-trichloroethoxycarbonyl, 2-ethynyl (2) propoxy-carbonyl, cyclopropylmethoxycarbonyl, isobornyloxycarbonyl, 1-piperidyloxycarbonyl, benzyloxycarbonyl ("Z"), 4-phenylbenzyloxycarbonyl, 2-methylbenzyloxy-carbonyl, α-2,4,5-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl, and the like, the benzoylmethylsulfonyl group, dithiasuccinoyl ("Dts") group, the 2-(nitro)-phenylsulfenyl group ("Nps"), the 2- or 4-nitro-phenylsulfonyl ("Nos") group, 4-toluenesulfonyl ("Ts"), the diphenylphosphine oxide group, and like amino-protecting groups.

The species of amine-protecting group employed is usually not critical so long as the derivatized amino group is stable to the conditions of the subsequent reactions and can be removed at the appropriate point without disrupting the remainder of the compound. A preferred amine-protecting group is a phthalimido group.

Further examples of amino-protecting groups embraced to by the above term are well known in organic synthesis and the peptide art and are described by, for example: T. W. Greene and P. G. M. Wuts, *Protective Groups in Organic Synthesis*, 2nd ed., John Wiley and Sons, New York. N.Y., Chapter 7, 1991; M. Bodanzsky, *Principles of Peptide Synthesis*, 1st and 2nd revised ed., Springer-Verlag, New York, N.Y., 1984 and 1993; and Stewart and Young, *Solid Phase Peptide Synthesis*, 2nd ed., Pierce Chemical Co, Rockford, Ill. 1984.

The related term "protected amino" or "protected amine" defines an amino group substituted with an amino-protecting group discussed above.

The terms "hydroxy-protecting group" and "hydroxyl-protecting group" refer to readily cleavable groups bonded to hydroxyl groups, such as the tetrahydropyranyl, 2-methoxyprop-2-yl, 1-ethoxyeth-1-yl, methoxymethyl, methylthiomethyl, β-methoxyethoxymethyl, t-butyl, t-amyl, trityl, 4-methoxytrityl, 4,4'-dimethoxytrityl, 4,4',4"-trimethoxytrityl, benzyl, allyl, trimethylsilyl ("TMS"), t-butyldiphenylsilyl ("TBDPS"), (t-butyl)dimethylsilyl ("TBS" or "TBDMS"), triisopropylsilyl ("TIPS"), and 2,2,2-trichloroethoxycarbonyl groups, and the like. Ester groups such as $C_1$-$C_6$-hydrocarboyl esters such as acetate ("OAc"), propionate and hexanoate are also useful, as is a benzyl ether ("Bn") group. The species of hydroxyl-protecting groups is also usually not critical so long as the derivatized (protected) hydroxyl group is stable to the conditions of subsequent reaction(s) and the protecting group can be removed at the appropriate point without disrupting the remainder of the compound.

Further examples of hydroxy-protecting groups are described by C. B. Reese and E Haslam, *Protective Groups in Organic Chemistry*, J. G. W. McOmie Ed., Plenum Press, New York, N.Y., Chapters 3 and 4, 1973, and T. W. Greene and P. G. M. Wuts, *Protective Groups in Organic Synthesis*, 2nd ed., John Wiley and Sons, New York, N.Y., Chapters 2 and 3, 1991.

DETAILED DESCRIPTION OF PREFERRED EMBODIMENTS

In an attempt to expand the scope of norbornene-mediated meta-C—H arylation reactions, aniline was selected as a model substrate. Meta-functionalization of this class of substrates[20-22] is highly valuable as electrophilic substitution reactions predominantly afford ortho- and/or para-substituted products due to the electronic directing effects of the aniline nitrogen atom.

Because of the multiple possible reaction pathways at several steps of the catalytic cycle, development of a ligand to orchestrate each step is a tremendous challenge. The discovery of mono-protected 3-amino-2-hydroxypyridine ligands (MPAHPs) that promote a highly efficient meta-C—H arylation of anilines, phenols, phenylacetic acids and heterocycles is disclosed hereinafter. This class of ligands has also enabled a meta-C—H amination reaction and a meta-C—H alkynylation reaction both of which, have not previously been achieved so far as is known.

Thus, a method of forming a reaction product containing carbon-to-carbon (C—C) bond to an aryl or heteroaryl substituent at a position meta to a substituent previously present on the ring of an aromatic reactive substrate compound is contemplated. Particularly contemplated in conjunction with that reaction is a substituted 3-amino-2-hydroxy-pyridine ligand useful in that reaction.

A contemplated method comprises the steps of heating a reaction mixture to a temperature of about 70° to about 120° C. The reaction mixture contains i) an aromatic reactive substrate compound of Formula I dissolved or dispersed in a non-aqueous solvent having a boiling point at 1 atmosphere of about 40° to about 200° C. That reaction mixture further contains dissolved or dispersed therein ii) a catalytic amount of a Pd(II) catalyst, iii) a substituted 3-amino-2-hydroxy-pyridine ligand of Formula III is present at about 10 to about 50 mole percent based on the moles of reactive substrate, iv) an ethylenically unsaturated bicyclic compound of Formula II as a transient mediator present in excess over the amount of reactive substrate, v) about 1.5 to about 5 equivalents of an oxidant based on the amount of said reactive substrate, and vi) about 1.1 to about 10 equivalents of a iodo-substituted aryl or heteroaryl coupling agent (Ar—I). The temperature is maintained for a time period sufficient to carry out the C—C bond formation at a position meta to the substituent and form a reaction product whose structural formula is shown in Formula IA

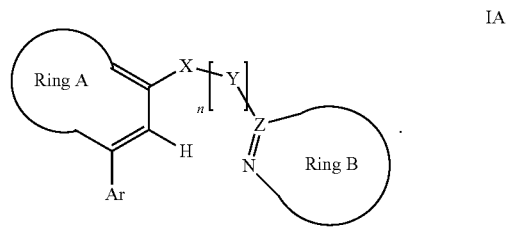

In some aspects, the reaction product is recovered from the reaction mixture. Where Y is methylene, the reacted A Ring can be separated from the B Ring by treatment with hydrogen in the presence of a catalyst such as palladium on charcoal, or by reaction with an acid such as trifluoroacetic acid. In other aspects, either treatment can be used without isolating the product from the reaction mixture.

In that reaction mixture, the iodo-substituted aryl or heteroaryl coupling agent can no further substituent that the iodo group; i.e., additionally be unsubstituted. Alternatively, the iodo-substituted aryl coupling agent can be further substituted a) at the meta and para positions with one or two substituents independently selected from the group consisting of halogen (fluoro, chloro, bromo or iodo), $C_1$-$C_7$-hydrocarbyl that is straight, branched or cyclic, $C_1$-$C_7$-hydrocarbyloxy ($C_1$-$C_7$—O—), $C_1$-$C_7$-hydrocarbylthioxy ($C_1$-$C_7$—S—), cyano, nitro, perfluoro-$C_1$-$C_3$-hydrocarbyl, carboxy $C_1$-$C_7$-hydrocarbyl, $C_1$-$C_7$-hydrocarboyl (acyl), protected hydroxyl, protected hydroxyl-substituted $C_1$-$C_7$-hydrocarbyl that is straight, branched or cyclic, di-($C_1$-$C_7$-hydrocarbyl) $C_1$-$C_7$-hydrocarbylphosphonate, protected amino wherein the protecting group(s) contains up to 10 carbon atoms and the amine nitrogen has no reactive hydrogen, and a fused ring that includes 3 or 4 added ring atoms. That iodo-substituted aryl coupling agent can also be substituted b) at the ortho position by a carboxy $C_1$-$C_7$-hydrocarbyl or NH—$C_1$-$C_7$-hydrocarboyl group.

An iodo-substituted heteroaryl coupling agent can also be further substituted with one or two substituents independently selected from the group consisting of halogen other than iodo, $C_1$-$C_7$-hydrocarbyl that is straight, branched or cyclic, $C_1$-$C_7$-hydrocarbyloxy ($C_1$-$C_7$—O—), $C_1$-$C_7$-hydrocarbylthioxy ($C_1$-$C_7$—S—), perfluoro-$C_1$-$C_3$-hydrocarbyl, carboxy $C_1$-$C_7$-hydrocarbyl, $C_1$-$C_7$-hydrocarboyl (acyl), a fused ring that includes 3 or 4 added ring atoms and in which any nitrogen atom present is free of reactive hydrogens.

The phrase "any nitrogen atom present is free of reactive hydrogens" and similar phrases are used herein to mean that a primary or secondary amine that normally contains one or two hydrogens bonded to the amine nitrogen atom are replaced by amine protecting groups (PG) that can be the same or different. Thus, a hydrogen that could otherwise react with a reactive group such as a isocyanate is absent. Illustrative protecting groups for a primary amine are benzyl (Bn) and t-butoxycarbonyl (Boc), and one or the other for a secondary amine.

The aromatic reactive substrate compound has a structural formula shown in Formula I, below:

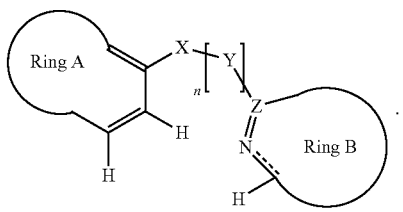

I

In Formula I, Ring A is a heteroaromatic or carbocyclic aromatic ring structure in which the bond shown to X is at the 1-position of the ring and the substituent bonded at the 1-position constitutes the substituent previously present on the ring that was noted above. The ring position rotated clock-wise from the 1-position is the ortho-position at which a hydrogen (H) is bonded, and the next position clock-wise from the ortho-position at which another hydrogen (H) is bonded is the meta-position and is the position at which the new C—C bond is formed.

The Ring A contains a single ring or two fused rings having a total of 5 to 10 ring atoms and in which the ring bonded to X is aromatic and any other ring fused to that aromatic ring is independently aromatic or aliphatic. A heteroaromatic ring structure that is all or a part of Ring A contains one, two or three heteroatoms that can independently be nitrogen, oxygen or sulfur atoms.

The Ring A optionally further contains 1, 2 or 3 substituents other than hydrido (H) bonded to the ring atoms. Those optional substituents when present are selected from the group consisting of halo other than iodo (fluoro, chloro or bromo), $C_1$-$C_7$-hydrocarbyl that is straight, branched or cyclic, $C_1$-$C_7$-hydrocarbyloxy ($C_1$-$C_7$—O—), $C_1$-$C_7$-hydrocarbylthioxy ($C_1$-$C_7$—S—), cyano, nitro, perfluoro-$C_1$-$C_3$-hydrocarbyl, carboxy $C_1$-$C_7$-hydrocarbyl, $C_1$-$C_7$-hydrocarboyl (acyl), protected amino wherein the protecting group(s) contains up to 10 carbon atoms, and a fused ring. Preferably, zero or 1 additional substituent is present bonded to a ring atom of Ring A.

Illustrative ring structures of Ring A include benzene and naphthalene rings, thiophene and furan rings, as well as pyridine, pyrazine, quinoline, quinoxaline, indole, indoline, indazole, dihydrobenzodioxine, and chromen-4-one rings. It is noted that in any of the Ring A heterocyclic rings that include a nitrogen ring atom, that nitrogen atom is bonded to a $C_1$-$C_7$-hydrocarbyl group as discussed above, or to a removable nitrogen protecting group so that no reactive hydrogen is present bonded to a Ring A nitrogen.

In structural Formula I, n is zero (0) or one. Thus, the methylene group ($CH_2$), Y, within the depicted brackets is absent when n is zero, and present when n is one. Z is carbon when n is zero or 1. Z is nitrogen (a) when n is zero, and (b) the double bond depicted is absent and replaced by a double bond at the position of the dashed line. In preferred aspects of the invention, n is 1.

X is O (oxygen) or NPG (a nitrogen bonded to a protecting group) when n is 1, and NPG or $CH_2$ (methylene) when n is zero. Additionally, when n is zero, the double bond depicted is absent and is replaced by a double bond at the position of the dashed line.

Ring B is a heteroaromatic single 5- or 6-membered ring or a fused 6,6- or 5,6-membered fused ring system containing the depicted nitrogen atom and 1 or 2 other nitrogen ring atoms. Ring B is often referred to herein as a directing group (DG or DG').

Preferably, when n is one, Ring B contains a single 6-membered ring and one nitrogen atom and up to three substituents other than hydrido (H) bonded to the ring atoms at ring positions other than that shown by the hydrido (hydrogen) bonded to the carbon atom adjacent to the depicted Ring B nitrogen in Formula I. Those optional substituents, $R^1$, $R^2$ and $R^3$, when present are selected from the group consisting of $C_1$-$C_7$-hydrocarbyl that is straight, branched or cyclic, $C_1$-$C_7$-hydrocarbyloxy, trifluoromethyl-$C_1$-$C_3$-hydrocarbyl, trifluoromethyl-$C_1$-$C_3$-hydrocarbyloxy.

In preferred aspects of this embodiment, a Ring B is a pyridine derivative whose structural formula is shown below, where the dotted line denotes

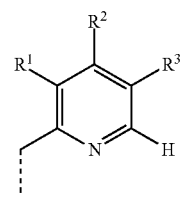

a bond to the methylene group Y of Formula I, $R^1$, $R^2$ and $R^3$ are independently hydrido, $C_1$-$C_6$-hydrocarbyl, $C_1$-$C_6$-hydrocarbyloxy or trifluoromethyl-$C_1$-$C_3$-hydrocarbyloxy. More preferably, at least one of $R^1$, $R^2$ and $R^3$ is other than hydrido. Preferred and particularly preferred Ring B groups are shown below with numerals identifying the compound of Formula I in which they are exemplified.

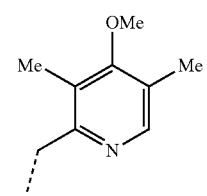

1a

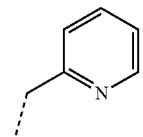

S3c

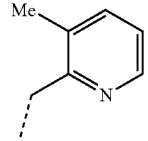

S5c

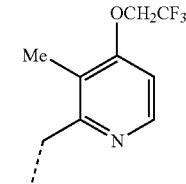

S5d

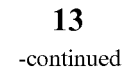

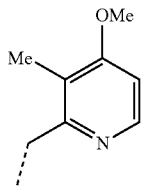

When n is zero, exemplary Ring B ring systems include pyridine, pyrimidine, pyrazine, pyrazole, indazole and quinolone. These B ring systems can contain one or two substituent groups such as a $C_1$-$C_7$-hydrocarbyl and a $C_1$-$C_7$-hydrocarbyloxy group.

The reaction mixture also contains a transient mediator that is an ethylenically unsaturated bicyclic compound of Formula II

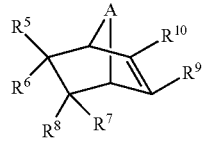

wherein

A is $CH_2$, C=O or O, each of $R^5$, $R^6$, $R^7$, $R^8$, $R^9$, and $R^{10}$ is independently H, $C_1$-$C_6$-hydrocarbyl, $C_1$-$C_6$-hydrocarbyloxy, $C_1$-$C_6$-hydrocarbyl carboxylate, $C_1$-$C_6$-hydrocarboyl, one or both of $R^5$ plus $R^6$ and $R^7$ plus $R^8$ together with the carbon atom to which they are bonded form one or two carbonyl groups, or one each of $R^5$ and $R^6$, or $R^7$ and $R^8$ together with the atoms to which they are bonded form a further 4- to 6-membered aliphatic or aromatic ring that itself can be independently substituted with one or two substituent groups selected from the group consisting of a $C_1$-$C_6$-hydrocarbyl, a $C_1$-$C_6$-hydrocarbyloxy, a $C_1$-$C_6$-hydrocarbyl carboxylate and a nitro group.

A ethylenically unsaturated bicyclic transient mediator compound of Formula II is present in excess over the amount of reactive substrate used. Preferably, that compound is present in an amount of about 1.2 to about 3 equivalents relative to the reactive substrate. More preferably, that amount is about 1.5 to about 2 times the moles of reactive substrate. Structural formulas of illustrative transient mediator ethylenically unsaturated bicyclic compounds are shown below.

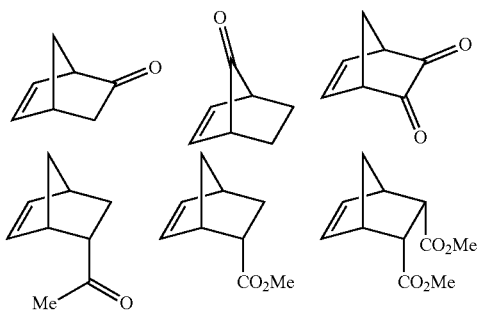

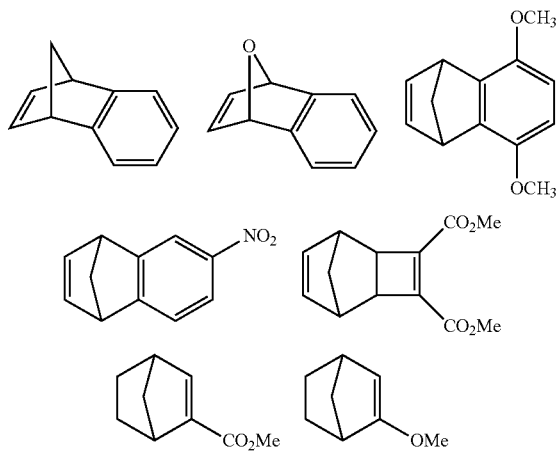

An improved transient mediator, methyl bicyclo[2.2.1]hept-2-ene-2-carboxylate (NBE-$CO_2$Me) whose structural formula is shown below is preferred in place of 2-norbornene that had been used in prior publications.[14]

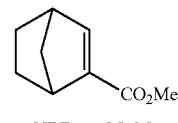

NBE—$CO_2$Me

A ligand that can be viewed as a substituted 3-amino-2-hydroxypyridine is also present in the reaction mixture has the structure of Formula III, below,

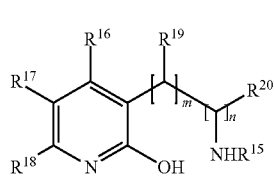

wherein $R^{15}$ is an acyl group containing 2 to about 12 carbon atoms or a perfluorinated acyl group containing 2 to about 6 carbon atoms, $R^{16}$ is hydrido or $C_1$-$C_6$-hydrocarbyl, $R^{17}$ is hydrido, $C_1$-$C_6$-hydrocarbyl or trifluoromethyl, $R^{18}$ is hydrido or $C_1$-$C_6$-hydrocarbyl, or $R^{16}$ and $R^{17}$ or $R^{17}$ and $R^{18}$ together with the carbon atoms to which they are bonded form a 6-membered ring with the depicted pyridine ring, m and p are the same and are zero or 1. When m and p are zero, the bracketed carbon atoms are absent and the NH$R^{15}$ group is bonded directly to the depicted pyridine ring. When $R^{16}$ and $R^{17}$ form a 6-membered ring with the depicted pyridine ring, it is preferred that $R^{18}$ be hydrido. When m and p are both one, $R^{19}$ and $R^{20}$ together with the carbons to which they are bonded form a phenyl ring.

In some embodiments, when m and p are both zero, $R^{16}$, $R^{17}$, $R^{17}$ and $R^{18}$ are independently hydrido, $C_1$-$C_6$-hydrocarbyl or trifluoromethyl as defined above so that the ligand is a 2-hydroxypyridine derivative as is shown in Formula IIIa, below. Here, preferably at least one of $R^{16}$,

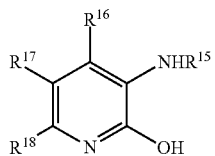

IIIa $R^{17}$ and $R^{18}$ is other than hydrido. In one aspect of a preferred embodiment, $R^{17}$ is trifluoromethyl. More preferably, $R^{15}$ is acetyl, 1-adamantoyl or trifluoroacetyl and $R^{16}$ is hydrido. In another preferred aspect, one of $R^{16}$ and $R^{17}$ is $C_1$-$C_6$-hydrocarbyl and the other is hydrido. In this aspect, $R^{15}$ is more preferably acetyl.

In other preferred aspects of this embodiment, $R^{16}$ and $R^{17}$, or $R^{17}$ and $R^{18}$ together with their bonded carbons form a 6-membered aromatic ring so that the ligand is a derivative of a quinoline or isoquinoline, as are shown in Formulas IIIb and IIIc, respectively, below.

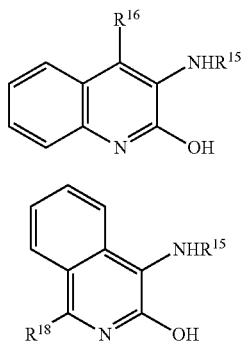

IIIb

IIIc

In a still further embodiment, m and p are both one and $R^{19}$ and $R^{20}$ together with the carbons to which they are bonded form a phenyl ring. In this case, the ligand is a 3-(ortho-aminophenyl)-2-hydroxypyridine derivative as is shown in Formula IIId, below, where $R^{16}$, $R^{17}$ and $R^{18}$ are as defined above.

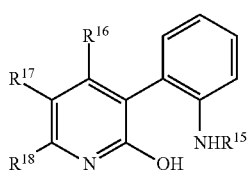

IIId

In preferred embodiments of a compound of Formula IIIa, at least one of $R^{16}$ and $R^{17}$ is other than hydrido. In one aspect of a preferred embodiment, $R^{17}$ is trifluoromethyl. More preferably, $R^{15}$ is acetyl, 1-adamantoyl or trifluoroacetyl and $R^{16}$ is hydrido. In another preferred aspect, one of $R^{16}$ and $R^{17}$ is $C_1$-$C_6$-hydrocarbyl and the other is hydrido. In this aspect, $R^{15}$ is more preferably acetyl. $R^{18}$ is preferably hydrido when not part of a ring system.

Structural formulas of six of these more preferred ligand compounds are shown below along with their numerical identifiers used herein.

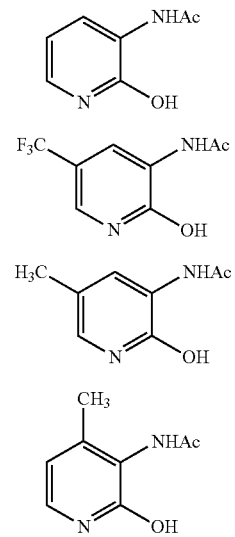

L12

L14

L16

L17

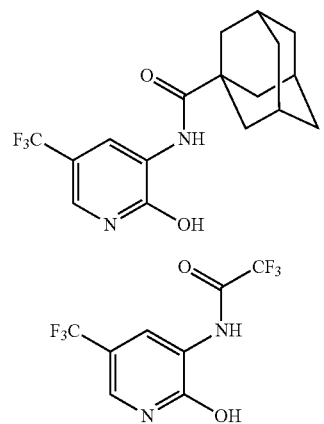

L24

L25

A ligand of Formula III is present in the reaction mixture in an amount of about 10 to about 50 mole percent based on the moles of reactive substrate. Preferably, that amount is about 20 to about 40 mole percent.

A contemplated method utilizes an excess, about 1.5 to about 5 equivalents (moles) of an oxidant per mole of reactive substrate, and preferably about 2 to about 4 equivalents of oxidant. A silver oxidant is typically used, although oxygen and other mild oxidants can also be used. Illustrative catalysts include Ag(Piv), Ag(OAc), $Ag_2O$, AgTFA, AgOTf, $Ag_2CO_3$,

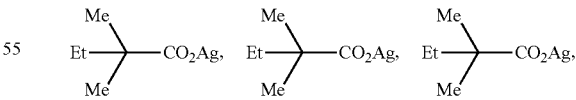

and $Cu(OAc)_2$. Ag(OAc) is a preferred oxidant.

A contemplated reaction is carried out with the ingredients dissolved or dispersed in a solvent and with agitation as can be provided by the use of a magnetic stir bar. Additional means of agitation such as shaking can also be utilized.

The reaction is carried out at a temperature of about 70° to about 120° C. More preferably, the reaction temperature is about 90° to about 110° C. Because many useful solvents boil at a temperature less than 70° C., the reactions are typically carried out in sealed containers under pressure greater than 1 atmosphere. Thus, the pressure under which the ingredients are maintained is mostly that created by the solvent used at the reaction temperature, with some contribution from the reactants.

The reaction is carried out at an above elevated temperature for a time period sufficient to carry out the electrophilic insertion and form a reaction product having the new carbon-carbon (C—C) bond. Reaction times are typically about 15 to about 50 hours, with times of about 18-30 hours being usual.

A contemplated solvent is a non-aqueous solvent having a boiling point at 1 atmosphere of about 40° to about 200° C. Exemplary solvents include $^tBuCO_2Me$, hexafluoro-isopropanol (HFIP), ethyl acetate (EtOAc or EA), acetonitrile, acetone, $^tBuCN$, $^tBuOMe$ (TBME), dioxane, toluene, t-amylOH, $^tBu(C=O)Me$, n-hexane, (trifluoromethyl)benzene, $C_6F_6$, chloroform ($CClH_3$), dichloromethane (DCM), and 1,2-dichloroethane (DCE). DCE, t-amylOH and HFIP are preferred among these materials.

Upon completion of the reaction, the desired product can be recovered by usual work-up procedures, or can be left in situ and reacted further as desired. In preferred situations in which Y is methylene and Z is carbon, the Ring B portion of the molecule is a pyridine derivative as discussed previously, a reaction product of Formula IA is chemically similar to a benzyl ether or benzyl amine.

As such, the two portions of the reaction product can be severed at the bond between X and Y in the structural formula to provide Ring A-Prod and Ring B-Prod whose structural formulas are shown below. This cleavage can be carried out using

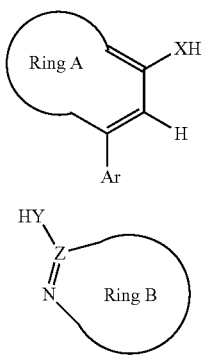

Ring A-Prod

Ring B-Prod chemistry utilized for benzyl protecting group cleavage as is discussed in Greene and Wuts, *Protective Groups in Organic Synthesis*, 3$^{rd}$ ed. John Wiley & Sons, Inc., New York (1999). Further illustrative cleavage reactions are illustrated hereinafter.

Results and Discussion

The initial evaluation of aniline substrates focused on finding a reactive and readily removable directing group that would be compatible with the desired catalytic cycle. The screening reaction used to identify a useful directing group (DG) is illustrated below in Table 1 along with eight aniline derivatives examined.

After a survey of the several directing groups, a benzylic-pyridine based directing group bonded to the aniline amine nitrogen along with a t-Boc protecting group (PG) was found to provide the meta-arylated product in 13% yield. Other directing groups were not reactive, as is shown.

TABLE 1

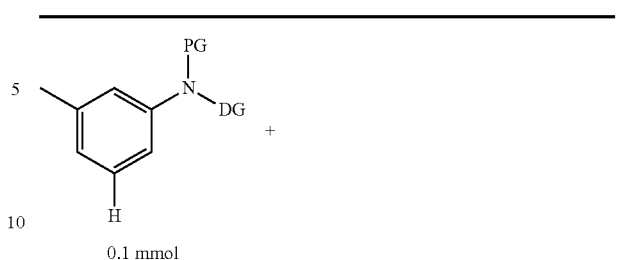

0.1 mmol

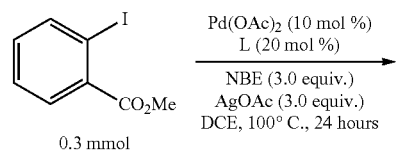 [SMILES: COC(=O)c1ccccc1I]

0.3 mmol

Pd(OAc)$_2$ (10 mol %)
L (20 mol %)
NBE (3.0 equiv.)
AgOAc (3.0 equiv.)
DCE, 100° C., 24 hours

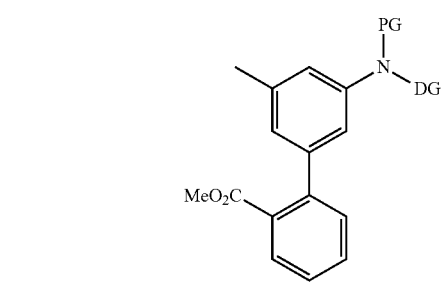

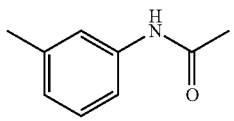

NR

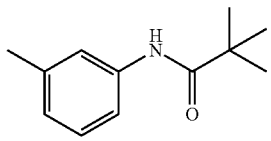

NR

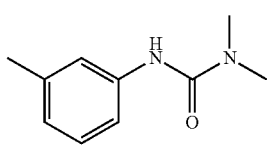

NR

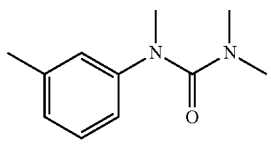

NR

TABLE 1-continued

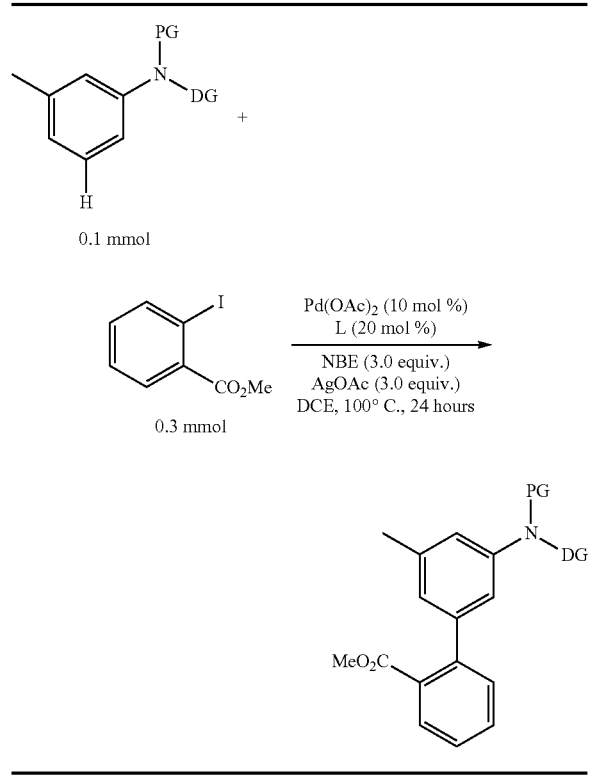

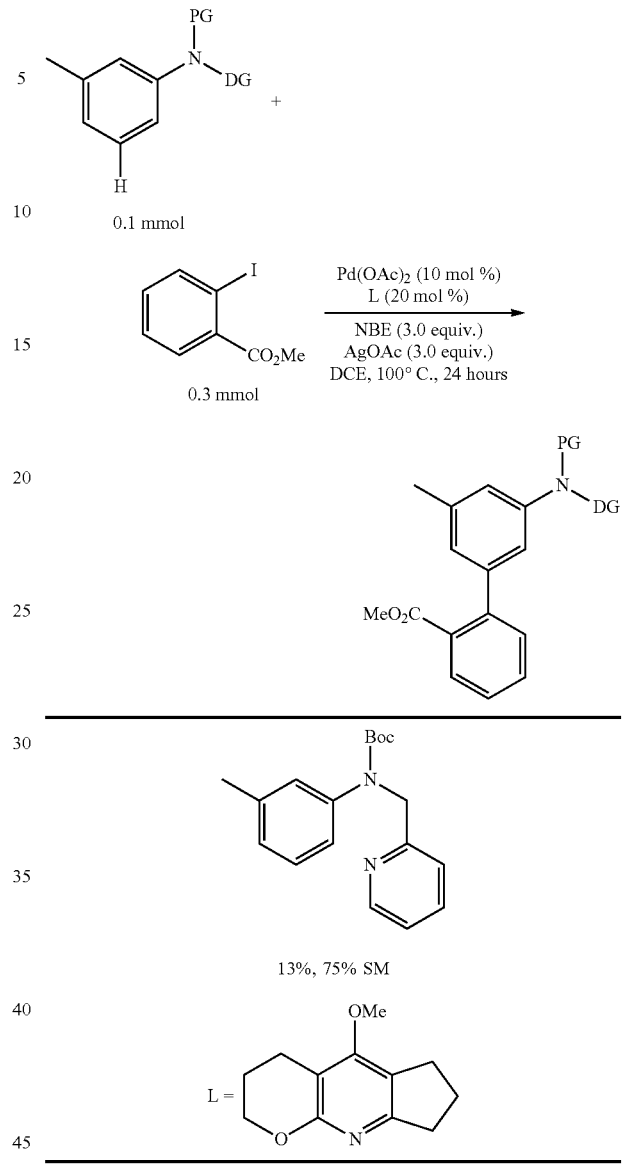

NR = no reaction;
SM = starting material;
The yield was determined by $^1$H NMR.

Ligands that could match with this directing group and promote the reaction were sought, starting with both amino acid- and heterocyclic base-derived ligands that have been shown to promote C—H activation reactions[7,12]. Unexpectedly, there was no significant improvement of the yield when utilizing either of these previously established ligand classes. These results are surprising given the enabling role of the pyridine-derived ligand L1 in the norbornene-mediated meta-C—H arylation of phenylacetic acid derived substrates previously reported by the inventor and co-workers.[12] Phosphine (L4 and L5) and N-heterocyclic carbene (L6) ligands were also evaluated, but neither class provided a significant improvement of the yield. This indicated that design of a new ligand would be crucial for developing broadly useful meta-C—H functionalizations of anilines utilizing this approach. See Table 2 below for results with ligands L1-L11.

TABLE 2*

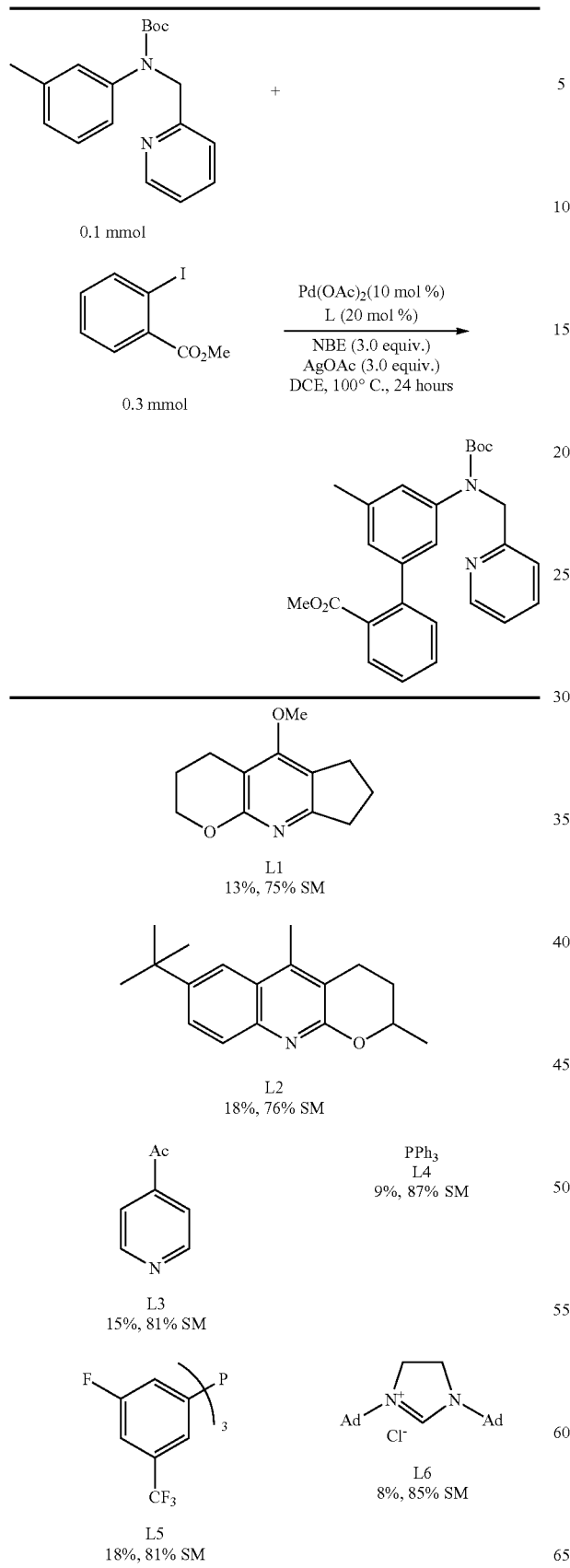

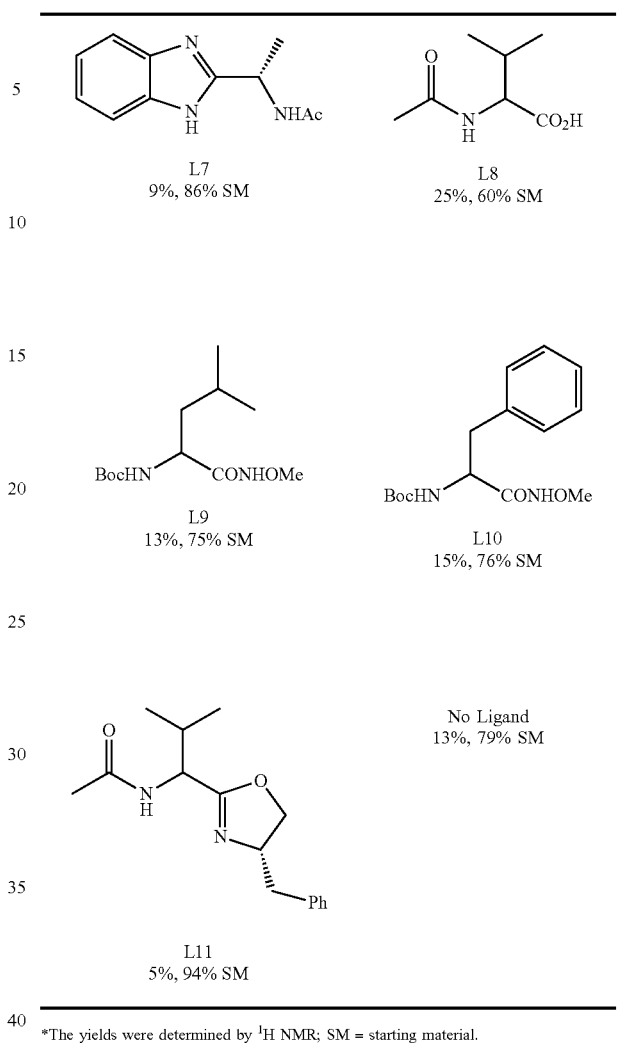

*The yields were determined by $^1$H NMR; SM = starting material.

Considering that the MPAAs have been shown to be highly versatile ligands that promote palladium(II) catalyzed C—H functionalization reactions of C(sp$^2$)-H and in some cases C(sp$^3$)-H bonds,[24,25] the vital structural features of this ligand were sought to be incorporated into other backbones that would enable new reactivity. Although varying the side chain of MPAA ligands permits tuning of their steric properties, modulation of the electronic properties of the C- and N-termini (COOH and NHPG, respectively, PG=protecting group such as Ac, Boc) remains limited. Notably, both computational studies and experimental investigations indicated the NHAc and COOH moieties are essential for forming a bis-dentate complex with Pd(II), generating the active catalytic species.[26,27]

Computational work has also identified a transition state in which the Pd—NAc or Pd-NBoc moiety can assist C—H deprotonation in the C—H cleavage step.[26,27] Recognizing the similarity of 2-hydroxypyridine and 2-pyridone tautomers with the various coordination modes of a carboxylate in MPAA ligands (below), MPAHP ligands were designed and prepared based on a hydroxypyridine scaffold that also incorporates the NHAc group from the MPAAs. A schematic that illustrates these ligands and their structural differences is shown below, where PG is a protecting group.

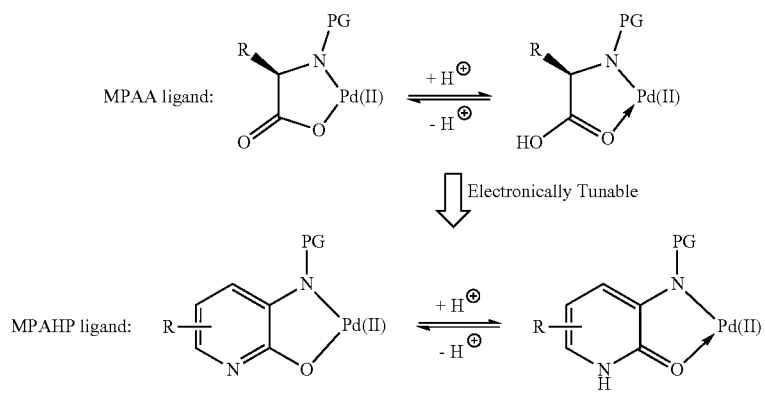

It is important to emphasize that MPAHP ligands were not only designed to act as structural mimics of the MPAAs but also to address the limited opportunities for electronic tuning of the latter ligand class. Specifically, as indicated above, substitution of the aromatic ring of MPAHP ligands permits significant modulation of electronic properties and hence, binding of the OH and NHAc groups (owing to their conjugation to the aromatic ring) to the Pd(II) catalyst. Illustrative ligands examined are shown in Table 3 below along with yield data for the use of each in the model ligand screening reaction shown in the previous table.

With these newly prepared ligands in hand, their use in a model system was investigated, and it was found that the yield approximately tripled with the introduction of L12.

TABLE 3*

TABLE 3*-continued

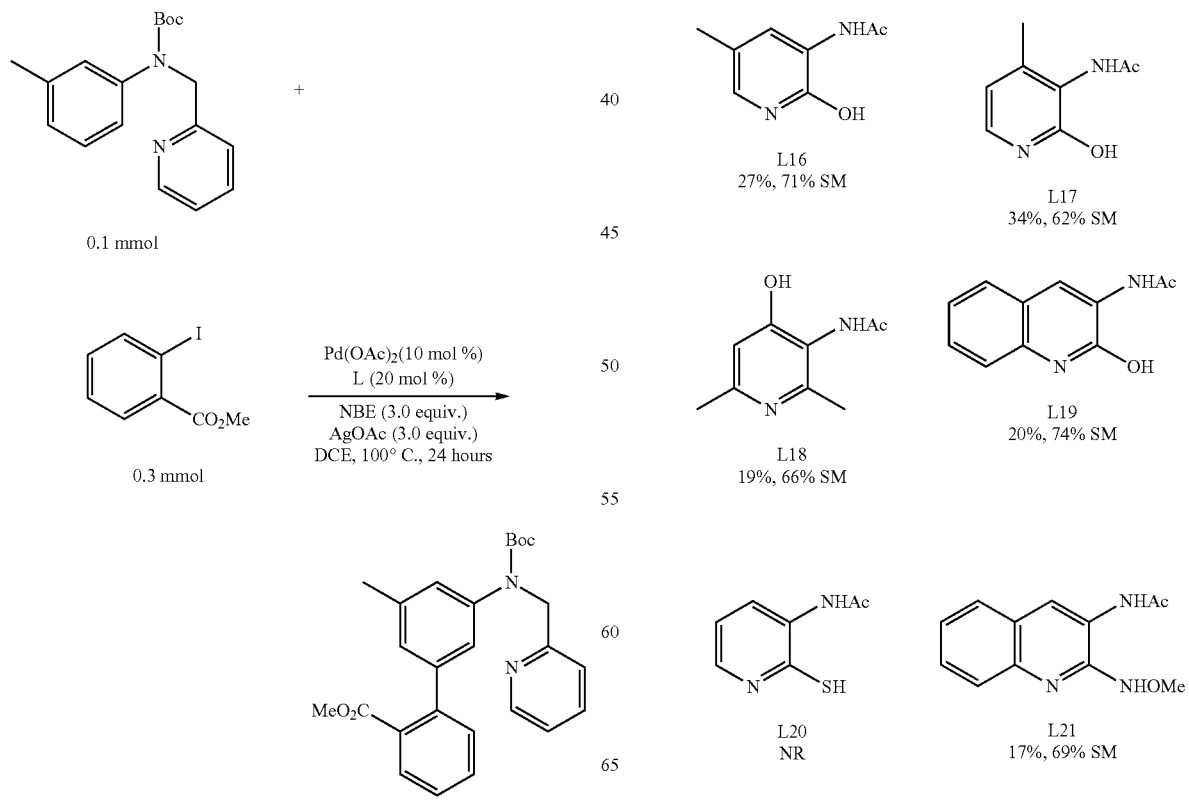

TABLE 3*-continued

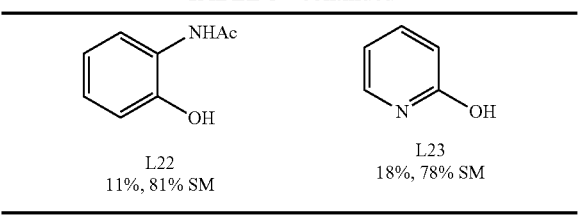

L22
11%, 81% SM

L23
18%, 78% SM

*The yields were determined by ¹H NMR; SM = starting material.

The use of a MPAHP ligand permits the use of a wide range of coupling partners such as a heteroaryl iodide, an alkynyl bromide and an N—OBz amine as are exemplarily illustrated below.

Coupling Partners Enabled by Use of a MPAHP Ligand

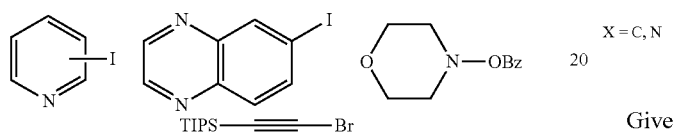

Similarly, use of a MPAHP ligand permits the use a wide range of substrates as are exemplarily shown below.

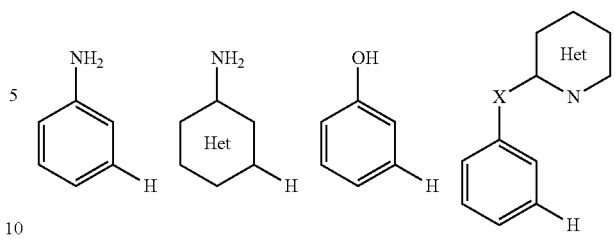

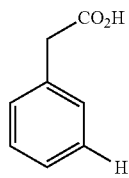

X = C, N

Given the importance of synergy between directing group and ligand for efficient C—H functionalization, the directing groups were re-examined. The effects of several directing groups were examined under standardized conditions as is shown in Table A, below. As shown by the data, it was

TABLE A

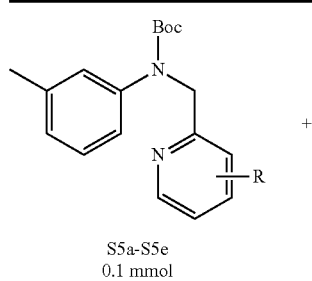

S5a-S5e
0.1 mmol

+

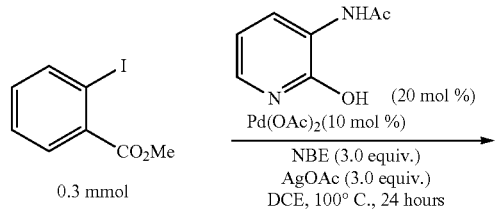 [SMILES: COC(=O)c1ccccc1I ; CC(=O)Nc1cccnc1O]

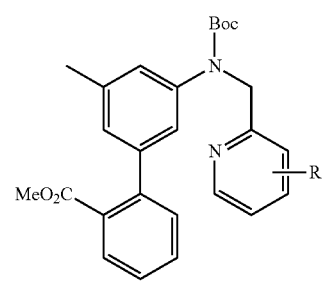

S6a-S6e

TABLE A-continued
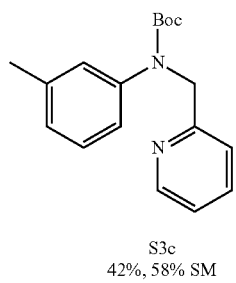 [SMILES: Cc1cccc(N(Cc2ccccn2)C(=O)OC(C)(C)C)c1]
S3c
42%, 58% SM
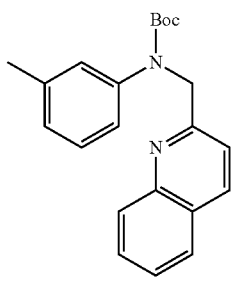
S5a
>2%, 40% SM
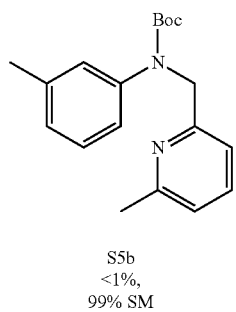 [SMILES: Cc1cccc(N(Cc2cccc(C)n2)C(=O)OC(C)(C)C)c1]
S5b
<1%,
99% SM
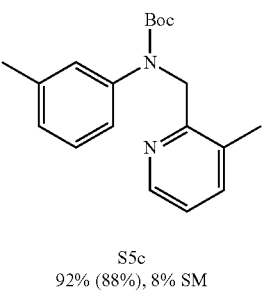
S5c
92% (88%), 8% SM
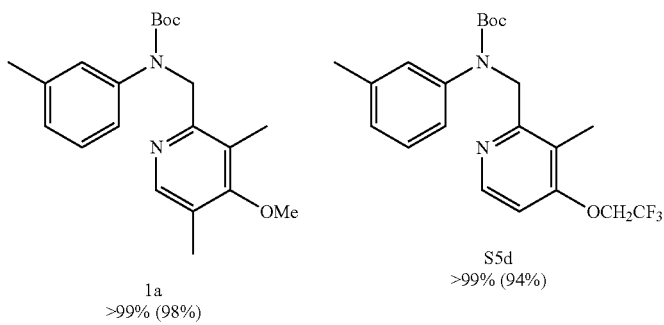
1a
>99% (98%)
S5d
>99% (94%)
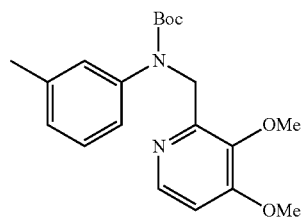
S5e
98%
(90%)
The yield was determined by $^1$H NMR; SM = starting material; The yields in parentheses are isolated yields.

found that electron rich benzylic pyridine-based directing groups matched well with this ligand scaffold, with a commercially available directing group (DG, shown below) cooperating with the ligand

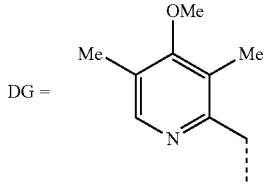

to provide the desired product in 98% isolated yield. With the optimized reaction conditions in hand, the scope of substrate reaction was examined.

As can be seen in Tables 4-7 below, the substrate scope of this transformation is very broad. Electron-donating and electron-withdrawing groups (5a-o) are well tolerated at both the ortho- and meta-positions of the aniline. It is noteworthy that the commonly troublesome cyano and nitro functionalities (5j, 5k) are well tolerated in this reaction when utilizing an improved transient mediator, methyl bicyclo[2.2.1]hept-2-ene-2-carboxylate (NBE-CO$_2$Me), in place of 2-norbornene.[14]

Interestingly, unsubstituted aniline 1j and para-substituted substrate 1p showed high selectivity for the di-substituted product, whereas 4-methoxy substituted aniline 1q showed high mono-selectivity. It is hypothesized that after the initial arylation of substrate 1q, a conformational change is induced wherein the methyl group on the methoxy is primarily positioned away from the newly installed aryl ring, blocking the alternative meta-position which prevents di-arylation.

TABLE 4*

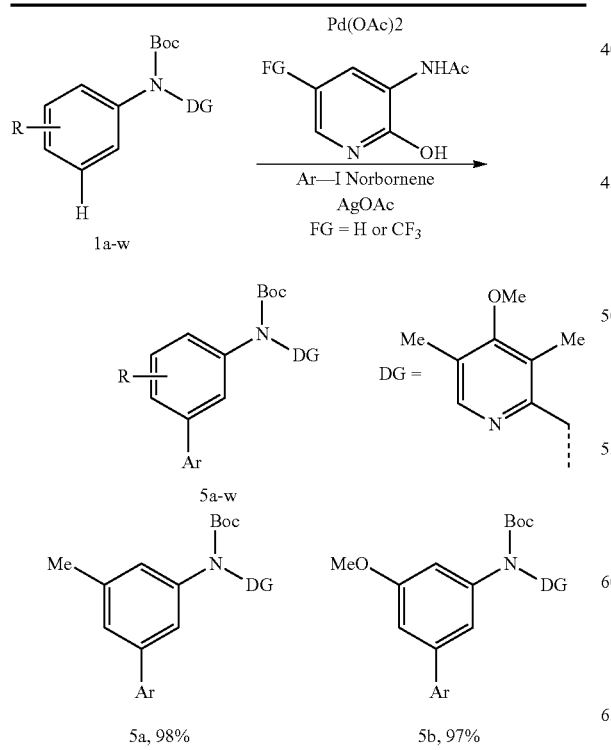

TABLE 4*-continued

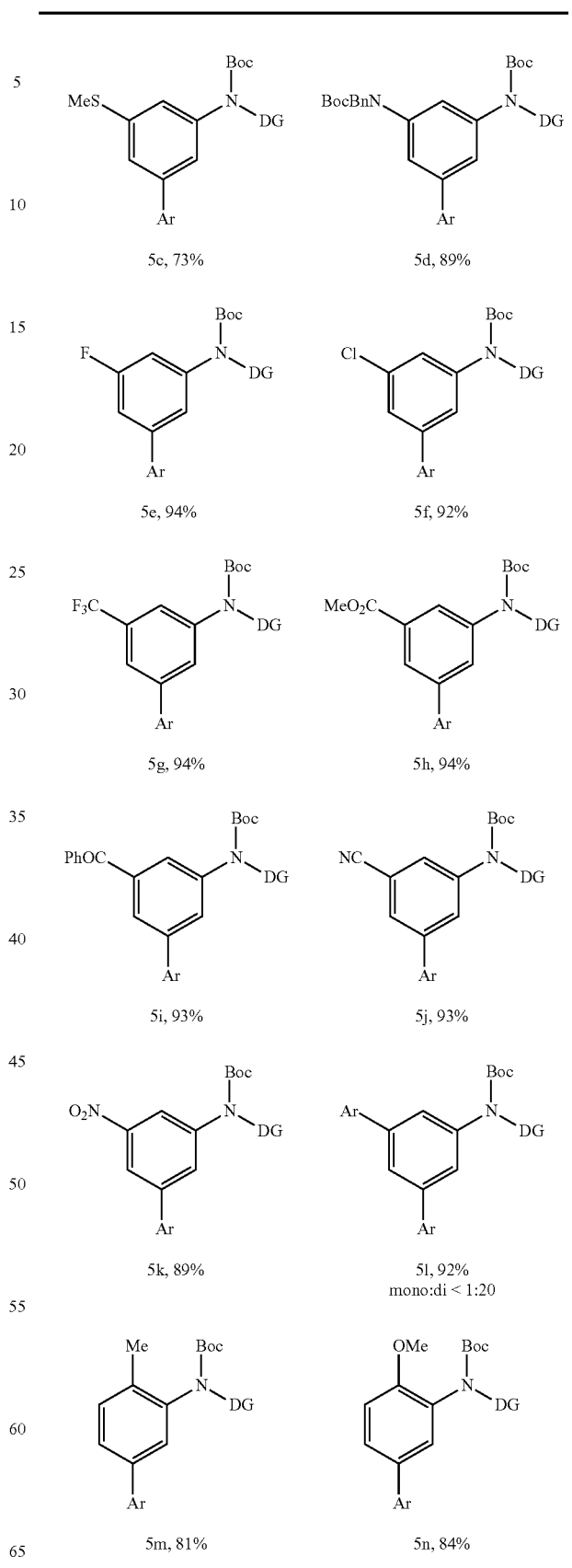

TABLE 4*-continued 5o, 90%

5p, 90%
mono:di < 1:20

5q, 64%
mono:di > 20:1

5r, 83%

5s, 94%

5t, 89%

5u, 87%

5v, 87%

5w, 68%

*In the above and following three tables: DG = directing group; Ar—I = methyl 2-iodobenzoate; Ar = 2-(carboxymethyl)phenyl; NBE—CO$_2$Me = methyl bicyclo[2.2.1]hept-2-ene-2-carboxylate; Boc = tert-butyloxycarbonyl; Ac = acetyl; Bn = benzyl.
The values under each structure indicate isolated yields. Substrates 1a-w and 2a-l were arylated using L12 in 1,2-dichloroethane. For substrates 1g, 1j, 1k, 2a, 2d and phenol substrates 3a-l, NBE—CO$_2$Me was used; other substrates were arylated using 2-norbornene as mediator. The selectivity of the mono- and di-arylated products was determined by $^1$H NMR analysis using CH$_2$Br$_2$ as an internal standard.

A deeper investigation into the scope of this reaction revealed that heterocyclic substrates (2a-l), which are commonly incompatible with C—H cross-coupling methodology, were well tolerated in this reaction providing good to excellent yields of products 6a-l, as shown in Table 5 below. Importantly, the yield of product 6b was reduced to 4% in the absence of L12, thus indicating the importance of the ligand to achieve a broad substrate scope for this transformation.

TABLE 5*

2a-l 6a-l

DG =

6a, 53%

6b, 72%

6c, 79%

6d, 56%

6e, 65%

6f, 76%

6g, 89%

6h, 66%

TABLE 5*-continued

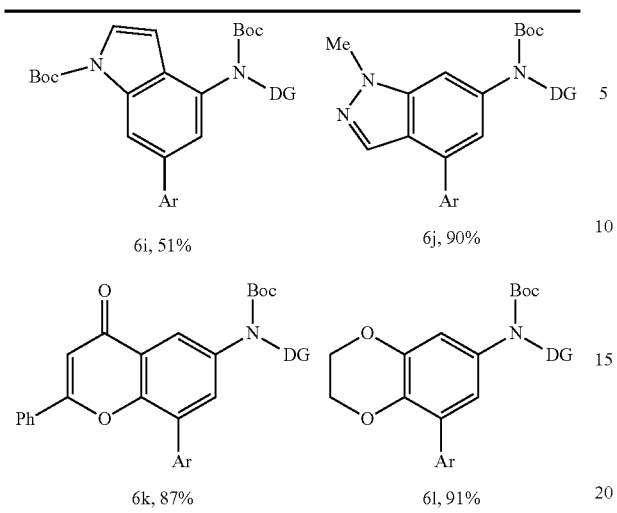

6i, 51%  6j, 90%  6k, 87%  6l, 91%

*Het = heteroaromatic.

Being interested in further examining the breadth of this reaction, was next evaluated meta-C—H arylation of phenol[28,29]-derived substrates bearing benzylic pyridine based directing groups was next evaluated.[30] Although good yields were obtained with the same directing group that was utilized for the aniline derived substrates, deprotection proved problematic. To circumvent this problem, a 2,3-lutidine derived directing group (DG', whose structure is shown adjacent to the reaction scheme in Table 6) was used that is removed by hydrogenolysis with catalytic palladium on carbon under 30 bar hydrogen.

As shown in Table 6, a variety of phenols could be successfully arylated at the meta-position utilizing methyl bicyclo[2.2.1]hept-2-ene-2-carboxylate (NBE-CO$_2$Me) and a modified ligand (L14). Successful use of both ligand attests to the importance of being able to tune the electronics of this newly disclosed ligand scaffold.

Intriguingly, although substrate 1j shows high selectivity for di-arylated product, phenolic substrate 3d provides a mono:di ratio of 1:1. This result is attributed to the phenolic substrates being slightly less reactive than their aniline counterparts.

TABLE 6*

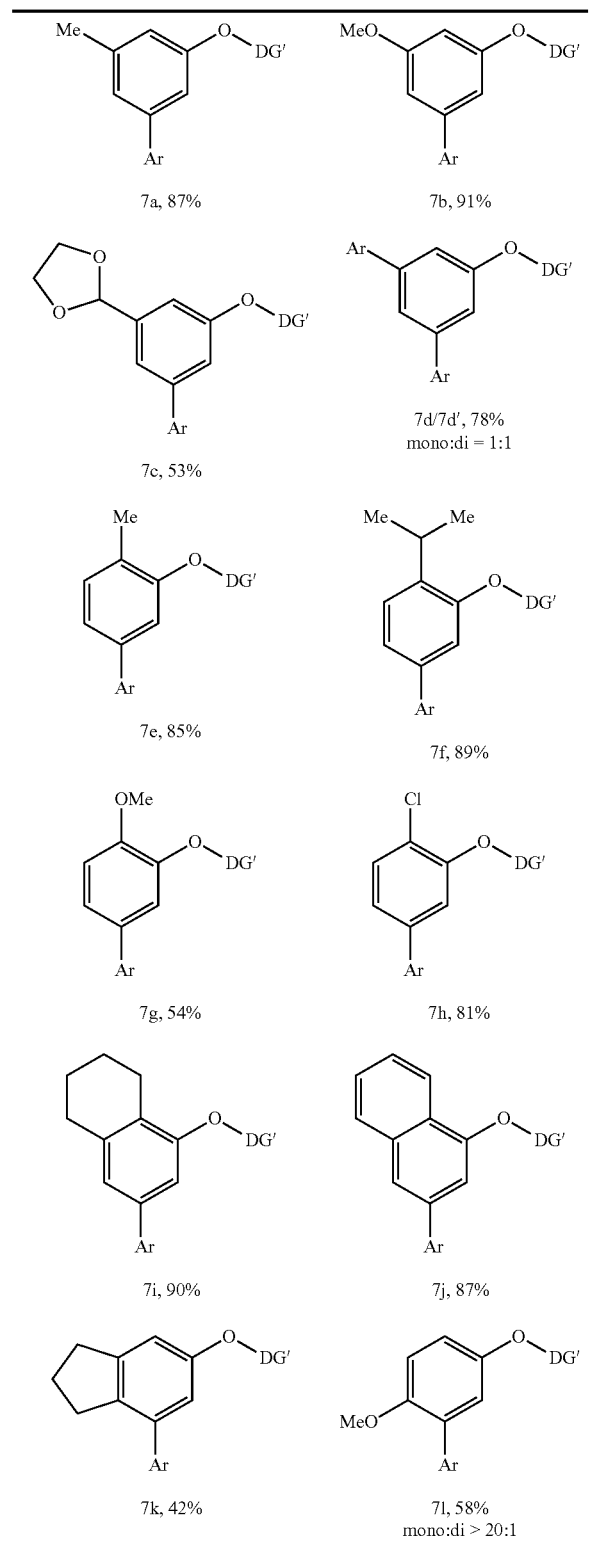

7a, 87%  7b, 91%  7c, 53%  7d/7d', 78% mono:di = 1:1
7e, 85%  7f, 89%  7g, 54%  7h, 81%
7i, 90%  7j, 87%  7k, 42%  7l, 58% mono:di > 20:1

*Substrates 3a-l and 4a-l were arylated using L14 in chloroform; substrate 3h was arylated using L12 in chloroform for 36 hours.

To more fully explore the scope of this methodology, the activity of this ligand was examined with substrates containing native heterocycles as directing groups. Gratifyingly, heterocyclic substrates that form 6-membered palladacycles upon cyclopalladation worked exceedingly well. Substrates directed by native pyridine, pyrimidine, pyrazine, pyrazole, indazole, isoindazole and isoquinoline were all successfully arylated at the previously inaccessible meta-positions as is seen in Table 7, below.

As all of these substrates are unsubstituted, the mono:di ratio appears to be loosely correlated to the coordination strength of the various heterocyclic directing groups with weaker coordinating directing groups tending away from highly di-selective arylations. Dotted bond lines in that table indicate the presence of diarylation products with the ratio of mono:di products being shown. Importantly, the ligand should be present for this reaction to proceed in synthetically useful yields with all of the substrate classes shown in Table 7.

TABLE 7*

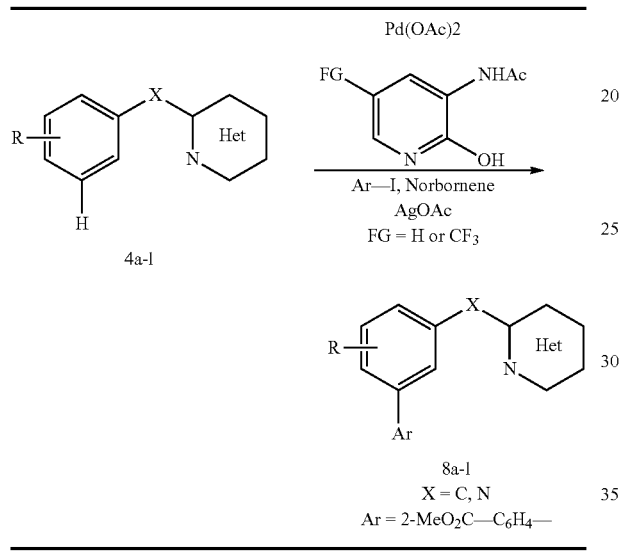

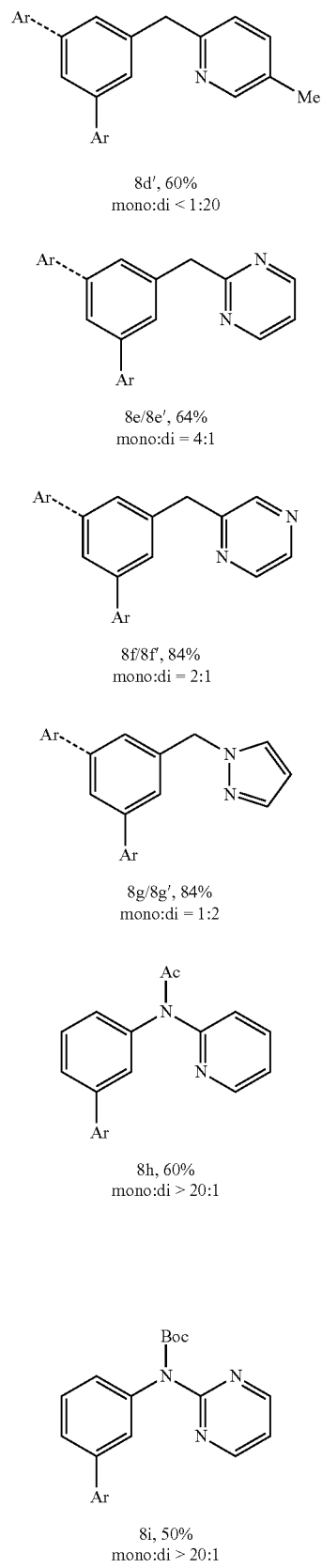

TABLE 7*-continued

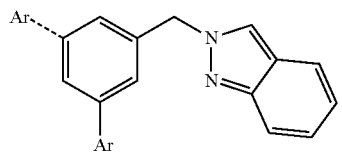

8j/8j', 74%
mono:di = 3:1

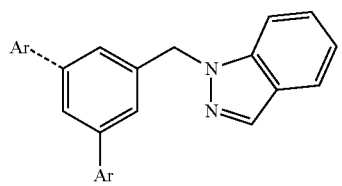

8k/8k', 50%
mono:di = 3:1

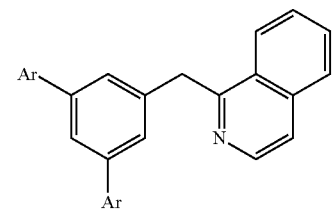

8l', 78%
mono:di < 1:20

*Het = heteroaromatic.

The effects of solvent and oxidation on the arylation in the standard reaction were also examined. Those results are illustrated by the reaction scheme and results shown below in Tables 8a and 8b.

TABLE 8a

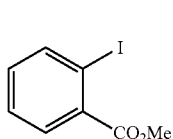

0.1 mmol
1

+

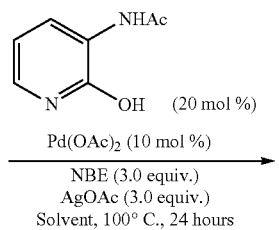

0.3 mmol

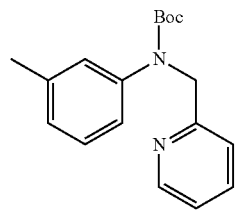
(20 mol %)
Pd(OAc)₂ (10 mol %)
―――――――――――→
NBE (3.0 equiv.)
AgOAc (3.0 equiv.)
Solvent, 100° C., 24 hours TABLE 8a-continued

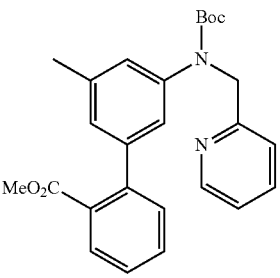

2

| Entry | Solvent | BP (° C.) | 2 (%) | 1 (%) |
|---|---|---|---|---|
| 1 | PhCH₃ | 110 | 24 | 65 |
| 2 | PhCF₃ | 101 | 31 | 64 |
| 3 | TBME | 131 | 20 | 78 |
| 4 | Dioxane | 101 | 37 | 51 |
| 5 | EA | 77 | 30 | 67 |
| 6 | CH₃CN | 82 | 36 | 47 |
| 7 | t-Amyl-OH | 102 | 35 | 53 |
| 8 | DCM | 40 | 34 | 64 |
| 9 | DCE | 84 | 42 | 58 |
| 10 | CHCl₃ | 61 | 42 | 57 |
| 11 | Acetone | 56 | 38 | 60 |
| 12 | DMF | 153 | 14 | 85 |

The yields were determined by ¹H NMR.

Thus, use of each of the above-listed solvents provided product. However, DCE and chloroform (CHCl₃) provided the highest yield of product (2) and the lowest amount of residual starting material (1).

TABLE 8b

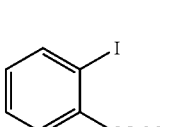

0.1 mmol
1

+

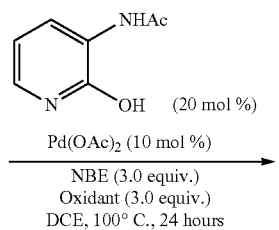

0.3 mmol

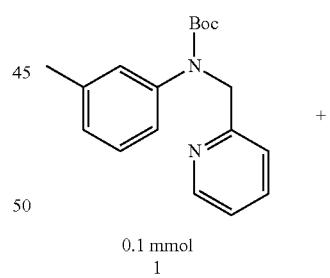
(20 mol %)
Pd(OAc)₂ (10 mol %)
―――――――――――→
NBE (3.0 equiv.)
Oxidant (3.0 equiv.)
DCE, 100° C., 24 hours

TABLE 8b-continued

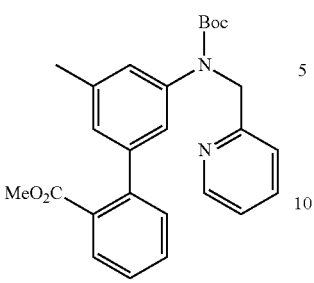

2

| Entry | Oxidant | 2 (%) | 1 (%) |
|---|---|---|---|
| 1 | — | 2 | 84 |
| 2 | AgOAc | 42 | 58 |
| 3 | Ag$_2$CO$_3$ | 12 | 82 |
| 4 | Ag$_2$O | 6 | 90 |
| 5 | AgF | <1 | <1 |
| 6 | AgNO$_3$ | 4 | 88 |
| 7 | AgOBz | 17 | 76 |
| 8 | AgOPiv | 10 | 87 |
| 9 | AgOTs | <1 | <1 |
| 10 | K$_2$S$_2$O$_8$ | <1 | <1 |
| 11 | Na$_2$S$_2$O$_8$ | <1 | <1 |
| 12 | BQ | <1 | 44 |
| 13 | PhI(OAc)$_2$ | 2 | 64 |
| 14 | Cu(OAc)$_2$ | <1 | <1 |

The yields were determined by $^1$H NMR.

As is seen from the data above, silver acetate (AgAOc) provided the best yields of the several oxidants examined.

Several removable aniline-nitrogen protecting groups (PG) were studied for their effect if any on product yield. As is seen from the data in Table 8c, below, most were useful, with t-boc providing the greatest yield in the conditions examined. The protecting groups (PG) used are

TABLE 8c*

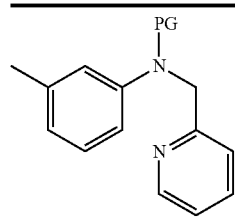

S3a-3i
0.1 mmol

+

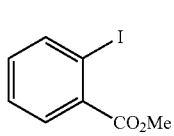 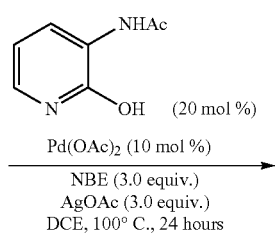

0.3 mmol

Pd(OAc)$_2$ (10 mol %)
NBE (3.0 equiv.)
AgOAc (3.0 equiv.)
DCE, 100° C., 24 hours

TABLE 8c*-continued

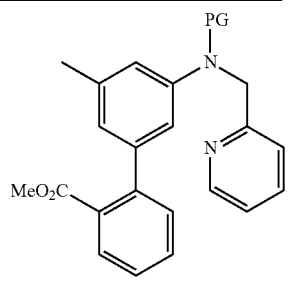

S4a-S4i

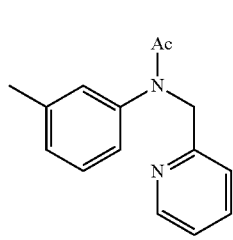 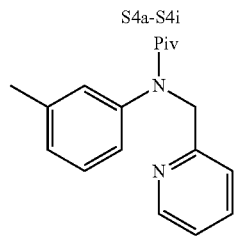

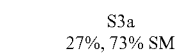 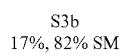

S3a
27%, 73% SM

S3b
17%, 82% SM

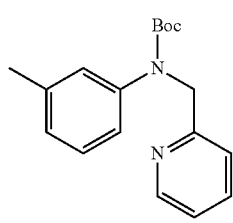 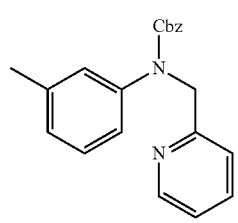

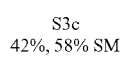 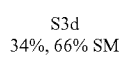

S3c
42%, 58% SM

S3d
34%, 66% SM

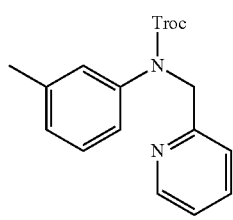 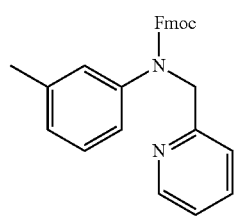

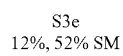 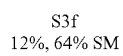

S3e
12%, 52% SM

S3f
12%, 64% SM

TABLE 8c*-continued

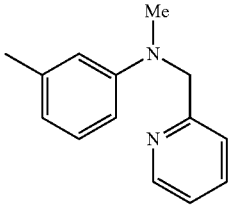

S3g
<5%, 89% SM

S3h
<1%, 12% SM

S3i
<1%, decomposed

*The yields were determined by $^1$H NMR; SM = starting material.
Ac = acetyl,
Piv = pivaloyl,
Boc = t-butoxycarbonyl,
Cbz = benzyloxycarbonyl,
Troc = 2,2,2-trichloro-ethoxycarbonyl,
Fmoc = 9-fluorenylmethoxycarbonyl,
Ms = methanedulfonyl,
Tf = trifluoromethanesulfonyl, and
Nos = nitrobenzenesulfonyl.

Having thoroughly examined the substrate scope of this reaction, focus was turned to evaluating the coupling partner scope using aniline 1a as the model substrate. Although 3-aryl-5-methyl anilines are alternatively accessible via Suzuki-coupling of the commercially available 3-bromo-5-methylaniline, Compound 1a was chosen as the model substrate to investigate the reactivity of a wide range of aryl iodides as it is relatively electron neutral when compared to alternatively substituted anilines.

Experimental results shown in Table 9, below, indicate that this reaction exhibited an exceptionally broad coupling partner scope when utilizing a modified norbornene.[14] Electron donating and electron withdrawing groups at the para- and meta-positions of the aryl iodide coupling partner were well tolerated, providing the desired products in good yields (9a-y).

TABLE 9*

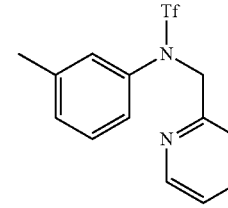

1a

TABLE 9*-continued

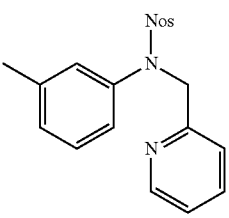

9a-ad

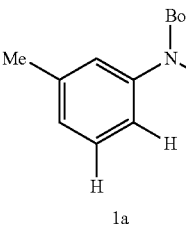

9a-s

| R = | | |
|---|---|---|
| H | 9a, | 87% |
| Ph | 9b, | 79% |
| Me | 9c, | 82% |
| CH$_2$OTBS | 9d, | 83% |
| OMe | 9e, | 81% |
| OTBS | 9f, | 65% |
| CH$_2$PO(OEt)$_2$ | 9g, | 92% |
| R = SMe | 9h, | 70% |
| NBnBoc | 9i, | 80% |
| F | 9j, | 92% |
| Cl | 9k, | 83% |
| Br | 9l, | 82% |
| I | 9m, | 67% |
| CO$_2$Me | 9n, | 92% |
| R = COMe | 9o, | 87% |
| CHO | 9p, | 96% |
| CF$_3$ | 9q, | 97% |
| NO$_2$ | 9r, | 88% |
| CN | 9s, | 89% |

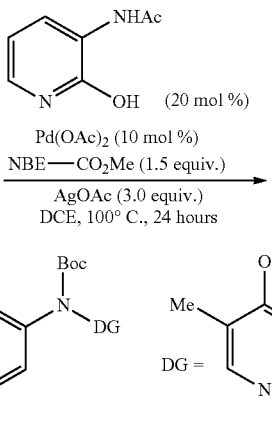

9t-x

| R = CO$_2$Me | 9t, | 88% |
|---|---|---|
| F | 9u, | 86% |

TABLE 9*-continued

| | |
|---|---|
| I | 9v, 74% |
| Me | 9w, 82% |
| OMe | 9x, 85% |

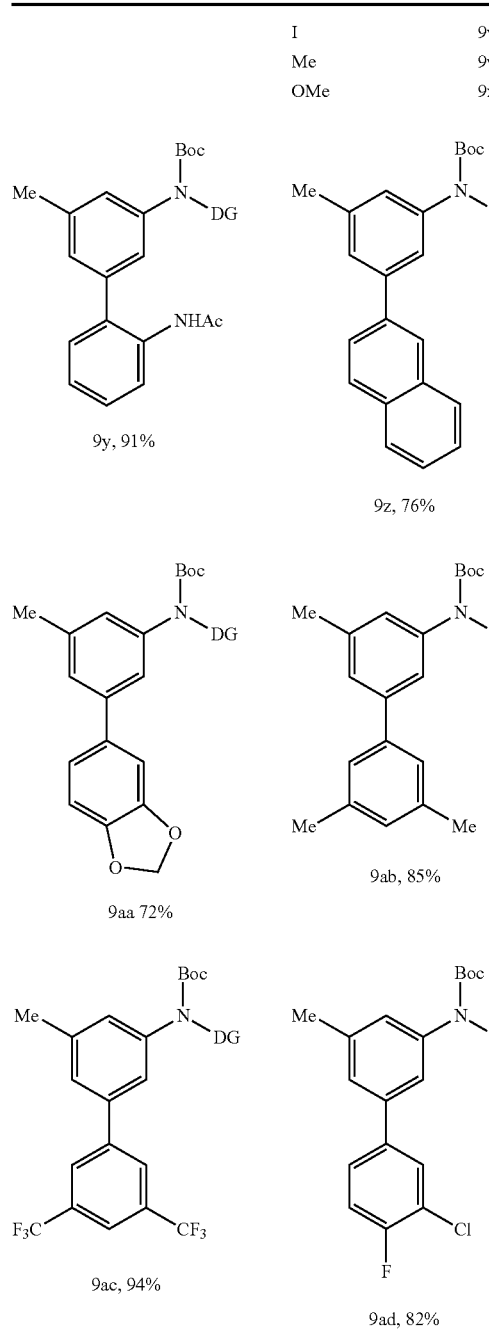

*In Tables 9-11: TBS = tert-butyldimethylsilyl; Ts = 4-toluenesulfonyl; NBE-CO₂Me = methyl bicyclo[2.2.1]hept-2-ene-2-carboxylate.
The values under each structure indicate isolated yields.

Reaction conditions: Substrate (0.1 mmol), Ar—I (0.2 mmol), Pd(OAc)₂ (10 mol %), L12 (20 mol %), NBE-CO₂Me (1.5 equiv.), AgOAc (3.0 equiv.), 1,2-dichloroethane (0.5 mL), 100° C., 24 hours.

Interestingly, this reaction was not limited to simple aryl iodides and an array of heterocyclic aryl iodides worked well in this reaction (9ae-ba). Indoles, thiophenes, furan, indazole, quinoline, quinazoline, and a range of pyridines were suitable coupling partners, showcasing the utility of this reaction for medicinal chemistry efforts where heterocyclic motifs are prevalent. These results are shown in Table 10, below.

TABLE 10

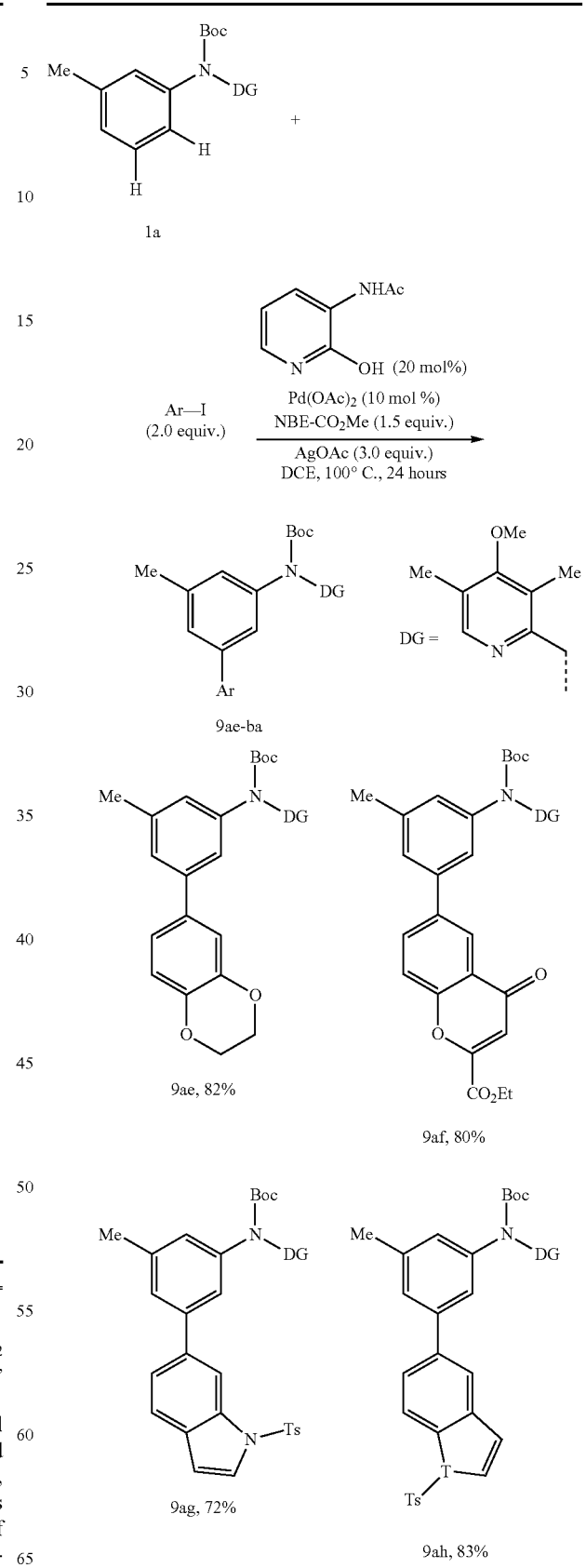

TABLE 10-continued
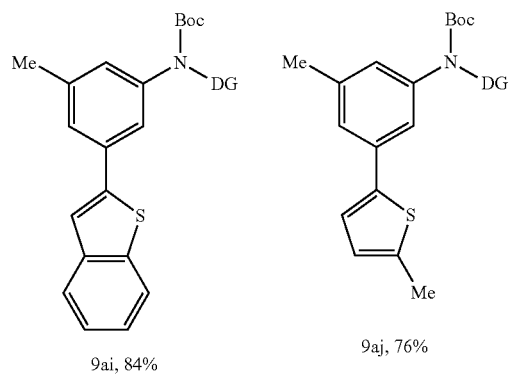
9ai, 84%   9aj, 76%
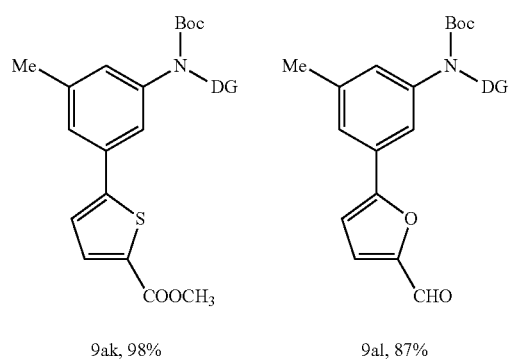
9ak, 98%   9al, 87%
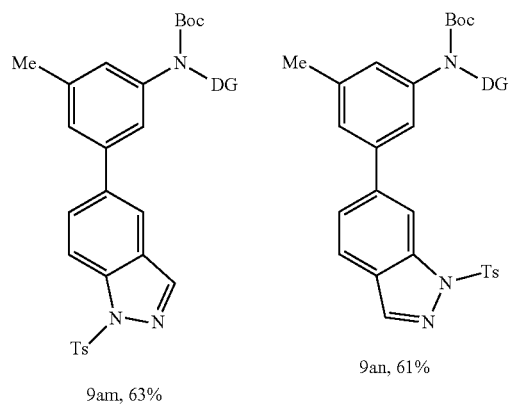
9am, 63%   9an, 61%
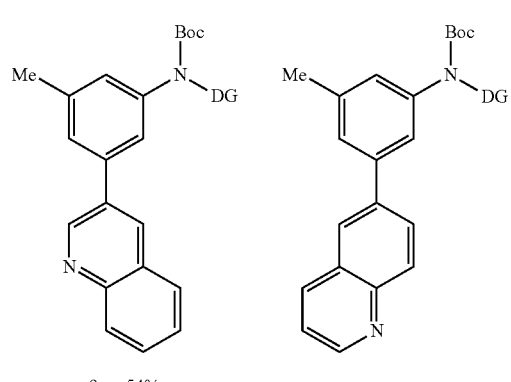
9ao, 54%   9ap, 41%
TABLE 10-continued
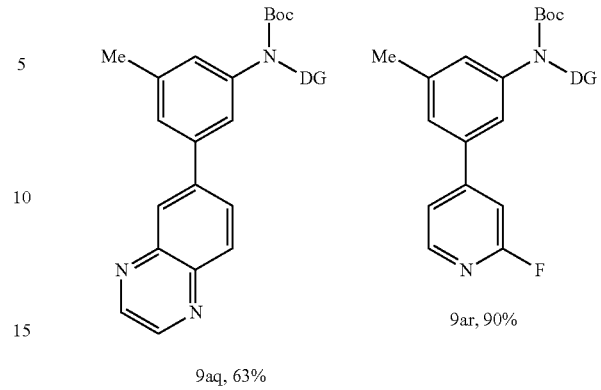
9aq, 63%   9ar, 90%
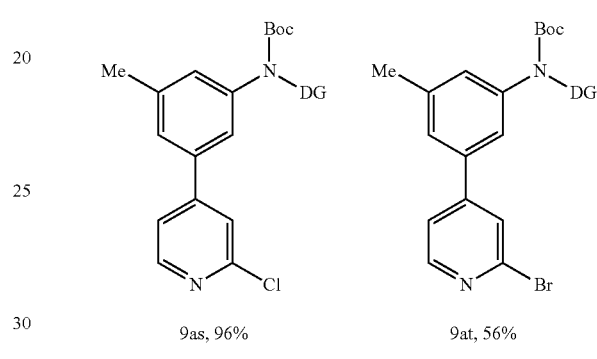
9as, 96%   9at, 56%
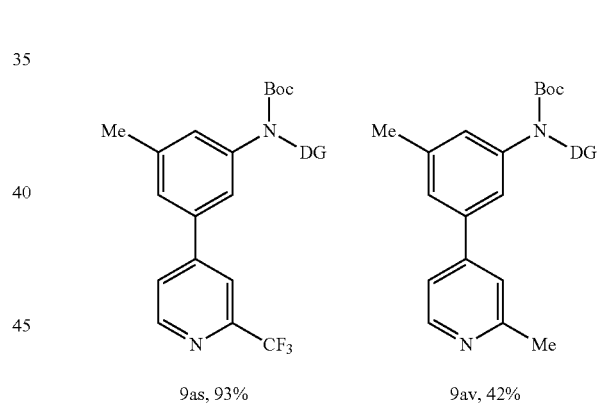
9as, 93%   9av, 42%
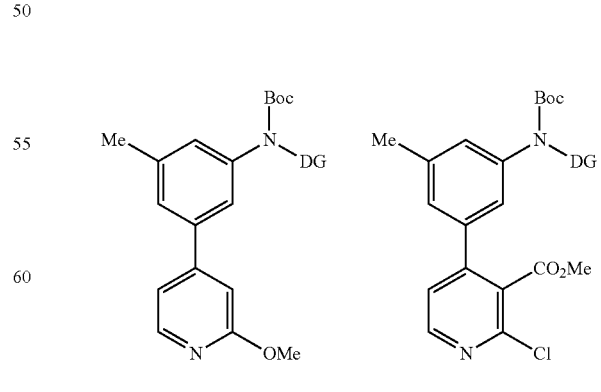
9aw, 55%   9ax, 51%

TABLE 10-continued

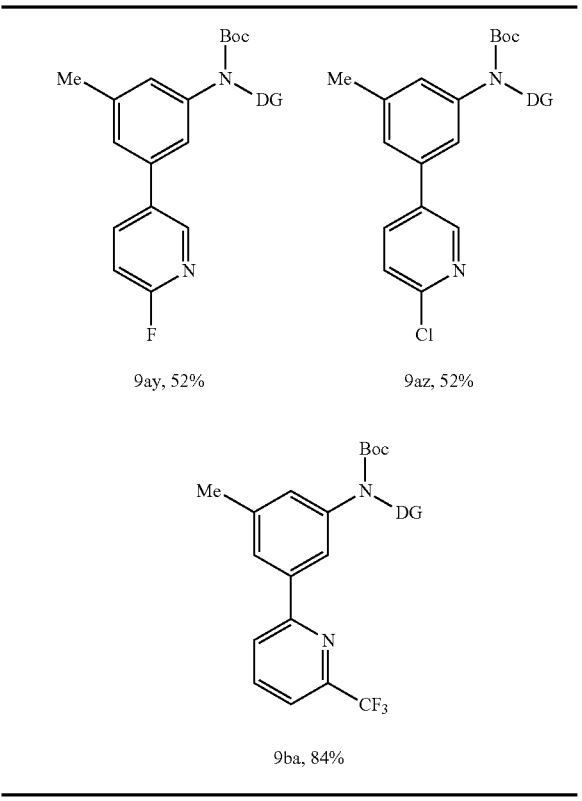

*For 9ap, 9av, 9ba, 9bb and 9bc, Pd(OAc)₂ (20 ml %) and L12 (40 mol %) were used.

To determine whether the broad coupling partner scope observed in this reaction was enabled by the ligand, the reaction was carried out under the optimized conditions with 2-chloro-4-iodopyridine in the absence of L12 and found the yield to be 9% by $^1$H NMR. This result highlights the importance of the MPAHP ligands for this transformation.

In order to fully investigate the compatibility of this reaction with heterocycles, the efficiency of coupling heterocyclic substrates with heterocyclic aryl iodides was examined. As can be seen in Table 11, (compounds 9bb-9bh), this ligand enables the coupling of heterocyclic coupling partners with heterocyclic substrates in good to excellent yields. Furthermore, the scalability of this reaction was demonstrated by performing the meta-C—H coupling of aniline substrate 1a on gram-scale with 5 mol % Pd(OAc)₂ and 5 mol % L12, providing the desired product cleanly in 93% yield.

TABLE 11*

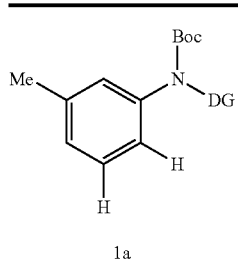

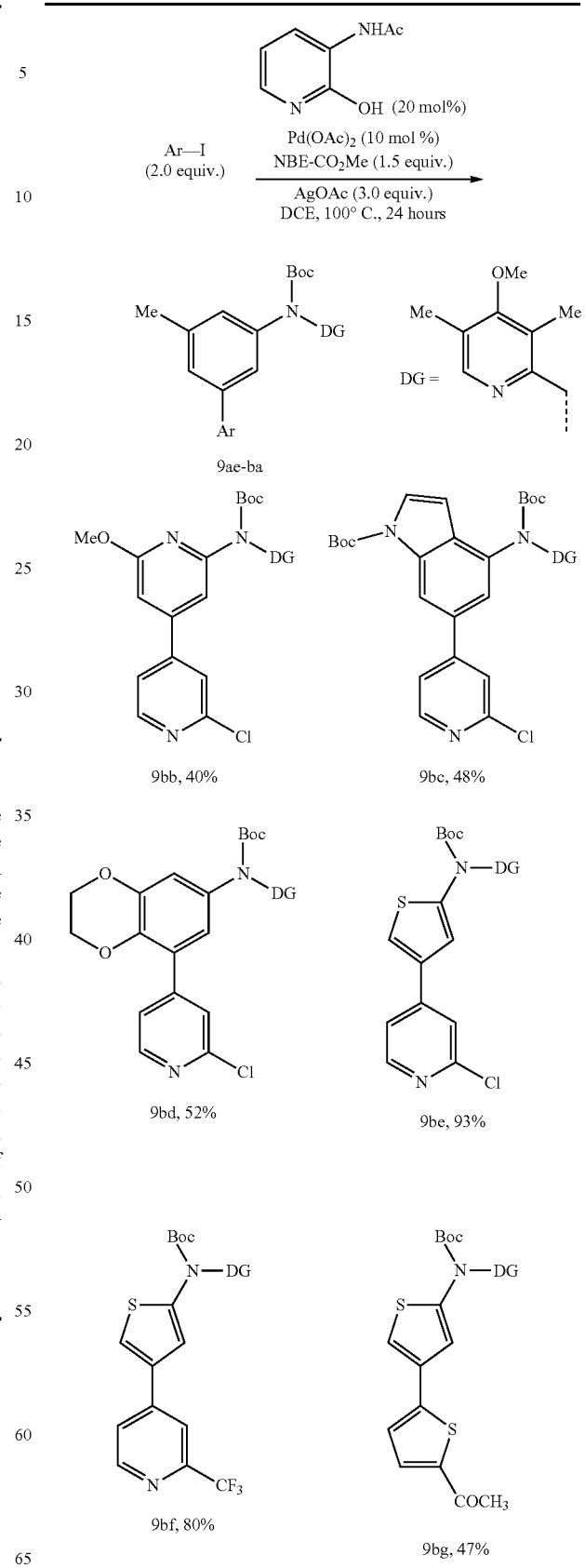

TABLE 11*-continued

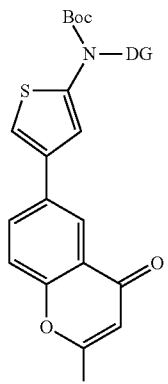

9bh, 41%

Given the efficiency of the meta-C—H coupling of aniline substrates on a preparative scale, the applicability of this methodology was sought to be demonstrated using medicinally relevant compounds. Recently, the drug thalidomide and its derivatives pomalidomide and lenalidomide (IMiDs) have been repurposed for several clinical indications including multiple myeloma (MM) and myelodysplasia. Crystallographic evidence for IMiD binding to a key target, cereblon (CREN),[31] suggests that chemical modification of the solvent-exposed phthalimide part of the IMiDs could lead to molecules with altered specificity.

Efforts were therefore initiated to evaluate the feasibility of applying the ligand enabled, meta-C—H arylation of aniline derivatives to functionalize the solvent-exposed, meta-position of lenalidomide. This exemplifies a scenario where utilizing norbornene-mediated meta-C—H functionalization is advantageous as it allows elaboration of the parent drug molecule in relatively few steps. Gratifyingly, the meta-arylation of a lenalidomide derivative proceeded smoothly to provide the desired product (Compound 11) in 61% isolated yield (below). The successful utilization of the

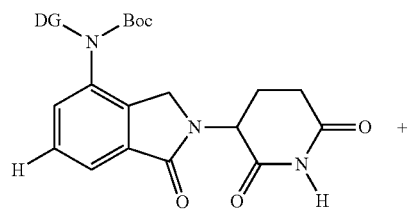

lenalidomide derivative

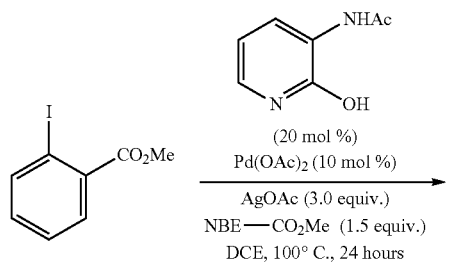

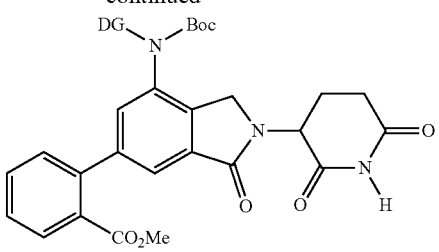

11, 61% yield

Boc = tert-butyloxycarbonyl; NBE—CO₂Me = methyl bicyclo[2.2.1]hept-2-ene-2-carboxylate; Ac = Acetyl; DCE = 1,2-dichloroethane norbornene mediated meta-C—H functionalization in this setting showcases the potential utility of this reaction in drug discovery.

Recognizing the robust nature of the MPAHP ligands, an improvement of the practicality of the reaction conditions in collaboration with Bristol-Myers Squibb. A high throughput screen was undertaken to establish Ag-free conditions with process friendly solvents. Through this screen, it was found that the use of CsOAc in place of AgOAc in t-Amyl-OH could provide excellent yields on gram-scale reactions with ortho-substituted aryl iodides, and synthetically useful yields with simple aryl iodides when utilizing L12 or L17 respectively as are illustrated in the reaction schemes below. The

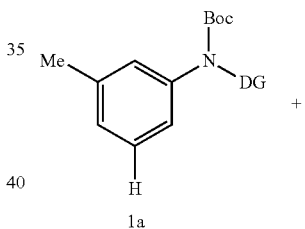

1a

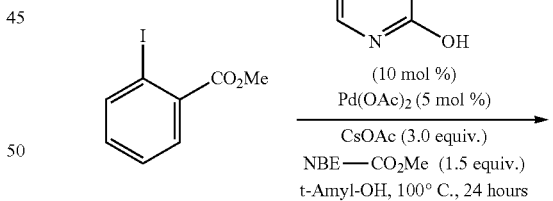

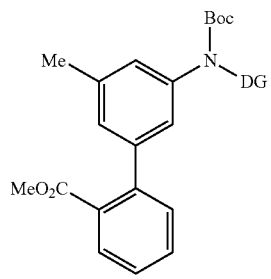

5a, 1.71 g, 87% yield

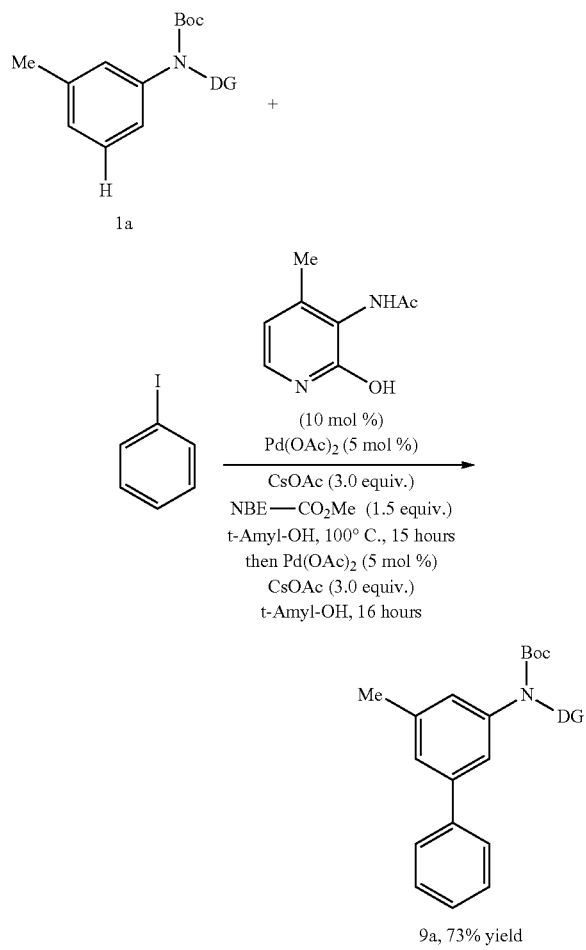

9a, 73% yield

DCM = dichloromethane.

removal of silver from the Pd(II) catalyzed, norbornene mediated meta-C—H arylation reaction for the first time is crucial for adopting this method in synthesis, especially when reactions need to be performed beyond gram-scale.

The applicability of this ligand scaffold in promoting other transformations was attempted in other challenging meta-C—H amination reactions. After systematic optimization, the MPAHP ligand L24 was found to promote the norbornene mediated meta-amination of a variety of anilines with N—O benzoyl morpholine to provide Compounds 10a-j in synthetically useful yields. These reactions are illustrated below in Table 12.

TABLE 12*

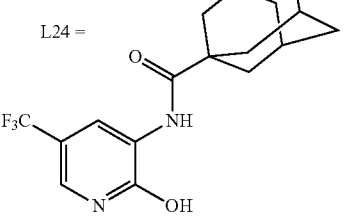

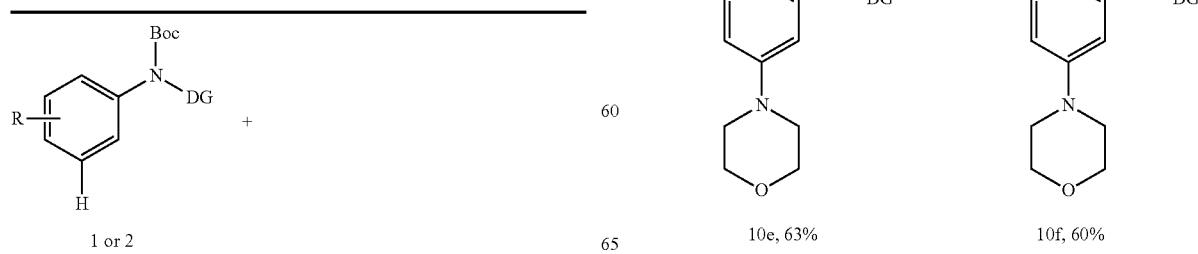

TABLE 12*-continued

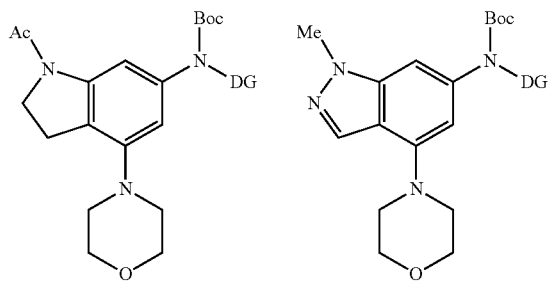
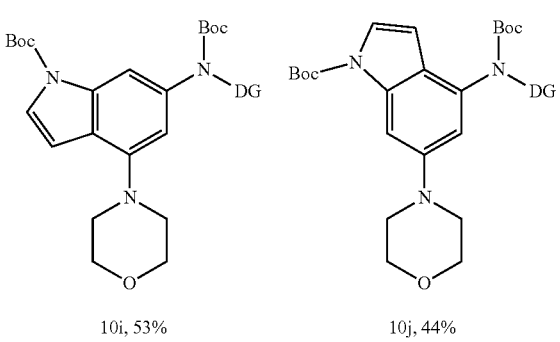
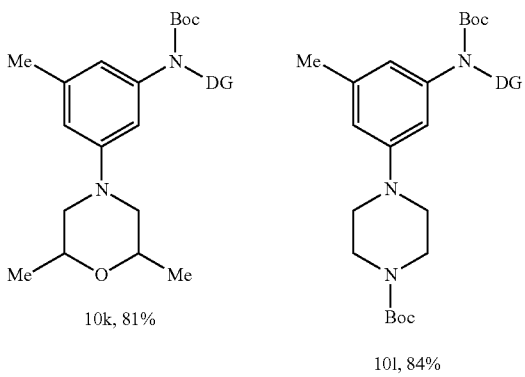
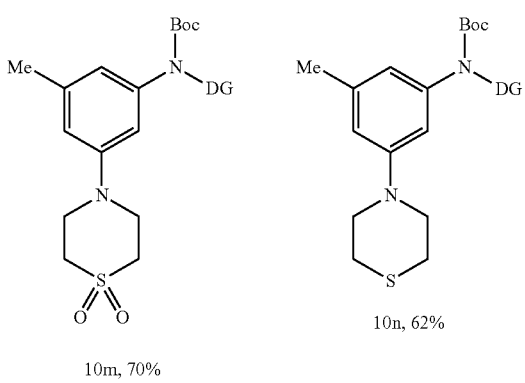

TABLE 12*-continued

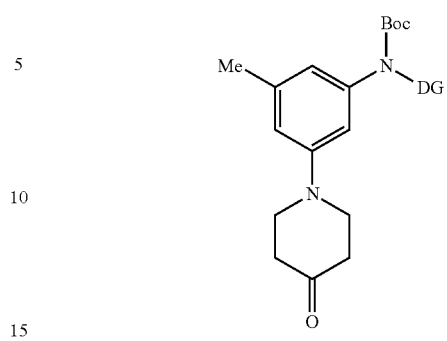

*Bz = benzoyl; DCM = dichloromethane; Boc = tert-butyloxycarbonyl; Bn = benzyl; NBE-CO$_2$Me = methyl bicyclo[2.2.1]hept-2-ene-2-carboxylate.

Reaction conditions: Compound 1 or 2 (0.1 mmol), aminating reagent (0.15 mmol), Pd(OAc)$_2$ (10 mol %), L24 (10 mol %), NBE-CO$_2$Me (1.5 equiv.), AgOAc (2.0 equiv.), dichloromethane (1.0 mL), 100° C., 24 hours.

For Compounds 10f, 10n and 10o, Pd(OAc)$_2$ (15 mol %), L24 (15 mol %), AgOAc (3.0 equiv.) and NBE-CO$_2$Me (3.0 equiv.) were used.

Although linear amines do not work well in this transformation under the current conditions, a variety of 6-membered amines can be smoothly coupled to provide 10k-o. These results are also shown in Table 12, above. This is believed to be the first report of a meta-C—H amination reaction in the literature.[32]

Furthermore, due to the robust catalysis enabled by the MPAHP ligands, the possibility of utilizing alkynyl bromides as coupling partners to provide meta-alkynylated products was considered. It is important to note that this reaction has no precedent in the Catellani reaction, and it is believed that no meta-C—H alkynylation reactions have been reported. To our great delight, after a brief evaluation of MPAHP ligands and reaction conditions, meta-C—H alkynylation of a variety of aniline-derived substrates could be achieved, providing Compounds 14a-j in good yields. This reaction scheme and results are shown in Table 13, below.

TABLE 13*

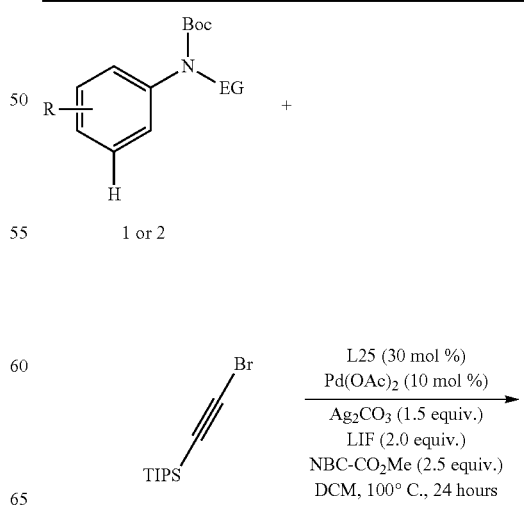

TABLE 13*-continued

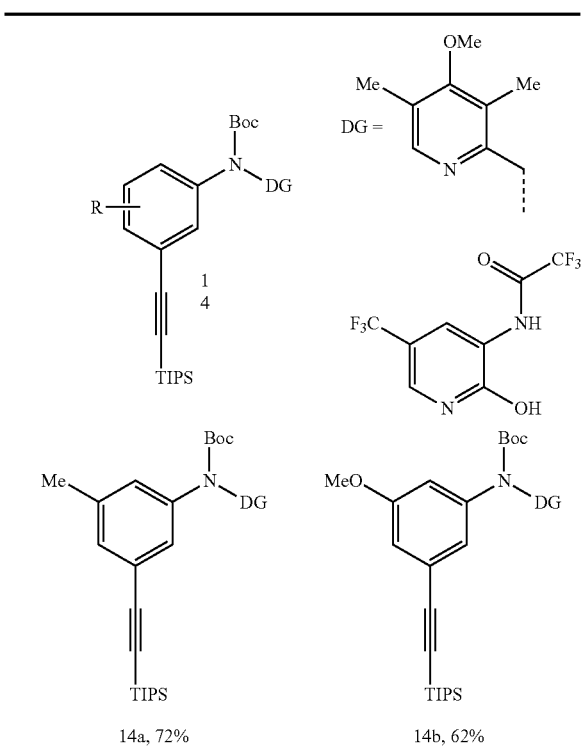

14a, 72%
14b, 62%
14c, 70%
14d, 50%
14e, 61%
14f, 44%

TABLE 13*-continued

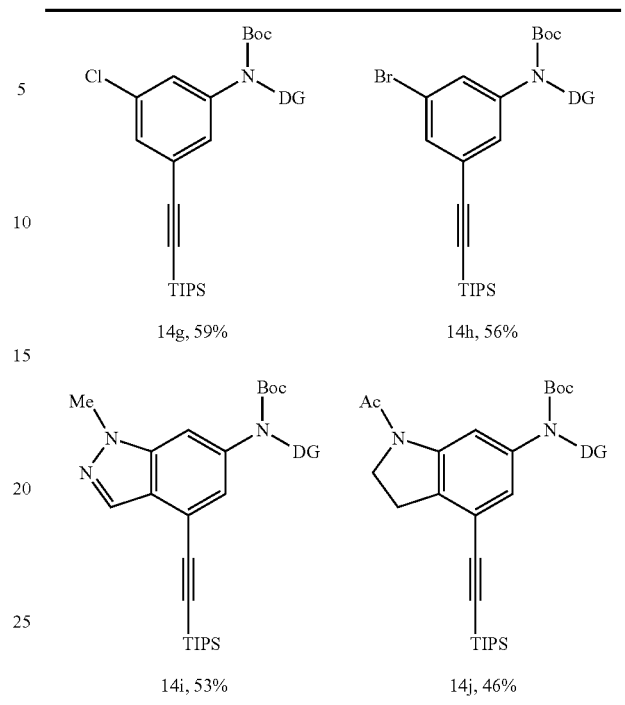

14g, 59%
14h, 56%
14i, 53%
14j, 46%

*TIPS = triisopropylsilyl;
TBS = tert-butyldimethylsilyl
Reaction conditions: Compounds 1 or 2 (0.1 mmol), alkynylating reagent (0.2 mmol), Pd(OAc)$_2$ (10 mol %), L25 (30 mol %), NBE-CO$_2$Me (2.5 equiv.), Ag$_2$CO$_3$ (1.5 equiv.), LiF (2.0 equiv.), dichloromethane (1.0 mL), 100° C., 24 hours.

Given that the original report[12,14] of this norbornene-mediated meta-C—H arylation strategy required installation of a directing group with phenylacetic acid substrates, whether the MPAHP ligands could enable a meta-C—H arylation of phenylacetic acids using the free acid as the directing group was examined. Indeed, as can be seen from the reaction scheme and results shown in the reaction scheme shown below, 2-methylphenylacetic acid could be arylated at the meta-position in the presence of MPAHP L24 to provide Compound 15 in 85% isolated yield. Importantly, all three of the palladium-catalyzed transformations shown in the reaction schemes of Tables 12 and 13, and that below that was carried out in hexafluoroisopropanol (HFIP) are ligand-enabled and provide only trace product amounts in the absence of an MPAHP ligand.

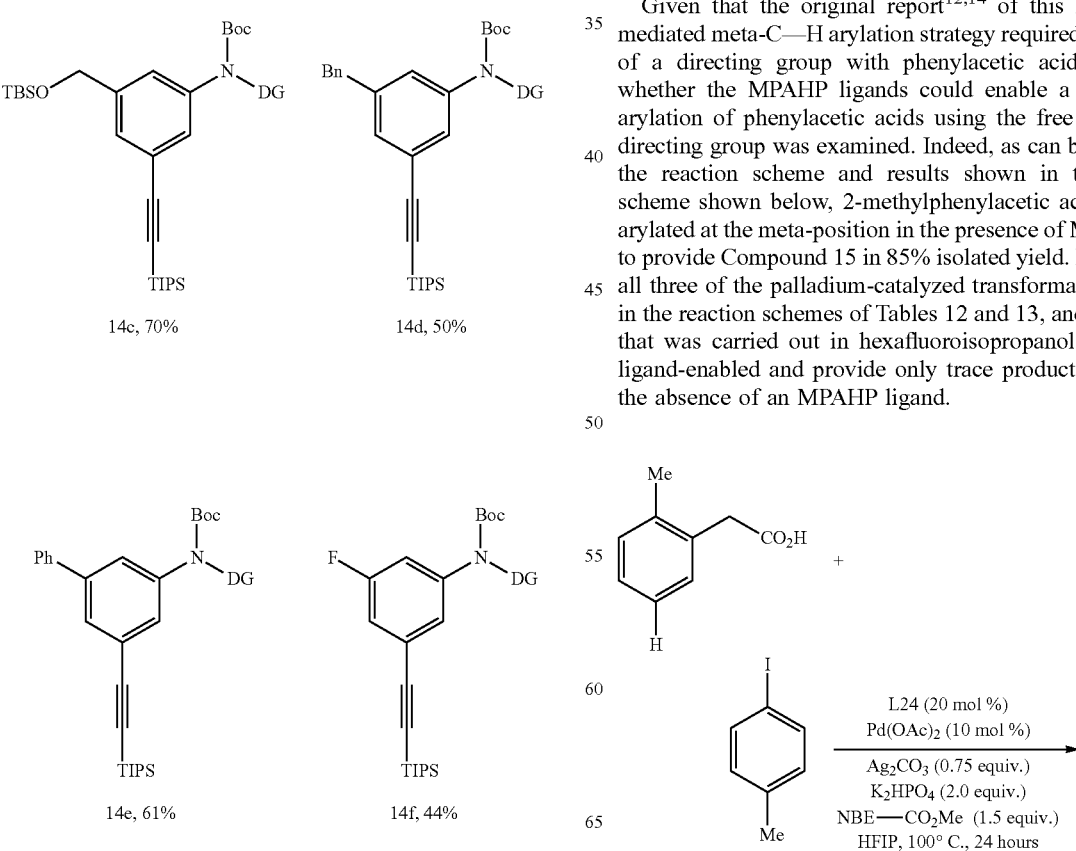

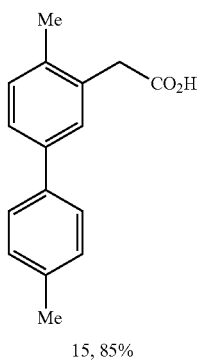

15, 85%

L24 = 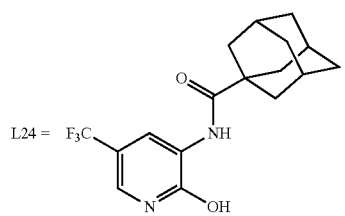

A versatile ligand scaffold for Pd(II) catalyzed meta-C—H arylation of a wide range of arenes using norbornene as a transient mediator is disclosed. Heterocyclic substrates and coupling partners are well tolerated under the developed reaction conditions, which should enable rapid uptake of this ligand enabled methodology in drug discovery. The utility of this ligand is further demonstrated by enabling the development of both a challenging meta-C—H amination reaction and an unprecedented meta-C—H alkynylation reaction. In addition, in the case of phenylacetic acid substrates, installation of a directing group is omitted as the MPAHP ligand promotes the meta-C—H functionalization of this class of substrates using the native acid as the directing group.

Methods Summary

General Procedure for the MPAHP-Promoted Norbornene-Mediated Meta-C—H Activation of Anilines.

Substrate (0.1 mmol), Ar—I (0.2 mmol), Pd(OAc)$_2$ (2.2 mg, 10 mol %), L12 (3.0 mg, 20 mol %), AgOAc (50.1 mg, 0.3 mmol), 2-norbornene (14.1 mg, 0.15 mmol) or NBE-CO$_2$Me (21.6 mg, 0.15 mmol) and 1,2-dichloroethane (0.5 mL) were added to a 2-dram vial. The vial was capped and closed tightly, then the reaction mixture was stirred at 100° C. for 24 hours. After cooling to room temperature, the mixture was passed through a pad of Celite® with dichloromethane as the eluent to remove the insoluble precipitate. The resulting solution was concentrated and purified by preparative TLC to afford the desired arylated product.

General Information

2-Norbornene and AgOAc were purchased from Sigma-Aldrich. NBE-CO$_2$Me (methyl bicyclo[2.2.1]hept-2-ene-2-carboxylate) was synthesized following literature procedures. [Shen et al., *J. Am. Chem. Soc.* 137:11574-11577 (2015).] Solvents were obtained from Sigma-Aldrich, Alfa-Aesar and Acros and used directly without further purification. Analytical thin layer chromatography was performed on 0.25 mm silica gel 60-F254. Visualization was carried out with UV light and Vogel's permanganate. $^1$H NMR was recorded on Bruker AMX-400 instrument (400 MHz) or Bruker DRX-600 instrument (600 MHz). Chemical shifts were quoted in parts per million (ppm) referenced to 0.0 ppm for tetramethylsilane. The following abbreviations (or combinations thereof) were used to explain multiplicities: s=singlet, d=doublet, t=triplet, q=quartet, p=pentet, sext=sextet, sep=septet m=multiplet, br=broad. Coupling constants, J, were reported in Hertz unit (Hz). $^{13}$C NMR spectra were recorded on Bruker AMX-400 instrument (100 MHz) or Bruker DRX-600 instrument (150 MHz), and were fully decoupled by broad band proton decoupling. $^{19}$F NMR spectra were recorded on Bruker AMX-400 instrument (376 MHz), and were fully decoupled by broad band proton decoupling. Chemical shifts were reported in ppm referenced to either the center line of a triplet at 77.0 ppm of chloroform-d or referenced to the center line of a septet at 39.52 ppm of DMSO-d$_6$. High-resolution mass spectra (HRMS) were recorded on an Agilent Mass spectrometer using ESI-TOF (electrospray ionization-time of flight).

Substrate Molecules

Aniline substrates

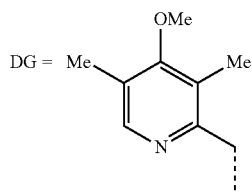

1a

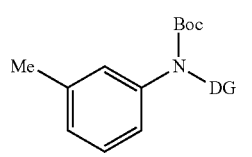

1b

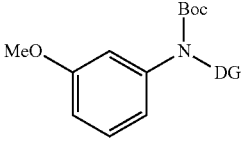

1c

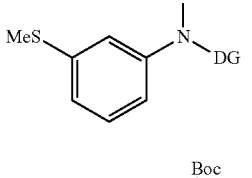

1d

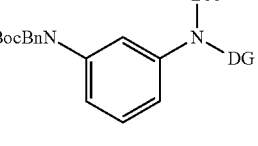

1e

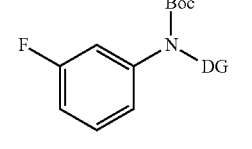

1f

-continued
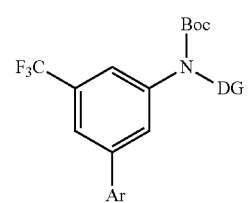 1g
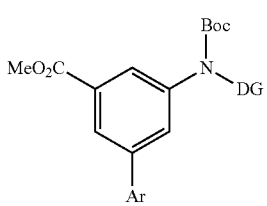 1h
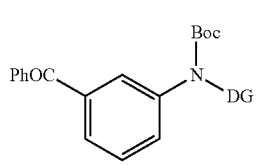 1i
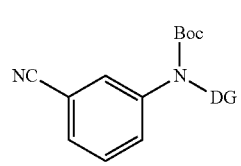 1j
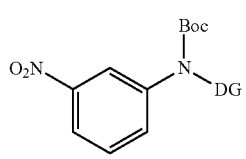 1k
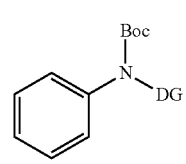 1l
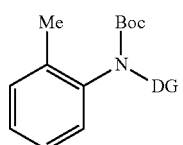 1m
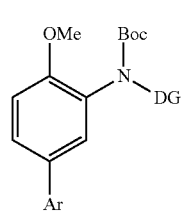 1n
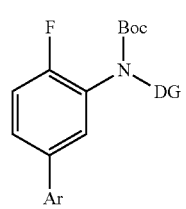 1o
-continued
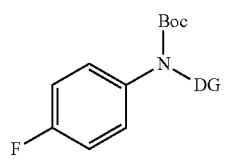 1p
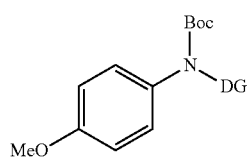 1q
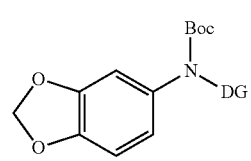 1r
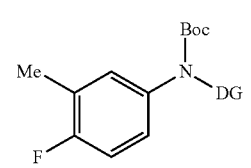 1s
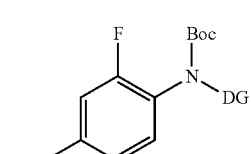 1t
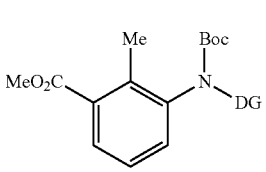 1u
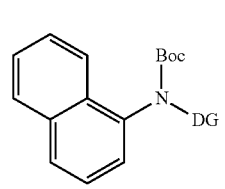 1v
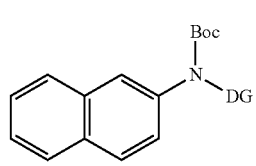 1w
Heterocycle-containing aromatic amine substrates
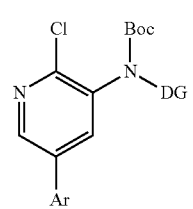 2a

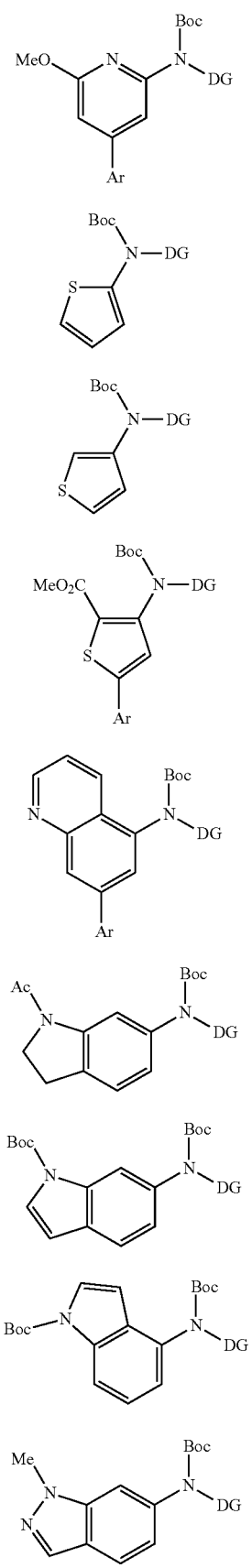
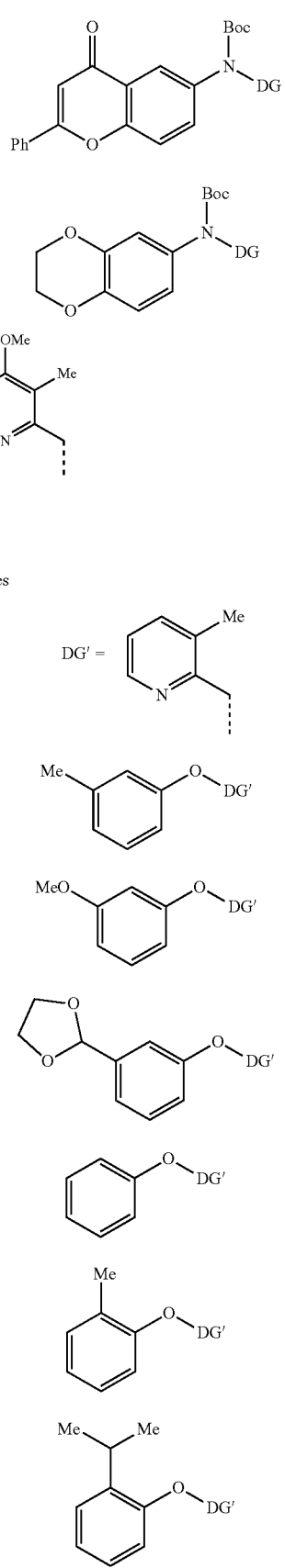
Phenol substrates

3g 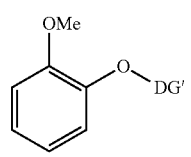
3h 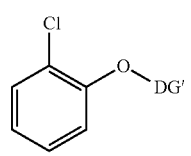
3i 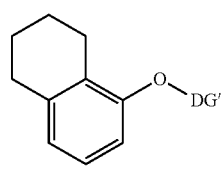
3j 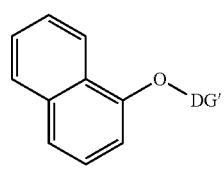
3k 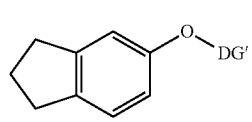
3l 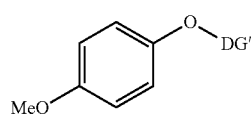
Other heterocycle substrates
4a 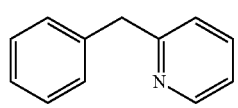
4b 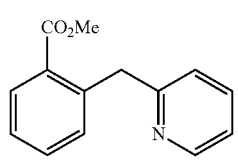
4c 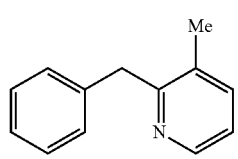
4d 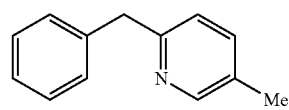
4e 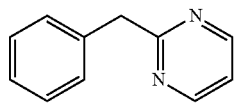
4f 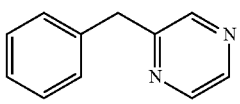
4g 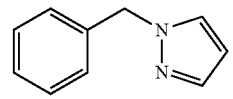
4h 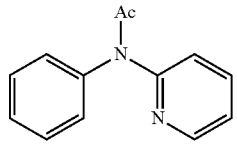
4i 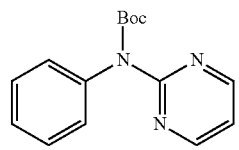
4j 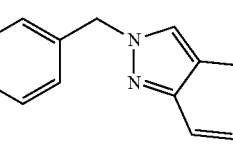
4k 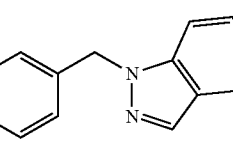
4l 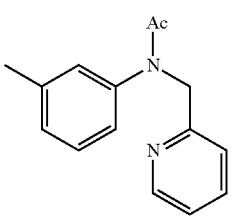
Other Substrates
S3a

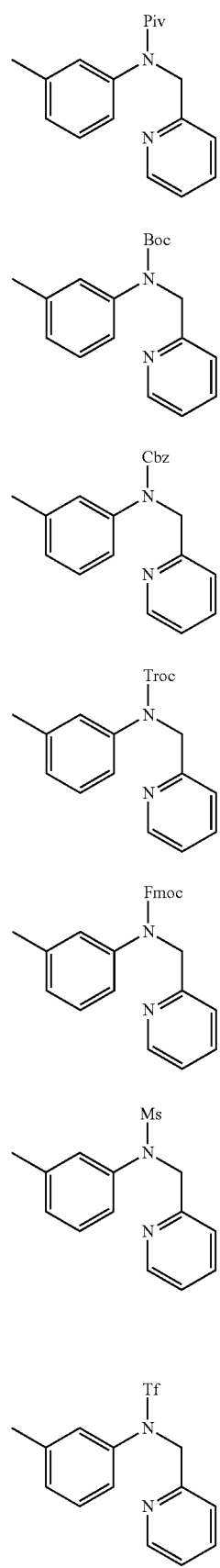
S3b
S3c
S3d
S3e
S3f
S3g
S3h
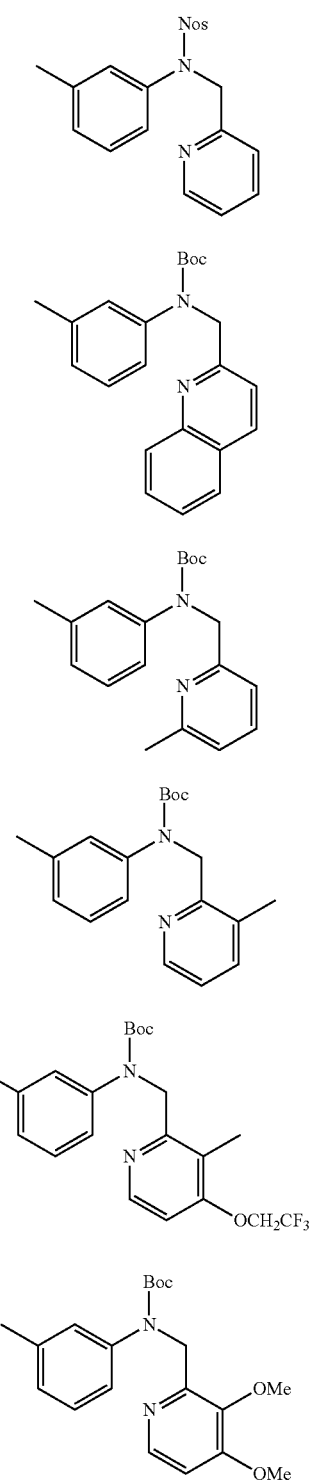
S3i
S5a
S5b
S5c
S5d
S5e
Preparation of Aniline Substrates
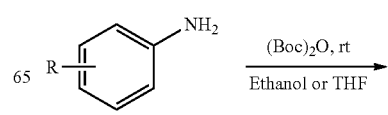

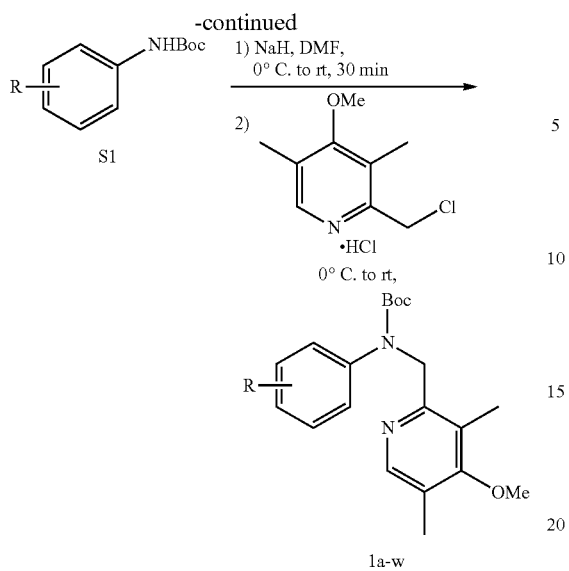

1a-w

Boc-protected anilines (S1) were synthesized following literature procedures starting from the free anilines. Substrates 1a-w were synthesized following the general procedure.

General Procedure for Synthesis of Boc-Protected Amines S1:

To a solution of anilines in ethanol was added (Boc)$_2$O (1.1 equiv.) at room temperature. After the reaction was completed, the solution was concentrated under vacuum to afford the Boc-protected amines in high yield. The Boc-protected amines were used for next step without further purification. [Vilaivan, *Tetrahedron Lett* 47, 6739-6742 (2006).]

General Procedure for Synthesis of Substrates 1a-w:

To a solution of Boc-protected anilines S1 (1.2 equiv.) in DMF was added NaH (3.0 equiv.) at 0° C., and the resulting mixture was allowed to warm up to room temperature for 30 min. The mixture was cooled to 0° C. again, then 2-chloromethyl-4-methoxy-3,5-dimethylpyridine hydrochloride (1.0 equiv.) was added into the mixture slowly. The resulting mixture was allowed to warm up to room temperature for another 12 hours. After the reaction completed, EtOAc was added to dilute the reaction mixture, then the organic phase was washed with water, brine and dried over Na$_2$SO$_4$. After concentrated by rotatory evaporation, the residue was purified by silica gel chromatography to afford the desired substrates 1a-w.

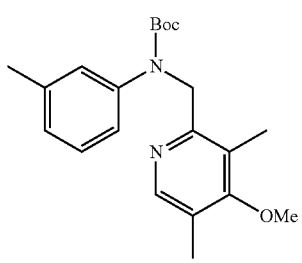

tert-Butyl ((4-methoxy-3,5-dimethylpyridin-2-yl)methyl)-(m-tolyl)carbamate (1a)

Colorless solid, mp=73° C., $^1$H NMR (400 MHz, CDCl$_3$) δ 8.15 (s, 1H), 7.10 (t, J=7.7 Hz, 1H), 7.06 (s, 1H), 7.02 (d, J=8.1 Hz, 1H), 6.91 (d, J=7.5 Hz, 1H), 4.90 (s, 2H), 3.72 (s, 3H), 2.27 (s, 3H), 2.21 (s, 6H), 1.39 (s, 9H); $^{13}$C NMR (150 MHz, CDCl$_3$) δ 163.62, 155.18, 154.78, 148.91, 142.70, 138.03, 128.05, 126.95, 126.29, 124.57, 123.68, 123.50, 80.14, 59.83, 53.54, 28.25, 21.34, 13.19, 10.40; HRMS (ESI-TOF) m/z Calcd for C$_{21}$H$_{29}$N$_2$O$_3$ [M+H]$^+$: 357.2173, found: 357.2172.

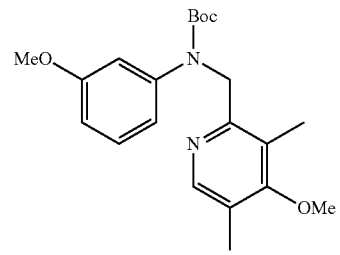

tert-Butyl ((4-methoxy-3,5-dimethylpyridin-2-yl)methyl)-(3-methoxyphenyl)carbamate (1b)

Colorless solid, mp=65° C., $^1$H NMR (400 MHz, CDCl$_3$) δ 8.15 (s, 1H), 7.13 (t, J=8.2 Hz, 1H), 6.84 (d, J=7.4 Hz, 2H), 6.70-6.63 (m, 1H), 4.90 (s, 2H), 3.73 (s, 3H), 3.72 (s, 3H), 2.21 (s, 3H), 2.20 (s, 3H), 1.40 (s, 9H); $^{13}$C NMR (150 MHz, CDCl$_3$) δ 163.62, 159.49, 155.04, 154.68, 148.97, 144.04, 128.84, 124.62, 123.67, 118.87, 112.47, 111.17, 80.29, 59.84, 55.23, 53.51, 28.27, 13.20, 10.39; HRMS (ESI-TOF) m/z Calcd for C$_{21}$H$_{29}$N$_2$O$_4$ [M+H]$^+$: 373.2122, found: 373.2121.

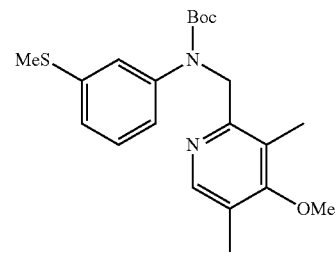

tert-Butyl ((4-methoxy-3,5-dimethylpyridin-2-yl)methyl)-(3-(methylthio)phenyl)carbamate (1c)

Colorless liquid, $^1$H NMR (400 MHz, CDCl$_3$) δ 8.16 (s, 1H), 7.18-7.11 (m, 2H), 7.07-6.97 (m, 2H), 4.89 (s, 2H), 3.72 (s, 3H), 2.40 (s, 3H), 2.21 (s, 3H), 2.20 (s, 3H), 1.40 (s, 9H); $^{13}$C NMR (150 MHz, CDCl$_3$) δ 163.62, 154.88, 154.56, 148.92, 143.30, 138.20, 128.52, 124.82, 124.65, 123.89, 123.65, 123.30, 80.37, 59.81, 53.31, 28.21, 15.89, 13.16, 10.36; HRMS (ESI-TOF) m/z Calcd for C$_{21}$H$_{29}$N$_2$O$_3$S [M+H]$^+$: 389.1893, found: 389.1893.

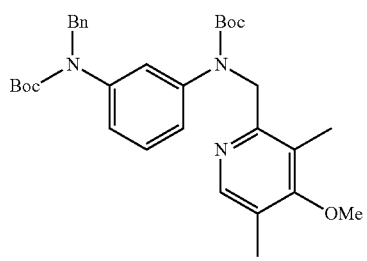

1d tert-Butyl (3-(benzyl(tert-butoxycarbonyl)-amino)phenyl)-((4-methoxy-3,5-dimethylpyridin-2-yl)methyl)carbamate (1d)

Colorless liquid, $^1$H NMR (400 MHz, CDCl$_3$) δ 8.10 (s, 1H), 7.31-7.02 (m, 8H), 6.88 (d, J=7.4 Hz, 1H), 4.84 (s, 2H), 4.73 (s, 2H), 3.71 (s, 3H), 2.19 (s, 3H), 2.16 (s, 3H), 1.44-1.30 (m, 18H); $^{13}$C NMR (150 MHz, CDCl$_3$) δ 163.55, 154.78, 154.50, 154.46, 148.85, 143.15, 142.72, 138.49, 128.17, 128.02, 127.20, 126.84, 124.51, 124.17, 123.87, 123.73, 123.50, 80.29, 80.19, 59.73, 53.82, 53.27, 28.13, 28.11, 13.09, 10.25; HRMS (ESI-TOF) m/z Calcd for C$_{32}$H$_{42}$N$_3$O$_5$ [M+H]$^+$: 548.3119, found: 548.3120.

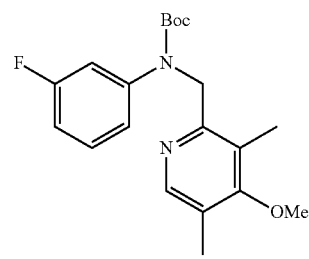

1e tert-Butyl (3-fluorophenyl)((4-methoxy-3,5-dimethylpyridin-2-yl)methyl)carbamate (1e)

Colorless solid, $^1$H NMR (400 MHz, CDCl$_3$) δ 8.16 (s, 1H), 7.18 (q, J=7.4 Hz, 1H), 7.10-6.97 (m, 2H), 6.86-6.76 (m, 1H), 4.89 (s, 2H), 3.73 (s, 3H), 2.22 (s, 3H), 2.21 (s, 3H), 1.40 (s, 9H); $^{13}$C NMR (150 MHz, CDCl$_3$) δ 163.68, 162.38 (d, J=245.3 Hz), 154.63, 154.37, 149.03, 144.52 (d, J=10.3 Hz), 129.15 (d, J=9.6 Hz), 124.76, 123.52, 121.78, 113.69 (d, J=23.4 Hz), 112.25 (d, J=21.0 Hz), 80.68, 59.86, 53.27, 28.17, 13.20, 10.33; $^{19}$F NMR (376 MHz, CDCl$_3$) δ -113.42; HRMS (ESI-TOF) m/z Calcd for C$_{20}$H$_{26}$FN$_2$O$_3$ [M+H]$^+$: 361.1922, found: 361.1920.

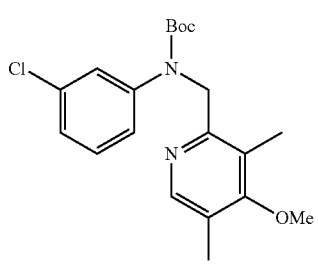

1f tert-Butyl (3-chlorophenyl)((4-methoxy-3,5-dimethylpyridin-2-yl)methyl)carbamate (1f)

Colorless solid, mp=68° C., $^1$H NMR (400 MHz, CDCl$_3$) δ 8.16 (s, 1H), 7.29 (s, 1H), 7.21-7.12 (m, 2H), 7.12-7.04 (m, 1H), 4.88 (s, 2H), 3.73 (s, 3H), 2.22 (s, 3H), 2.20 (s, 3H), 1.39 (s, 9H); $^{13}$C NMR (150 MHz, CDCl$_3$) δ 163.68, 154.60, 154.35, 149.06, 144.17, 133.61, 129.15, 126.59, 125.52, 124.78, 124.51, 123.52, 80.72, 59.88, 53.23, 28.19, 13.22, 10.36; HRMS (ESI-TOF) m/z Calcd for C$_{20}$H$_{26}$ClN$_2$O$_3$ [M+H]$^+$: 377.1626, found: 377.1628.

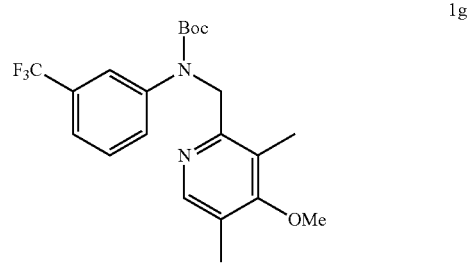 [SMILES: COc1c(C)cnc(CN(C(=O)OC(C)(C)C)c2cccc(C(F)(F)F)c2)c1C]

1g tert-Butyl ((4-methoxy-3,5-dimethylpyridin-2-yl)methyl)-3-(trifluoromethyl)phenyl)carbamate (1g)

Colorless solid, $^1$H NMR (400 MHz, CDCl$_3$) δ 8.15 (s, 1H), 7.54 (s, 1H), 7.47 (s, 1H), 7.39-7.31 (m, 2H), 4.92 (s, 2H), 3.73 (s, 3H), 2.21 (s, 6H), 1.40 (s, 9H); $^{13}$C NMR (150 MHz, CDCl$_3$) δ 163.75, 154.49, 154.30, 149.08, 143.44, 130.58 (q, J=32.2 Hz), 129.39, 128.76, 124.89, 123.88 (d, J=272.3 Hz); 123.59, 123.54, 121.95, 80.92, 59.86, 53.10, 28.16, 13.20, 10.38; $^{19}$F NMR (376 MHz, CDCl$_3$) δ -62.90; HRMS (ESI-TOF) m/z Calcd for C$_{21}$H$_{26}$F$_3$N$_2$O$_3$ [M+H]$^+$: 411.1890, found: 411.1890.

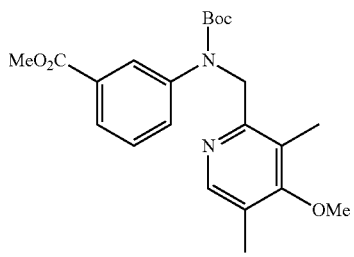

1h

Methyl 3-((tert-butoxycarbonyl)((4-methoxy-3,5-dimethylpyridin-2-yl)methyl)amino)benzoate (1h)

Colorless solid, $^1$H NMR (400 MHz, CDCl$_3$) δ 8.14 (s, 1H), 7.92 (s, 1H), 7.78 (d, J=7.7 Hz, 1H), 7.48 (d, J=8.0 Hz, 1H), 7.30 (t, J=7.9 Hz, 1H), 4.93 (s, 2H), 3.87 (s, 3H), 3.73 (s, 3H), 2.22 (s, 3H), 2.20 (s, 3H), 1.40 (s, 9H); $^{13}$C NMR (100 MHz, CDCl$_3$) δ 166.64, 163.67, 154.63, 154.42, 148.94, 142.99, 131.04, 128.26, 127.55, 126.54, 124.72, 123.66, 80.59, 59.79, 53.10, 52.01, 28.13, 13.13, 10.36; HEMS (ESI-TOF) m/z Calcd for C$_{22}$H$_{29}$N$_2$O$_5$ [M+H]$^+$: 401.2071, found: 401.2072.

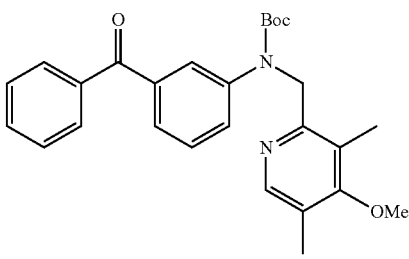

tert-Butyl (3-benzoylphenyl)((4-methoxy-3,5-dimethylpyridin-2-yl)methyl)carbamate (1i)

Light yellow liquid, $^1$H NMR (400 MHz, CDCl$_3$) δ 8.13 (s, 1H), 7.75 (d, J=7.4 Hz, 2H), 7.67 (s, 1H), 7.61-7.50 (m, 3H), 7.45 (t, J=7.6 Hz, 2H), 7.36 (t, J=7.8 Hz, 1H), 4.93 (s, 2H), 3.72 (s, 3H), 2.26-2.16 (m, 6H), 1.40 (s, 9H); $^{13}$C NMR (150 MHz, CDCl$_3$) δ 196.04, 163.69, 154.63, 154.51, 148.97, 142.97, 137.71, 137.35, 132.32, 130.55, 130.00, 128.21, 128.15, 127.87, 127.10, 124.75, 123.63, 80.66, 59.83, 53.16, 28.18, 13.18, 10.36; HRMS (ESI-TOF) m/z Calcd for C$_{27}$H$_{31}$N$_2$O$_4$ [M+H]$^+$: 447.2278, found: 447.2278.

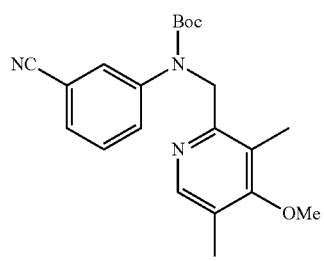

tert-Butyl (3-cyanophenyl)((4-methoxy-3,5-dimethylpyridin-2-yl)methyl)carbamate (1j)

Colorless solid, $^1$H NMR (400 MHz, CDCl$_3$) δ 8.16 (s, 1H), 7.66-7.54 (m, 2H), 7.43-7.31 (m, 2H), 4.87 (s, 2H), 3.75 (s, 3H), 2.23 (s, 3H), 2.21 (s, 3H), 1.38 (s, 9H); $^{13}$C NMR (150 MHz, CDCl$_3$) δ 163.76, 154.14, 149.14, 144.04, 130.83, 129.57, 129.11, 128.74, 124.98, 123.37, 118.61, 112.31, 81.20, 59.92, 52.98, 28.12, 13.23, 10.32; HRMS (ESI-TOF) m/z Calcd for C$_{21}$H$_{26}$N$_3$O$_3$ [M+H]$^+$: 368.1969, found: 368.1969.

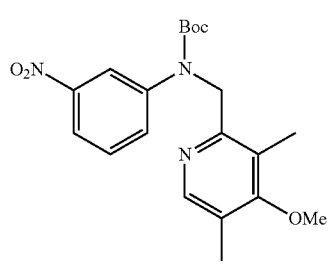

tert-Butyl ((4-methoxy-3,5-dimethylpyridin-2-yl)methyl)(3-nitrophenyl)carbamate (1k)

Light yellow solid, $^1$H NMR (400 MHz, CDCl$_3$) δ 8.18 (t, J=2.2 Hz, 1H), 8.16 (s, 1H), 8.00-7.93 (m, 1H), 7.68 (d, J=8.0 Hz, 1H), 7.41 (t, J=8.1 Hz, 1H), 4.93 (s, 2H), 3.75 (s, 3H), 2.23 (s, 3H), 2.22 (s, 3H), 1.40 (s, 9H); $^{13}$C NMR (150 MHz, CDCl$_3$) δ 163.81, 154.13, 154.07, 149.15, 148.12, 144.24, 132.19, 128.82, 125.02, 123.49, 121.22, 119.98, 81.36, 59.92, 52.91, 28.12, 13.22, 10.36; HRMS (ESI-TOF) m/z Calcd for C$_{20}$H$_{26}$N$_3$O$_5$ [M+H]$^+$: 388.1867, found: 388.1865.

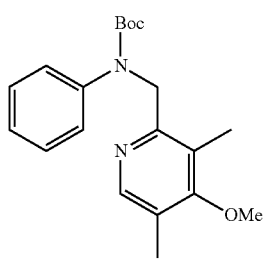

tert-Butyl ((4-methoxy-3,5-dimethylpyridin-2-yl)methyl)(phenyl)carbamate (1l)

Light yellow solid, mp=60° C., $^1$H NMR (400 MHz, CDCl$_3$) δ 8.14 (s, 1H), 7.26-7.18 (m, 4H), 7.14-7.15 (m, 1H), 4.92 (s, 2H), 3.72 (s, 3H), 2.25-2.17 (m, 6H), 1.39 (s, 9H); $^{13}$C NMR (150 MHz, CDCl$_3$) δ 163.63, 155.06, 154.74, 148.93, 142.74, 128.29, 126.46, 125.49, 124.63, 123.76, 80.23, 59.82, 53.45, 28.23, 13.19, 10.39; HRMS (ESI-TOF) m/z Calcd for C$_{20}$H$_{27}$N$_2$O$_3$ [M+H]$^+$: 343.2016, found: 343.2015.

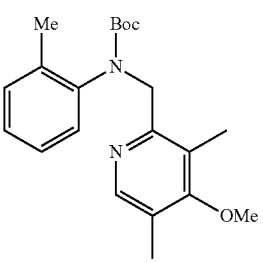

tert-Butyl ((4-methoxy-3,5-dimethylpyridin-2-yl)methyl)-(o-tolyl)carbamate (1m)

Light yellow liquid, rotameric mixture; $^1$H NMR (400 MHz, CDCl$_3$) δ 8.09 (s, 1H), 7.25-6.87 (m, 4H), 5.13 (d, J=14.8 Hz, 1H), 4.70-4.39 (m, 1H), 3.71 (s, 3H), 2.20 (s, 6H), 2.13 (s, 3H), 1.54-1.28 (m, 9H); $^{13}$C NMR (150 MHz, CDCl$_3$) rotameric mixture, resonances for the minor rotamer are enclosed in parenthesis ( ): δ 163.68, 154.95 (155.19), 154.85 (154.37), 148.85, 140.63 (141.16), 135.87 (136.15), 130.22 (130.55), 128.28, 126.87, 126.06 (126.40), 124.97 (124.72), 124.87 (124.00), 79.71 (80.05), 59.71, 52.50 (53.38), 28.22, 17.49 (17.63), 13.18, 10.60; HRMS (ESI-TOF) m/z Calcd for C$_{21}$H$_{29}$N$_2$O$_3$ [M+H]$^+$: 357.2173, found: 357.2172.

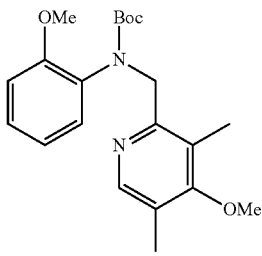

1n tert-Butyl ((4-methoxy-3,5-dimethylpyridin-2-yl)methyl)-(2-methoxyphenyl)carbamate (1n)

Colorless liquid, $^1$H NMR (400 MHz, CDCl$_3$) δ 8.05 (s, 1H), 7.12 (t, J=7.6 Hz, 1H), 6.93-6.65 (m, 3H), 5.46-4.37 (m, 2H), 3.77 (brs, 3H), 3.72 (s, 3H), 2.25 (s, 3H), 2.18 (brs, 3H), 1.55-1.26 (m, 9H); $^{13}$C NMR (150 MHz, CDCl$_3$) rotameric mixture, resonances for the minor rotamer the the minor rotamer are enclosed in parenthesis ( ): δ 163.68 (163.60), 155.45 (155.59), 155.32, 155.10 (154.83), 148.58, 130.61 (130.28), 129.42, 127.79 (128.02), 125.35 (124.59), 124.76 (124.49), 119.95 (120.39), 110.89 (111.68), 79.47 (80.09), 59.72, 55.14 (55.59), 52.42 (53.29), 28.17 (28.26), 13.16, 10.57; HRMS (ESI-TOF) m/z Calcd for C$_{21}$H$_{29}$N$_2$O$_4$ [M+H]$^+$: 373.2122, found: 373.2121.

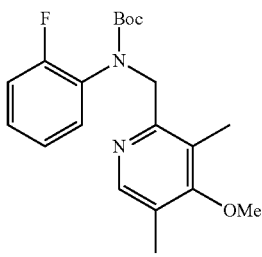

1o tert-Butyl (2-fluorophenyl)((4-methoxy-3,5-dimethylpyridin-2-yl)methyl)carbamate (1o)

Colorless solid, mp=59° C., rotameric mixture, ratio of the rotamers=75/25; $^1$H NMR (400 MHz, CDCl$_3$) δ 8.07 (s, 1H), 7.40-7.06 (m, 2H), 7.05-6.89 (m, 2H), 4.93 (s, 2H), 3.72 (s, 3H), 2.25 (s, 3H), 2.18 (s, 3H), 1.40 (s, 9H); $^{13}$C NMR (150 MHz, CDCl$_3$) rotameric mixture, resonances for the minor rotamer the the minor rotamer are enclosed in parenthesis ( ): δ 163.79, 158.15 (d, J=248.9 Hz), 154.68, 154.30, 148.72, 129.69 (d, J=12.0 Hz), 129.28, 127.90 (d, J=7.8 Hz), 125.12, 124.97, 123.79, 115.56 (d, J=21.3 Hz), 80.48, 59.75, 52.69 (53.39), 28.07, 13.16, 10.49; $^{19}$F NMR (376 MHz, CDCl$_3$) for major isomer: δ -121.13; $^{19}$F NMR (376 MHz, CDCl$_3$) for minor isomer: δ -120.82; HRMS (ESI-TOF) m/z Calcd for C$_{20}$H$_{26}$FN$_2$O$_3$ [M+H]$^+$: 361.1922, found: 361.1922.

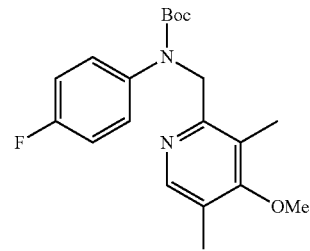

1p tert-Butyl (4-fluorophenyl)((4-methoxy-3,5-dimethylpyridin-2-yl)methyl)carbamate (1p)

Light yellow solid, $^1$H NMR (400 MHz, CDCl$_3$) δ 8.13 (s, 1H), 7.19 (s, 2H), 6.91 (t, J=8.6 Hz, 2H), 4.88 (s, 2H), 3.72 (s, 3H), 2.21 (s, 6H), 1.39 (s, 9H); $^{13}$C NMR (150 MHz, CDCl$_3$) δ 163.72, 160.46 (d, J=244.4 Hz), 154.82, 154.78, 148.96, 138.65, 128.43 (d, J=8.0 Hz), 124.81, 123.93, 115.06 (d, J=22.8 Hz), 80.39, 59.85, 53.50, 28.22, 13.20, 10.40; $^{19}$F NMR (376 MHz, CDCl$_3$) δ -117.08; HRMS (ESI-TOF) m/z Calcd for C$_{20}$H$_{26}$FN$_2$O$_3$ [M+H]$^+$: 361.1922, found: 361.1923.

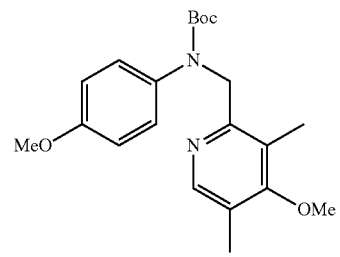

1q tert-Butyl ((4-methoxy-3,5-dimethylpyridin-2-yl)methyl)-(4-methoxyphenyl)carbamate (1q)

Red solid, $^1$H NMR (400 MHz, CDCl$_3$) δ 8.12 (s, 1H), 7.10 (brs, 2H), 6.74 (d, J=8.4 Hz, 2H), 4.89 (s, 2H), 3.74 (s, 3H), 3.72 (s, 3H), 2.25-2.16 (m, 6H), 1.39 (s, 9H); $^{13}$C NMR (150 MHz, CDCl$_3$) δ 163.67, 157.34, 155.15, 155.08, 148.88, 135.52, 127.99, 124.68, 124.09, 113.56, 80.04, 59.81, 55.31, 53.67, 28.28, 13.19, 10.43; HRMS (ESI-TOF) m/z Calcd for C$_{21}$H$_{29}$N$_2$O$_4$ [M+H]$^+$: 373.2122, found: 373.2123.

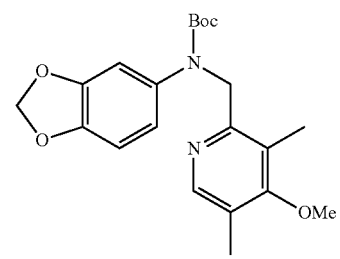

1r tert-Butyl benzo[d][1,3]dioxol-5-yl((4-methoxy-3,5-dimethylpyridin-2-yl)methyl)carbamate (1r)

Colorless solid, mp=87° C., $^1$H NMR (400 MHz, CDCl$_3$) δ 8.14 (s, 1H), 6.77 (s, 1H), 6.65 (s, 2H), 5.90 (s, 2H), 4.84 (s, 2H), 3.73 (s, 3H), 2.21 (s, 3H), 2.20 (s, 3H), 1.39 (s, 9H); $^{13}$C NMR (150 MHz, CDCl$_3$) δ 163.24, 154.58, 154.53, 148.48, 146.76, 145.02, 136.32, 124.28, 123.48, 119.75, 108.27, 107.11, 100.71, 79.75, 59.40, 53.38, 27.82, 12.76, 9.98; HRMS (ESI-TOF) m/z Calcd for C$_{21}$H$_{27}$N$_2$O$_5$ [M+H]$^+$: 387.1914, found: 387.1914.

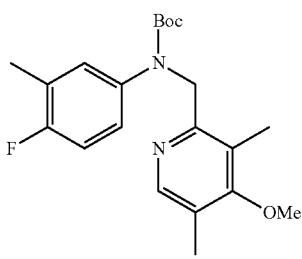

1s tert-Butyl (4-fluoro-3-methylphenyl)((4-methoxy-3,5-dimethylpyridin-2-yl)methyl)carbamate (1s)

Colorless solid, mp=78° C., $^1$H NMR (400 MHz, CDCl$_3$) δ 8.14 (s, 1H), 7.07 (s, 1H), 6.98 (s, 1H), 6.83 (t, J=9.0 Hz, 1H), 4.86 (s, 2H), 3.73 (s, 3H), 2.24-2.19 (m, 6H), 2.18 (d, J=1.9 Hz, 3H), 1.39 (s, 9H); $^{13}$C NMR (150 MHz, CDCl$_3$) δ 163.68, 159.05 (d, J=243.2 Hz), 154.94, 154.81, 148.90, 138.26, 129.63 (d, J=5.3 Hz), 125.69, 124.72, 124.59 (d, J=18.6 Hz), 123.83, 114.59 (d, J=23.3 Hz), 80.26, 59.81, 53.58, 28.22, 14.51, 13.18, 10.40; $^{19}$F NMR (376 MHz, CDCl$_3$) δ −121.37; HRMS (ESI-TOF) m/z Calcd for C$_{21}$H$_{28}$FN$_2$O$_3$ [M+H]$^+$: 375.2078, found: 375.2079.

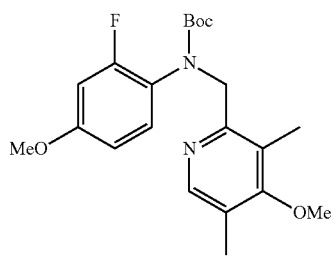

1t tert-butyl (2-fluoro-4-methoxyphenyl)((4-methoxy-3,5-dimethylpyridin-2-yl)methyl)carbamate (1t)

Red liquid, rotameric mixture, ratio of the rotamers=75/25; $^1$H NMR (400 MHz, CDCl$_3$) δ 8.06 (brs, 1H), 7.18 (s, 0.25H), 7.00 (d, J=9.1 Hz, 0.75H), 6.63-6.44 (m, 2H), 5.02-4.75 (m, 2H), 3.73 (s, 3H), 3.72 (s, 3H), 2.26 (s, 3H), 2.19 (s, 3H), 1.52-1.31 (m, 9H); $^{13}$C NMR (150 MHz, CDCl$_3$) rotameric mixture: δ 163.81, 159.63, 159.41, 159.20, 159.16, 159.03, 158.95, 158.01, 157.76, 154.96, 154.81, 154.66, 148.69, 130.50, 129.73, 125.28, 124.99, 124.42, 122.33, 122.24, 109.53, 108.98, 101.75, 101.59, 80.62, 80.22, 76.79, 59.73, 55.48, 53.61, 52.77, 28.10, 13.17, 10.52; $^{13}$C NMR (150 MHz, CDCl$_3$) for major isomer: δ 163.81, 159.03, 158.95, 158.58 (d, J=248.7 Hz), 154.74 (d, J=22.2 Hz), 148.69, 129.73, 125.28, 124.99, 122.29 (d, J=13.1 Hz), 108.98, 101.67 (d, J=24.2 Hz), 80.22, 59.73, 55.48, 52.77, 28.10, 13.17, 10.52; $^{19}$F NMR (376 MHz, CDCl$_3$) for major isomer: δ −119.19; $^{19}$F NMR (376 MHz, CDCl$_3$) for minor isomer: δ −118.92; HRMS (ESI-TOF) m/z Calcd for C$_{21}$H$_{28}$FN$_2$O$_4$ [M+H]$^+$: 391.2028, found: 391.2028.

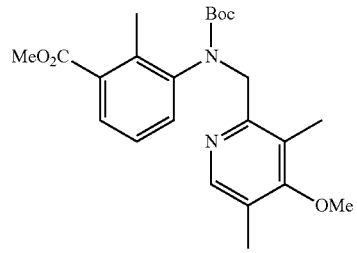

1u

Methyl 3-((tert-butoxycarbonyl)((4-methoxy-3,5-dimethylpyridin-2-yl)methyl)amino)-2-methylbenzoate (1u)

Colorless liquid, rotameric mixture, ratio of the rotamers=70/30; $^1$H NMR (400 MHz, CDCl$_3$) δ 8.09 (brs, 1H), 7.72 (d, J=7.8 Hz, 1H), 7.47 (s, 0.3H), 7.21 (d, J=7.8 Hz, 0.7H), 7.16-7.00 (m, 1H), 5.16 (d, J=14.9 Hz, 1H), 4.66-4.30 (m, 1H), 3.87 (s, 3H), 3.71 (s, 3H), 2.50-2.30 (m, 3H), 2.20 (s, 6H), 1.52-1.28 (m, 9H); $^{13}$C NMR (150 MHz, CDCl$_3$) rotameric mixture, resonances for the minor rotamer the the minor rotamer are enclosed in parenthesis ( ): δ 168.05, 163.75 (163.65), 154.70 (154.79), 154.48, 148.89, 141.94 (142.56), 137.93 (138.10), 132.50 (132.90), 130.91 (131.28), 129.15, 125.50 (125.79), 124.98, 124.86 (123.85), 80.07, 59.72, 52.44 (53.27), 51.85, 28.16, 15.07, 13.17, 10.61; HRMS (ESI-TOF) m/z Calcd for C$_{23}$H$_{31}$N$_2$O$_5$ [M+H]$^+$: 415.2227, found: 415.2226.

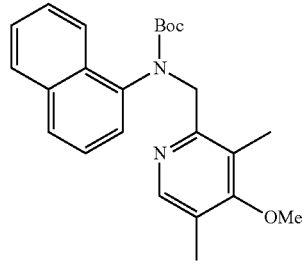

1v tert-Butyl ((4-methoxy-3,5-dimethylpyridin-2-yl)methyl)(naphthalen-1-yl)carbamate (1v)

Colorless solid, rotameric mixture, $^1$H NMR (400 MHz, CDCl$_3$) δ 8.11 (s, 1H), 7.87 (s, 1H), 7.84-7.77 (m, 1H), 7.70 (d, J=8.2 Hz, 1H), 7.52-7.39 (m, 2H), 7.38-7.18 (m, 2H), 5.37 (d, J=15.2 Hz, 1H), 4.66 (d, J=15.1 Hz, 1H), 3.66 (s, 3H), 2.17 (s, 3H), 2.13 (s, 3H), 1.70-1.05 (m, 9H); $^{13}$C NMR (150 MHz, CDCl$_3$) rotameric mixture, resonances for the minor rotamer are enclosed in parenthesis ( ): δ 163.63, 155.46, 154.99, 148.89, 138.66, 134.23, 130.76, 128.14, 127.27, 126.37, 125.99, 125.66, 125.32, 124.75, 124.66, 122.88, 79.93, 59.69, 53.00 (53.86), 28.06, 13.13, 10.54; HRMS (ESI-TOF) m/z Calcd for $C_{24}H_{29}N_2O_3$ [M+H]$^+$: 393.2173, found: 393.2173.

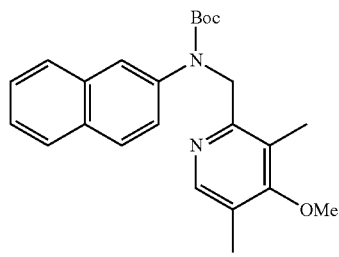

tert-butyl ((4-methoxy-3,5-dimethylpyridin-2-yl)methyl)(naphthalen-2-yl)carbamate (1w)

Colorless solid, mp=81° C., $^1$H NMR (400 MHz, CDCl$_3$) δ 8.14 (s, 1H), 7.78-7.72 (m, 1H), 7.72-7.67 (m, 2H), 7.65 (s, 1H), 7.44 (d, J=8.6 Hz, 1H), 7.42-7.34 (m, 2H), 5.03 (s, 2H), 3.71 (s, 3H), 2.23 (s, 3H), 2.19 (s, 3H), 1.41 (s, 9H); $^{13}$C NMR (150 MHz, CDCl$_3$) δ 163.66, 154.99, 154.78, 148.97, 140.41, 133.41, 131.37, 127.73, 127.70, 127.37, 126.03, 125.78, 125.36, 124.67, 123.75, 123.52, 80.43, 59.80, 53.63, 28.25, 13.17, 10.43; HRMS (ESI-TOF) m/z Calcd for $C_{24}H_{29}N_2O_3$ [M+H]$^+$: 393.2173, found: 393.2172.

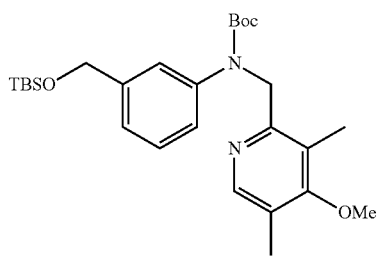

tert-Butyl (3-(((tert-butyldimethylsilyl)oxy)methyl)phenyl)((4-methoxy-3,5-dimethylpyridin-2-yl)methyl)-carbamate (1x)

Light yellow liquid, $^1$H NMR (400 MHz, CDCl$_3$) δ 8.14 (s, 1H), 7.23-7.15 (m, 2H), 7.12 (d, J=7.9 Hz, 1H), 7.06 (d, J=7.5 Hz, 1H), 4.91 (s, 2H), 4.66 (s, 2H), 3.72 (s, 3H), 2.24-2.16 (m, 6H), 1.39 (s, 9H), 0.89 (s, 9H), 0.04 (s, 6H); $^{13}$C NMR (150 MHz, CDCl$_3$) δ 163.60, 155.03, 154.79, 148.95, 142.79, 141.69, 128.05, 124.93, 124.55, 123.81, 123.61, 123.03, 80.17, 64.61, 64.59, 59.81, 53.46, 28.24, 25.88, 25.86, 18.32, 13.17, 10.34, −5.33; HRMS (ESI-TOF) m/z Calcd for $C_{27}H_{43}N_2O_4Si$ [M+H]$^+$: 487.2987, found: 487.2986.

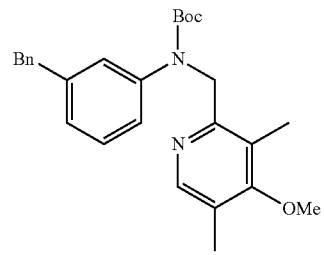

tert-Butyl (3-benzylphenyl)((4-methoxy-3,5-dimethylpyridin-2-yl)methyl)carbamate (1y)

Colorless liquid, $^1$H NMR (400 MHz, CDCl$_3$) δ 8.11 (s, 1H), 7.28-7.20 (m, 2H), 7.20-6.99 (m, 6H), 6.91 (d, J=7.1 Hz, 1H), 4.89 (s, 2H), 3.89 (s, 2H), 3.69 (s, 3H), 2.19 (s, 3H), 2.18 (s, 3H), 1.36 (s, 9H); $^{13}$C NMR (150 MHz, CDCl$_3$) δ 163.64, 155.04, 154.72, 148.88, 142.70, 141.02, 140.89, 128.85, 128.35, 128.29, 127.34, 126.19, 125.94, 124.60, 123.96, 123.82, 80.21, 59.79, 53.44, 41.62, 28.21, 13.20, 10.39; HRMS (ESI-TOF) m/z Calcd for $C_{27}H_{33}N_2O_3$ [M+H]$^+$: 433.2486, found: 433.2484.

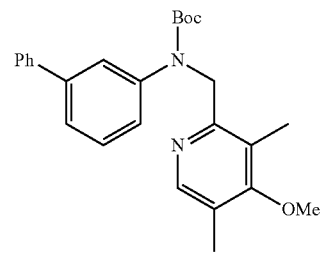

tert-Butyl [1,1'-biphenyl]-3-yl((4-methoxy-3,5-dimethylpyridin-2-yl)methyl)carbamate (1z)

Light yellow liquid, $^1$H NMR (400 MHz, CDCl$_3$) δ 8.16 (s, 1H), 7.52-7.46 (m, 2H), 7.44 (s, 1H), 7.42-7.36 (m, 2H), 7.36-7.27 (m, 3H), 7.23 (d, J=8.3 Hz, 1H), 4.97 (s, 2H), 3.71 (s, 3H), 2.22 (s, 3H), 2.20 (s, 3H), 1.42 (s, 9H); $^{13}$C NMR (150 MHz, CDCl$_3$) δ 163.68, 155.08, 154.72, 148.97, 143.09, 141.32, 140.87, 128.61, 127.19, 127.07, 125.43, 125.32, 124.70, 124.30, 123.82, 80.33, 59.81, 53.46, 28.28, 13.18, 10.43; HRMS (ESI-TOF) m/z Calcd for $C_{26}H_{31}N_2O_3$ [M+H]$^+$: 419.2329, found: 419.2327.

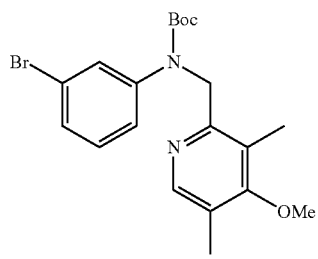

tert-Butyl (3-bromophenyl)((4-methoxy-3,5-dimethylpyridin-2-yl)methyl)carbamate (1aa)

Colorless solid, $^1$H NMR (400 MHz, CDCl$_3$) δ 8.17 (s, 1H), 7.45 (s, 1H), 7.26-7.18 (m, 2H), 7.10 (t, J=8.0 Hz, 1H), 4.87 (s, 2H), 3.74 (s, 3H), 2.22 (s, 3H), 2.20 (s, 3H), 1.39 (s, 9H); $^{13}$C NMR (150 MHz, CDCl$_3$) δ 163.68, 154.57, 154.33, 149.04, 149.03, 144.29, 129.46, 128.43, 125.00, 124.79, 123.53, 121.55, 80.74, 59.88, 53.21, 28.18, 13.21, 10.36; HRMS (ESI-TOF) m/z Calcd for C$_{20}$H$_{26}$BrN$_2$O$_3$ [M+H]$^+$: 421.1121, found: 421.1121.

Preparation of Heterocyclic-Amine Substrates

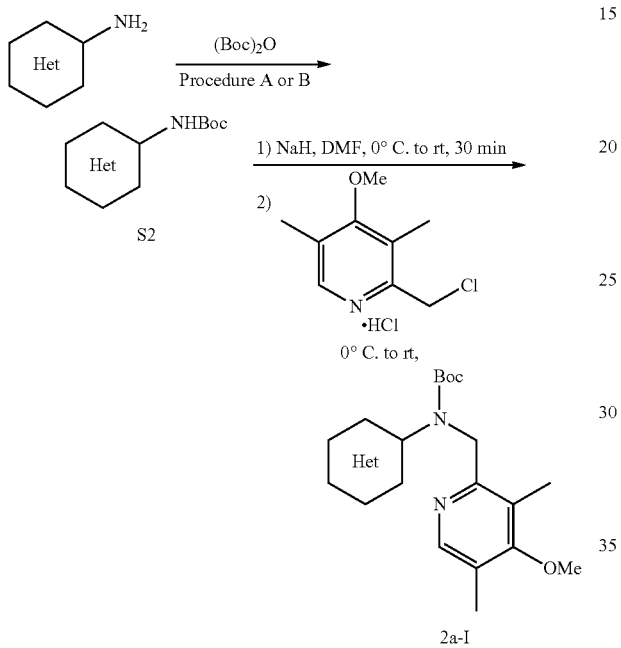

S2a and S2b were synthesized following the General Procedure A; Aminothiophenes bearing Boc-protecting group S2c-e were commercial available; Boc-protected amines S2f-l were synthesized following the General Procedure B. Substrates 2a-l were synthesized following the general procedure.

General Procedure A for Synthesis of Boc-Protected Amines S2:

To a solution of amine (5 mmol) in THF (20 mL) was added a solution of sodium bis(trimethylsilyl)amide (2.5 N in THF) slowly at −15° C. under nitrogen, and the resulting mixture was stirred for 30 min at the same temperature. Next, (Boc)$_2$O (1.1 equiv.) was added at the same temperature. The reaction mixture was allowed to warm up to room temperature. After the reaction was completed, the resulting mixture was diluted with EtOAc (50 mL), and the organic phase was washed with water (50 mL) and then brine (50 mL), dried over MgSO$_4$, and concentrated in vacuo. Purification of the residue by flash chromatography on silica gel gave S2. [Demont ert al., Med. Chem., 58:5649-5673 (2015).]

General Procedure B for Synthesis of Boc-Protected Amines S2:

To a solution of amine in ethanol was added (Boc)$_2$O (1.1 equiv.) at room temperature. After the reaction was completed, the solution was concentrated under vacuum to afford the Boc-protected amines in high yield. The Boc-protected amines were used for next step without further purification. [Vilaivan, Tetrahedron Lett 47:6739-6742 (2005).]

General Procedure for Synthesis of Substrates 2a-l:

To a solution of Boc-protected amine S2 (1.2 equiv.) in DMF was added NaH (3.0 equiv.) at 0° C., and the resulting mixture was allowed to warm up to room temperature for 30 minutes. The mixture was cooled to 0° C. again, then 2-chloromethyl-4-methoxy-3,5-dimethylpyridine hydrochloride (1.0 equiv.) was added into the mixture slowly. The resulting mixture was allowed to warm to room temperature for another 12 hours. After the reaction completed, EtOAc was added to dilute the reaction mixture, then the organic phase was washed with water, brine and dried over Na$_2$SO$_4$. After concentrated in vacuo, the residue was purified by flash chromatography on silica gel to afford 2.

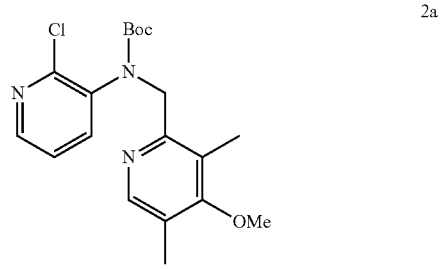 [SMILES: COc1c(C)cnc(CN(C(=O)OC(C)(C)C)c2cccnc2Cl)c1C]

tert-Butyl (2-chloropyridin-3-yl)((4-methoxy-3,5-dimethylpyridin-2-yl)methyl)carbamate (2a)

Colorless solid, rotameric mixture, ratio of the rotamers=76/24; $^1$H NMR (400 MHz, CDCl$_3$) δ 8.22 (d, J=4.7 Hz, 1H), 8.13 (s, 0.24H), 8.07 (s, 0.76H), 7.92 (s, 0.24H), 7.66 (d, J=7.7 Hz, 0.76H), 7.22-7.10 (m, 1H), 5.16 (d, J=15.4 Hz, 1H), 4.72-4.38 (m, 1H), 3.73 (s, 3H), 2.27 (s, 3H), 2.20 (s, 3H), 1.50-1.29 (m, 9H); $^{13}$C NMR (100 MHz, CDCl$_3$) for major isomer: δ 163.86, 154.04, 153.75, 150.49, 148.80, 147.43, 139.21, 136.43, 125.23, 125.07, 122.51, 81.02, 59.75, 51.62, 28.03, 13.17, 10.66; HRMS (ESI-TOF) m/z Calcd for C$_{19}$H$_{25}$ClN$_3$O$_3$ [M+H]$^+$: 378.1579, found: 378.1579.

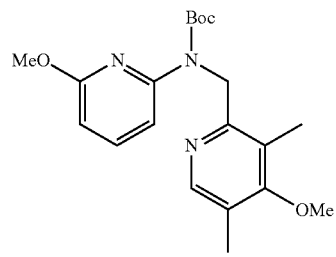

tert-Butyl ((4-methoxy-3,5-dimethylpyridin-2-yl)methyl)(6-methoxypyridin-2-yl)carbamate (2b)

Light yellow liquid, $^1$H NMR (400 MHz, CDCl$_3$) δ 8.12 (s, 1H), 7.50 (t, J=7.9 Hz, 1H), 7.38 (d, J=7.9 Hz, 1H), 6.37 (d, J=7.9 Hz, 1H), 5.20 (s, 2H), 3.72 (s, 3H), 3.62 (s, 3H), 2.24 (s, 3H), 2.19 (s, 3H), 1.43 (s, 9H); $^{13}$C NMR (150 MHz, CDCl$_3$) δ 163.32, 162.09, 155.91, 154.45, 152.20, 148.85, 139.43, 123.84, 122.42, 110.75, 104.67, 80.95, 59.82, 52.84, 49.28, 28.15, 13.13, 10.32; HRMS (ESI-TOF) m/z Calcd for $C_{20}H_{28}N_3O_4$ [M+H]$^+$: 374.2074, found: 374.2073.

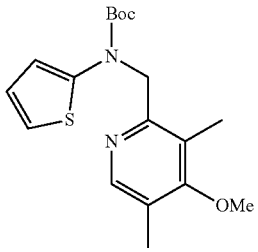

tert-Butyl ((4-methoxy-3,5-dimethylpyridin-2-yl)methyl)(thiophen-2-yl)carbamate (2c)

Light yellow liquid, $^1$H NMR (400 MHz, CDCl$_3$) δ 8.17 (s, 1H), 6.89 (d, J=5.5 Hz, 1H), 6.73 (dd, J=5.6, 3.8 Hz, 1H), 6.57 (d, J=3.6 Hz, 1H), 4.96 (s, 2H), 3.73 (s, 3H), 2.21 (s, 3H), 2.20 (s, 3H), 1.46 (s, 9H); $^{13}$C NMR (150 MHz, CDCl$_3$) δ 163.71, 154.15, 154.00, 149.00, 145.12, 124.83, 124.21, 123.75, 120.38, 116.32, 81.52, 59.85, 53.87, 28.16, 13.19, 10.26; HRMS (ESI-TOF) m/z Calcd for $C_{18}H_{25}N_2O_3S$ [M+H]$^+$: 349.1580, found: 349.1579.

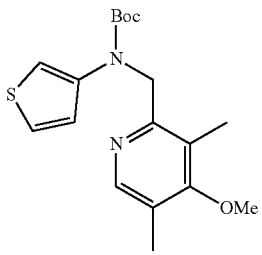

tert-Butyl ((4-methoxy-3,5-dimethylpyridin-2-yl)methyl)(thiophen-3-yl)carbamate (2d)

Light yellow liquid, $^1$H NMR (400 MHz, CDCl$_3$) δ 8.16 (s, 1H), 7.12-7.08 (m, 1H), 7.06 (s, 1H), 6.91 (s, 1H), 4.90 (s, 2H), 3.73 (s, 3H), 2.21 (s, 3H), 2.20 (s, 3H), 1.44 (s, 9H); $^{13}$C NMR (150 MHz, CDCl$_3$) δ 163.67, 154.80, 154.25, 149.00, 141.18, 125.41, 124.68, 123.61, 123.18, 114.83, 80.65, 59.84, 53.33, 28.23, 13.18, 10.27; HRMS (ESI-TOF) m/z Calcd for $C_{18}H_{25}N_2O_3S$ [M+H]$^+$: 349.1580, found: 349.1581.

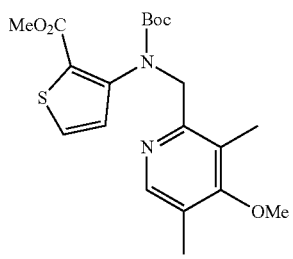

Methyl 3-((tert-butoxycarbonyl)((4-methoxy-3,5-dimethylpyridin-2-yl)methyl)amino)thiophene-2-carboxylate (2e)

Light yellow liquid, rotameric mixture, ratio of rotamers=34/64, $^1$H NMR (400 MHz, CDCl$_3$) δ 8.20-7.98 (m, 1H), 7.37-7.16 (m, 1H), 6.99 (s, 0.34H), 6.76 (s, 0.66H), 5.14-4.68 (m, 2H), 3.84 (s, 3H), 3.72 (s, 3H), 2.25 (s, 3H), 2.20 (s, 3H), 1.50-1.28 (m, 9H); $^{13}$C NMR (150 MHz, CDCl$_3$) rotameric mixture, resonances for the minor rotamer are enclosed in parenthesis ( ): δ 163.74 (163.60), 161.44 (161.32), 154.71 (155.16), 154.07 (154.16), 148.67 (148.75), 144.92 (145.84), 128.91 (129.28), 128.51 (128.78), 124.97 (125.02), 124.78 (124.71), 123.92, 80.28 (80.62), 59.75, 52.49 (53.43), 51.83, 28.08, 13.15, 10.50; HRMS (ESI-TOF) m/z Calcd for $C_{20}H_{27}N_2O_5S$ [M+H]$^+$: 407.1635, found: 407.1635.

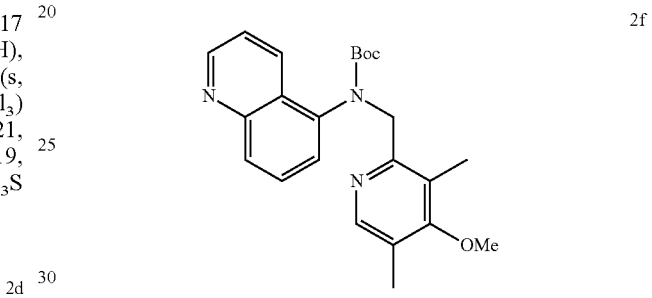

tert-Butyl ((4-methoxy-3,5-dimethylpyridin-2-yl)methyl)(quinolin-5-yl)carbamate (2f)

Red liquid, $^1$H NMR (400 MHz, CDCl$_3$) δ 8.88 (dd, J=4.2, 1.6 Hz, 1H), 8.27 (s, 1H), 8.09 (s, 1H), 7.98 (d, J=8.5 Hz, 1H), 7.59 (t, J=7.9 Hz, 1H), 7.38 (dd, J=8.5, 4.2 Hz, 2H), 5.21 (d, J=15.3 Hz, 1H), 4.80 (d, J=15.2 Hz, 1H), 3.67 (s, 3H), 2.17 (s, 6H), 1.25 (brs, 9H); $^{13}$C NMR (150 MHz, CDCl$_3$) δ 163.73, 155.09, 154.54, 150.19, 148.97, 148.73, 138.85, 131.91, 128.89, 128.74, 126.24, 125.75, 124.95, 124.53, 120.89, 80.46, 59.75, 53.26, 28.07, 13.16, 10.60; HRMS (ESI-TOF) m/z Calcd for $C_{23}H_{28}N_3O_3$ [M+H]$^+$: 394.2125, found: 394.2124.

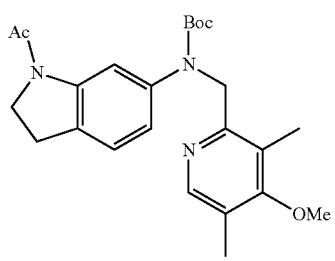

tert-Butyl (1-acetylindolin-6-yl)((4-methoxy-3,5-dimethylpyridin-2-yl)methyl)carbamate (2g)

Light yellow solid, mp=140° C., rotameric mixture, ratio of rotamer=22/78, $^1$H NMR (400 MHz, CDCl$_3$) δ 8.18-8.08 (m, 1.78H), 7.15 (s, 0.22H), 7.08 (d, J=7.4 Hz, 0.22H), 7.00 (d, J=8.0 Hz, 0.78H), 6.96-6.85 (m, 1H), 4.95-4.84 (m, 2H), 4.09 (t, J=8.1 Hz, 0.44H), 4.02 (t, J=8.4 Hz, 1.56H), 3.72 (s, 3H), 3.11 (t, J=8.5 Hz, 1.56H), 2.98 (t, J=8.5 Hz, 0.44H), 2.32-2.14 (m, 9H), 1.40 (s, 9H); $^{13}$C NMR (150 MHz, CDCl$_3$) rotameric mixture, resonances for the minor rotamer are enclosed in parenthesis ( ): δ 168.34 (168.19), 163.61 (163.68), 155.12 (154.97), 154.79, 148.78 (148.86), 142.93 (142.18), 142.08 (141.68), 128.43 (131.15), 125.15, 124.52 (124.79), 123.75 (123.89), 122.25 (121.66), 115.85 (113.80), 80.16 (80.38), 59.79, 53.55 (53.60), 49.18 (48.33), 28.21, 27.56 (26.39), 24.11 (24.31), 13.15, 10.44 (10.39); HRMS (ESI-TOF) m/z Calcd for $C_{24}H_{32}N_3O_4$ [M+H]$^+$: 426.2387, found: 426.2387.

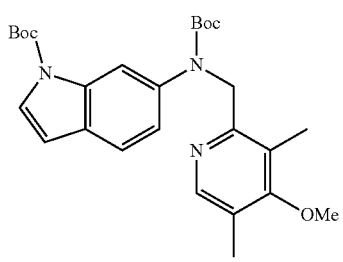

tert-Butyl 6-((tert-butoxycarbonyl)((4-methoxy-3,5-dimethylpyridin-2-yl)methyl)amino)-1H-indole-1-carboxylate (2h)

Colorless liquid, $^1$H NMR (400 MHz, CDCl$_3$) δ 8.11 (s, 1H), 7.95 (s, 1H), 7.53 (d, J=3.7 Hz, 1H), 7.38 (d, J=8.3 Hz, 1H), 7.12 (d, J=8.4 Hz, 1H), 6.47 (d, J=3.7 Hz, 1H), 4.99 (s, 2H), 3.72 (s, 3H), 2.23 (s, 3H), 2.19 (s, 3H), 1.59 (s, 9H), 1.40 (s, 9H); $^{13}$C NMR (150 MHz, CDCl$_3$) δ 163.73, 154.75, 154.55, 149.01, 143.94, 139.80, 139.25, 124.81, 123.72, 123.58, 123.39, 120.34, 111.99, 84.65, 80.74, 59.85, 53.78, 28.20, 28.01, 13.19, 10.43; HRMS (ESI-TOF) m/z Calcd for $C_{27}H_{36}N_3O_5$ [M+H]$^+$: 482.2649, found: 482.2650.

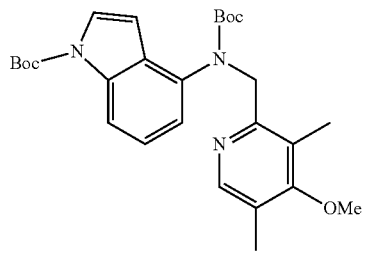

tert-Butyl 4-((tert-butoxycarbonyl)((4-methoxy-3,5-dimethylpyridin-2-yl)methyl)amino)-1H-indole-1-carboxylate (2i)

Colorless solid, $^1$H NMR (400 MHz, CDCl$_3$) δ 8.10 (s, 1H), 7.97 (d, J=8.3 Hz, 1H), 7.52 (d, J=3.8 Hz, 1H), 7.15 (t, J=8.0 Hz, 1H), 7.01 (s, 1H), 6.52 (d, J=3.7 Hz, 1H), 4.99 (s, 2H), 3.68 (s, 3H), 2.18 (s, 6H), 1.65 (s, 9H), 1.35 (brs, 9H); $^{13}$C NMR (150 MHz, CDCl$_3$) δ 163.59, 154.98, 154.85, 149.65, 148.85, 135.80, 134.93, 128.51, 125.42, 124.33, 124.16, 121.07, 113.58, 105.56, 83.62, 80.08, 59.70, 53.18, 28.16, 28.13, 13.14, 10.52; HRMS (ESI-TOF) m/z Calcd for $C_{27}H_{36}N_3O_5$ [M+H]$^+$: 482.2649, found: 482.2649.

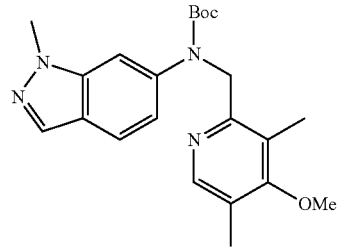

tert-Butyl ((4-methoxy-3,5-dimethylpyridin-2-yl)methyl)-(1-methyl-1H-indazol-6-yl)carbamate (2j)

Colorless solid, $^1$H NMR (400 MHz, CDCl$_3$) δ 8.15 (s, 1H), 7.87 (s, 1H), 7.55 (d, J=8.6 Hz, 1H), 7.33 (s, 1H), 7.05 (d, J=8.6 Hz, 1H), 4.99 (s, 2H), 3.98 (s, 3H), 3.73 (s, 3H), 2.24 (s, 3H), 2.21 (s, 3H), 1.40 (s, 9H); $^{13}$C NMR (150 MHz, CDCl$_3$) δ 163.70, 155.02, 154.81, 148.94, 141.45, 140.01, 132.47, 124.76, 123.84, 121.90, 120.82, 120.45, 106.53, 80.50, 59.84, 53.92, 35.50, 28.25, 13.21, 10.46; HRMS (ESI-TOF) m/z Calcd for $C_{22}H_{29}N_4O_3$ [M+H]$^+$: 397.2234, found: 397.2234.

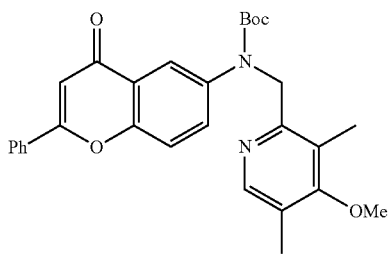

tert-Butyl ((4-methoxy-3,5-dimethylpyridin-2-yl)methyl)-(4-oxo-2-phenyl-4H-chromen-6-yl)carbamate (2k)

Yellow solid, $^1$H NMR (400 MHz, CDCl$_3$) δ 8.14 (s, 1H), 7.99 (d, J=2.6 Hz, 1H), 7.94-7.87 (m, 2H), 7.78 (d, J=9.1 Hz, 1H), 7.57-7.49 (m, 3H), 7.47 (d, J=9.0 Hz, 1H), 6.77 (s, 1H), 4.98 (s, 2H), 3.74 (s, 3H), 2.24 (s, 3H), 2.20 (s, 3H), 1.40 (s, 9H); $^{13}$C NMR (150 MHz, CDCl$_3$) δ 177.99, 163.75, 163.22, 154.50, 153.76, 149.03, 140.32, 133.36, 131.73, 131.53, 128.99, 126.22, 124.84, 123.84, 123.68, 121.85, 117.95, 107.19, 80.83, 59.89, 53.24, 28.18, 13.19, 10.42; HRMS (ESI-TOF) m/z Calcd for $C_{29}H_{31}N_2O_5$ [M+H]$^+$: 487.2227, found: 487.2226.

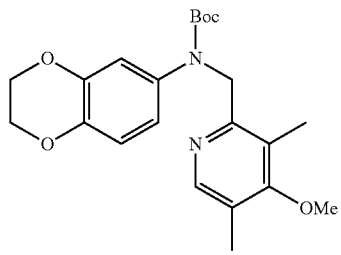

tert-Butyl (2,3-dihydrobenzo[b][1,4]dioxin-6-yl)((4-methoxy-3,5-dimethylpyridin-2-yl)methyl)carbamate (2l)

Colorless solid, $^1$H NMR (500 MHz, CDCl$_3$) δ 8.15 (s, 1H), 6.78 (s, 1H), 6.70 (s, 2H), 4.84 (s, 2H), 4.19 (s, 4H), 3.72 (s, 3H), 2.21 (s, 3H), 2.19 (s, 3H), 1.39 (s, 9H); $^{13}$C NMR (150 MHz, CDCl$_3$) δ 163.62, 155.05, 154.99, 148.92, 142.85, 141.48, 136.34, 124.59, 123.75, 120.17, 116.54, 115.81, 80.10, 64.24, 64.19, 59.82, 53.68, 28.25, 13.18, 10.37; HRMS (ESI-TOF) m/z Calcd for C$_{22}$H$_{29}$N$_2$O$_5$ [M+H]$^+$: 401.2071, found: 401.2071.

Preparation of Phenol Substrates

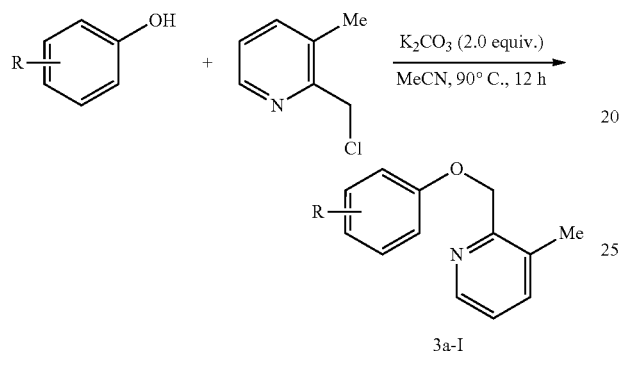

2-(Chloromethyl)-3-methylpyridine was synthesized following the literature. [Narendara et al., *Synthetic Commun*, 34:1097-1103 (2004)]

General Procedure for Preparation of Phenol Substrates[1]:

Phenol derivative (10 mmol) and K$_2$CO$_3$ (20 mmol) were added to a 100 mL round bottom flask equipped with a reflux condenser and diluted with 20 mL MeCN. Next, 2-(chloromethyl)-3-methylpyridine (12 mmol) was added to the mixture via syringe and the reaction mixture was stirred at 90° C. for 12 hours. After cooling to room temperature, the mixture was diluted with EtOAc and washed with 2 N NaOH three times. The resulting solution was dried over sodium sulfate, concentrated by rotatory evaporation and purified by silica gel chromatography to afford the desired phenol substrate Compounds 3a-l.

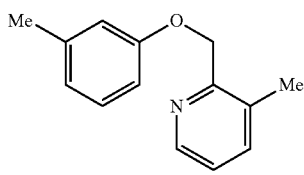

3a

3-Methyl-2-((m-tolyloxy)methyl)pyridine (3a)

Light yellow liquid, $^1$H NMR (400 MHz, CDCl$_3$) δ 8.45 (d, J=4.8 Hz, 1H), 7.51 (d, J=7.7 Hz, 1H), 7.21-7.13 (m, 2H), 6.82-6.88 (m, 2H), 6.78 (d, J=7.5 Hz, 1H), 5.20 (s, 2H), 2.43 (s, 3H), 2.33 (s, 3H); $^{13}$C NMR (100 MHz, CDCl$_3$) δ 158.70, 154.40, 146.47, 139.42, 138.37, 133.26, 129.11, 123.35, 121.79, 115.69, 111.61, 70.73, 21.48, 18.14; HRMS (ESI-TOF) m/z Calcd for C$_{14}$H$_{15}$NO [M+H]$^+$: 214.1226, found: 214.1228.

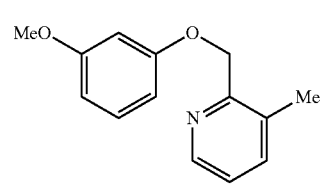

3b

2-((3-Methoxyphenoxy)methyl)-3-methylpyridine (3b)

Light yellow liquid, $^1$H NMR (400 MHz, CDCl$_3$) δ 8.45 (d, J=4.7 Hz, 1H), 7.51 (d, J=7.6 Hz, 1H), 7.23-7.10 (m, 2H), 6.66-6.59 (m, 2H), 6.52 (dd, J=8.3, 2.4 Hz, 1H), 5.19 (s, 2H), 3.78 (s, 3H), 2.42 (s, 3H); $^{13}$C NMR (100 MHz, CDCl$_3$) δ 160.75, 159.96, 154.24, 146.57, 138.39, 133.21, 129.81, 123.41, 106.93, 106.75, 101.26, 70.83, 55.23, 18.14; HRMS (ESI-TOF) m/z Calcd for C$_{14}$H$_{16}$NO$_2$ [M+H]$^+$: 230.1176, found: 230.1180.

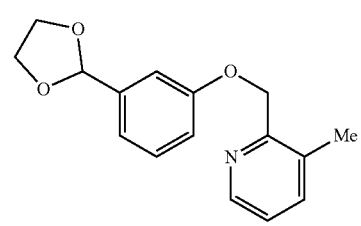

3c

2-((3-(1,3-Dioxolan-2-yl)phenoxy)methyl)-3-methylpyridine (3c)

Clear liquid, $^1$H NMR (400 MHz, CDCl$_3$) δ 8.45 (d, J=4.7 Hz, 1H), 7.50 (d, J=7.7 Hz, 1H), 7.33-7.27 (m, 1H), 7.21-7.15 (m, 2H), 7.09 (d, J=7.5 Hz, 1H), 7.05 (dd, J=8.2, 2.7 Hz, 1H), 5.81 (s, 1H), 5.23 (s, 2H), 4.16-3.97 (m, 4H), 2.42 (s, 3H); $^{13}$C NMR (100 MHz, CDCl$_3$) δ 158.64, 154.04, 146.37, 139.42, 138.27, 133.16, 129.31, 123.32, 118.96, 115.54, 112.55, 103.32, 103.31, 70.71, 65.09, 18.01; HRMS (ESI-TOF) m/z Calcd for C$_{16}$H$_{18}$NO$_3$ [M+H]$^+$: 272.1281, found: 272.1284.

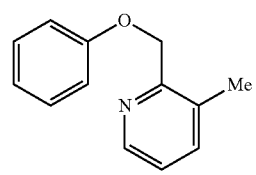

3d

3-Methyl-2-(phenoxymethyl)pyridine (3d)

Clear liquid, $^1$H NMR (400 MHz, CDCl$_3$) δ 8.44 (d, J=4.7 Hz, 1H), 7.49 (d, J=7.6 Hz, 1H), 7.31-7.23 (m, 2H), 7.16 (dd, J=7.7, 4.8 Hz, 1H), 7.06-7.00 (m, 2H), 6.94 (t, J=7.6, 1H) 5.20 (s, 2H), 2.41 (s, 3H); $^{13}$C NMR (100 MHz, CDCl$_3$) δ 158.63, 154.26, 146.46, 138.30, 133.17, 129.32, 123.32, 120.88, 114.76, 70.73, 18.07; HRMS (ESI-TOF) m/z Calcd for C$_{13}$H$_{14}$NO [M+H]$^+$: 200.1070, found: 200.1073.

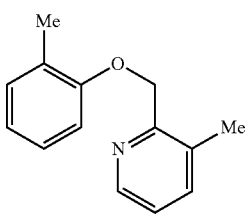

3-Methyl-2-((o-tolyloxy)methyl)pyridine (3e)

Light yellow liquid, $^1$H NMR (400 MHz, CDCl$_3$) δ 8.44 (d, J=4.9 Hz, 1H), 7.52 (d, J=7.2 Hz, 1H), 7.19 (dd, J=7.7, 4.9 Hz, 1H), 7.16-7.10 (m, 2H), 7.03 (d, J=8.1 Hz, 1H), 6.86 (t, J=7.4 Hz, 1H), 5.22 (s, 2H), 2.45 (s, 3H), 2.22 (s, 3H); $^{13}$C NMR (100 MHz, CDCl$_3$) δ 156.74, 154.66, 146.37, 138.37, 133.46, 130.62, 126.82, 126.75, 123.35, 120.54, 111.51, 71.16, 18.14, 16.23; HRMS (ESI-TOF) m/z Calcd for C$_{14}$H$_{16}$NO [M+H]$^+$: 214.1226, found: 214.1236.

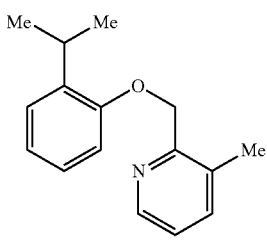

2-((2-Isopropylphenoxy)methyl)-3-methylpyridine (3f)

Clear liquid, $^1$H NMR (400 MHz, CDCl$_3$) δ 8.45 (d, J=4.4, Hz, 1H), 7.52 (d, J=8.0 Hz, 1H), 7.24-7.16 (m, 2H), 7.14 (d, J=7.2 Hz, 1H), 7.07 (d, J=8.1 Hz, 1H), 6.94 (t, J=7.4 Hz, 1H), 5.22 (s, 2H) 3.34 (sep, J=6.9 Hz, 1H), 2.45 (s, 3H), 1.18 (d, J=6.9 Hz, 6H); $^{13}$C NMR (100 MHz, CDCl$_3$) δ 155.77, 154.74, 146.44, 138.35, 137.20, 133.43, 126.50, 126.05, 123.38, 120.86, 111.81, 71.31, 26.36, 22.90, 18.16; HRMS (ESI-TOF) m/z Calcd for C$_{16}$H$_{19}$NO [M+H]$^+$: 242.1539, found: 242.1539.

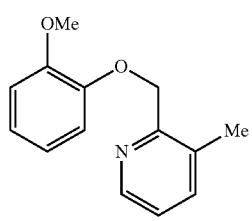

2-((2-Methoxyphenoxy)methyl)-3-methylpyridine (3g)

Yellow liquid, $^1$H NMR (400 MHz, CDCl$_3$) δ 8.32 (d, J=4.4 Hz, 1H), 7.37 (d, J=7.6 Hz, 1H), 7.04 (dd, J=7.7, 4.8 Hz, 1H), 6.98 (d, J=8.6 Hz, 1H), 6.85-6.74 (m, 3H), 5.16 (s, 2H), 3.73 (s, 3H), 2.36 (s, 3H); $^{13}$C NMR (100 MHz, CDCl$_3$) δ 154.25, 149.65, 147.97, 146.22, 138.26, 133.36, 123.19, 121.41, 120.62, 114.42, 111.69, 71.86, 55.66, 18.02; HRMS (ESI-TOF) m/z Calcd for C$_{14}$H$_{16}$NO$_2$ [M+H]$^+$: 230.1176, found: 230.1179.

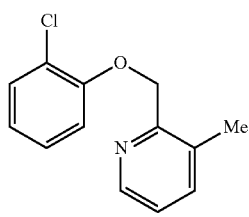

2-((2-Chlorophenoxy)methyl)-3-methylpyridine (3h)

Colorless solid, $^1$H NMR (400 MHz, CDCl$_3$) δ 8.43 (d, J=4.8 Hz, 1H), 7.52 (d, J=7.7 Hz, 1H), 7.34 (d, J=8.0 Hz, 1H), 7.23-7.14 (m, 3H), 6.92-6.84 (m, 1H), 5.31 (s, 2H), 2.49 (s, 3H); $^{13}$C NMR (100 MHz, CDCl$_3$) δ 153.98, 153.78, 146.24, 138.62, 133.90, 130.25, 127.65, 123.60, 122.95, 121.59, 114.23, 72.02, 18.22; HRMS (ESI-TOF) m/z Calcd for C$_{13}$H$_{13}$ClNO [M+H]$^+$: 234.0680, found: 234.0682.

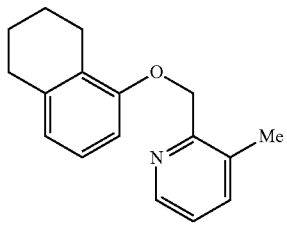

3-Methyl-2-(((5,6,7,8-tetrahydronaphthalen-1-yl)oxy)methyl)pyridine (3i)

Orange solid, $^1$H NMR (400 MHz, CDCl$_3$) δ 8.44 (d, J=4.7 Hz, 1H), 7.51 (d, J=7.6 Hz, 1H), 7.19 (dd, J=7.6, 4.8 Hz, 1H), 7.06 (t, J=7.9 Hz, 1H), 6.86 (d, J=8.0 Hz, 1H), 6.71 (d, J=7.6 Hz, 1H), 5.21 (s, 2H), 2.75 (t, J=5.1 Hz, 2H), 2.66 (t, J=6.3 Hz, 2H), 2.44 (s, 3H), 1.84-1.68 (m, J=3.3 Hz, 4H); $^{13}$C NMR (100 MHz, CDCl$_3$) δ 156.34, 154.77, 146.34, 138.49, 138.35, 133.49, 126.13, 125.62, 123.32, 121.62, 108.20, 71.06, 29.61, 23.10, 22.79, 22.75, 18.20; HRMS (ESI-TOF) m/z Calcd for C$_{17}$H$_{20}$NO [M+H]$^+$: 254.1539, found: 254.1537.

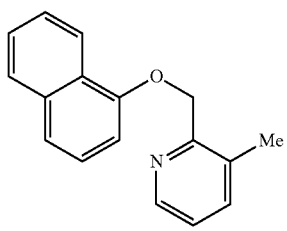

3-Methyl-2-((naphthalen-1-yloxy)methyl)pyridine (3j)

Orange liquid, $^1$H NMR (400 MHz, CDCl$_3$) δ 8.48 (d, J=4.9 Hz, 1H), 8.25 (d, J=8.2 Hz, 1H), 7.78 (d, J=8.1 Hz, 1H), 7.54 (d, J=7.6 Hz, 1H), 7.50-7.42 (m, 3H), 7.38 (t, J=7.9 Hz, 1H), 7.27-7.20 (m, 1H), 7.05 (d, J=7.5 Hz, 1H), 5.42 (s, 2H), 2.48 (s, 3H); $^{13}$C NMR (100 MHz, CDCl$_3$) δ 154.40, 154.31, 146.40, 138.54, 134.49, 133.69, 127.43, 126.31, 125.85, 125.64, 125.14, 123.52, 122.00, 120.46, 105.40, 71.32, 18.27; HRMS (ESI-TOF) m/z Calcd for C$_{17}$H$_{16}$NO [M+H]$^+$: 250.1226, found: 250.1228.

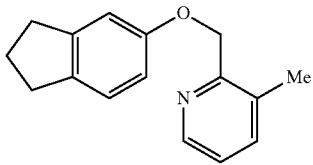

2-(((2,3-Dihydro-1H-inden-5-yl)oxy)methyl)-3-methylpyridine (3k)

Yellow liquid, $^1$H NMR (400 MHz, CDCl$_3$) δ 8.44 (d, J=4.8 Hz, 1H), 7.51 (d, J=7.5 Hz, 1H), 7.18 (dd, J=7.7, 4.8 Hz, 1H), 7.11 (d, J=8.2 Hz, 1H), 6.92 (s, 1H), 6.81 (dd, J=8.0, 2.2 Hz, 1H), 5.18 (s, 2H), 2.92-2.79 (m, 4H), 2.43 (s, 3H), 2.06 (p, J=7.4 Hz, 2H); $^{13}$C NMR (100 MHz, CDCl$_3$) δ 157.60, 154.53, 146.38, 145.64, 138.43, 136.52, 133.33, 124.66, 123.34, 112.78, 110.91, 71.05, 33.13, 31.95, 25.77, 18.16; HRMS (ESI-TOF) m/z Calcd for C$_{16}$H$_{18}$NO [M+H]$^+$: 240.1383, found: 240.1386.

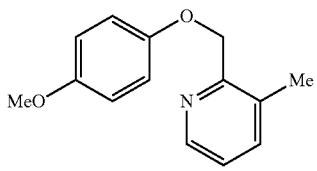

2-((4-Methoxyphenoxy)methyl)-3-methylpyridine (3l)

Light yellow liquid, $^1$H NMR (400 MHz, CDCl$_3$) δ 8.44 (d, J=4.8 Hz, 1H), 7.50 (d, J=7.6 Hz, 1H), 7.18 (dd, J=7.7, 4.8 Hz, 1H), 6.96 (d, J=9.0 Hz, 2H), 6.82 (d, J=9.0 Hz, 2H), 5.16 (s, 2H), 3.76 (s, 3H), 2.43 (s, 3H); $^{13}$C NMR (100 MHz, CDCl$_3$) δ 154.53, 154.00, 152.87, 146.56, 138.37, 133.21, 123.36, 115.85, 114.58, 71.55, 55.68, 18.17; HRMS (ESI-TOF) m/z Calcd for C$_{14}$H$_{16}$NO$_2$ [M+H]$^+$: 230.1176, found: 230.1179.

Preparation of Other Heterocyclic Substrates

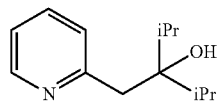

2,4-Dimethyl-3-(2-pyridylmethyl)-3-pentanol (S7)

n-BuLi (1.6 M in hexane, 13 mL, 20 mmol) was slowly added to a solution of 2-picoline (2.0 mL, 20 mmol) in tetrahydrofuran (20 mL) at −30° C. and the reaction mixture was stirred for 30 minutes. Diisopropyl ketone (3.4 mL, 24 mmol) was then added, the reaction mixture was stirred for 2 hours at ambient temperature. Water (30 mL) was added, and the product was extracted with ethyl acetate (3×20 mL). The combined organic layer was dried over sodium sulfate, and concentrated in vacuo. Silica gel column purification (Hexane:EtOAc=3:1) gave the pyridyl alcohol S7 (3.5 g, 17 mmol) in 85% yield.

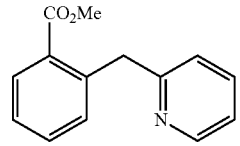

Methyl 2-(pyridin-2-ylmethyl)benzoate (4b)

[Niwa et al., *Angew. Chem. Int. Ed.* 46:2643-2645 (2007).]

Cesium carbonate (0.714 g, 2.0 mmol) was placed in a 50-mL two-necked reaction flask. Cesium carbonate was dried in vacuo with heating with a heat gun for 2 minutes. The flask was then filled with argon using standard Schlenk technique. Palladium trifluoroacetate (34 mg, 0.10 mmol), tricyclohexylphosphine (53 mg, 0.20 mmol), xylene (10 mL), pyridyl alcohol S7 (0.414 g, 2.0 mmol), and methyl 2-iodobenzoate (576 mg, 2.2 mmol) were sequentially added at room temperature. The resulting mixture was heated at reflux for 10 hours. After the mixture was cooled to room temperature, water (30 mL) was added. The product was extracted with ethyl acetate (30 mL×3). The combined organic layers were dried over sodium sulfate, and concentrated in vacuo. Silica gel column purification (Hexane:EtOAc=5:1) gave product Compound 4b (272 mg, 1.2 mmol) in 60% yield. $^1$H NMR (400 MHz, CDCl$_3$) δ 8.53 (d, J=4.6 Hz, 1H), 7.93 (d, J=7.8 Hz, 1H), 7.54 (td, J=7.7, 1.9 Hz, 1H), 7.50-7.42 (m, 1H), 7.36-7.28 (m, 2H), 7.13-7.02 (m, 2H), 4.56 (s, 2H), 3.81 (s, 3H); $^{13}$C NMR (100 MHz, CDCl$_3$) δ 167.93, 160.81, 149.15, 140.44, 136.28, 132.12, 131.98, 130.72, 129.96, 126.54, 122.96, 120.99, 51.91, 42.52; HRMS (ESI-TOF) m/z Calcd for C$_{14}$H$_{14}$NO$_2$ [M+H]$^+$: 228.1019, found: 228.1019.

2-Benzyl-3-methylpyridine (4c)

Anhydrous cobalt(II) acetylacetonate (77 mg, 0.30 mmol) was placed in a 50 mL flask. Anhydrous dioxane (10 mL) was then added under argon. After the solution became red, benzylmagnesium chloride (2.0 M in THF, 4.5 mL, 9.0 mmol) was added at 0° C. The mixture was stirred for about 5 minutes at 25° C. Then, 2-bromo-3-methylpyridine (526 mg, 3.0 mmol) was added dropwise to the reaction mixture. After stirring for 2 hours at 25° C., the reaction mixture was poured into water. The products were extracted with ethyl acetate (3×30 mL) and the combined organic layers were dried over sodium sulfate and concentrated. Purification of the crude product by silica gel column chromatography (Hexane:EtOAc=4:1) provided the corresponding product Compound 4c (384 mg, 2.1 mmol) in 70% yield. $^1$H NMR (400 MHz, CDCl$_3$) δ 8.42 (d, J=4.6 Hz, 1H), 7.40 (d, J=7.5 Hz, 1H), 7.25 (t, J=7.5 Hz, 2H), 7.22-7.13 (m, 3H), 7.07 (dd, J=7.6, 4.9 Hz, 1H), 4.19 (s, 2H), 2.24 (s, 3H); $^{13}$C NMR (100 MHz, CDCl$_3$) δ 158.76, 146.74, 138.99, 137.96, 131.70, 128.61, 128.33, 126.04, 121.66, 42.21, 18.92; HRMS (ESI-TOF) m/z Calcd for C$_{13}$H$_{14}$N [M+H]$^+$: 184.1121, found: 184.1121.

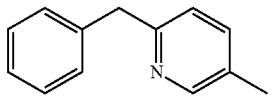

2-Benzyl-5-methylpyridine (4d)

[Ohmiya et al., *Chem. Lett.*, 33:1240-1241 (2004).]

Anhydrous cobalt(II) acetylacetonate (77 mg, 0.30 mmol) was placed in a 50 mL flask. Anhydrous dioxane (10 mL) was then added under argon. After the solution became red, benzylmagnesium chloride (2 M in THF, 4.5 mL, 9.0 mmol) was added at 0° C. The mixture was stirred for about 5 minutes at 25° C. Then, 2-bromo-5-methylpyridine (526 mg, 3.0 mmol) was added dropwise to the reaction mixture. After being stirred for 2 hours at 25° C., the reaction mixture was poured into water. The products were extracted with ethyl acetate (30 mL×3). The combined organic layers were dried over sodium sulfate and concentrated. Purification of the crude product by silica gel column chromatography (Hexane:EtOAc=4:1) provided the corresponding product Compound 4d (455 mg, 2.4 mmol) in 83% yield. $^1$H NMR (400 MHz, CDCl$_3$) δ 8.52 (s, 1H), 7.57-7.50 (m, 1H), 7.49-7.38 (m, 4H), 7.38-7.32 (m, 1H), 7.15 (d, J=7.9 Hz, 1H), 4.27 (s, 2H), 2.43 (s, 3H); $^{13}$C NMR (100 MHz, cdcl$_3$) δ 157.96, 149.60, 139.77, 137.09, 130.43, 128.98, 128.49, 126.22, 122.53, 44.18, 17.98; HRMS (ESI-TOF) m/z Calcd for C$_{13}$H$_{14}$N [M+H]$^+$: 184.1121, found: 184.1121.

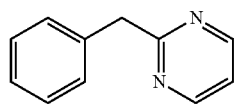

2-benzylpyrimidine (4e)

According to procedure for Compound 4c, Compound 4e was afforded in 83% yield using 2-(bromomethyl)pyrimidine. $^1$H NMR (400 MHz, CDCl$_3$) δ 8.68 (d, J=4.9 Hz, 2H), 7.36 (d, J=7.6 Hz, 2H), 7.30 (t, J=7.5 Hz, 2H), 7.22 (t, J=7.3 Hz, 1H), 7.12 (t, J=4.9 Hz, 1H), 4.30 (s, 2H); $^{13}$C NMR (150 MHz, CDCl$_3$) δ 170.03, 157.29, 138.19, 129.12, 128.52, 126.57, 118.63, 46.05; HRMS (ESI-TOF) m/z Calcd for C$_{11}$H$_{11}$N$_2$ [M+H]$^+$: 171.0917, found: 171.0916.

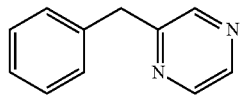

2-Benzylpyrazine (4f)

According to procedure for Compound 4c, Compound 4f was afforded in 70% yield using 2-(bromomethyl)pyrazine. $^1$H NMR (400 MHz, CDCl$_3$) δ 8.50 (t, J=2.0 Hz, 1H), 8.47 (s, 1H), 8.40 (d, J=2.5 Hz, 1H), 7.36-7.20 (m, 5H), 4.17 (s, 2H); $^{13}$C NMR (100 MHz, cdcl$_3$) δ 156.44, 144.73, 144.04, 142.34, 138.08, 128.96, 128.72, 126.72, 41.94; HRMS (ESI-TOF) m/z Calcd for C$_{11}$H$_{11}$N$_2$ [M+H]$^+$: 171.0917, found: 171.0917.

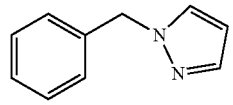

1-Benzyl-1H-pyrazole (4g)

[Kumpulainen et al., *Adv. Synth. Catal.* 356:1555-1561 (2014).]

A round bottomed flask was charged with pyrazole (504 mg, 12.6 mmol), benzyl bromide (1.0 mL, 8.4 mmol), potassium carbonate (1.738 g, 12.6 mmol), potassium iodide (70 mg, 0.043 mmol) and dimethylformamide (10 mL). The mixture was heated to 80° C. for 13 hours. The reaction mixture was allowed to cool to room temperature and poured into a beaker containing water (20 mL) and ethyl acetate (50 mL). Next, the phases were separated and aqueous phase was extracted with ethyl acetate (50 mL). Combined organic extracts were dried with anhydrous sodium sulfate and solvents were evaporated. Purification by silica gel column chromatography (Hexane:EtOAc=20:1) provided the corresponding product (796 mg, 5.0 mmol) in 60% yield. $^1$H NMR (600 MHz, CDCl$_3$) δ 7.58 (d, J=1.9 Hz, 1H), 7.40 (d, J=2.3 Hz, 1H), 7.39-7.34 (m, 2H), 7.34-7.30 (m, 1H), 7.26-7.22 (m, 2H), 6.31 (t, J=2.1 Hz, 1H), 5.35 (s, 2H); $^{13}$C NMR (150 MHz, CDCl$_3$) δ 139.43, 136.59, 129.12, 128.69, 127.89, 127.52, 105.86, 55.82; HRMS (ESI-TOF) m/z Calcd for C$_{10}$H$_{11}$N$_2$ [M+H]$^+$: 159.0917, found: 159.0917.

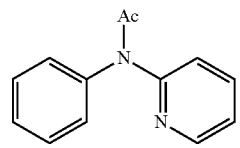

N-phenyl-N-(pyridin-2-yl)acetamide (4h)

[Wang et al., *Tetrahedron Lett* 55:7121-7123 (2014).]

A 10 mL flask equipped with a magnetic stir bar and a Teflon valve was charged with CuI (19 mg, 1 mol %), pyridin-2-amine (1.41 g, 15 mmol), and KOtBu (2.12 g, 20 mmol). The tube was evacuated and backfilled with argon. Under a counter flow of argon, 1,4-dioxane (25 mL) and bromobenzene (1.57 g, 10 mmol) were added via syringe and the tube was sealed. The reaction mixture was allowed to stir at 110° C. for 24 hours. The mixture was cooled to room temperature and 5.0 mL of brine was added. Subsequently, the mixture was extracted with ethyl acetate. The organic layers were collected, dried over sodium sulfate, filtered and the solvent was removed under vacuum. The residue was purified by column chromatography on silica gel (hexanes:EtOAc=8:1) to give the secondary amine as a colorless solid (1.35 g, 8.2 mmol) in 82% yield.

NaH (60% in mineral oil, 50 mg, 1.2 mmol) was added into the solution of secondary amine (170 mg, 10 mmol) in THF. The reaction mixture was stirred at room temperature for 30 minutes. Then acetyl chloride (110 mg, 1.5 mmol) was added and the reaction was monitored by TLC. Upon completion, the mixture was extracted with ethyl acetate (3×30 mL). The combined organic phases were washed with brine and dried over sodium sulfate and concentrated. The crude product was purified by column chromatography on silica gel (Hexanes:EtOAc=20:1) to give the title product Compound 4h (174 mg, 0.85 mmol) in 85% yield. $^1$H NMR (600 MHz, CDCl$_3$) δ 8.43 (dd, J=4.9, 1.9 Hz, 1H), 7.71 (td, J=7.8, 2.0 Hz, 1H), 7.46 (d, J=8.4 Hz, 1H), 7.44-7.38 (m, 2H), 7.33 (d, J=7.5 Hz, 1H), 7.32-7.27 (m, 2H), 7.13 (dd, J=7.0, 5.1 Hz, 1H), 2.11 (s, 3H); $^{13}$C NMR (150 MHz, CDCl$_3$) δ 170.89, 155.18, 148.74, 141.96, 137.86, 129.38, 128.31, 127.54, 121.38, 121.13, 24.21; HRMS (ESI-TOF) m/z Calcd for C$_{13}$H$_{13}$N$_2$O [M+H]$^+$: 213.1022, found: 213.1021.

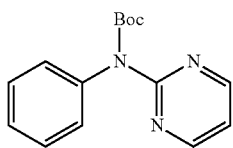

4i tert-Butyl phenyl (pyrimidin-2-yl)carbamate (4i)

[Qian et al., Eur. J. Org. Chem. 4837-4843 (2014).]

To an oven-dried flask containing aniline (1.39 g, 15.0 mmol) was added a solution of 2-chloro-pyrimidine (1.14 g, 10.0 mmol) and acetic acid (0.6 g, 10 mmol) in 1,4-dioxane (30.0 mL). The reaction mixture was stirred at 110° C. overnight. Upon completion, the mixture was extracted with CH$_2$Cl$_2$ (3×30 mL). The combined organic phases were washed with brine, dried over sodium sulfate and concentrated. The crude product was purified by column chromatography on silica gel (hexanes:EtOAc=5:1) to give the secondary amine as a colorless solid (1.28 g, 7.5 mmol) in 75% yield.

The secondary amine (513 mg, 3.0 mmol) was dissolved in anhydrous DMF (30 mL), and the solution was cooled to 0° C. in an ice/water bath. Sodium hydride (132 mg, 60% suspension in oil, 3.3 mmol) was added in portions. The suspension was stirred vigorously for an additional 20 minutes while maintaining the temperature below 5° C. and then (Boc)$_2$O (719 mg, 3.3 mmol) was added dropwise. After stirring for 30 minutes, the reaction mixture was brought to room temperature over a 1 hour period before water (5.0 mL) was added. The mixture was then diluted with water (20 mL) and extracted with ethyl acetate (3×30 mL). The organic layer was separated and extracted with water, 0.1 M HCl, sat. aqueous NaHCO$_3$ solution, and brine, then dried and concentrated. The resulting residue was then purified by silica gel chromatography (Hexanes:EtOAc=10:1) to afford Compound 4i (650 mg, 80%) as a clear, colorless oil.

$^1$H NMR (400 MHz, CDCl$_3$) δ 8.66 (d, J=4.8 Hz, 2H), 7.44-7.35 (m, 2H), 7.32-7.26 (m, 1H), 7.25-7.20 (m, 2H), 7.04 (t, J=4.8 Hz, 1H), 1.45 (s, 9H); $^{13}$C NMR (150 MHz, CDCl$_3$) δ 161.35, 158.21, 153.16, 141.25, 128.95, 127.69, 126.84, 117.14, 82.04, 28.05; HRMS (ESI-TOF) m/z Calcd for C$_{15}$H$_{18}$N$_3$O$_2$ [M+H]$^+$: 272.1394, found: 272.1394.

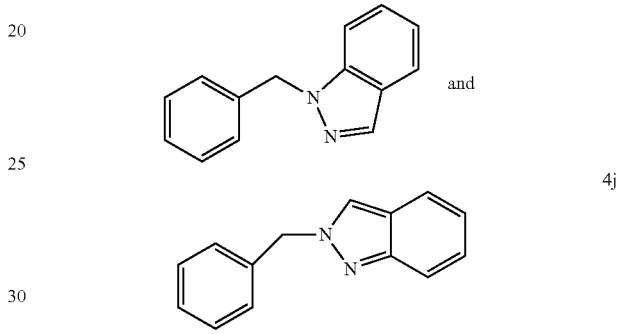

1-Benzyl-1H-indazole and 2-Benzyl-2H-indazole

[Shumeiko et al., Russ. J. Org. Chem. 42:294-295 (2006).] A round-bottom flask was charged with indazole (1.18 g, 10.0 mmol), benzyl bromide (1.44 mL, 10.0 mmol), potassium hydroxide (0.56 g, 10.0 mmol), tetrabutylammonium chloride (189 mg, 0.5 mmol) and toluene (50 mL). The mixture was heated to 110° C. overnight (about 18 hours). The reaction mixture was allowed to cool to room temperature and poured into a beaker containing water (20 mL) and ethyl acetate (50 mL). Phases were separated and the aqueous phase was extracted with ethyl acetate (50 mL). Combined organic extracts were dried over anhydrous sodium sulfate and solvents were evaporated. The resulting residue was then purified by silica gel column chromatography (Hexanes:EtOAc=20:1-10:1) to provide the corresponding 1-benzyl-1H-indazole 4k (1.1 g, 5.5 mmol) in 55% yield and 2-benzyl-2H-indazole 4k' (561 mg, 2.7 mmol) in 27% yield.

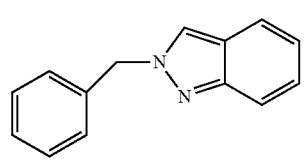

2-Benzyl-2H-indazole (4j)

$^1$H NMR (400 MHz, CDCl$_3$) δ 7.89-7.85 (m, 1H), 7.73 (d, J=8.8 Hz, 1H), 7.61 (d, J=8.4 Hz, 1H), 7.38-7.30 (m, 3H), 7.30-7.23 (m, 3H), 7.06 (dd, J=8.3, 6.7 Hz, 1H), 5.58 (s,

2H); $^{13}$C NMR (100 MHz, CDCl$_3$) δ 148.90, 135.73, 128.87, 128.32, 127.92, 125.91, 122.78, 122.06, 121.71, 120.09, 117.50, 57.47; HRMS (ESI-TOF) m/z Calcd for C$_{14}$H$_{13}$N$_2$ [M+H]$^+$: 209.1073, found: 209.1074.

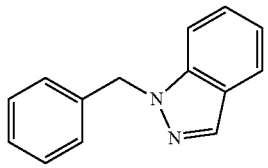

1-Benzyl-1H-indazole (4k)

$^1$H NMR (600 MHz, CDCl$_3$) δ 8.04 (d, J=0.9 Hz, 1H), 7.74 (dt, J=8.1, 1.0 Hz, 1H), 7.36-7.31 (m, 2H), 7.30-7.26 (m, 2H), 7.26-7.23 (m, 1H), 7.21-7.19 (m, 1H), 7.19-7.17 (m, 1H), 7.15-7.12 (m, 1H), 5.60 (s, 2H); $^{13}$C NMR (150 MHz, CDCl$_3$) δ 139.52, 136.86, 133.36, 128.69, 127.70, 127.14, 126.35, 124.34, 121.12, 120.61, 109.26, 52.95; HRMS (ESI-TOF) m/z Calcd for C$_{14}$H$_{13}$N$_2$ [M+H]$^+$: 209.1073, found: 209.1074.

1-Benzylisoquinoline (4l)

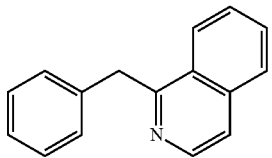

Anhydrous cobalt(II) acetylacetonate (77 mg, 0.30 mmol) was placed in a 50 mL flask. Anhydrous 1,4-dioxane (10 mL) was then added under argon. After the solution became red, benzylmagnesium chloride (2 M in THF solution, 4.5 mL, 9.0 mmol) was added at 0° C. The mixture was stirred for about 5 minutes at 25° C. Next, 2-chloroquinoline (491 mg, 3.0 mmol) was added dropwise to the reaction mixture. After being stirred for 2 hours at 25° C., the reaction mixture was poured into water. The products were extracted with ethyl acetate (3×30 mL). The combined organic layers were dried over sodium sulfate and concentrated. Purification of the crude product by silica gel column chromatography (Hexanes:EtOAc=4:1) provided the corresponding product Compound 4l (328 mg, 1.5 mmol) in 50% yield. $^1$H NMR (400 MHz, CDCl$_3$) δ 8.09 (d, J=8.5 Hz, 1H), 7.99 (d, J=8.5 Hz, 1H), 7.73 (d, J=8.2 Hz, 1H), 7.68 (t, J=7.6 Hz, 1H), 7.47 (t, J=7.5 Hz, 1H), 7.33-7.25 (m, 4H), 7.25-7.16 (m, 2H), 4.34 (s, 2H); $^{13}$C NMR (100 MHz, CDCl$_3$) δ 161.14, 147.74, 139.15, 136.42, 129.41, 129.15, 128.92, 128.56, 127.44, 126.70, 126.42, 125.91, 121.46, 45.50; HRMS (ESI-TOF) m/z Calcd for C$_{16}$H$_{14}$N [M+H]$^+$: 220.1121, found: 220.1121.

Synthesis of Substrates Bearing Different Protecting Groups

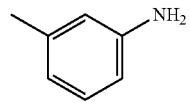 

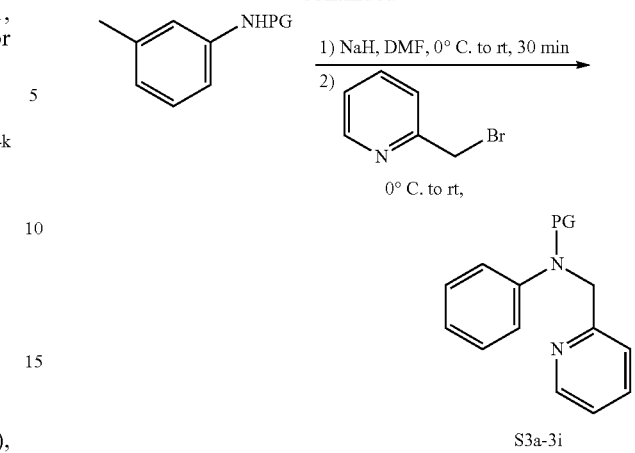

S3a-3i were synthesized following a similar procedure to make substrate 1. The protected amines were prepared as previously described. [Pialat et al., *Org. Lett.* 15:1764-1767 (2013); Brasche et al., *Org. Lett.* 10:2207-2210 (2008); Wipf et al., *Org. Lett.* 10:4383-4386 (2008); Imanishi et al., *Adv. Synth. Catal.* 354:771-776 (2012); Gawande et al., *Green Chem.* 13:3355-3359 (2011); Johnson et al., *J. Org. Chem.* 68:5300-5309 (2003); and Le Pera et al., *Tetrahedron* 62:100-6106 (2006).]

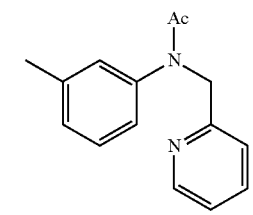

N-(Pyridin-2-ylmethyl)-N-(m-tolyl)acetamide (S3a)

Colorless liquid, $^1$H NMR (400 MHz, CDCl$_3$) δ 8.49 (d, J=4.9 Hz, 1H), 7.64 (td, J=7.7, 1.8 Hz, 1H), 7.38 (d, J=7.8 Hz, 1H), 7.20 (t, J=7.7 Hz, 1H), 7.14 (dd, J=7.5, 5.0 Hz, 1H), 7.09 (d, J=7.6 Hz, 1H), 6.97 (s, 1H), 6.92 (d, J=7.9 Hz, 1H), 5.02 (s, 2H), 2.31 (s, 3H), 1.95 (s, 3H); $^{13}$C NMR (150 MHz, CDCl$_3$) δ 170.69, 157.40, 149.02, 143.16, 139.55, 136.44, 129.22, 128.59, 128.31, 124.85, 122.40, 122.03, 54.87, 22.57, 21.20; HRMS (ESI-TOF) m/z Calcd for C$_{15}$H$_{17}$N$_2$O [M+H]$^+$: 241.1335, found: 241.1335.

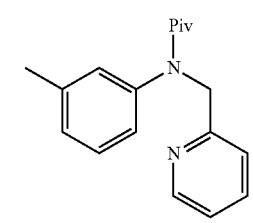

N-(Pyridin-2-ylmethyl)-N-(m-tolyl)pivalamide (S3b)

Colorless liquid, $^1$H NMR (400 MHz, CDCl$_3$) δ 8.46 (d, J=4.8 Hz, 1H), 7.65 (td, J=7.7, 1.8 Hz, 1H), 7.39 (d, J=7.8 Hz, 1H), 7.21-7.05 (m, 3H), 6.99 (s, 1H), 6.95 (d, J=7.8 Hz, 1H), 4.95 (s, 2H), 2.30 (s, 3H), 1.07 (s, 9H); $^{13}$C NMR (100 MHz, CDCl$_3$) δ 177.81, 157.95, 148.84, 143.71, 138.86, 136.35, 130.05, 128.62, 128.59, 126.50, 122.23, 121.82, 58.48, 40.96, 29.46, 21.17; HRMS (ESI-TOF) m/z Calcd for C$_{18}$H$_{23}$N$_2$O [M+H]$^+$: 283.1805, found: 283.1805.

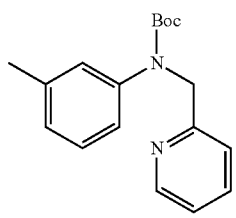

tert-Butyl (pyridin-2-ylmethyl)(m-tolyl)carbamate (S3c)

Colorless liquid, $^1$H NMR (400 MHz, CDCl$_3$) δ 8.53 (d, J=4.6 Hz, 1H), 7.66 (td, J=7.7, 1.8 Hz, 1H), 7.36 (d, J=7.9 Hz, 1H), 7.20-7.09 (m, 3H), 7.06 (d, J=8.0 Hz, 1H), 6.96 (d, J=7.4 Hz, 1H), 4.96 (s, 2H), 2.30 (s, 3H), 1.40 (s, 9H); $^{13}$C NMR (100 MHz, cdcl$_3$) δ 158.73, 154.67, 149.09, 142.87, 138.39, 136.46, 128.35, 126.41, 126.36, 122.80, 121.79, 120.73, 80.59, 55.92, 28.17, 21.33; HRMS (ESI-TOF) m/z Calcd for C$_{18}$H$_{23}$N$_2$O$_2$ [M+H]$^+$: 299.1754, found: 299.1754.

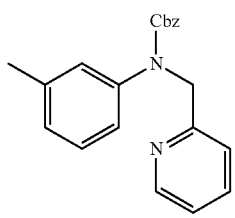

Benzyl (pyridin-2-ylmethyl)(m-tolyl)carbamate (S3d)

Colorless liquid, $^1$H NMR (400 MHz, CDCl$_3$) δ 8.52 (d, J=4.7 Hz, 1H), 7.60 (t, J=7.6 Hz, 1H), 7.33-7.25 (m, 4H), 7.25-7.11 (m, 4H), 7.09 (s, 1H), 7.05 (d, J=7.6 Hz, 1H), 6.99 (d, J=7.6 Hz, 1H), 5.18 (s, 2H), 5.00 (s, 2H), 2.29 (s, 3H); $^{13}$C NMR (150 MHz, CDCl$_3$) δ 157.83, 155.60, 149.20, 142.14, 138.65, 136.52, 136.40, 128.57, 128.29, 127.80, 127.63, 127.18, 126.94, 123.26, 122.00, 121.25, 67.37, 56.10, 21.29; HRMS (ESI-TOF) m/z Calcd for C$_{21}$H$_{21}$N$_2$O$_2$ [M+H]$^+$: 333.1598, found: 333.1598.

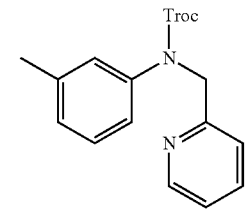

2,2,2-Trichloroethyl (pyridin-2-ylmethyl)(m-tolyl)-carbamate (S3e)

Colorless solid, $^1$H NMR (400 MHz, CDCl$_3$) δ 8.54 (d, J=4.8 Hz, 1H), 7.66 (t, J=7.7 Hz, 1H), 7.38 (d, J=7.8 Hz, 1H), 7.25-7.06 (m, 4H), 7.03 (d, J=7.5 Hz, 1H), 5.05 (s, 2H), 4.79 (s, 2H), 2.31 (s, 3H); $^{13}$C NMR (150 MHz, CDCl$_3$) δ 157.16, 154.02, 149.35, 142.16, 141.00, 138.78, 136.61, 128.65, 127.70, 126.36, 123.82, 122.24, 121.66, 95.39, 77.25, 77.04, 76.83, 75.20, 56.43, 21.30; HRMS (ESI-TOF) m/z Calcd for C$_{16}$H$_{16}$Cl$_3$N$_2$O$_2$ [M+H]$^+$: 373.0272, found: 373.0271.

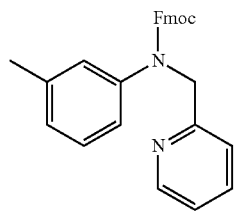

(9H-Fluoren-9-yl)methyl (pyridin-2-ylmethyl)(m-tolyl)-carbamate (S3f)

Light yellow solid, $^1$H NMR (400 MHz, CDCl$_3$) δ 8.52 (d, J=4.8 Hz, 1H), 7.69 (d, J=7.6 Hz, 2H), 7.62 (t, J=7.6 Hz, 1H), 7.34 (t, J=7.5 Hz, 2H), 7.30-7.21 (m, 3H), 7.21-7.12 (m, 4H), 7.11-7.02 (d, J=6.3 Hz, 2H), 6.99 (d, J=6.9 Hz, 1H), 4.97 (s, 2H), 4.45 (d, J=7.0 Hz, 2H), 4.10 (t, J=7.0 Hz, 1H), 2.32 (s, 3H); $^{13}$C NMR (150 MHz, CDCl$_3$) δ 157.65, 155.75, 149.23, 143.71, 141.89, 141.19, 138.84, 136.57, 128.73, 127.51, 126.86, 125.09, 124.26, 122.07, 121.54, 119.78, 67.60, 56.08, 47.11, 21.32; HRMS (ESI-TOF) m/z Calcd for C$_{28}$H$_{25}$N$_2$O$_2$ [M+H]$^+$: 421.1911, found: 421.1911.

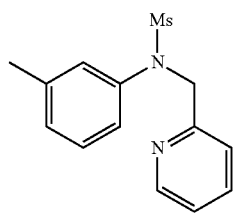

N-(Pyridin-2-ylmethyl)-N-(m-tolyl)methanesulfonamide (S3g)

Light yellow solid, $^1$H NMR (400 MHz, CDCl$_3$) δ 8.49 (d, J=4.7 Hz, 1H), 7.64 (td, J=7.7, 1.8 Hz, 1H), 7.45 (d, J=7.9

Hz, 1H), 7.24-7.11 (m, 4H), 7.06 (d, J=7.3 Hz, 1H), 5.01 (s, 2H), 3.04 (s, 3H), 2.30 (s, 3H); $^{13}$C NMR (150 MHz, CDCl$_3$) δ 156.70, 149.06, 139.37, 136.70, 129.07, 128.82, 128.75, 124.96, 122.46, 122.35, 56.53, 38.13, 21.28; HRMS (ESI-TOF) m/z Calcd for C$_{14}$H$_{17}$N$_2$O$_2$S [M+H]$^+$: 277.1005, found: 277.1005.

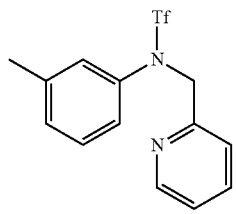

1,1,1-Trifluoro-N-(pyridin-2-ylmethyl)-N-(m-tolyl)-methanesulfonamide (S3h)

Yellow solid, $^1$H NMR (400 MHz, CDCl$_3$) δ 8.48 (d, J=4.8 Hz, 1H), 7.68 (td, J=7.7, 1.8 Hz, 1H), 7.45 (d, J=7.8 Hz, 1H), 7.24-7.15 (m, 2H), 7.14-7.04 (m, 3H), 5.07 (s, 2H), 2.30 (s, 3H); $^{13}$C NMR (150 MHz, CDCl$_3$) δ 154.65, 149.38, 139.53, 136.84, 129.97, 129.42, 129.10, 125.91, 122.99, 122.61, 120.46 (q, J=324.2 Hz), 58.52, 21.22; $^{19}$F NMR (376 MHz, CDCl$_3$) δ −73.54; HRMS (ESI-TOF) m/z Calcd for C$_{14}$H$_{14}$F$_3$N$_2$O$_2$S [M+H]$^+$: 331.0723, found: 331.0723.

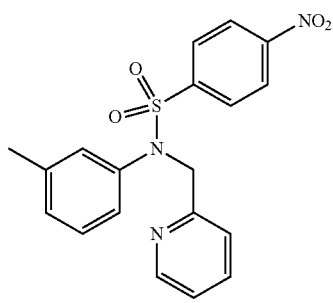

4-Nitro-N-(pyridin-2-ylmethyl)-N-(m-tolyl)benzene-sulfonamide (S3i)

Light yellow solid, $^1$H NMR (400 MHz, CDCl$_3$) δ 8.41 (d, J=4.7 Hz, 1H), 8.30 (d, J=8.7 Hz, 2H), 7.81 (d, J=8.7 Hz, 2H), 7.66 (td, J=7.7, 1.7 Hz, 1H), 7.52 (d, J=7.9 Hz, 1H), 7.17-7.09 (m, 2H), 7.06 (d, J=7.6 Hz, 1H), 6.96 (s, 1H), 6.83 (d, J=7.7 Hz, 1H), 4.93 (s, 2H), 2.26 (s, 3H); $^{13}$C NMR (150 MHz, CDCl$_3$) δ 155.77, 150.05, 149.06, 144.00, 139.35, 138.44, 136.76, 129.34, 129.22, 128.96, 125.09, 123.93, 122.62, 122.44, 56.87, 21.22; HRMS (ESI-TOF) m/z Calcd for C$_{19}$H$_{18}$N$_3$O$_4$S [M+H]$^+$: 384.1013, found: 384.1013.

Synthesis of Substrates Bearing Different Directing Groups

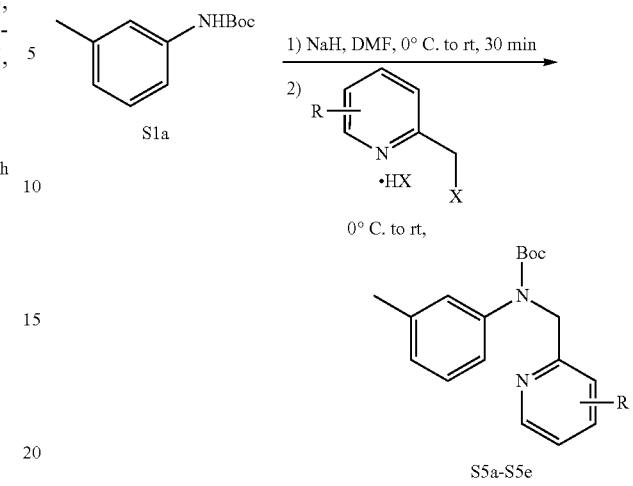

S5a-5e were synthesized following a similar procedure to prepare substrate 1.

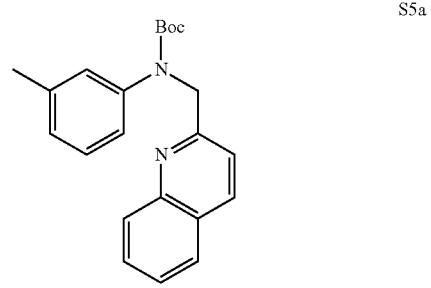 [SMILES: Cc1cccc(N(Cc2ccc3ccccc3n2)C(=O)OC(C)(C)C)c1]

tert-Butyl (quinolin-2-ylmethyl)(m-tolyl)carbamate (S5a)

Light yellow solid, $^1$H NMR (400 MHz, CDCl$_3$) δ 8.15 (d, J=8.5 Hz, 1H), 8.02 (d, J=8.5 Hz, 1H), 7.80 (d, J=8.1 Hz, 1H), 7.72-7.66 (m, 1H), 7.55-7.47 (m, 2H), 7.21-7.12 (m, 2H), 7.09 (d, J=8.1 Hz, 1H), 6.95 (d, J=7.3 Hz, 1H), 5.13 (s, 2H), 2.29 (s, 3H), 1.40 (s, 9H); $^{13}$C NMR (150 MHz, CDCl$_3$) δ 159.14, 154.91, 147.63, 142.84, 138.47, 136.63, 129.51, 128.97, 128.42, 127.53, 127.16, 126.62, 126.57, 126.09, 123.04, 118.88, 80.73, 56.48, 28.22, 21.37; HRMS (ESI-TOF) m/z Calcd for C$_{22}$H$_{25}$N$_2$O$_2$ [M+H]$^+$: 349.1911, found: 349.1911.

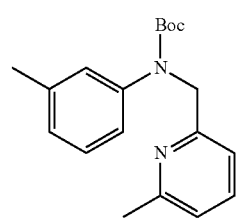

tert-Butyl (quinolin-2-ylmethyl)(m-tolyl)carbamate (S5b)

Light yellow solid, $^1$H NMR (400 MHz, CDCl$_3$) δ 7.55 (t, J=7.7 Hz, 1H), 7.19-7.10 (m, 3H), 7.07 (d, J=8.1 Hz, 1H), 7.00 (d, J=7.6 Hz, 1H), 6.95 (d, J=7.4 Hz, 1H), 4.92 (s, 2H), 2.51 (s, 3H), 2.30 (s, 3H), 1.40 (s, 9H); $^{13}$C NMR (150 MHz, CDCl$_3$) δ 158.07, 157.70, 154.71, 142.95, 138.32, 136.68, 128.31, 126.36, 126.32, 122.76, 121.23, 117.34, 80.53, 55.96, 28.18, 24.34, 21.34; HRMS (ESI-TOF) m/z Calcd for C$_{19}$H$_{25}$N$_2$O$_2$ [M+H]$^+$: 313.1911, found: 313.1911.

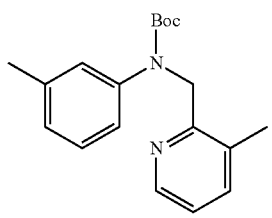

tert-Butyl ((3-methylpyridin-2-yl)methyl)(m-tolyl)-carbamate (S5c)

Light yellow solid, $^1$H NMR (400 MHz, CDCl$_3$) δ 8.37 (d, J=4.6 Hz, 1H), 7.38 (d, J=7.6 Hz, 1H), 7.16-7.00 (m, 4H), 6.92 (d, J=7.4 Hz, 1H), 4.93 (s, 2H), 2.30 (s, 3H), 2.27 (s, 3H), 1.37 (s, 9H); $^{13}$C NMR (150 MHz, CDCl$_3$) δ 155.32, 154.74, 146.51, 142.81, 138.05, 137.46, 130.61, 128.06, 126.85, 126.26, 123.39, 121.90, 80.10, 53.44, 28.16, 21.29, 18.00; HRMS (ESI-TOF) m/z Calcd for C$_{19}$H$_{25}$N$_2$O$_2$ [M+H]$^+$: 313.1911, found: 313.1911.

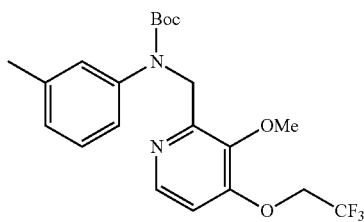

tert-Butyl ((3-methoxy-4-(2,2,2-trifluoroethoxy)pyridin-2-yl)methyl)(m-tolyl)carbamate (S5d)

Colorless solid, $^1$H NMR (400 MHz, CDCl$_3$) δ 8.31 (d, J=5.6 Hz, 1H), 7.16-6.98 (m, 3H), 6.92 (d, J=7.4 Hz, 1H), 6.59 (d, J=5.6 Hz, 1H), 4.93 (s, 2H), 4.37 (q, J=7.9 Hz, 2H), 2.27 (s, 3H), 2.20 (s, 3H), 1.38 (s, 9H); $^{13}$C NMR (150 MHz, CDCl$_3$) δ 161.13, 157.09, 154.73, 147.71, 142.75, 138.09, 128.08, 126.81, 126.30, 123.38, 122.98 (q, J=278.34 Hz), 119.92, 105.10, 80.21, 65.31 (q, J=36.2 Hz), 53.37, 28.18, 21.30, 9.64; $^{19}$F NMR (376 MHz, CDCl$_3$) δ −74.21; HRMS (ESI-TOF) m/z Calcd for C$_{21}$H$_{26}$F$_3$N$_2$O$_4$[M+H]$^+$: 411.1890, found: 411.1890.

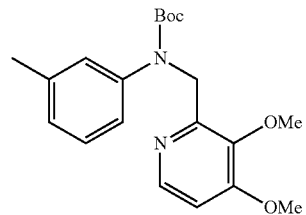

tert-Butyl ((3,4-dimethoxypyridin-2-yl)methyl)(m-tolyl)-carbamate (S5e)

Colorless solid, $^1$H NMR (400 MHz, CDCl$_3$) δ 8.21 (d, J=5.5 Hz, 1H), 7.19-7.03 (m, 3H), 6.91 (d, J=7.0 Hz, 1H), 6.74 (d, J=5.5 Hz, 1H), 4.97 (s, 2H), 3.88 (s, 3H), 3.78 (s, 3H), 2.28 (s, 3H), 1.39 (s, 9H); $^{13}$C NMR (150 MHz, CDCl$_3$) δ 157.99, 154.90, 151.47, 145.59, 143.22, 142.90, 138.01, 128.04, 126.85, 126.11, 123.41, 106.49, 79.97, 60.41, 55.54, 50.72, 28.24, 21.33; HRMS (ESI-TOF) m/z Calcd for C$_{20}$H$_{27}$N$_2$O$_4$ [M+H]$^+$: 359.1965, found: 359.1964.

Synthesis of MPAHP Ligands

Ligands L12-19 were synthesized from commercially available amines S9. In cases where the amines were not commercially available, the free amines S9 were synthesized by the reduction of the nitro group.

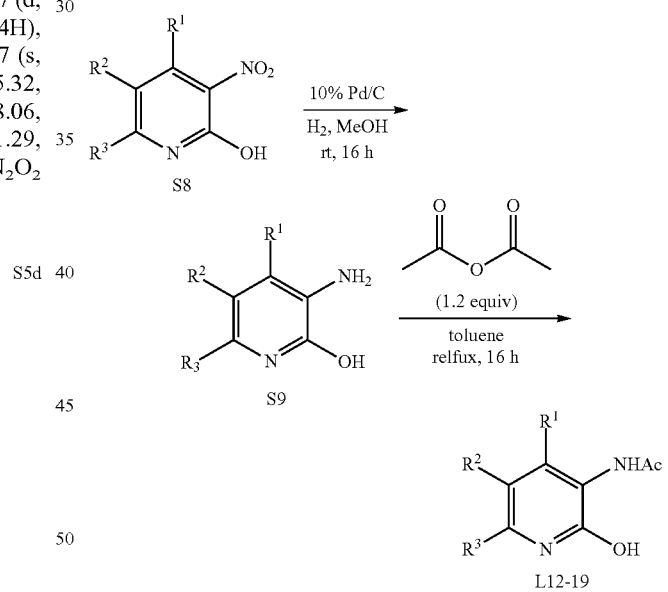

Reduction:

In a 100 mL round bottom flask, S8 (10.0 mmol), 10% Pd/C (1.0 mmol) were added and the flask was sealed with a rubber stopper. Next, 50 mL methanol was added under nitrogen. The nitrogen was removed and the flask was back filled with hydrogen three times. Then a hydrogen balloon was left on the flask and the reaction mixture was stirred for 16 hours at room temperature. After the 16 hours, the reaction mixture was filtered through a pad of Celite® and the solvent was evaporated to obtain the pure amino product in quantitative yields.

Acetyl Protection:

In a 50 mL round bottom flask, S9 (8.0 mmol), acetic anhydride (9.6 mmol) and 20 mL toluene were added and the reaction mixture was refluxed for 16 hours. The solvent was removed and the residue was washed with diethyl ether (5.0 mL) twice to remove impurities. The left over residue was recrystallized with methanol to obtain the product.

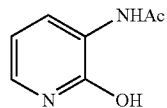

N-(2-Hydroxypyridin-3-yl)acetamide (L12)

Black solid, $^1$H NMR (400 MHz, DMSO-d$_6$) δ 11.89 (s, 1H), 9.18 (s, 1H), 8.20 (dd, J=7.4, 1.8 Hz, 1H), 7.06 (dd, J=6.6, 1.9 Hz, 1H), 6.18 (t, J=6.9 Hz, 1H), 2.11 (s, 3H); $^{13}$C NMR (150 MHz, DMSO-d$_6$) δ 169.30, 157.25, 129.45, 127.53, 123.25, 105.20, 24.00; HRMS (ESI-TOF) m/z Calcd for C$_7$H$_9$N$_2$O$_2$ [M+H]$^+$: 153.0659, found: 153.0659.

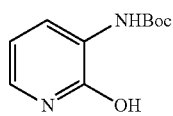

tert-Butyl (2-hydroxypyridin-3-yl)carbamate (L13)

Beige solid, $^1$H NMR (400 MHz, DMSO-d$_6$) δ 11.91 (s, 1H), 7.79 (dd, J=7.1, 2.0 Hz, 1H), 7.68 (s, 1H), 7.03 (dd, J=6.6, 1.8 Hz, 1H), 6.21 (t, J=6.9 Hz, 1H), 1.45 (s, 9H); $^{13}$C NMR (150 MHz, DMSO-d$_6$) δ 157.01, 152.11, 129.01, 126.59, 120.66, 105.35, 80.01, 27.88; HRMS (ESI-TOF) m/z Calcd for C$_{10}$H$_{15}$N$_2$O$_3$ [M+H]$^+$: 211.1077, found: 211.1077.

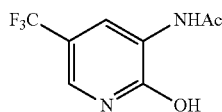

N-(2-Hydroxy-5-(trifluoromethyl)pyridin-3-yl)acetamide (L14)

Beige solid, $^1$H NMR (400 MHz, DMSO-d$_6$) δ 12.51 (s, 1H), 9.55 (s, 1H), 8.41 (d, J=2.6 Hz, 1H), 7.69-7.61 (m, 1H), 2.15 (s, 3H); $^{13}$C NMR (150 MHz, DMSO-d$_6$) δ 170.23, 157.16, 130.11, 127.64 (q, J=4.7 Hz), 123.86 (q, J=269.5 Hz), 116.81, 107.23 (q, J=34.1 Hz), 24.00; $^{19}$F NMR (376 MHz, DMSO-d$_6$) δ −60.60; HRMS (ESI-TOF) m/z Calcd for C$_8$H$_8$F$_3$N$_2$O$_2$ [M+H]$^+$: 221.0532, found: 221.0532.

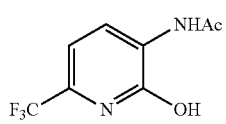

N-(2-Hydroxy-6-(trifluoromethyl)pyridin-3-yl)acetamide (L15)

Beige solid, $^1$H NMR (400 MHz, DMSO-d$_6$) δ 9.54 (s, 1H), 8.46 (d, J=7.9 Hz, 1H), 7.13 (d, J=7.9 Hz, 1H), 2.15 (s, 3H); $^{13}$C NMR (150 MHz, DMSO-d$_6$) δ 169.98, 155.31, 132.92, 127.74, 124.99, 121.16 (q, J=272.7 Hz), 110.60, 23.99; $^{19}$F NMR (376 MHz, DMSO-d$_6$) 5-65.22; HRMS (ESI-TOF) m/z Calcd for C$_8$H$_8$F$_3$N$_2$O$_2$ [M+H]$^+$: 221.0532, found: 221.0532.

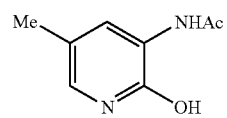

N-(2-Hydroxy-5-methylpyridin-3-yl)acetamide (L16)

Colorless solid, $^1$H NMR (400 MHz, DMSO-d$_6$) δ 11.68 (s, 1H), 9.15 (s, 1H), 8.11 (d, J=2.4 Hz, 1H), 6.85 (dd, J=2.3, 1.2 Hz, 1H), 2.10 (s, 3H), 2.01 (d, J=1.1 Hz, 3H); $^{13}$C NMR (150 MHz, DMSO-d$_6$) δ 169.27, 156.32, 128.89, 125.50, 124.50, 113.60, 24.03, 17.10; HRMS (ESI-TOF) m/z Calcd for C$_8$H$_{11}$N$_2$O$_2$ [M+H]$^+$: 167.0815, found: 167.0815.

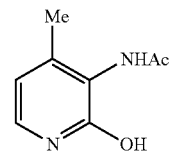

N-(2-Hydroxy-4-methylpyridin-3-yl)acetamide (L17)

Colorless solid, $^1$H NMR (400 MHz, DMSO-d$_6$) δ 11.60 (s, 1H), 9.08 (s, 1H), 7.16 (d, J=6.7 Hz, 1H), 6.06 (d, J=6.7 Hz, 1H), 1.99 (s, 3H), 1.97 (s, 3H); $^{13}$C NMR (150 MHz, DMSO-d$_6$) δ 167.97, 159.90, 145.60, 130.99, 125.64, 107.86, 22.75, 18.49; HRMS (ESI-TOF) m/z Calcd for C$_8$H$_{11}$N$_2$O$_2$ [M+H]$^+$: 167.0815, found: 167.0815.

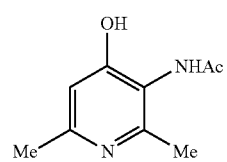

N-(4-Hydroxy-2,6-dimethylpyridin-3-yl)acetamide (L18)

Colorless solid, $^1$H NMR (400 MHz, DMSO-d$_6$) δ 11.12 (s, 1H), 8.84 (s, 1H), 5.91 (s, 1H), 2.17 (s, 3H), 2.04 (s, 3H), 1.96 (s, 3H); $^{13}$C NMR (150 MHz, DMSO-d$_6$) δ 174.23, 168.04, 145.41, 142.63, 122.97, 113.63, 22.77, 18.35, 16.19; HRMS (ESI-TOF) m/z Calcd for C$_9$H$_{13}$N$_2$O$_2$ [M+H]$^+$: 181.0972, found: 181.0972.

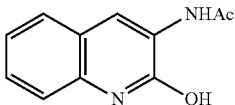

L19

N-(2-Hydroxyquinolin-3-yl)acetamide (L19)

Beige solid, $^1$H NMR (400 MHz, DMSO-$d_6$) δ 12.22 (s, 1H), 9.43 (s, 1H), 8.63 (s, 1H), 7.62 (d, J=7.8 Hz, 1H), 7.43-7.35 (m, 1H), 7.28 (d, J=8.1 Hz, 1H), 7.17 (t, J=7.5 Hz, 1H), 2.18 (s, 3H); $^{13}$C NMR (150 MHz, DMSO-$d_6$) δ 169.70, 157.43, 134.32, 128.76, 128.10, 127.25, 122.41, 120.49, 119.72, 114.87, 24.11; HRMS (ESI-TOF) m/z Calcd for $C_{11}H_{11}N_2O_2$ [M+H]$^+$: 203.0815, found: 203.0815.

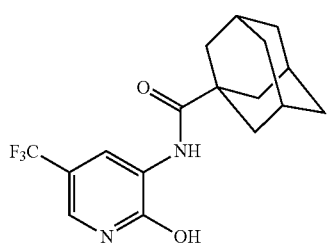

L24

To a solution of amine (2.0 mmol) and 1-adamantanecarbonyl chloride (437.1 mg, 2.2 mmol) in DCM (10.0 mL) was added triethylamine (0.56 mL, 4.0 mmol) at 0° C.

The mixture was allowed to warm to room temperature and stirred at room temperature. After the reaction was completed, the solvent was removed under vacuum and the resulting residue was then purified by silica gel chromatography to afford L24 as a colorless solid.

(3r,5r,7r)-N-(2-Hydroxy-5-(trifluoromethyl)pyridin-3-yl)adamantane-1-carboxamide (L24)

Colorless solid, $^1$H NMR (400 MHz, CDCl$_3$) δ 12.80 (brs, 1H), 8.76 (d, J=2.4 Hz, 1H), 8.56 (s, 1H), 7.50 (s, 1H), 2.13 (s, 3H), 2.07-1.90 (m, 6H), 1.84-1.69 (m, 6H); $^{13}$C NMR (150 MHz, CDCl$_3$) δ 177.36, 159.30, 129.79, 125.78, 125.32, 125.28, 125.24, 125.20, 123.99, 122.20, 120.41, 119.15, 112.65, 112.41, 112.18, 111.95, 42.05, 39.10, 38.74, 36.43, 36.32, 28.00, 27.86; HRMS (ESI-TOF) m/z Calcd for $C_{17}H_{20}F_3N_2O_2$ [M+H]$^+$: 341.1471, found: 341.1474.

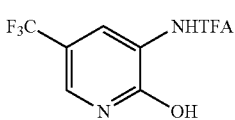

L25

2,2,2-Trifluoro-N-(2-hydroxy-5-(trifluoromethyl)pyridin-3-yl)acetamide (L25)

Colorless solid, $^1$H NMR (400 MHz, DMSO-$d_6$) δ 11.66 (brs, 2H), 8.12 (d, J=2.6 Hz, 1H), 7.98-7.88 (m, 1H); $^{13}$C NMR (150 MHz, DMSO-$d_6$) δ 157.45, 155.22 (q, J=37.5 Hz), 132.36 (q, J=5.3 Hz), 126.82, 124.67 (q, J=3.0 Hz), 123.52 (q, J=269.6 Hz), 115.37 (q, J=286.2 Hz), 106.75 (q, J=34.5 Hz); HRMS (ESI-TOF) m/z Calcd for $C_8H_5F_6N_2O_2$ [M+H]$^+$: 275.0250, found: 275.0250.

Condition Screening

Ligand Screened

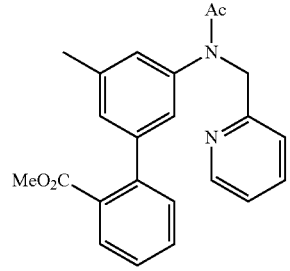

S4a

Methyl 3'-methyl-5'-(N-(pyridin-2-ylmethyl)acetamido)-[1,1'-biphenyl]-2-carboxylate (S4a)

Colorless liquid, $^1$H NMR (400 MHz, CDCl$_3$) δ 8.50 (d, J=4.8 Hz, 1H), 7.82 (d, J=7.7 Hz, 1H), 7.67 (t, J=7.5 Hz, 1H), 7.51 (t, J=7.5 Hz, 1H), 7.41 (t, J=6.9 Hz, 2H), 7.26 (d, J=6.9 Hz, 1H), 7.20-7.13 (m, 1H), 7.07 (s, 1H), 6.98 (s, 1H), 6.90 (s, 1H), 5.05 (s, 2H), 3.60 (s, 3H), 2.36 (s, 3H), 2.02 (s, 3H); $^{13}$C NMR (150 MHz, CDCl$_3$) δ 170.85, 168.42, 157.30, 148.81, 142.85, 142.64, 141.45, 139.37, 136.77, 131.33, 130.56, 130.50, 129.91, 128.59, 127.47, 127.03, 125.32, 122.39, 122.14, 54.85, 51.94, 22.64, 21.29; HRMS (ESI-TOF) m/z Calcd for $C_{23}H_{23}N_2O_3$ [M+H]$^+$: 375.1703, found: 375.1703.

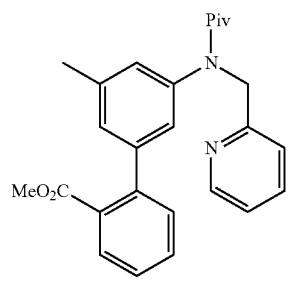

S4b

Methyl 3'-methyl-5'-(N-(pyridin-2-ylmethyl)pivalamido)-[1,1'-biphenyl]-2-carboxylate (S4b)

Colorless liquid, $^1$H NMR (400 MHz, CDCl$_3$) δ 8.48 (d, J=4.4 Hz, 1H), 7.81 (d, J=7.7 Hz, 1H), 7.66 (td, J=7.8, 1.8 Hz, 1H), 7.49 (t, J=7.2 Hz, 1H), 7.43-7.37 (m, 2H), 7.21-7.11 (m, 2H), 7.04-6.98 (m, 2H), 6.92 (s, 1H), 4.98 (s, 2H), 3.56 (s, 3H), 2.34 (s, 3H), 1.12 (s, 9H); $^{13}$C NMR (150 MHz, CDCl$_3$) δ 177.91, 168.61, 157.94, 148.84, 143.60, 142.35, 141.50, 138.56, 136.59, 131.27, 130.63, 130.53, 129.88, 128.84, 128.73, 127.43, 126.57, 122.25, 121.94, 58.58, 51.89, 41.09, 29.60, 21.26; HRMS (ESI-TOF) m/z Calcd for $C_{26}H_{29}N_2O_3$ [M+H]$^+$: 417.2173, found: 417.2172.

Directing Group

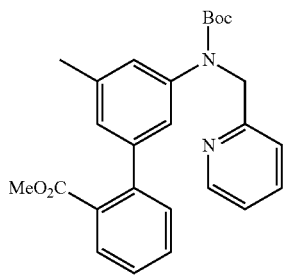

S4c

Methyl 3'-((tert-butoxycarbonyl)(pyridin-2-ylmethyl)-amino)-5'-methyl-[1,1'-biphenyl]-2-carboxylate (S4c)

Colorless liquid, $^1$H NMR (400 MHz, CDCl$_3$) δ 8.54 (d, J=4.8 Hz, 1H), 7.76 (d, J=7.7 Hz, 1H), 7.69 (t, J=7.7 Hz, 1H), 7.49 (t, J=7.5 Hz, 1H), 7.41-7.35 (m, 2H), 7.32 (d, J=7.6 Hz, 1H), 7.22-7.15 (m, 1H), 7.11 (s, 1H), 7.06 (s, 1H), 6.93 (s, 1H), 4.99 (s, 2H), 3.57 (s, 3H), 2.34 (s, 3H), 1.39 (s, 9H); $^{13}$C NMR (150 MHz, CDCl$_3$) δ 169.09, 158.62, 154.60, 148.87, 142.66, 141.80, 141.58, 138.13, 136.77, 131.10, 130.92, 130.55, 129.61, 127.14, 126.53, 125.36, 123.13, 121.90, 120.81, 80.68, 55.92, 51.89, 28.18, 21.38; HRMS (ESI-TOF) m/z Calcd for C$_{26}$H$_{29}$N$_2$O$_4$ [M+H]$^+$: 433.2122, found: 433.2122.

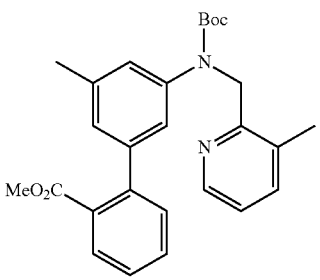

S6c

Methyl 3'-((tert-butoxycarbonyl)((3-methylpyridin-2-yl)-methyl)amino)-5'-methyl-[1,1'-biphenyl]-2-carboxylate (S6c)

Colorless liquid, $^1$H NMR (400 MHz, CDCl$_3$) δ 8.39 (d, J=4.4 Hz, 1H), 7.74 (d, J=7.7 Hz, 1H), 7.47 (t, J=7.1 Hz, 1H), 7.42-7.33 (m, 2H), 7.30 (d, J=7.6 Hz, 1H), 7.12 (s, 1H), 7.10-7.03 (m, 2H), 6.89 (s, 1H), 4.93 (s, 2H), 3.57 (s, 3H), 2.31 (s, 3H), 2.30 (s, 3H), 1.36 (s, 9H); $^{13}$C NMR (150 MHz, CDCl$_3$) δ 169.26, 155.35, 154.68, 146.58, 142.78, 141.97, 141.19, 137.69, 137.45, 131.02, 130.93, 130.56, 129.53, 126.98, 126.33, 125.88, 123.55, 121.90, 80.12, 53.50, 51.81, 28.18, 21.34, 18.03; HRMS (ESI-TOF) m/z Calcd for C$_{27}$H$_{31}$N$_2$O$_4$ [M+H]$^+$: 447.2278, found: 447.2278.

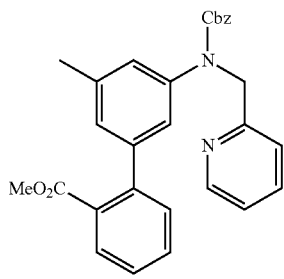

S4d

Methyl 3'-(((benzyloxy)carbonyl)(pyridin-2-ylmethyl)-amino)-5'-methyl-[1,1'-biphenyl]-2-carboxylate (S4d)

Colorless liquid, $^1$H NMR (400 MHz, CDCl$_3$) δ 8.53 (d, J=4.9 Hz, 1H), 7.77 (d, J=7.7 Hz, 1H), 7.62 (t, J=7.8 Hz, 1H), 7.48 (t, J=7.5 Hz, 1H), 7.38 (t, J=7.6 Hz, 1H), 7.35-7.18 (m, 7H), 7.18-7.12 (m, 1H), 7.09 (s, 1H), 7.05 (s, 1H), 6.96 (s, 1H), 5.18 (s, 2H), 5.03 (s, 2H), 3.50 (s, 3H), 2.33 (s, 3H); $^{13}$C NMR (150 MHz, CDCl$_3$) δ 169.02, 157.82, 155.59, 149.25, 141.97, 141.81, 141.65, 138.36, 136.61, 136.35, 131.15, 131.13, 130.87, 130.56, 129.68, 128.32, 127.85, 127.68, 127.23, 127.19, 125.72, 123.60, 122.05, 121.22, 67.47, 56.19, 51.87, 21.36; HRMS (ESI-TOF) m/z Calcd for C$_{29}$H$_{27}$N$_2$O$_4$ [M+H]$^+$: 467.1965, found: 467.1965.

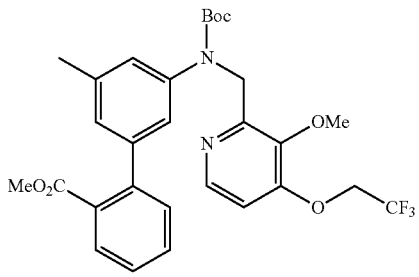

S6d

Methyl 3'-((tert-butoxycarbonyl)((3-methoxy-4-(2,2,2-trifluoroethoxy)pyridin-2-yl)methyl)amino)-5'-methyl-[1,1'-biphenyl]-2-carboxylate (S6d)

Colorless liquid, $^1$H NMR (400 MHz, CDCl$_3$) δ 8.34 (d, J=5.6 Hz, 1H), 7.75 (d, J=7.5 Hz, 1H), 7.47 (t, J=7.5 Hz, 1H), 7.36 (t, J=7.3 Hz, 1H), 7.30 (d, J=7.5 Hz, 1H), 7.10 (s, 1H), 7.06 (s, 1H), 6.89 (s, 1H), 6.60 (d, J=5.6 Hz, 1H), 4.94 (s, 2H), 4.37 (q, J=7.9 Hz, 2H), 3.59 (s, 3H), 2.32 (s, 3H), 2.20 (s, 3H), 1.37 (s, 9H); $^{13}$C NMR (150 MHz, CDCl$_3$) δ 169.22, 161.11, 157.10, 154.67, 147.78, 142.73, 141.97, 141.18, 137.70, 131.04, 130.91, 130.55, 129.55, 127.00, 126.34, 125.83, 123.49, 122.99 (q, J=277.9 Hz), 119.77, 105.10, 80.19, 65.33 (q, J=36.3 Hz), 53.41, 51.81, 28.19, 21.34, 9.64; $^{19}$F NMR (376 MHz, CDCl$_3$) δ −74.20; HRMS (ESI-TOF) m/z Calcd for C$_{29}$H$_{32}$F$_3$N$_2$O$_6$ [M+H]$^+$: 545.2258, found: 545.2258.

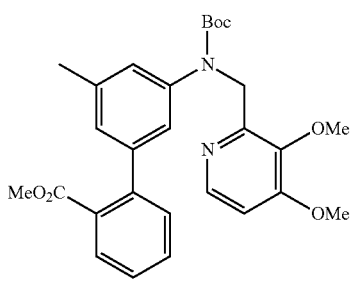

S6e

Methyl 3'-((tert-butoxycarbonyl)((3,4-dimethoxy-pyridin-2-yl)methyl)amino)-5'-methyl-[1,1'-biphenyl]-2-carboxylate (S6e)

Colorless liquid, $^1$H NMR (400 MHz, CDCl$_3$) δ 8.23 (d, J=5.5 Hz, 1H), 7.74 (d, J=7.5 Hz, 1H), 7.47 (t, J=7.5 Hz, 1H), 7.40-7.28 (m, 2H), 7.14 (s, 1H), 7.11 (s, 1H), 6.89 (s, 1H), 6.75 (d, J=5.5 Hz, 1H), 4.98 (s, 2H), 3.89 (s, 3H), 3.80 (s, 3H), 3.58 (s, 3H), 2.32 (s, 3H), 1.37 (s, 9H); $^{13}$C NMR (150 MHz, CDCl$_3$) δ 169.31, 157.99, 154.82, 151.39, 145.57, 143.14, 142.81, 141.99, 141.15, 137.65, 131.01, 131.00, 130.94, 130.58, 129.52, 126.94, 126.21, 125.89, 123.52, 106.51, 80.00, 60.40, 55.55, 51.84, 50.86, 28.22, 21.35; HRMS (ESI-TOF) m/z Calcd for C$_{28}$H$_{33}$N$_2$O$_6$ [M+H]$^+$: 493.2333, found: 493.2332.

Meta-Arylation of Anilines

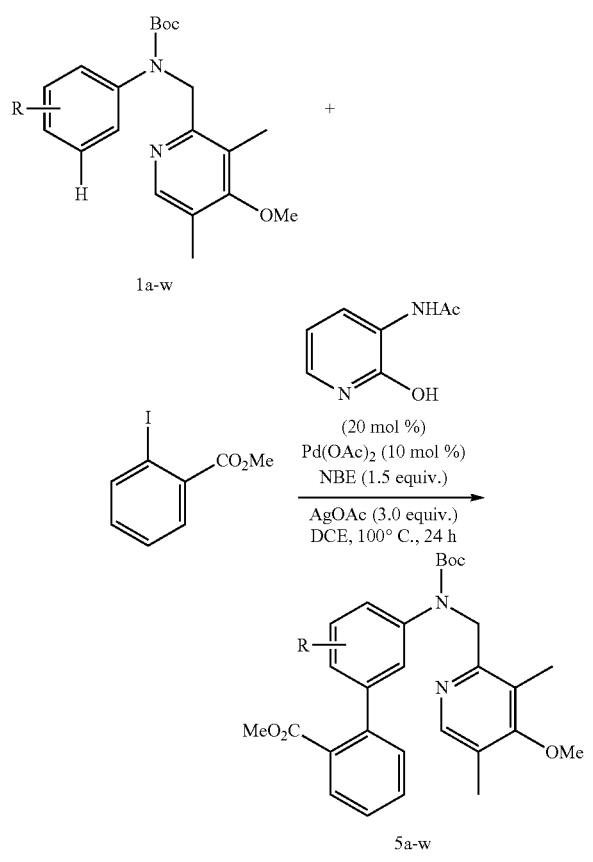

General Procedure for Meta-Arylation of Anilines:

Substrate 1 (0.1 mmol), Ar—I (0.2 mmol), Pd(OAc)$_2$ (2.2 mg, 10 mol %), L12 (3.0 mg, 20 mol %), AgOAc (50.1 mg, 0.3 mmol), 2-Norbornene (14.1 mg, 0.15 mmol) or NBE-CO$_2$Me (21.6 mg, 0.15 mmol) and DCE (0.5 mL) were added to a 2 dram vial. The vial was capped and closed tightly. Then the reaction mixture was then stirred at 100° C. for 24 hours. After cooling to room temperature, the mixture was passed through a pad of Celite® with DCM as the eluent to remove the insoluble precipitate. The resulted solution was concentrated and purified by preparative TLC to afford the desired arylated product. (In cases where mono:di ratios are possible, the selectivity was determined by $^1$H NMR.)

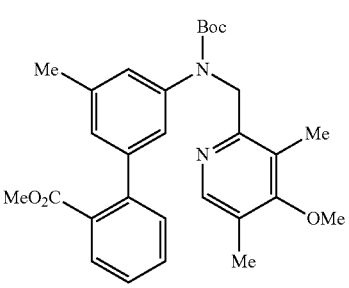

5a

Methyl 3'-((tert-butoxycarbonyl)((4-methoxy-3,5-dimethylpyridin-2-yl)methyl)amino)-5'-methyl-[1,1'-biphenyl]-2-carboxylate (5a)

Substrate 1a was arylated following the general meta-arylation procedure using 2-norbornene. After purification by preparative thin-layer chromatography, Compound 5a was obtained in 98% yield as a light yellow liquid. $^1$H NMR (400 MHz, CDCl$_3$) δ 8.17 (s, 1H), 7.74 (d, J=7.6 Hz, 1H), 7.47 (t, J=7.4 Hz, 1H), 7.36 (t, J=7.5 Hz, 1H), 7.27 (d, J=9.1 Hz, 1H), 7.09 (s, 1H), 7.02 (s, 1H), 6.87 (s, 1H), 4.90 (s, 2H), 3.71 (s, 3H), 3.57 (s, 3H), 2.31 (s, 3H), 2.21 (s, 6H), 1.38 (s, 9H); $^{13}$C NMR (150 MHz, CDCl$_3$) δ 169.24, 163.59, 155.18, 154.67, 148.91, 142.61, 141.97, 141.13, 137.63, 131.00, 130.92, 130.54, 129.52, 126.97, 126.33, 125.93, 124.54, 123.64, 123.57, 80.09, 59.79, 53.54, 51.77, 28.22, 21.33, 13.16, 10.38; HRMS (ESI-TOF) m/z Calcd for C$_{29}$H$_{35}$N$_2$O$_5$ [M+H]$^+$: 491.2540, found: 491.2540.

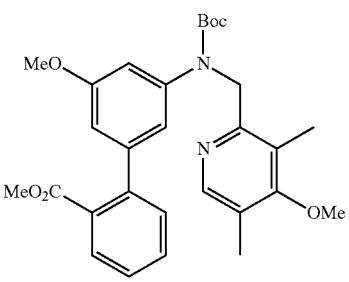

5b

Methyl 3'-((tert-butoxycarbonyl)((4-methoxy-3,5-dimethylpyridin-2-yl)methyl)amino)-5'-methoxy-[1,1'-biphenyl]-2-carboxylate (5b)

Substrate 1b was arylated following the general meta-arylation procedure using 2-norbornene. After purification by preparative thin-layer chromatography, Compound 5b was obtained in 97% yield as a colorless liquid. $^1$H NMR (400 MHz, CDCl$_3$) δ 8.18 (s, 1H), 7.75 (dd, J=7.7, 1.5 Hz, 1H), 7.48 (td, J=7.5, 1.5 Hz, 1H), 7.37 (td, J=7.6, 1.4 Hz, 1H), 7.30 (d, J=7.4 Hz, 1H), 6.86 (s, 1H), 6.83 (s, 1H), 6.62 (t, J=1.9 Hz, 1H), 4.91 (s, 2H), 3.75 (s, 3H), 3.71 (s, 3H), 3.59 (s, 3H), 2.21 (s, 3H), 2.20 (s, 3H), 1.40 (s, 9H); $^{13}$C NMR (126 MHz, CDCl$_3$) δ 169.10, 163.62, 159.09, 155.01, 154.56, 148.91, 143.74, 142.09, 141.80, 131.00, 130.45, 129.49, 127.15, 124.58, 123.60, 119.21, 111.54, 111.26, 80.23, 59.79, 55.31, 53.46, 51.85, 28.23, 13.14, 10.36; HRMS (ESI-TOF) m/z Calcd for C$_{29}$H$_{35}$N$_2$O$_6$ [M+H]$^+$: 507.2490, found: 507.2490.

by preparative thin-layer chromatography, Compound 5d was obtained in 89% yield as a colorless solid. $^1$H NMR (400 MHz, CDCl$_3$) δ 8.11 (s, 1H), 7.75 (d, J=7.7 Hz, 1H), 7.46 (t, J=7.4 Hz, 1H), 7.36 (t, J=7.5 Hz, 1H), 7.30-7.15 (m, 6H), 7.11 (s, 1H), 7.05 (s, 1H), 6.89 (s, 1H), 4.84 (s, 2H), 4.78 (s, 2H), 3.70 (s, 3H), 3.49 (s, 3H), 2.19 (s, 3H), 2.16 (s, 3H), 1.37 (s, 9H), 1.36 (s, 9H); $^{13}$C NMR (150 MHz, CDCl$_3$) δ 168.82, 163.59, 154.82, 154.49, 154.47, 148.94, 142.97, 142.38, 141.48, 141.42, 138.51, 131.07, 130.84, 130.55, 129.65, 128.26, 127.27, 127.20, 126.91, 124.55, 124.08, 123.91, 123.46, 123.16, 80.41, 80.26, 59.80, 53.94, 53.38, 51.75, 28.21, 28.18, 13.15, 10.32; HRMS (ESI-TOF) m/z Calcd for C$_{40}$H$_{48}$N$_3$O$_7$ [M+H]$^+$: 682.3487, found: 682.3486.

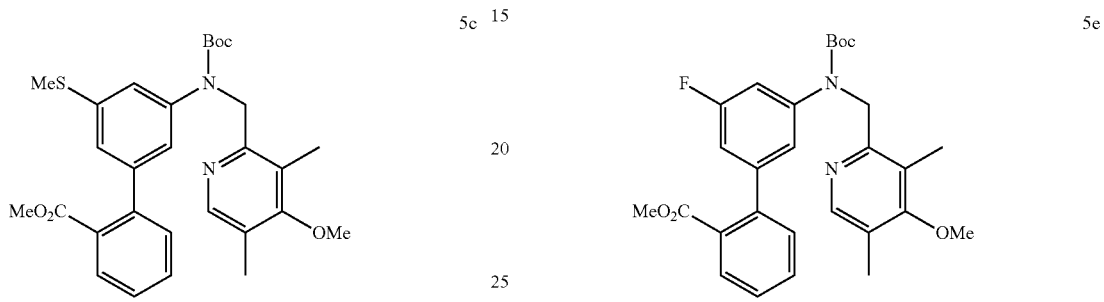

Methyl 3'-((tert-butoxycarbonyl)((4-methoxy-3,5-dimethylpyridin-2-yl)methyl)amino)-5'-(methylthio)-[1,1'-biphenyl]-2-carboxylate (5c)

Substrate 1c was arylated following the general meta-arylation procedure using 2-norbornene. After purification by preparative thin-layer chromatography, Compound 5c was obtained in 73% yield as a colorless liquid. $^1$H NMR (400 MHz, CDCl$_3$) δ 8.18 (s, 1H), 7.77 (d, J=7.7 Hz, 1H), 7.49 (t, J=7.5 Hz, 1H), 7.38 (t, J=7.6 Hz, 1H), 7.30 (d, J=7.6 Hz, 1H), 7.18 (s, 1H), 7.03 (s, 1H), 6.95 (s, 1H), 4.90 (s, 2H), 3.72 (s, 3H), 3.59 (s, 3H), 2.42 (s, 3H), 2.21 (s, 3H), 2.20 (s, 3H), 1.39 (s, 9H); $^{13}$C NMR (150 MHz, CDCl$_3$) δ 168.98, 163.62, 154.91, 154.50, 148.96, 143.14, 141.75, 141.41, 137.98, 131.14, 130.87, 130.50, 129.66, 127.31, 124.65, 123.64, 123.53, 80.36, 59.83, 53.37, 51.88, 28.23, 15.90, 13.17, 10.38; HRMS (ESI-TOF) m/z Calcd for C$_{29}$H$_{35}$N$_2$O$_5$S [M+H]$^+$: 523.2261, found: 523.2261.

Methyl 3'-((tert-butoxycarbonyl)((4-methoxy-3,5-dimethylpyridin-2-yl)methyl)amino)-5'-fluoro-[1,1'-biphenyl]-2-carboxylate (5e)

Substrate 1e was arylated following the general meta-arylation procedure using 2-norbornene. After purification by preparative thin-layer chromatography, Compound 5e was obtained in 94% yield as a colorless solid. mp=97° C., $^1$H NMR (400 MHz, CDCl$_3$) δ 8.18 (s, 1H), 7.80 (dd, J=7.7, 1.4 Hz, 1H), 7.50 (td, J=7.6, 1.5 Hz, 1H), 7.40 (td, J=7.6, 1.3 Hz, 1H), 7.29 (dd, J=7.7, 1.4 Hz, 1H), 7.11-7.00 (m, 2H), 6.83-6.75 (m, 1H), 4.89 (s, 2H), 3.73 (s, 3H), 3.62 (s, 3H), 2.22 (s, 3H), 2.20 (s, 3H), 1.39 (s, 9H); $^{13}$C NMR (150 MHz, CDCl$_3$) δ 168.59, 163.64, 161.86 (d, J=244.6 Hz), 154.63, 154.28, 149.03, 144.18 (d, J=10.2 Hz), 142.71 (d, J=9.7 Hz), 140.98 (d, J=1.8 Hz), 131.28, 130.65, 130.50, 129.83, 127.56, 124.72, 123.39, 122.00, 112.39 (d, J=22.4 Hz), 80.65, 59.84, 53.29, 51.92, 28.17, 13.18, 10.32; $^{19}$F NMR (376 MHz, CDCl$_3$) δ −114.11; HRMS (ESI-TOF) m/z Calcd for C$_{28}$H$_{32}$FN$_2$O$_5$ [M+H]$^+$: 495.2290, found: 495.2289.

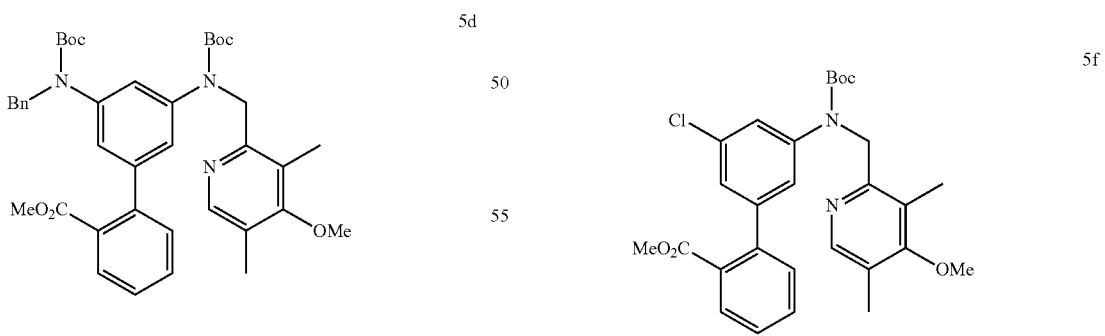

Methyl 3'-(benzyl(tert-butoxycarbonyl)amino)-5'-((tert-butoxycarbonyl)((4-methoxy-3,5-dimethylpyridin-2-yl)methyl)amino)-[1,1'-biphenyl]-2-carboxylate (5d)

Substrate 1d was arylated following the general meta-arylation procedure using 2-norbornene. After purification Methyl 3'-((tert-butoxycarbonyl)((4-methoxy-3,5-dimethylpyridin-2-yl)methyl)amino)-5'-chloro-[1,1'-biphenyl]-2-carboxylate (5f)

Substrate 1f was arylated following the general meta-arylation procedure using 2-norbornene. After purification by preparative thin-layer chromatography, Compound 5f was obtained in 92% yield as a colorless solid. mp=98° C., $^1$H NMR (400 MHz, CDCl$_3$) δ 8.21 (s, 1H), 7.82 (d, J=7.7 Hz, 1H), 7.51 (t, J=7.5 Hz, 1H), 7.41 (t, J=7.5 Hz, 1H), 7.36-7.28 (m, 2H), 7.18 (s, 1H), 7.05 (s, 1H), 5.01 (s, 2H), 3.78 (s, 3H), 3.63 (s, 3H), 2.25 (s, 3H), 2.24 (s, 3H), 1.40 (s, 9H); $^{13}$C NMR (150 MHz, CDCl$_3$) δ 168.38, 165.08, 154.14, 153.64, 147.26, 143.18, 142.84, 140.70, 133.18, 131.43, 130.64, 130.42, 129.95, 127.68, 125.79, 125.55, 125.31, 124.82, 81.08, 60.11, 52.20, 51.92, 28.16, 28.13, 13.43, 10.58; HRMS (ESI-TOF) m/z Calcd for C$_{28}$H$_{32}$ClN$_2$O$_5$ [M+H]$^+$: 511.1994, found: 511.1994.

by preparative thin-layer chromatography, Compound 5h was obtained in 94% yield as a colorless solid. $^1$H NMR (400 MHz, CDCl$_3$) δ 8.16 (s, 1H), 7.95 (s, 1H), 7.84 (d, J=7.6 Hz, 1H), 7.75 (s, 1H), 7.56-7.45 (m, 2H), 7.41 (t, J=7.6 Hz, 1H), 7.30 (d, J=7.6 Hz, 1H), 4.93 (s, 2H), 3.88 (s, 3H), 3.72 (s, 3H), 3.58 (s, 3H), 2.22 (s, 3H), 2.21 (s, 3H), 1.39 (s, 9H); $^{13}$C NMR (150 MHz, CDCl$_3$) δ 168.41, 166.57, 163.67, 154.70, 154.38, 149.00, 142.92, 141.68, 141.21, 131.37, 130.99, 130.71, 130.43, 130.01, 127.54, 126.56, 126.36, 124.71, 123.54, 80.60, 59.81, 53.18, 52.10, 51.83, 28.16, 13.16, 10.38; HRMS (ESI-TOF) m/z Calcd for C$_{30}$H$_{35}$N$_2$O$_7$ [M+H]$^+$: 535.2439, found: 535.2439.

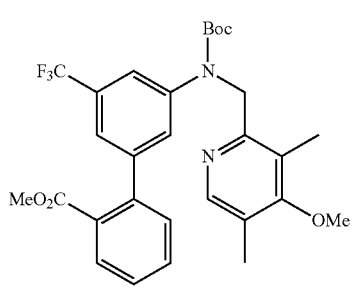

Methyl 3'-((tert-butoxycarbonyl)((4-methoxy-3,5-dimethylpyridin-2-yl)methyl)amino)-5'-(trifluoromethyl)-[1,1'-biphenyl]-2-carboxylate (5g)

Substrate 1g was arylated following the general meta-arylation procedure using NBE-CO$_2$Me. After purification by preparative thin-layer chromatography, Compound 5g was obtained in 94% yield as a colorless liquid. $^1$H NMR (400 MHz, CDCl$_3$) δ 8.17 (s, 1H), 7.85 (d, J=7.6 Hz, 1H), 7.57 (s, 1H), 7.53 (t, J=7.3 Hz, 1H), 7.48 (s, 1H), 7.43 (t, J=7.5 Hz, 1H), 7.35-7.28 (m, 2H), 4.93 (s, 2H), 3.72 (s, 3H), 3.59 (s, 3H), 2.21 (s, 6H), 1.39 (s, 9H); $^{13}$C NMR (150 MHz, CDCl$_3$) δ 168.40, 163.70, 154.52, 154.22, 149.07, 143.32, 142.18, 140.70, 131.48, 130.63, 130.57, 130.18 (q, J=32.5 Hz), 130.12, 129.39, 127.81, 124.82, 123.85 (q, J=272.8 Hz), 123.47, 122.18, 122.07 (q, J=3.8 Hz), 80.87, 59.84, 53.13, 51.85, 28.15, 13.18, 10.36; $^{19}$F NMR (376 MHz, CDCl$_3$) δ −62.70; HRMS (ESI-TOF) m/z Calcd for C$_{29}$H$_{32}$F$_3$N$_2$O$_5$ [M+H]$^+$: 545.2258, found: 545.2259.

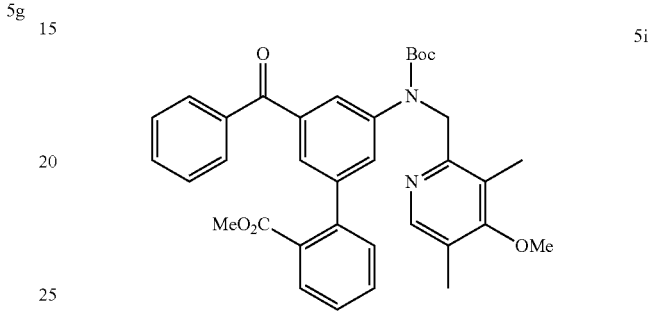

Methyl 3'-benzoyl-5'-((tert-butoxycarbonyl)((4-methoxy-3,5-dimethylpyridin-2-yl)methyl)amino)-[1,1'-biphenyl]-2-carboxylate (5i)

Substrate 1i was arylated following the general meta-arylation procedure using 2-norbornene. After purification by preparative thin-layer chromatography, Compound 5i was obtained in 93% yield as a colorless solid. $^1$H NMR (400 MHz, CDCl$_3$) δ 8.15 (s, 1H), 7.84 (d, J=7.7 Hz, 1H), 7.80 (s, 1H), 7.78 (s, 1H), 7.70 (s, 1H), 7.61-7.37 (m, 7H), 7.33 (d, J=7.6 Hz, 1H), 4.95 (s, 2H), 3.71 (s, 3H), 3.63 (s, 3H), 2.21 (s, 6H), 1.39 (s, 9H); $^{13}$C NMR (150 MHz, CDCl$_3$) δ 195.85, 168.29, 163.68, 154.67, 154.43, 148.98, 142.87, 141.50, 141.26, 137.35, 137.33, 132.36, 131.42, 130.82, 130.48, 130.41, 130.05, 130.02, 128.18, 127.56, 127.13, 126.67, 124.71, 123.52, 80.63, 59.83, 53.20, 51.89, 28.19, 13.18, 10.37; HRMS (ESI-TOF) m/z Calcd for C$_{35}$H$_{37}$N$_2$O$_6$ [M+H]$^+$: 581.2646, found: 581.2646.

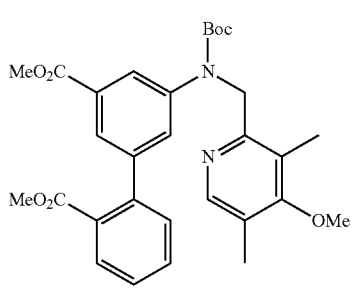

Dimethyl 5'-((tert-butoxycarbonyl)((4-methoxy-3,5-dimethylpyridin-2-yl)methyl)amino)-[1,1'-biphenyl]-2,3'-dicarboxylate (5h)

Substrate 1h was arylated following the general meta-arylation procedure using 2-norbornene. After purification

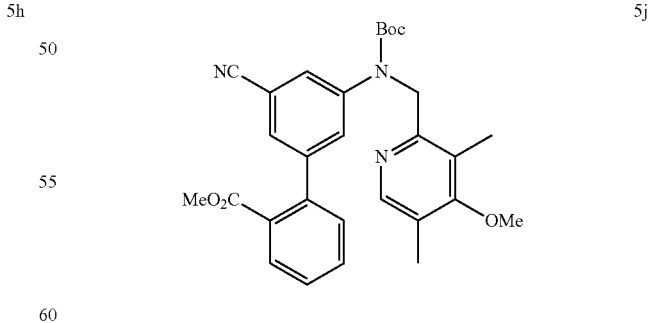

Methyl 3'-((tert-butoxycarbonyl)((4-methoxy-3,5-dimethylpyridin-2-yl)methyl)amino)-5'-cyano-[1,1'-biphenyl]-2-carboxylate (5j)

Substrate 1j was arylated following the general meta-arylation procedure using NBE-CO$_2$Me. After purification by preparative thin-layer chromatography, Compound 5j was obtained in 93% yield as a colorless solid. mp=106° C., ¹H NMR (400 MHz, CDCl₃) δ 8.18 (s, 1H), 7.89 (d, J=7.7 Hz, 1H), 7.62 (s, 1H), 7.60-7.50 (m, 2H), 7.45 (t, J=7.6 Hz, 1H), 7.33 (s, 1H), 7.28 (d, J=9.0 Hz, 1H), 4.88 (s, 2H), 3.75 (s, 3H), 3.65 (s, 3H), 2.23 (s, 3H), 2.21 (s, 3H), 1.38 (s, 9H); ¹³C NMR (150 MHz, CDCl₃) δ 167.80, 163.70, 154.19, 154.05, 149.12, 143.79, 142.73, 140.27, 131.68, 130.88, 130.67, 130.31, 130.10, 128.52, 128.08, 124.90, 123.22, 118.55, 111.81, 81.11, 59.88, 53.00, 51.99, 28.10, 13.20, 10.28; HRMS (ESI-TOF) m/z Calcd for $C_{29}H_{32}N_3O_5$ [M+H]⁺: 502.2336, found: 502.2336.

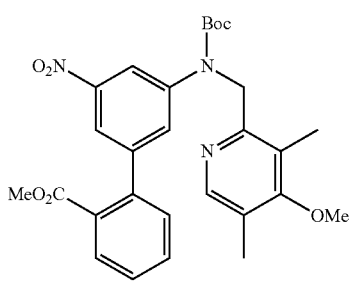

Methyl 3'-((tert-butoxycarbonyl)((4-methoxy-3,5-dimethylpyridin-2-yl)methyl)amino)-5'-nitro-[1,1'-biphenyl]-2-carboxylate (5k)

Substrate 1k was arylated following the general meta-arylation procedure using NBE-CO₂Me. After purification by preparative thin-layer chromatography, Compound 5k was obtained in 89% yield as a light yellow solid. ¹H NMR (400 MHz, CDCl₃) δ 8.20 (q, J=2.1 Hz, 1H), 8.18 (s, 1H), 7.96-7.88 (m, 2H), 7.67 (s, 1H), 7.56 (t, J=7.5 Hz, 1H), 7.46 (t, J=7.5 Hz, 1H), 7.33 (d, J=7.6 Hz, 1H), 4.93 (s, 2H), 3.75 (s, 3H), 3.65 (s, 3H), 2.23 (s, 6H), 1.39 (s, 9H); ¹³C NMR (150 MHz, CDCl₃) δ 167.74, 163.75, 154.21, 154.02, 149.15, 147.71, 143.89, 142.56, 140.27, 132.22, 131.76, 130.75, 130.40, 130.08, 128.19, 124.93, 123.33, 119.80, 81.27, 59.90, 52.96, 52.02, 28.11, 13.22, 10.34; HRMS (ESI-TOF) m/z Calcd for $C_{28}H_{32}N_3O_7$ [M+H]⁺: 522.2235, found: 522.2235.

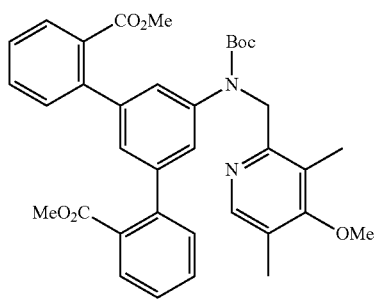

Dimethyl 5'-((tert-butoxycarbonyl)((4-methoxy-3,5-dimethylpyridin-2-yl)methyl)amino)-[1,1':3',1''-terphenyl]-2,2''-dicarboxylate (5l)

Substrate 1l was arylated following the general meta-arylation procedure using 2-norbornene. Analysis of crude reaction mixture by ¹H NMR showed the selectivity of mono- and di-products (mono:di<20:1). After purification by preparative thin-layer chromatography, Compound 5l was obtained in 92% yield as a light yellow liquid. ¹H NMR (400 MHz, CDCl₃) δ 8.18 (s, 1H), 7.78 (dd, J=7.7, 1.4 Hz, 2H), 7.49 (td, J=7.5, 1.5 Hz, 2H), 7.38 (td, J=7.6, 1.3 Hz, 2H), 7.34 (s, 1H), 7.32 (s, 1H), 7.29-7.21 (m, 2H), 7.01 (t, J=1.7 Hz, 1H), 4.93 (s, 2H), 3.70 (s, 3H), 3.61 (s, 6H), 2.21 (s, 6H), 1.39 (s, 9H); ¹³C NMR (150 MHz, CDCl₃) δ 168.99, 163.58, 155.04, 154.55, 148.94, 142.56, 141.68, 141.13, 131.09, 130.93, 130.64, 129.68, 127.17, 125.60, 125.36, 124.58, 123.52, 80.18, 59.79, 53.50, 51.84, 28.21, 13.15, 10.37; HRMS (ESI-TOF) m/z Calcd for $C_{36}H_{39}N_2O_7$ [M+H]⁺: 611.2752, found: 611.2754.

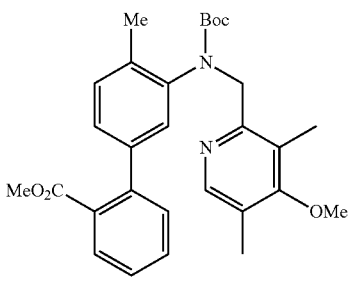

Methyl 3'-((tert-butoxycarbonyl)((4-methoxy-3,5-dimethylpyridin-2-yl)methyl)amino)-4'-methyl-[1,1'-biphenyl]-2-carboxylate (5m)

Substrate 1m was arylated following the general meta-arylation procedure using 2-norbornene. After purification by preparative thin-layer chromatography, Compound 5m was obtained in 81% yield as a colorless liquid. Rotameric mixture, ratio of the rotamers=70/30; ¹H NMR (400 MHz, CDCl₃) δ 8.11 (s, 1H), 7.73 (d, J=7.7 Hz, 1H), 7.44 (t, J=7.5 Hz, 1H), 7.34 (t, J=7.6 Hz, 1H), 7.31-6.98 (m, 3.3H), 6.86 (s, 0.7H), 5.26 (d, J=14.9 Hz, 0.7H), 5.18-5.04 (m, 0.3H), 4.51 (d, J=14.7 Hz, 1H), 3.66 (s, 3H), 3.55 (s, 3H), 2.33-2.12 (m, 9H), 1.38 (s, 9H); ¹³C NMR (150 MHz, CDCl₃) rotameric mixture, resonances for the minor rotamer are enclosed in parenthesis ( ): δ 169.20 (169.50), 163.76 (163.54), 155.07 (155.34), 154.75 (154.09), 148.88, 141.49 (141.25), 140.41, 139.11, 134.90 (135.29), 130.95, 130.86, 130.47, 130.27, 129.89, 129.59, 128.31, 126.87, 124.95 (124.65), 123.71, 79.77 (79.90), 59.69, 52.52 (53.54), 51.72 (51.84), 28.22, 17.31 (17.52), 13.13, 10.61; HRMS (ESI-TOF) m/z Calcd for $C_{29}H_{35}N_2O_5$ [M+H]⁺: 491.2540, found: 491.2540.

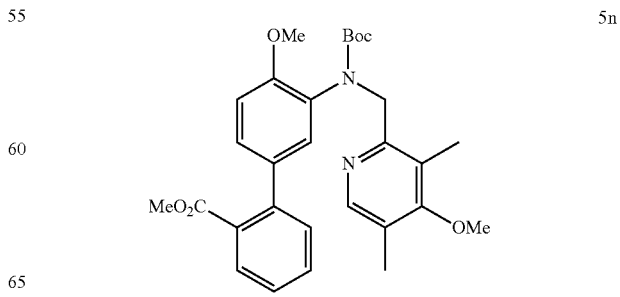

Methyl 3'-((tert-butoxycarbonyl)((4-methoxy-3,5-dimethylpyridin-2-yl)methyl)amino)-4'-methoxy-[1,1'-biphenyl]-2-carboxylate (5n)

Substrate 1n was arylated following the general meta-arylation procedure using 2-norbornene. After purification by preparative thin-layer chromatography, Compound 5n was obtained in 84% yield as a colorless liquid. Rotameric mixture, ratio of the rotamers=75/25; $^1$H NMR (400 MHz, CDCl$_3$) δ 8.07 (s, 1H), 7.70 (d, J=7.6 Hz, 1H), 7.42 (t, J=7.6 Hz, 1H), 7.32 (t, J=7.5 Hz, 1H), 7.26-6.76 (m, 4H), 5.33 (s, 0.75H), 4.91-4.30 (m, 1.25H), 3.83 (s, 3H), 3.67 (s, 3H), 3.55 (s, 3H), 2.26 (s, 3H), 2.19 (s, 3H), 1.49-1.30 (m, 9H); $^{13}$C NMR (150 MHz, CDCl$_3$) rotameric mixture: δ 169.56, 169.35, 163.76, 163.59, 155.70, 155.53, 155.24, 154.82, 154.49, 148.62, 141.28, 133.15, 132.99, 130.88, 130.85, 130.63, 130.45, 130.38, 129.53, 127.78, 127.71, 126.68, 126.62, 125.28, 124.84, 124.56, 124.19, 111.22, 110.42, 79.98, 79.51, 59.70, 55.72, 55.31, 53.50, 52.50, 51.86, 51.70, 28.19, 13.11, 10.58; HRMS (ESI-TOF) m/z Calcd for C$_{29}$H$_{35}$N$_2$O$_6$ [M+H]$^+$: 507.2490, found: 507.2491.

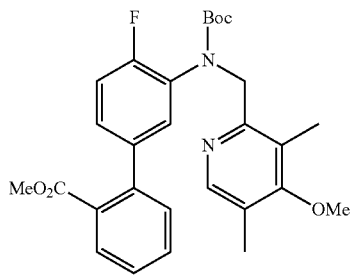

Methyl 3'-((tert-butoxycarbonyl)((4-methoxy-3,5-dimethylpyridin-2-yl)methyl)amino)-4'-fluoro-[1,1'-biphenyl]-2-carboxylate (5o)

Substrate 1o was arylated following the general meta-arylation procedure using 2-norbornene. After purification by preparative thin-layer chromatography, Compound 5o was obtained in 90% yield as a colorless liquid. Rotameric mixture, ratio of the rotamers=75/25; $^1$H NMR (400 MHz, CDCl$_3$) δ 8.10 (s, 1H), 7.77 (dd, J=7.7, 1.4 Hz, 1H), 7.47 (td, J=7.5, 1.5 Hz, 1H), 7.37 (t, J=7.3 Hz, 1H), 7.25-6.91 (m, 4H), 4.94 (s, 2H), 3.70 (s, 3H), 3.56 (s, 3H), 2.26 (s, 3H), 2.19 (s, 3H), 1.41 (s, 9H); $^{13}$C NMR (150 MHz, CDCl$_3$) δ 168.85, 163.77, 157.50 (d, J=249.6 Hz), 154.68, 154.23, 148.77, 140.84, 137.07 (d, J=3.7 Hz), 131.16, 130.73, 130.55, 129.80, 129.50, 129.36, 129.28, 127.78 (d, J=7.8 Hz), 127.24, 124.96, 115.06 (d, J=21.6 Hz), 80.50, 59.74, 52.70, 51.74, 28.07, 13.14, 10.48; $^{19}$F NMR (376 MHz, CDCl$_3$) for major isomer: δ −123.17; $^{19}$F NMR (376 MHz, CDCl$_3$) for minor isomer: δ −122.57; HRMS (ESI-TOF) m/z Calcd for C$_{28}$H$_{32}$FN$_2$O$_5$ [M+H]$^+$: 495.2290, found: 495.2291.

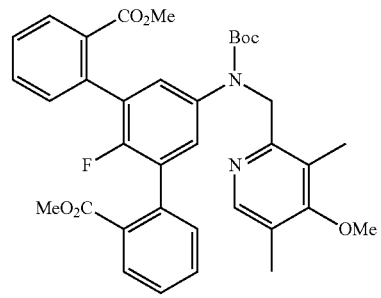

Dimethyl 5'-((tert-butoxycarbonyl)((4-methoxy-3,5-dimethylpyridin-2-yl)methyl)amino)-2'-fluoro-[1,1':3',1''-terphenyl]-2,2''-dicarboxylate (5p)

Substrate 1p was arylated following the general meta-arylation procedure using 2-norbornene. Analysis of the crude reaction mixture by $^1$H NMR showed the selectivity of mono- and di-products (mono:di<20:1). After purification by preparative thin-layer chromatography, Compound 5p was obtained in 90% yield as a light yellow solid. $^1$H NMR (400 MHz, CDCl$_3$) δ 8.17 (s, 1H), 7.91 (d, J=7.7 Hz, 2H), 7.53 (t, J=7.5 Hz, 2H), 7.41 (t, J=7.6 Hz, 2H), 7.29 (d, J=7.7 Hz, 2H), 7.18 (s, 2H), 4.95 (s, 2H), 3.70 (s, 3H), 3.64 (s, 6H), 2.21 (s, 6H), 1.41 (s, 9H); $^{13}$C NMR (150 MHz, CDCl$_3$) δ 167.79, 163.69, 154.99, 154.58, 153.56 (d, J=244.3 Hz), 148.91, 138.04, 136.02, 131.52, 131.42, 130.96, 130.01, 128.54 (d, J=18.4 Hz), 127.98, 127.80, 124.74, 123.92, 80.29, 59.78, 53.54, 51.87, 28.24, 13.16, 10.44; $^{19}$F NMR (376 MHz, CDCl$_3$) δ −123.88; HRMS (ESI-TOF) m/z Calcd for C$_{36}$H$_{38}$FN$_2$O$_7$ [M+H]$^+$: 629.2658, found: 629.2657.

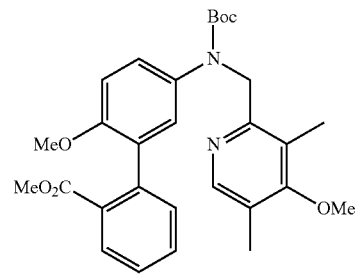

Methyl 5'-((tert-butoxycarbonyl)((4-methoxy-3,5-dimethylpyridin-2-yl)methyl)amino)-2'-methoxy-[1,1'-biphenyl]-2-carboxylate (5q)

Substrate 1q was arylated following the general meta-arylation procedure using 2-norbornene. Analysis of crude reaction mixture by $^1$H NMR showed the selectivity of mono- and di-products (mono:di>20:1). After purification by preparative thin-layer chromatography, Compound 5q was obtained in 64% yield as a colorless liquid. $^1$H NMR (400 MHz, CDCl$_3$) δ 8.14 (s, 1H), 7.83 (d, J=7.7 Hz, 1H), 7.50 (t, J=7.5 Hz, 1H), 7.37 (t, J=7.6 Hz, 1H), 7.16 (brs, 2H), 7.01 (s, 1H), 6.73 (d, J=8.7 Hz, 1H), 4.93 (brs, 2H), 3.70 (s, 3H), 3.65 (s, 3H), 3.56 (s, 3H), 2.30-2.10 (m, 6H), 1.41 (s, 9H); $^{13}$C NMR (150 MHz, CDCl$_3$) δ 168.60, 163.75, 155.29, 154.99, 153.89, 148.84, 138.17, 135.35, 131.60, 131.49, 131.20, 130.30, 129.32, 128.85, 127.12, 126.88, 124.74, 124.39, 109.71, 80.03, 59.79, 55.35, 53.66, 51.48, 28.30, 13.17, 10.51; HRMS (ESI-TOF) m/z Calcd for C$_{29}$H$_{35}$N$_2$O$_6$ [M+H]$^+$: 507.2490, found: 507.2491.

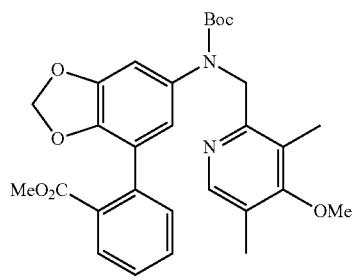

Methyl 2-(6-((tert-butoxycarbonyl)((4-methoxy-3,5-dimethylpyridin-2-yl)methyl)amino)benzo[d][1,3]dioxol-4-yl)benzoate (5r)

Substrate 1r was arylated following the general meta-arylation procedure using 2-norbornene. After purification by preparative thin-layer chromatography, Compound 5r was obtained in 83% yield as a light yellow liquid. $^1$H NMR (400 MHz, CDCl$_3$) δ 8.18 (s, 1H), 7.86 (d, J=7.7 Hz, 1H), 7.51 (t, J=7.5 Hz, 1H), 7.39 (t, J=7.6 Hz, 1H), 7.30 (d, J=7.7 Hz, 1H), 6.81 (s, 1H), 6.68 (s, 1H), 5.87 (s, 2H), 4.88 (s, 2H), 3.71 (s, 3H), 3.67 (s, 3H), 2.22 (s, 3H), 2.21 (s, 3H), 1.40 (s, 9H); $^{13}$C NMR (150 MHz, CDCl$_3$) δ 168.36, 163.70, 155.02, 154.92, 148.85, 146.61, 142.64, 136.74, 135.93, 131.57, 130.88, 130.76, 130.06, 127.66, 124.71, 123.99, 121.88, 120.87, 107.96, 101.15, 80.15, 59.79, 53.76, 51.89, 28.24, 13.16, 10.41; HRMS (ESI-TOF) m/z Calcd for C$_{29}$H$_{33}$N$_2$O$_7$ [M+H]$^+$: 521.2282, found: 521.2283.

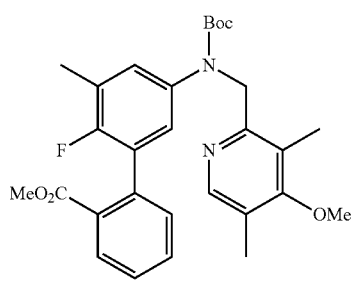

Methyl 5'-((tert-butoxycarbonyl)((4-methoxy-3,5-dimethylpyridin-2-yl)methyl)amino)-2'-fluoro-3'-methyl-[1,1'-biphenyl]-2-carboxylate (5s)

Substrate 1s was arylated following the general meta-arylation procedure using 2-norbornene. After purification by preparative thin-layer chromatography, Compound 5s was obtained in 94% yield as a light yellow liquid. $^1$H NMR (400 MHz, CDCl$_3$) δ 8.17 (s, 1H), 7.92 (d, J=7.7 Hz, 1H), 7.52 (td, J=7.6, 1.4 Hz, 1H), 7.41 (t, J=7.6 Hz, 1H), 7.23 (d, J=7.6 Hz, 1H), 7.10 (s, 1H), 6.96 (s, 1H), 4.90 (s, 2H), 3.71 (s, 3H), 3.63 (s, 3H), 2.21 (d, J=2.3 Hz, 9H), 1.39 (s, 9H); $^{13}$C NMR (150 MHz, CDCl$_3$) δ 167.87, 163.69, 155.58 (d, J=243.2 Hz), 155.03, 154.69, 148.85, 137.86, 136.35, 131.58, 131.32, 130.77, 129.96, 128.67 (d, J=5.1 Hz), 128.35 (d, J=18.1 Hz), 127.66, 126.39, 124.71, 124.08 (d, J=19.5 Hz), 123.89, 80.20, 59.78, 53.57, 51.74, 28.22, 14.66 (d, J=4.0 Hz), 13.15, 10.41; $^{19}$F NMR (376 MHz, CDCl$_3$) δ −124.82; HRMS (ESI-TOF) m/z Calcd for C$_{29}$H$_{34}$FN$_2$O$_5$ [M+H]$^+$: 509.2446, found: 509.2447.

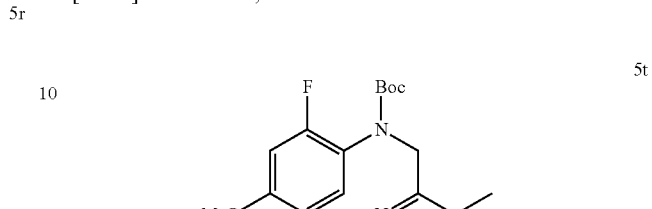

Methyl 5'-((tert-butoxycarbonyl)((4-methoxy-3,5-dimethylpyridin-2-yl)methyl)amino)-4'-fluoro-2'-methoxy-[1,1'-biphenyl]-2-carboxylate (5t)

Substrate 1t was arylated following the general meta-arylation procedure using 2-norbornene. After purification by preparative thin-layer chromatography, Compound 5t was obtained in 92% yield as a colorless solid. Rotameric mixture, ratio of the rotamers=76/24; $^1$H NMR (400 MHz, CDCl$_3$) δ 8.09 (s, 1H), 7.82 (d, J=7.7 Hz, 1H), 7.47 (t, J=7.5 Hz, 1H), 7.36 (t, J=7.6 Hz, 1H), 7.14 (s, 0.48H), 6.99 (s, 0.76H), 6.83 (s, 0.76H), 6.54 (d, J=11.7 Hz, 1H), 5.30-4.60 (m, 2H), 3.68 (s, 3H), 3.64 (s, 3H), 3.56 (s, 3H), 2.27 (s, 3H), 2.20 (s, 3H), 1.41 (s, 9H); $^{13}$C NMR (150 MHz, CDCl$_3$) rotameric mixture: δ 168.42, 163.89, 163.80, 158.89, 157.23, 155.41, 155.35, 155.02, 154.66, 154.29, 148.71, 137.20, 131.49, 131.12, 130.76, 130.71, 130.56, 129.44, 127.23, 125.97, 125.40, 125.07, 124.87, 124.36, 121.96, 121.54, 121.46, 99.03, 98.88, 98.52, 98.35, 80.59, 59.71, 55.55, 53.83, 52.66, 51.41, 28.12, 13.14, 10.57; $^{19}$F NMR (376 MHz, CDCl$_3$) for major isomer: δ −119.67; $^{19}$F NMR (376 MHz, CDCl$_3$) for minor isomer: δ −118.80; HRMS (ESI-TOF) m/z Calcd for C$_{29}$H$_{34}$FN$_2$O$_6$ [M+H]$^+$: 525.2395, found: 525.2395.

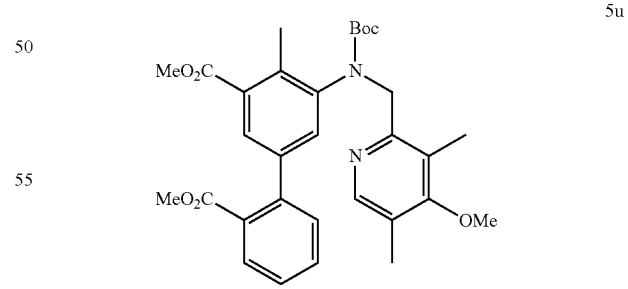

Dimethyl 5'-((tert-butoxycarbonyl)((4-methoxy-3,5-dimethylpyridin-2-yl)methyl)amino)-4'-methyl-[1,1'-biphenyl]-2,3'-dicarboxylate (5u)

Substrate 1u was arylated following the general meta-arylation procedure using 2-norbornene. After purification by preparative thin-layer chromatography, Compound 5u was obtained in 92% yield as a colorless liquid. Rotameric mixture, ratio of the rotamers=74/26; $^1$H NMR (400 MHz, CDCl$_3$) δ 8.22-8.05 (m, 1H), 7.79 (d, J=7.7 Hz, 1H), 7.70 (s, 0.74H), 7.59 (d, J=3.7 Hz, 0.26H), 7.47 (t, J=7.5 Hz, 1H), 7.38 (t, J=7.6 Hz, 1H), 7.34-7.04 (m, 2H), 5.35-5.05 (m, 1H), 4.54-4.30 (m, 1H), 3.87 (s, 3H), 3.67 (s, 3H), 3.55 (s, 3H), 2.57-2.38 (m, 3H), 2.27-2.15 (m, 6H), 1.37 (s, 9H); $^{13}$C NMR (150 MHz, CDCl$_3$) rotameric mixture: δ 169.05, 168.64, 167.81, 163.78, 163.55, 155.01, 154.64, 154.30, 148.94, 142.67, 141.82, 140.66, 138.61, 137.22, 136.92, 132.94, 132.41, 131.20, 130.57, 130.50, 129.93, 129.13, 127.38, 124.99, 124.77, 124.67, 123.49, 80.13, 59.70, 53.43, 52.55, 51.92, 51.75, 28.17, 15.00, 13.12, 10.61; HRMS (ESI-TOF) m/z Calcd for C$_{31}$H$_{37}$N$_2$O$_7$ [M+H]$^+$: 549.2595, found: 549.2596.

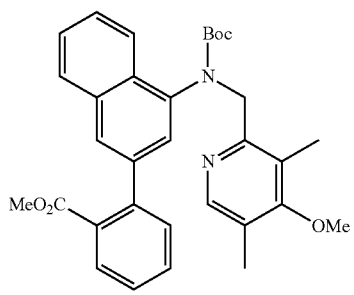

5v

Methyl 2-(4-((tert-butoxycarbonyl)((4-methoxy-3,5-dimethylpyridin-2-yl)methyl)amino) naphthalen-2-yl)benzoate (5v)

Substrate 1v was arylated following the general meta-arylation procedure using 2-norbornene. After purification by preparative thin-layer chromatography, Compound 5v was obtained in 92% yield as a colorless solid. Rotameric mixture, $^1$H NMR (400 MHz, CDCl$_3$) δ 8.13 (s, 1H), 7.92 (s, 1H), 7.87-7.77 (m, 2H), 7.66 (s, 1H), 7.56-7.44 (m, 3H), 7.40 (t, J=7.5 Hz, 1H), 7.34-7.18 (m, 2H), 5.56-5.18 (m, 1H), 4.61 (d, J=15.2 Hz, 1H), 3.63 (s, 3H), 3.46 (s, 3H), 2.18 (s, 3H), 2.16 (s, 3H), 1.56-1.14 (m, 9H); $^{13}$C NMR (150 MHz, CDCl$_3$) rotameric mixture: δ 169.07, 163.64, 155.33, 155.03, 148.96, 141.59, 138.49, 138.37, 134.01, 131.13, 131.01, 130.80, 129.82, 128.36, 127.66, 127.20, 126.76, 126.17, 126.07, 124.76, 124.46, 123.31, 122.91, 79.96, 59.67, 53.15, 51.75, 50.06, 28.07, 13.10, 10.52; HRMS (ESI-TOF) m/z Calcd for C$_{32}$H$_{35}$N$_2$O$_5$ [M+H]$^+$: 527.2540, found: 527.2541.

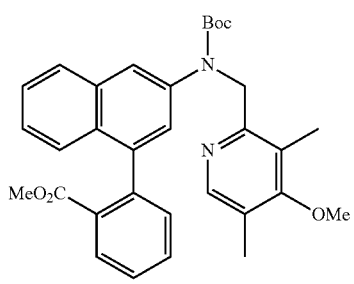

5w

Methyl 2-(3-((tert-butoxycarbonyl)((4-methoxy-3,5-dimethylpyridin-2-yl)methyl)amino)naphthalene-1-yl)benzoate (5w)

Substrate 1w was arylated following the general meta-arylation procedure using 2-norbornene. After purification by preparative thin-layer chromatography Compound 5w was obtained in 92% yield as a colorless solid. $^1$H NMR (400 MHz, CDCl$_3$) δ 8.15 (s, 1H), 8.00 (d, J=7.8 Hz, 1H), 7.74 (d, J=8.1 Hz, 1H), 7.66 (s, 1H), 7.58 (t, J=7.3 Hz, 1H), 7.49 (t, J=7.6 Hz, 1H), 7.41-7.22 (m, 5H), 5.06 (s, 2H), 3.70 (s, 3H), 3.23 (s, 3H), 2.24 (s, 3H), 2.20 (s, 3H), 1.40 (s, 9H); $^{13}$C NMR (150 MHz, CDCl$_3$) δ 167.79, 163.68, 155.11, 154.65, 148.94, 140.85, 139.61, 139.57, 133.26, 131.79, 131.61, 131.43, 130.13, 130.00, 128.09, 127.57, 126.09, 125.60, 125.52, 125.10, 124.67, 123.85, 122.79, 80.40, 59.81, 53.70, 51.56, 28.27, 13.17, 10.48; HRMS (ESI-TOF) m/z Calcd for C$_{32}$H$_{35}$N$_2$O$_5$ [M+H]$^+$: 527.2540, found: 527.2538.

Meta-Arylation of Heterocycle-Containing Aromatic Amines

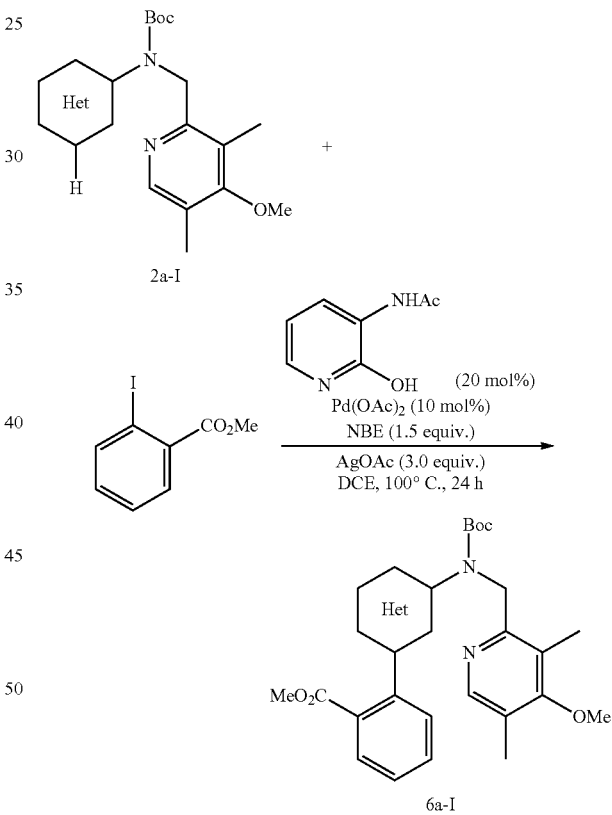

General Procedures for Meta-Arylation of Heterocycle-Containing Aromatic Amines:

Substrate 2 (0.1 mmol), Ar—I (0.2 mmol), Pd(OAc)$_2$ (2.2 mg, 10 mol %), L12 (3.0 mg, 20 mol %), AgOAc (50.1 mg, 0.3 mmol), 2-Norbornene (14.1 mg, 0.15 mmol) or NEE-CO$_2$Me (21.6 mg, 0.15 mmol) and DCE (0.5 mL) were added to a 2-dram vial. The vial was capped and closed tightly. Then the reaction mixture was then stirred at 100° C. for 24 hours. After cooling to room temperature, the mixture was passed through a pad of Celite® with DCM as the eluent to remove the insoluble precipitate. The resultant solution was concentrated and purified by preparative TLC plate to afford the desired arylated product.

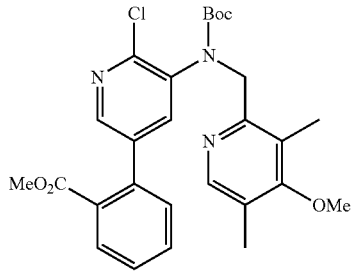

6a

Methyl 2-(5-((tert-butoxycarbonyl)((4-methoxy-3,5-dimethylpyridin-2-yl)methyl)amino)-6-chloropyridin-3-yl)benzoate (6a)

Substrate 2a was arylated following the general meta-arylation procedure using NBE-CO$_2$Me. After purification by preparative thin-layer chromatography, Compound 6a was obtained in 53% yield as a colorless liquid. Rotameric mixture, ratio of the rotamers=77/23; $^1$H NMR (400 MHz, CDCl$_3$) δ 8.25-8.12 (m, 1H), 8.10 (s, 0.77H), 7.99 (s, 0.23H), 7.92 (d, J=7.7 Hz, 1H), 7.65 (s, 0.77H), 7.55 (t, J=7.4 Hz, 1H), 7.47 (t, J=7.6 Hz, 1H), 7.27 (s, 0.46H), 7.17 (d, J=7.6 Hz, 0.77H), 5.24 (d, J=15.5 Hz, 1H), 4.56 (d, J=15.5 Hz, 1H), 3.71 (s, 3H), 3.60 (s, 3H), 2.33-2.23 (m, 3H), 2.20 (s, 3H), 1.40 (s, 9H); $^{13}$C NMR (150 MHz, CDCl$_3$) rotameric mixture: δ 167.98, 167.68, 163.94, 163.69, 154.64, 154.12, 153.79, 149.03, 148.91, 148.78, 146.47, 140.22, 138.99, 137.15, 136.54, 136.33, 135.68, 131.78, 130.84, 130.60, 130.46, 130.29, 128.36, 128.26, 125.26, 124.97, 124.86, 123.59, 81.08, 59.79, 52.51, 51.91, 51.67, 28.09, 13.18, 10.67, 10.50; HRMS (ESI-TOF) m/z Calcd for C$_{27}$H$_{31}$ClN$_3$O$_5$ [M+H]$^+$: 512.1947, found: 512.1946.

3.65 (s, 3H), 2.26 (s, 3H), 2.21 (s, 3H), 1.41 (s, 9H); $^{13}$C NMR (150 MHz, CDCl$_3$) δ 168.27, 163.33, 161.85, 156.03, 154.28, 153.00, 151.84, 148.82, 140.63, 131.35, 130.42, 130.26, 129.83, 127.90, 123.82, 122.36, 110.87, 104.23, 80.92, 59.83, 53.00, 52.05, 49.35, 28.13, 13.14, 10.34; HRMS (ESI-TOF) m/z Calcd for C$_{28}$H$_{34}$N$_3$O$_6$ [M+H]$^+$: 508.2442, found: 508.2442.

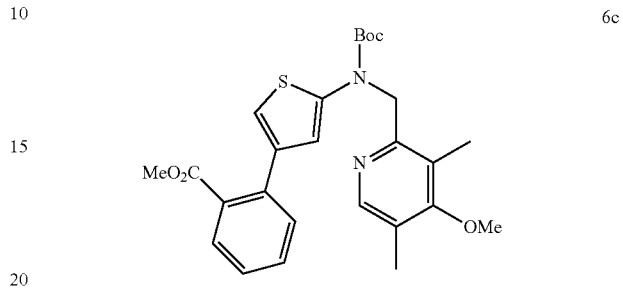

6c

Methyl 2-(5-((tert-butoxycarbonyl)((4-methoxy-3,5-dimethylpyridin-2-yl)methyl)amino)-thiophen-3-yl)benzoate (6c)

Substrate 2c was arylated following the general meta-arylation procedure using 2-norbornene. After purification by preparative thin-layer chromatography, Compound 6c was obtained in 79% yield as a colorless liquid. $^1$H NMR (400 MHz, CDCl$_3$) δ 8.30 (s, 1H), 7.71 (d, J=7.7 Hz, 1H), 7.56-7.39 (m, 2H), 7.34 (t, J=7.4 Hz, 1H), 6.97 (s, 1H), 6.80 (s, 1H), 5.48 (s, 2H), 3.96 (s, 3H), 3.73 (s, 3H), 2.35 (s, 6H), 1.50 (s, 9H); $^{13}$C NMR (150 MHz, CDCl$_3$) δ 169.58, 168.72, 153.40, 150.44, 141.74, 138.94, 136.46, 131.35, 130.71, 130.40, 129.44, 128.83, 128.72, 128.13, 127.24, 123.99, 118.73, 82.96, 60.92, 52.06, 49.86, 28.09, 14.16, 11.10; HRMS (ESI-TOF) m/z Calcd for C$_{26}$H$_{31}$N$_2$O$_5$S [M+H]$^+$: 483.1948, found: 483.1949.

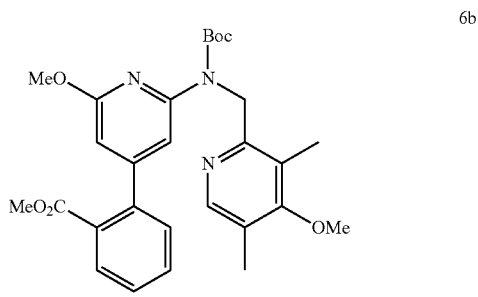 [SMILES: COC(=O)c1ccccc1-c1cc(N(Cc2ncc(C)c(OC)c2C)C(=O)OC(C)(C)C)cc([N+](=O)[O-])c1]

6b

Methyl 2-(2-((tert-butoxycarbonyl)((4-methoxy-3,5-dimethylpyridin-2-yl)methyl)amino)-6-methoxypyridin-4-yl)benzoate (6b)

Substrate 2b was arylated following the general meta-arylation procedure using 2-norbornene. After purification by preparative thin-layer chromatography, Compound 6b was obtained in 72% yield as a colorless liquid. Only 4% NMR yield was obtained in the absence of L12. $^1$H NMR (400 MHz, CDCl$_3$) δ 8.13 (s, 1H), 7.83 (d, J=7.6 Hz, 1H), 7.51 (t, J=7.5 Hz, 1H), 7.46-7.39 (m, 2H), 7.36 (d, J=7.5 Hz, 1H), 6.32 (s, 1H), 5.24 (s, 2H), 3.73 (s, 3H), 3.69 (s, 3H),

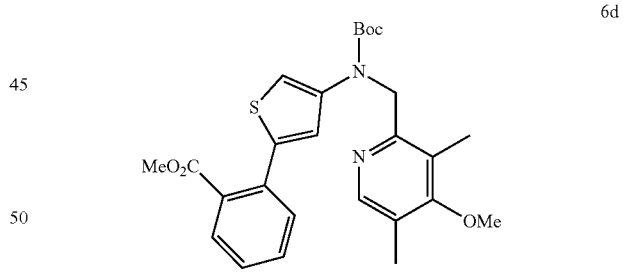

6d

Methyl 2-(4-((tert-butoxycarbonyl)((4-methoxy-3,5-dimethylpyridin-2-yl)methyl)amino)-thiophen-2-yl)benzoate (6d)

Substrate 2d was arylated following the general meta-arylation procedure using NBE-CO$_2$Me. After purification by preparative thin-layer chromatography, Compound 6d was obtained in 56% yield as a colorless liquid. $^1$H NMR (400 MHz, CDCl$_3$) δ 8.19 (s, 1H), 7.66 (d, J=7.6 Hz, 1H), 7.49-7.39 (m, 2H), 7.39-7.32 (m, 1H), 7.07 (s, 1H), 6.96 (s, 1H), 4.91 (s, 2H), 3.74 (s, 3H), 3.70 (s, 3H), 2.26-2.19 (m, 6H), 1.44 (s, 9H); $^{13}$C NMR (150 MHz, CDCl$_3$) δ 169.04, 163.69, 154.77, 154.18, 149.05, 140.87, 139.46, 134.13, 131.51, 130.88, 129.27, 127.64, 124.68, 123.50, 115.39, 80.72, 59.86, 53.21, 52.13, 28.25, 13.20, 10.29; HRMS (ESI-TOF) m/z Calcd for $C_{26}H_{31}N_2O_5S$ [M+H]$^+$: 483.1948, found: 483.1948.

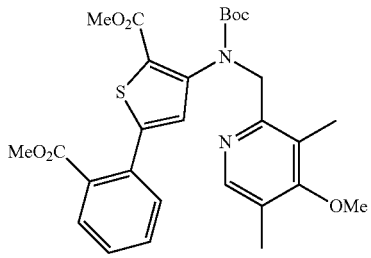

6e

Methyl 3-((tert-butoxycarbonyl)((4-methoxy-3,5-dimethylpyridin-2-yl)methyl)amino)-5-(2-(methoxy-carbonyl)-phenyl)thiophene-2-carboxylate (6e)

Substrate 2e was arylated following the general meta-arylation procedure using 2-norbornene. After purification by preparative thin-layer chromatography, Compound 6e was obtained in 65% yield as a colorless liquid. Rotameric mixture, ratio of the rotamers=65/35; $^1$H NMR (400 MHz, CDCl$_3$) δ 8.13 (s, 1H), 7.73 (d, J=7.6 Hz, 1H), 7.48 (t, J=7.5 Hz, 1H), 7.45-7.29 (m, 2H), 7.06 (s, 0.35H), 6.80 (s, 0.65H), 5.20-4.60 (m, 2H), 3.85 (s, 3H), 3.72 (s, 3H), 3.66 (s, 3H), 2.26 (s, 3H), 2.20 (s, 3H), 1.39 (s, 9H); $^{13}$C NMR (150 MHz, CDCl$_3$) rotameric mixture: δ 168.16, 167.85, 163.31, 163.14, 161.03, 160.90, 154.89, 154.29, 153.70, 132.81, 131.11, 131.03, 130.72, 130.38, 129.28, 128.41, 128.18, 128.10, 127.77, 124.49, 124.38, 124.28, 124.12, 124.05, 123.05, 79.91, 59.37, 53.02, 52.14, 51.79, 51.68, 51.47, 27.72, 12.74, 10.07; HRMS (ESI-TOF) m/z Calcd for $C_{28}H_{33}N_2O_7S$ [M+H]$^+$: 541.2003, found: 541.2003.

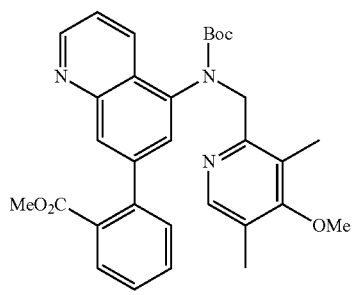

6f

Methyl 2-(5-((tert-butoxycarbonyl)((4-methoxy-3,5-dimethylpyridin-2-yl)methyl)amino)-quinolin-7-yl)benzoate (6f)

Substrate 2f was arylated following the general meta-arylation procedure using 2-norbornene. After purification by preparative thin-layer chromatography, Compound 6f was obtained in 76% yield as a red liquid. $^1$H NMR (400 MHz, CDCl$_3$) δ 8.91 (dd, J=4.2, 1.6 Hz, 1H), 8.34 (d, J=8.4 Hz, 1H), 8.12 (s, 1H), 7.97 (s, 1H), 7.87 (d, J=7.6 Hz, 1H), 7.55 (t, J=7.3 Hz, 1H), 7.51-7.30 (m, 4H), 5.24 (d, J=15.5 Hz, 1H), 4.76 (d, J=15.3 Hz, 1H), 3.65 (s, 3H), 3.52 (s, 3H), 2.28-2.10 (m, 6H), 1.54-1.10 (m, 9H); $^{13}$C NMR (150 MHz, CDCl$_3$) δ 168.50, 163.67, 154.97, 154.56, 150.52, 148.99, 148.57, 142.19, 141.25, 138.52, 132.00, 131.46, 130.91, 130.66, 130.17, 127.65, 127.48, 126.97, 125.23, 124.87, 124.23, 120.86, 80.44, 59.72, 53.40, 51.82, 28.08, 13.12, 10.51; HRMS (ESI-TOF) m/z Calcd for $C_{31}H_{34}N_3O_5$ [M+H]$^+$: 528.2493, found: 528.2493.

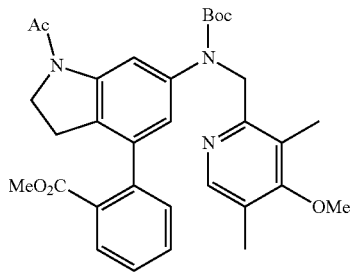

6g

Methyl 2-(1-acetyl-6-((tert-butoxycarbonyl)((4-methoxy-3,5-dimethylpyridin-2-yl)methyl)-amino)-indolin-4-yl)-benzoate (6g)

Substrate 2g was arylated following the general meta-arylation procedure using 2-norbornene. After purification by preparative thin-layer chromatography, Compound 6g was obtained in 89% yield as a light yellow solid. Rotameric mixture, ratio of the rotamers=78/22; mp=79° C., $^1$H NMR (400 MHz, CDCl$_3$) δ 8.20-8.08 (m, 1.78H), 7.96-7.84 (m, 1H), 7.50 (t, J=7.6 Hz, 1H), 7.40 (t, J=7.6 Hz, 1H), 7.26-7.09 (m, 1.22H), 6.74 (s, 1H), 5.00-4.80 (m, 2H), 4.12-3.90 (m, 2H), 3.70 (s, 2H), 3.66-3.52 (m, 3H), 2.82 (t, J=8.4 Hz, 1.56H), 2.69 (t, J=8.4 Hz, 0.44H), 2.38-2.08 (m, 9H), 1.40 (s, 9H); $^{13}$C NMR (150 MHz, CDCl$_3$) resonances for the minor rotamer are enclosed in parenthesis ( ): δ 168.46 (168.29), 167.88 (167.52), 163.60 (163.66), 155.15 (155.03), 154.68, 148.74 (148.82), 142.41, 142.00 (141.16), 140.54 (140.45), 137.49 (138.91), 131.49 (131.67), 130.52 (130.47), 130.13 (129.85), 129.97 (129.28), 127.41 (127.61), 126.70, 124.50 (124.75), 123.90, 122.52 (121.91), 114.62 (112.46), 80.12 (80.33), 59.74 (59.79), 53.54, 51.87 (51.92), 49.12 (48.19), 28.21, 26.81 (25.60), 24.14 (24.36), 13.12, 10.45 (10.37); HRMS (ESI-TOF) m/z Calcd for $C_{32}H_{38}N_3O_6$ [M+H]$^+$: 560.2755, found: 560.2755.

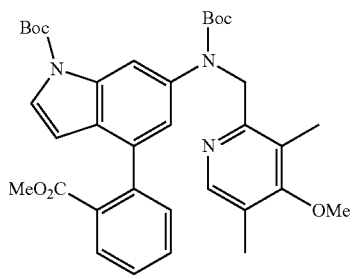

6h tert-Butyl 6-((tert-butoxycarbonyl)((4-methoxy-3,5-dimethylpyridin-2-yl)methyl)amino)-4-(2-(methoxy-carbonyl)-phenyl)-1H-indole-1-carboxylate (6h)

Substrate 2h was arylated following the general meta-arylation procedure using 2-norbornene. After purification by preparative thin-layer chromatography, Compound 6h was obtained in 66% yield as a colorless solid. $^1$H NMR (400 MHz, CDCl$_3$) δ 8.14 (s, 1H), 7.99 (s, 1H), 7.89 (d, J=7.7 Hz, 1H), 7.57-7.47 (m, 2H), 7.43 (t, J=7.6 Hz, 1H), 7.31 (d, J=7.5 Hz, 1H), 7.03 (s, 1H), 6.22 (d, J=3.7 Hz, 1H), 5.01 (s, 2H), 3.71 (s, 3H), 3.42 (s, 3H), 2.24 (s, 3H), 2.20 (s, 3H), 1.60 (s, 9H), 1.40 (s, 9H); $^{13}$C NMR (150 MHz, CDCl$_3$) δ 168.58, 163.70, 155.30, 154.94, 149.55, 148.84, 140.23, 139.22, 134.48, 133.59, 131.39, 131.32, 131.14, 129.92, 127.36, 127.32, 126.33, 124.64, 124.05, 122.40, 112.86, 105.68, 83.59, 80.08, 59.76, 54.11, 51.88, 28.27, 28.04, 13.12, 10.50; HRMS (ESI-TOF) m/z Calcd for C$_{35}$H$_{42}$N$_3$O$_7$ [M+H]$^+$: 616.3017, found: 616.3018.

by preparative thin-layer chromatography, Compound 6j as obtained in 90% yield as a colorless solid. mp=79° C., $^1$H NMR (400 MHz, CDCl$_3$) δ 8.18 (s, 1H), 7.90 (d, J=7.7 Hz, 1H), 7.63 (s, 1H), 7.56 (t, J=7.5 Hz, 1H), 7.46 (t, J=7.6 Hz, 1H), 7.39 (d, J=7.6 Hz, 1H), 7.35 (s, 1H), 6.98 (s, 1H), 5.00 (s, 2H), 4.00 (s, 3H), 3.71 (s, 3H), 3.44 (s, 3H), 2.24 (s, 3H), 2.22 (s, 3H), 1.40 (s, 9H); $^{13}$C NMR (150 MHz, CDCl$_3$) δ 168.39, 163.70, 155.05, 154.71, 148.89, 141.40, 139.77, 139.61, 134.29, 131.56, 131.45, 131.09, 131.02, 130.00, 127.64, 124.73, 123.79, 121.46, 120.66, 105.64, 80.43, 59.80, 53.89, 51.89, 35.65, 28.23, 13.17, 10.45; HRMS (ESI-TOF) m/z Calcd for C$_{30}$H$_{35}$N$_4$O$_5$ [M+H]$^+$: 531.2602, found: 531.2604.

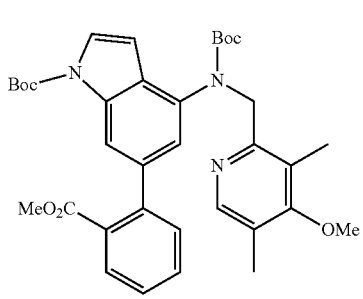

tert-Butyl 4-((tert-butoxycarbonyl)((4-methoxy-3,5-dimethylpyridin-2-yl)methyl)amino)-6-(2-(methoxycarbonyl)-phenyl)-1H-indole-1-carboxylate (6i)

Substrate 2i was arylated following the general meta-arylation procedure using 2-norbornene. After purification by preparative thin-layer chromatography, Compound 6i as obtained in 51% yield as a colorless solid. $^1$H NMR (400 MHz, CDCl$_3$) δ 8.13 (s, 1H), 8.01 (s, 1H), 7.75 (d, J=7.7 Hz, 1H), 7.56 (d, J=3.7 Hz, 1H), 7.48 (t, J=7.4 Hz, 1H), 7.41-7.28 (m, 2H), 7.02 (brs, 1H), 6.58 (d, J=3.7 Hz, 1H), 4.97 (brs, 2H), 3.66 (s, 3H), 3.54 (s, 3H), 2.18 (s, 6H), 1.64 (s, 9H), 1.35 (s, 9H); $^{13}$C NMR (150 MHz, CDCl$_3$) δ 169.41, 163.58, 155.02, 154.78, 149.61, 148.93, 142.31, 137.48, 135.73, 134.72, 131.18, 130.97, 130.92, 129.65, 127.71, 126.83, 125.87, 124.67, 124.15, 121.93, 113.59, 105.71, 83.78, 80.07, 59.72, 53.36, 51.76, 28.20, 28.13, 13.15, 10.50; HRMS (ESI-TOF) m/z Calcd for C$_{35}$H$_{42}$N$_3$O$_7$ [M+H]$^+$: 616.3017, found: 616.3018.

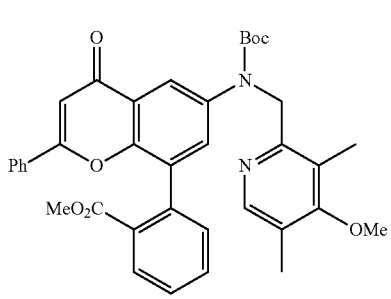

Methyl 2-(6-((tert-butoxycarbonyl)((4-methoxy-3,5-dimethylpyridin-2-yl)methyl)amino)-4-oxo-2-phenyl-4H-chromen-8-yl)benzoate (6k)

Substrate 2k was arylated following the general meta-arylation procedure using 2-norbornene. After purification by preparative thin-layer chromatography, Compound 6k was obtained in 87% yield as a colorless solid. $^1$H NMR (400 MHz, CDCl$_3$) δ 8.16 (s, 1H), 8.11 (d, J=7.7 Hz, 1H), 8.01 (d, J=2.6 Hz, 1H), 7.78-7.62 (m, 2H), 7.61-7.49 (m, 3H), 7.48-7.33 (m, 4H), 6.77 (s, 1H), 5.02 (q, J=15.1, 14.2 Hz, 2H), 3.74 (s, 3H), 3.40 (s, 3H), 2.25 (s, 3H), 2.21 (s, 3H), 1.41 (s, 9H); $^{13}$C NMR (150 MHz, CDCl$_3$) δ 178.08, 167.21, 163.75, 162.67, 154.60, 154.40, 150.81, 149.03, 139.91, 136.59, 134.50, 133.25, 132.19, 131.89, 131.69, 131.39, 131.27, 130.74, 130.52, 130.27, 128.83, 128.39, 126.00, 124.81, 123.70, 123.49, 120.74, 106.72, 80.78, 59.88, 53.26, 51.70, 28.20, 13.19, 10.44; HRMS (ESI-TOF) m/z Calcd for C$_{37}$H$_{37}$N$_2$O$_7$ [M+H]$^+$: 621.2595, found: 621.2596.

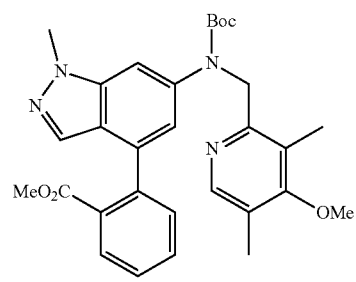

Methyl 2-(6-((tert-butoxycarbonyl)((4-methoxy-3,5-dimethylpyridin-2-yl)methyl)amino)-1-methyl-1H-indazol-4-yl)benzoate (6j)

Substrate 2j was arylated following the general meta-arylation procedure using 2-norbornene. After purification

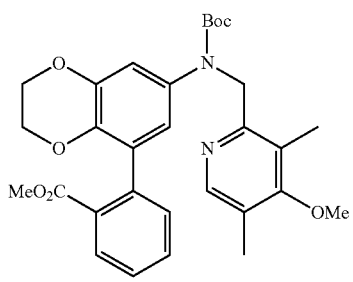

Methyl 2-(7-((tert-butoxycarbonyl)((4-methoxy-3,5-dimethylpyridin-2-yl)methyl)amino)-2,3-dihydrobenzo[b][1,4]dioxin-5-yl)benzoate (6l)

Substrate 2l was arylated following the general meta-arylation procedure using 2-norbornene. After purification by preparative thin-layer chromatography, Compound 61 was obtained in 91% yield as a colorless solid. $^1$H NMR (400 MHz, CDCl$_3$) δ 8.17 (s, 1H), 7.84 (d, J=7.7 Hz, 1H), 7.50 (t, J=7.5 Hz, 1H), 7.36 (s, 1H), 7.21 (d, J=6.4 Hz, 1H), 6.81 (s, 1H), 6.67 (s, 1H), 4.89 (s, 2H), 4.15 (dd, J=5.6, 2.8 Hz, 2H), 4.09 (dd, J=5.7, 2.8 Hz, 2H), 3.71 (s, 3H), 3.64 (s, 3H), 2.21 (s, 3H), 2.20 (s, 3H), 1.41 (s, 9H); $^{13}$C NMR (150 MHz, CDCl$_3$) δ 168.41, 163.63, 155.14, 154.84, 148.86, 142.40, 138.20, 137.39, 135.73, 131.50, 131.39, 131.22, 129.88, 129.41, 127.28, 124.60, 123.90, 120.95, 115.08, 80.03, 64.11, 64.02, 59.77, 53.66, 51.62, 28.25, 13.14, 10.39; HRMS (ESI-TOF) m/z Calcd for C$_{30}$H$_{35}$N$_2$O$_7$ [M+H]$^+$: 535.2439, found: 535.2438.

Meta-Arylation of Phenols

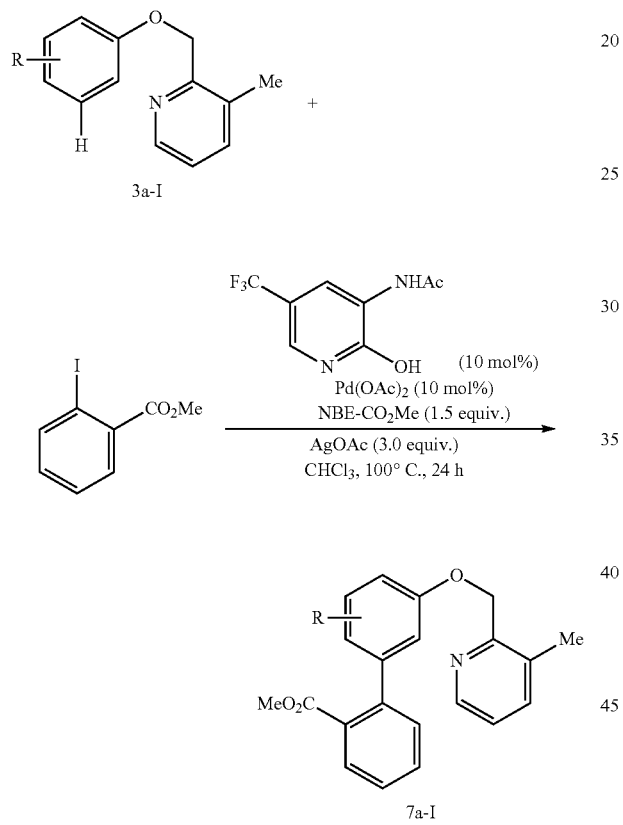

General Procedure for Meta-Arylation of Phenols:

Substrate 3 (0.2 mmol), Ar—I (0.6 mmol), Pd(OAc)$_2$ (4.5 mg, 10 mol %), L14 (4.4 mg, 10 mol %), AgOAc (100.0 mg, 0.6 mmol), NBE-CO$_2$Me (45.6 mg, 0.3 mmol) and CHCl$_3$ (1.0 mL) were added to a 50 mL schlenk tube. The tube was capped and closed tightly. The reaction mixture was then stirred at 100° C. for 24 hours. After cooling to room temperature, the mixture was passed through a pad of Celite® with EtOAc as the eluent to remove the insoluble precipitate. The resulting solution was concentrated and purified by preparative TLC plate to afford the desired arylated product. (In cases where mono:di ratios are possible, the selectivity was determined by $^1$H NMR.)

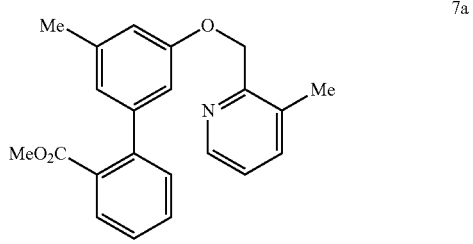 [SMILES: COC(=O)c1ccccc1-c1cc(C)cc(OCc2ncccc2C)c1]

Methyl 3'-methyl-5'-((3-methylpyridin-2-yl)methoxy)-[1,1'-biphenyl]-2-carboxylate (7a)

Substrate 3a was arylated following the general meta-arylation procedure for phenols. After purification by preparative thin-layer chromatography, Compound 7a was obtained in 87% yield as a light yellow liquid. $^1$H NMR (400 MHz, CDCl$_3$) δ 8.45 (d, J=4.4 Hz, 1H), 7.77 (d, J=7.5 Hz, 1H), 7.54-7.45 (m, 1H), 7.41-7.34 (m, 2H), 7.19 (dd, J=7.7, 4.8 Hz, 2H), 6.86 (s, 1H), 6.80 (s, 1H), 6.74 (s, 1H), 5.20 (s, 2H), 3.63 (s, 3H), 2.43 (s, 3H), 2.36 (s, 3H); $^{13}$C NMR (100 MHz, CDCl$_3$) δ 169.26, 158.48, 154.32, 146.55, 142.35, 142.13, 139.01, 138.34, 133.22, 131.04, 131.02, 130.46, 129.49, 127.06, 123.38, 122.02, 114.56, 111.92, 70.81, 51.92, 21.53, 18.16; HRMS (ESI-TOF) m/z Calcd for C$_{22}$H$_{22}$NO$_3$ [M+H]$^+$: 348.1594, found: 348.1598.

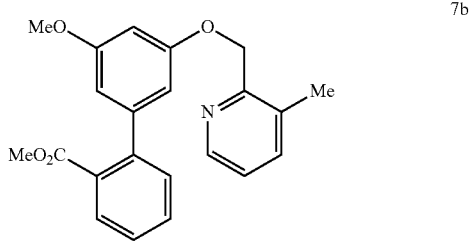 [SMILES: COC(=O)c1ccccc1-c1cc(OC)cc(OCc2ncccc2C)c1]

Methyl 3'-methoxy-5'-((3-methylpyridin-2-yl)methoxy)-[1,1'-biphenyl]-2-carboxylate (7b)

Substrate 3b was arylated following the general meta-arylation procedure for phenols. After purification by preparative thin-layer chromatography, Compound 7b was obtained in 91% yield as a light yellow liquid $^1$H NMR (400 MHz, CDCl$_3$) δ 8.45 (d, J=4.7 Hz, 1H), 7.76 (d, J=7.6 Hz, 1H), 7.54-7.46 (m, 2H), 7.42-7.35 (m, 2H), 7.19 (dd, J=7.7, 4.8 Hz, 1H), 6.26-6.58 (m, 2H), 6.48 (s, 1H), 5.19 (s, 2H), 3.79 (s, 3H), 3.64 (s, 3H), 2.42 (s, 3H); $^{13}$C NMR (100 MHz, CDCl$_3$) δ 169.18, 160.32, 159.56, 154.14, 146.61, 143.23, 142.00, 138.36, 133.17, 131.09, 131.05, 130.34, 129.47, 127.24, 123.42, 107.40, 107.03, 100.18, 70.86, 55.33, 51.99, 18.14; HRMS (ESI-TOF) m/z Calcd for C$_{22}$H$_{22}$NO$_4$ [M+H]$^+$: 364.1543, found: 364.1552.

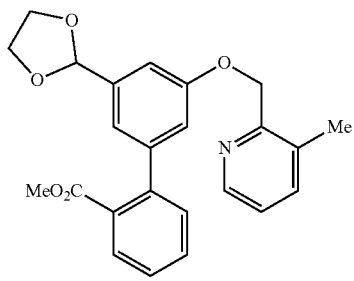

7c

Methyl 3'-(1,3-dioxolan-2-yl)-5'-((3-methylpyridin-2-yl)methoxy)-[1,1'-biphenyl]-2-carboxylate (7c)

Substrate 3c was arylated following the general meta-arylation procedure for phenols. After purification by preparative thin-layer chromatography, Compound 7c was obtained in 53% yield as a clear liquid. $^1$H NMR (400 MHz, CDCl$_3$) δ 8.45 (d, J=4.8 Hz, 1H), 7.79 (d, J=7.6 Hz, 1H), 7.55-7.46 (m, 2H), 7.43-7.34 (m, 2H), 7.19 (dd, J=7.7, 4.8 Hz, 1H), 7.16 (s, 1H), 7.03 (s, 1H), 7.01 (t, J=1.9 Hz, 1H); 5.82 (s, 1H), 5.23 (s, 2H), 4.16-3.95 (m, 4H), 3.61 (s, 3H), 2.43 (s, 3H); $^{13}$C NMR (100 MHz, CDCl$_3$) δ 169.21, 158.58, 154.15, 146.61, 142.68, 141.68, 139.35, 138.39, 133.30, 131.15, 131.06, 130.54, 129.68, 127.31, 123.48, 119.50, 115.78, 111.57, 103.46, 71.00, 65.27, 51.98, 18.20; HRMS (ESI-TOF) m/z Calcd for C$_{24}$H$_{24}$NO$_5$ [M+H]$^+$: 406.1649, found: 406.1656.

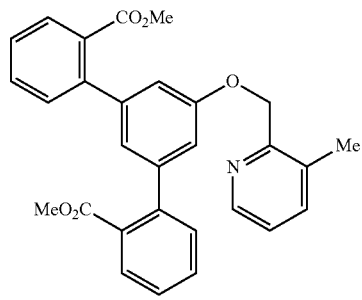

7d'

Dimethyl 5'-((3-methylpyridin-2-yl)methoxy)-[1,1':3',1''-terphenyl]-2,2''-dicarboxylate (7d')

Substrate 3d was arylated following the general meta-arylation procedure for phenols. After purification by preparative thin-layer chromatography, Compound 7d' was obtained in 40% yield as a clear liquid. $^1$H NMR (400 MHz, CDCl$_3$) δ 8.45 (d, J=4.9 Hz, 1H), 7.81-7.76 (m, 2H), 7.55-7.48 (m, 3H), 7.43-7.37 (m, 4H), 7.20 (dd, J=7.7, 4.8 Hz, 1H), 6.99 (s, 2H), 6.86 (s, 1H), 5.23 (s, 2H), 3.65 (s, 6H), 2.44 (s, 3H); $^{13}$C NMR (100 MHz, CDCl$_3$) δ 169.09, 158.22, 154.11, 146.58, 142.40, 141.86, 138.43, 133.25, 131.13, 131.05, 130.58, 129.67, 127.27, 123.47, 121.51, 113.81, 70.88, 51.98, 18.19; HRMS (ESI-TOF) m/z Calcd for C$_{29}$H$_{26}$NO$_5$ [M+H]$^+$: 468.1805, found: 468.1809.

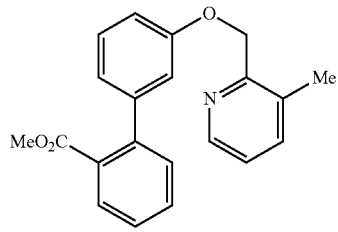

7d

Methyl 3'-((3-methylpyridin-2-yl)methoxy)-[1,1'-biphenyl]-2-carboxylate (7d)

Substrate 3d was arylated following the general meta-arylation procedure for phenols. Analysis of crude reaction mixture by $^1$H NMR showed the selectivity of mono- and di-products (mono:di=1:1). After purification by preparative thin-layer chromatography, Compound 7d was obtained in 38% yield as a clear liquid. $^1$H NMR (400 MHz, CDCl$_3$) δ 8.45 (d, J=4.3 Hz, 1H), 7.81-7.77 (m, 1H), 7.54-7.49 (m, 2H), 7.40 (td, J=7.6, 1.3 Hz, 1H), 7.38-7.35 (m, 1H), 7.30 (t, J=7.9 Hz, 1H), 7.19 (dd, J=7.7, 4.8 Hz, 1H), 7.03 (ddd, J=8.3, 2.6, 0.9 Hz, 1H), 7.00 (s, 1H), 6.90 (ddd, J=7.5, 1.7, 0.9 Hz, 1H), 5.22 (s, 2H), 3.62 (s, 3H), 2.44 (s, 3H); $^{13}$C NMR (100 MHz, CDCl$_3$) δ 169.15, 158.53, 154.28, 146.61, 142.68, 142.10, 138.40, 133.27, 131.15, 130.99, 130.55, 129.64, 128.99, 127.20, 123.44, 121.24, 114.99, 113.63, 70.89, 51.95, 18.20; HRMS (ESI-TOF) m/z Calcd for C$_{21}$H$_{20}$NO$_3$ [M+H]$^+$: 334.1438, found: 334.1443.

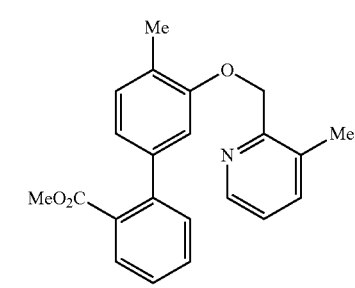

7e

Methyl 4'-methyl-3'-((3-methylpyridin-2-yl)methoxy)-[1,1'-biphenyl]-2-carboxylate (7e)

Substrate 3e was arylated following the general meta-arylation procedure for phenols. After purification by preparative thin-layer chromatography, Compound 7e was obtained in 85% yield as a light yellow liquid. $^1$H NMR (400 MHz, CDCl$_3$) δ 8.44 (d, J=4.6 Hz, 1H), 7.78 (d, J=7.6 Hz, 1H), 7.55-7.47 (m, 2H), 7.42-7.33 (m, 2H), 7.20 (dd, J=7.7, 4.8 Hz, 1H), 7.15 (d, J=7.5 Hz, 1H), 7.01 (s, 1H), 6.82 (d, J=7.6 Hz, 1H), 5.21 (s, 2H), 3.64 (d, J=0.7 Hz, 3H), 2.45 (s, 3H), 2.25 (s, 3H); $^{13}$C NMR (100 MHz, CDCl$_3$) δ 169.32, 156.53, 154.54, 146.49, 142.29, 139.95, 138.32, 133.39, 131.09, 131.00, 130.62, 130.27, 129.54, 126.94, 125.90, 123.39, 120.64, 111.72, 71.19, 51.97, 18.16, 16.08; HRMS (ESI-TOF) m/z Calcd for C$_{22}$H$_{22}$NO$_3$ [M+H]$^+$: 348.1594, found: 348.1597.

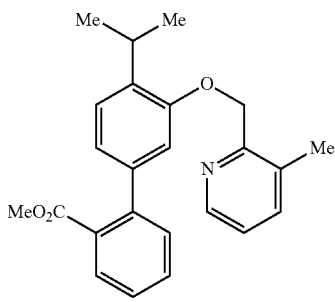

7f

Methyl 4'-isopropyl-3'-((3-methylpyridin-2-yl)methoxy)-[1,1'-biphenyl]-2-carboxylate (7f)

Substrate 3f was arylated following the general meta-arylation procedure for phenols. After purification by preparative thin-layer chromatography, Compound 7f was obtained in 89% yield as clear liquid. $^1$H NMR (400 MHz, CDCl$_3$) δ 8.44 (d, J=4.6 Hz, 1H), 7.77 (d, J=7.2 Hz, 1H), 7.56-7.46 (m, 2H), 7.42-7.35 (m, 2H), 7.26-7.16 (m, 2H), 7.04 (s, 1H), 6.89 (d, J=7.8 Hz, 1H), 5.20 (s, 2H), 3.63 (s, 3H), 3.34 (hept, J=7.0 Hz, 1H), 2.45 (s, 3H), 1.20 (d, J=6.9 Hz, 6H); $^{13}$C NMR (100 MHz, CDCl$_3$) δ 169.43, 155.58, 154.58, 146.52, 142.18, 139.50, 138.28, 136.18, 133.32, 131.09, 131.03, 130.59, 129.49, 126.90, 125.70, 123.39, 120.94, 111.96, 71.28, 51.93, 26.36, 22.84, 18.14; HRMS (ESI-TOF) m/z Calcd for C$_{24}$H$_{26}$NO$_3$ [M+H]$^+$: 376.1907, found: 376.1907.

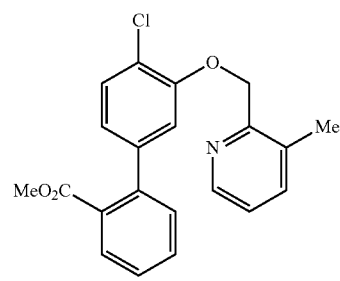

7h

Methyl 4'-chloro-3'-((3-methylpyridin-2-yl)methoxy)-[1,1'-biphenyl]-2-carboxylate (7h)

Substrate 3h was arylated following a slightly modified meta-arylation procedure for phenols. For this substrate, L12 was used in place of L14 and the reaction was run for 36 hours. After purification by preparative thin-layer chromatography, Compound 7h was obtained in 81% yield as a colorless solid. $^1$H NMR (400 MHz, CDCl$_3$) δ 8.42 (d, J=4.7 Hz, 1H), 7.83 (d, J=7.7 Hz, 1H), 7.56-7.49 (m, 2H), 7.42 (t, J=7.6 Hz, 1H), 7.35 (d, J=8.1 Hz, 1H), 7.30 (d, J=7.7 Hz, 1H), 7.20 (dd, J=7.7, 4.8 Hz, 1H), 7.14 (d, J=1.9 Hz, 1H), 6.82 (dd, J=8.1, 1.9 Hz, 1H), 5.29 (s, 2H), 3.62 (s, 3H), 2.50 (s, 3H); $^{13}$C NMR (100 MHz, CDCl$_3$) δ 168.71, 153.72, 153.63, 146.40, 141.40, 141.18, 138.50, 133.78, 131.33, 130.65, 130.56, 129.89, 129.65, 127.48, 123.60, 122.11, 121.68, 114.38, 72.13, 51.98, 18.23; HRMS (ESI-TOF) m/z Calcd for C$_{21}$H$_{19}$ClNO$_3$ [M+H]$^+$: 368.1048, found: 368.1053.

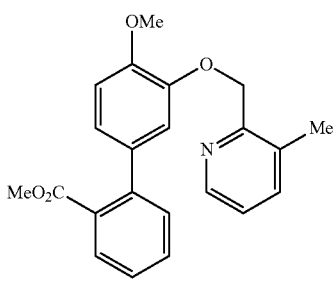

7g

Methyl 4'-methoxy-3'-((3-methylpyridin-2-yl)methoxy)-[1,1'-biphenyl]-2-carboxylate (7g)

Substrate 3g was arylated following the general meta-arylation procedure for phenols. After purification by preparative thin-layer chromatography, Compound 7g was obtained in 54% yield as a light yellow liquid. $^1$H NMR (400 MHz, CDCl3) δ 8.42 (d, J=4.9 Hz, 1H), 7.76 (d, J=7.7 Hz, 1H), 7.53-7.47 (m, 2H), 7.37 (t, J=7.6 Hz, 1H), 7.32 (d, J=7.7 Hz, 1H), 7.17 (dd, J=7.7, 4.8 Hz, 1H), 7.07 (d, J=1.2 Hz, 1H), 6.94-6.84 (m, 2H), 5.25 (s, 2H), 3.88 (s, 3H), 3.63 (s, 3H), 2.47 (s, 3H); $^{13}$C NMR (100 MHz, CDCl3) δ 169.39, 154.26, 149.19, 147.74, 146.49, 141.84, 138.36, 133.85, 133.43, 131.08, 130.96, 130.63, 129.58, 126.81, 123.35, 121.44, 114.84, 111.27, 72.02, 55.89, 51.96, 18.20; HRMS (ESI-TOF) m/z Calcd for C$_{22}$H$_{22}$NO$_4$[M+H]$^+$: 364.1543, found: 364.1547.

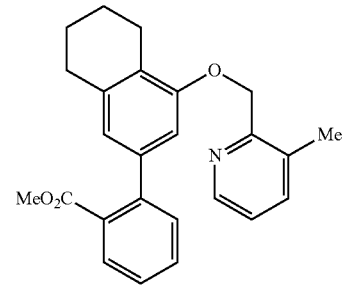

7i

Methyl 2-(4-((3-methylpyridin-2-yl)methoxy)-5,6,7,8-tetrahydronaphthalen-2-yl)benzoate (7i)

Substrate 3i was arylated following the general meta-arylation procedure for phenols. After purification by preparative thin-layer chromatography, Compound 7i was obtained in 90% yield as a light yellow liquid. $^1$H NMR (400 MHz, CDCl$_3$) δ 8.43 (d, J=4.7 Hz, 1H), 7.75 (d, J=7.9 Hz, 1H), 7.54-7.46 m, 2H), 7.41-7.33 (m, 2H), 7.18 (dd, J=7.6, 4.8 Hz, 1H), 6.82 (s, 1H), 6.68 (s, 1H), 5.17 (s, 2H), 3.66 (s, 3H), 2.78-2.74 (m, 2H), 2.71-2.65 (m, 2H), 2.43 (s, 3H), 1.82-1.72 m, 4H); $^{13}$C NMR (100 MHz, CDCl$_3$) δ 169.50, 156.15, 154.63, 146.45, 142.35, 138.65, 138.27, 138.14, 133.37, 131.08, 130.98, 130.58, 129.38, 126.80, 125.29, 123.33, 121.58, 108.53, 71.05, 51.99, 29.67, 23.04, 22.79, 22.70, 18.19; HRMS (ESI-TOF) m/z Calcd for C$_{25}$H$_{26}$NO$_3$ [M+H]$^+$: 388.1907, found: 388.1910.

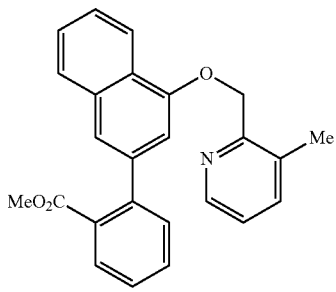

7j

Methyl 2-(4-((3-methylpyridin-2-yl)methoxy)naphthalen-2-yl)benzoate (7j)

Substrate 3j was arylated following the general meta-arylation procedure for phenols. After purification by preparative thin-layer chromatography, Compound 7j was obtained in 87% yield as a yellow liquid. $^1$H NMR (400 MHz, CDCl$_3$) δ 8.47 (d, J=4.8, 1.5 Hz, 1H), 8.24 (d, J=8.2 Hz, 1H), 7.84 (dd, J=7.6 Hz, 1H), 7.79 (d, J=8.0 Hz, 1H), 7.59-7.52 (m, 2H), 7.51-7.40 (m, 4H), 7.39 (s, 1H), 7.23 (dd, J=7.7, 4.9 Hz, 1H), 7.02 (d, J=1.4 Hz, 1H), 5.38 (s, 2H), 3.55 (s, 3H), 2.47 (s, 3H); $^{13}$C NMR (100 MHz, CDCl$_3$) δ 169.27, 154.25, 154.04, 146.57, 142.43, 139.06, 138.40, 134.23, 133.52, 131.19, 131.15, 130.84, 129.71, 127.66, 127.22, 126.70, 125.25, 124.76, 123.52, 121.98, 119.70, 106.67, 71.33, 51.97, 18.23; HRMS (ESI-TOF) m/z Calcd for C$_{25}$H$_{22}$NO$_3$ [M+H]$^+$: 384.1594, found: 384.1598.

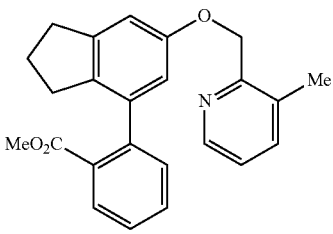

7k

Methyl 2-(6-((3-methylpyridin-2-yl)methoxy)-2,3-dihydro-1H-inden-4-yl)benzoate (7k)

Substrate 3k was arylated following the general meta-arylation procedure for phenols. After purification by preparative thin-layer chromatography, Compound 7k was obtained in 42% yield as a clear liquid. $^1$H NMR (400 MHz, CDCl$_3$) δ 8.44 (d, J=4.9 Hz, 1H), 7.88 (d, J=7.8 Hz, 1H), 7.54-7.48 (m, 2H), 7.39 (t, J=7.6 Hz, 1H), 7.31-7.23 (m, 1H), 7.18 (dd, J=7.7, 4.8 Hz, 1H), 6.92 (s, 1H), 6.69 (d, J=2.3 Hz, 1H), 5.18 (s, 2H), 3.62 (s, 3H), 2.93 (t, J=7.4 Hz, 2H), 2.55 (t, J=7.3 Hz, 2H), 2.43 (s, 3H), 2.06-1.94 (m, 2H); $^{13}$C NMR (100 MHz, CDCl$_3$) δ 168.28, 157.49, 154.57, 146.50, 145.21, 142.14, 138.50, 138.34, 134.70, 133.27, 131.35, 130.67, 130.38, 129.80, 127.03, 123.32, 113.01, 109.93, 71.11, 51.94, 33.41, 31.11, 25.59, 18.21; HRMS (ESI-TOF) m/z Calcd for C$_{24}$H$_{24}$NO$_3$ [M+H]$^+$: 374.1757, found: 374.1757.

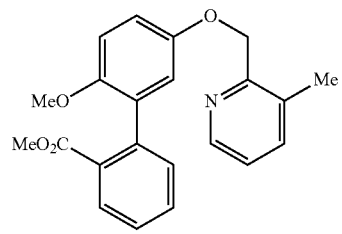

7l

Methyl 2'-methoxy-5'-((3-methylpyridin-2-yl)methoxy)-[1,1'-biphenyl]-2-carboxylate (7l)

Substrate 3l was arylated following the general meta-arylation procedure for phenols. Analysis of crude reaction mixture by $^1$H NMR showed the selectivity of mono- and di-products (mono:di=20>1). After purification by preparative thin-layer chromatography, Compound 7l was obtained in 58% yield as a light yellow liquid. $^1$H NMR (400 MHz, CDCl$_3$) δ 8.45 (d, J=4.3 Hz, 1H), 7.85 (dd, J=7.7, 1.4 Hz, 1H), 7.57-7.49 (m, 2H), 7.39 (td, J=7.6, 1.2 Hz, 1H), 7.31 (dd, J=7.6, 1.3 Hz, 1H), 7.19 (dd, J=7.6, 4.8 Hz, 1H), 7.02-6.96 (m, 2H), 6.80 (d, J=8.5 Hz, 1H), 5.19 (s, 2H), 3.63-3.68 (m, 6H), 2.44 (s, 3H); $^{13}$C NMR (100 MHz, CDCl$_3$) δ 168.52, 154.52, 152.76, 150.57, 146.55, 138.40, 138.36, 133.23, 131.62, 131.51, 131.37, 131.20, 129.30, 127.18, 123.36, 117.34, 114.11, 111.00, 71.48, 55.73, 51.68, 18.21; HRMS (ESI-TOF) m/z Calcd for C$_{22}$H$_{22}$NO$_4$ [M+H]$^+$: 364.1543, found: 364.1543.

Meta-Arylation of Other Heterocyclic Substrates

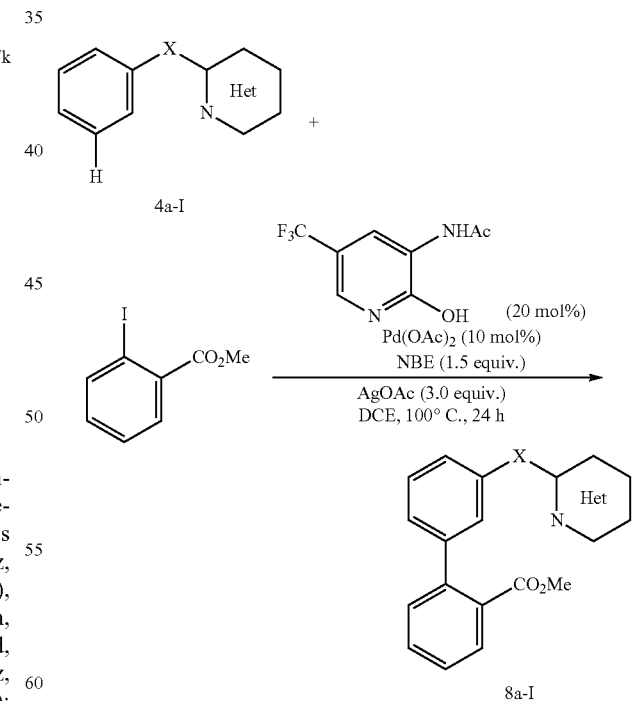

General Procedure for Meta-Arylation of Other Heterocycle Substrates:

Substrate 4 (0.1 mmol), methyl 2-iodobenzoate (43.0 μL, 0.3 mmol), Pd(OAc)$_2$ (2.2 mg, 10 mol %), L14 (4.4 mg, 20 mol %), AgOAc (50.1 mg, 0.3 mmol), 2-Norbornene (14.1 mg, 0.15 mmol) and CHCl₃ (1.0 mL) were added to a 2-dram vial. The vial was capped and closed tightly. Then the reaction mixture was then stirred at 90° C. for 24 hours. After cooling to room temperature, the mixture was passed through a pad of Celite® with DCM as the eluent to remove the insoluble precipitate. The resultant solution was concentrated and purified by preparative TLC to afford the desired arylated product. (In cases where mono:di ratios are possible, the selectivity was determined by $^1$H NMR.)

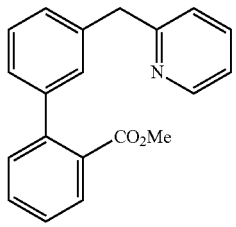

Methyl 3'-(pyridin-2-ylmethyl)-[1,1'-biphenyl]-2-carboxylate (8a)

Substrate 4a was arylated following the general meta-arylation procedure using 2-norbornene. Analysis of crude reaction mixture by $^1$H NMR showed the selectivity of mono- and di-products (mono:di=2:1). After purification by preparative thin-layer chromatography, Compounds 8a and 8a' were obtained in 92% total yield.

$^1$H NMR (400 MHz, CDCl₃) δ 8.58-8.53 (m, 1H), 7.79 (d, J=7.5 Hz, 1H), 7.58 (td, J=7.7, 1.8 Hz, 1H), 7.50 (t, J=7.5 Hz, 1H), 7.42-7.31 (m, 3H), 7.30-7.24 (m, 1H), 7.23-7.16 (m, 2H), 7.16-7.08 (m, 2H), 4.19 (s, 2H), 3.55 (s, 3H); $^{13}$C NMR (150 MHz, CDCl₃) δ 169.11, 160.85, 149.30, 142.23, 141.50, 139.17, 136.53, 131.15, 130.88, 130.64, 129.66, 129.10, 128.30, 128.04, 127.09, 126.38, 123.11, 121.25, 51.84, 44.62; HRMS (ESI-TOF) m/z Calcd for C₂₀H₁₈NO₂ [M+H]⁺: 304.1332, found: 304.1332.

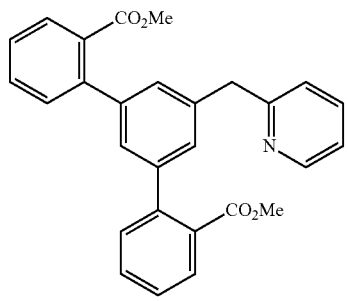

Dimethyl 5'-(pyridin-2-ylmethyl)-[1,1':3',1''-terphenyl]-2,2''-dicarboxylate (8a')

$^1$H NMR (400 MHz, CDCl₃) δ 8.55 (d, J=3.6 Hz, 1H), 7.82-7.76 (m, 2H), 7.60 (td, J=7.7, 1.8 Hz, 1H), 7.54-7.47 (m, 2H), 7.43-7.36 (m, 4H), 7.20 (s, 2H), 7.19-7.15 (m, 2H), 7.12 (dd, J=7.5, 5.0 Hz, 1H), 4.23 (s, 2H), 3.58 (s, 6H); $^{13}$C NMR (150 MHz, CDCl₃) δ 169.10, 160.77, 149.30, 141.94, 141.44, 138.84, 136.54, 131.15, 131.02, 130.67, 129.70, 128.12, 127.19, 126.46, 123.13, 121.30, 51.87, 44.56; HRMS (ESI-TOF) m/z Calcd for C₂₈H₂₄NO₄ [M+H]⁺: 438.1700, found: 438.1698.

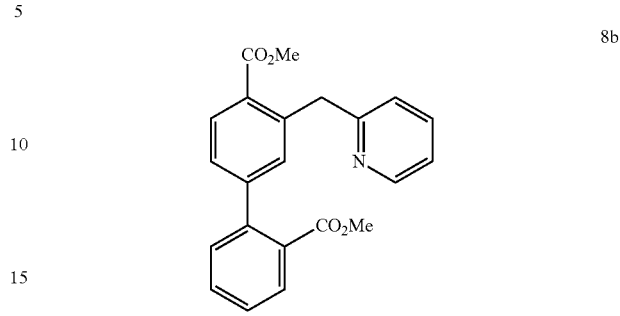

Dimethyl 5'-(pyridin-2-ylmethyl)-[1,1':3',1''-terphenyl]-2,2''-dicarboxylate (8b)

Substrate 4b was arylated following the general meta-arylation procedure using 2-norbornene. After purification by preparative thin-layer chromatography, Compound 8b was obtained in 92% yield. $^1$H NMR (400 MHz, CDCl₃) δ 8.55-8.49 (m, 1H), 8.00 (d, J=7.9 Hz, 1H), 7.84 (dd, J=7.7, 1.4 Hz, 1H), 7.59-7.48 (m, 2H), 7.42 (td, J=7.6, 1.3 Hz, 1H), 7.35 (dd, J=7.6, 1.3 Hz, 1H), 7.30-7.24 (m, 2H), 7.12-7.04 (m, 2H), 4.61 (s, 2H), 3.83 (s, 3H), 3.59 (s, 3H); $^{13}$C NMR (150 MHz, CDCl₃) δ 168.53, 167.72, 160.74, 149.08, 145.28, 141.29, 140.29, 136.36, 132.08, 131.38, 130.72, 130.56, 130.54, 129.98, 128.63, 127.70, 126.57, 122.88, 121.04, 51.96, 51.95, 42.53; HRMS (ESI-TOF) m/z Calcd for C₂₂H₂₀NO₄ [M+H]⁺: 362.1387, found: 362.1387.

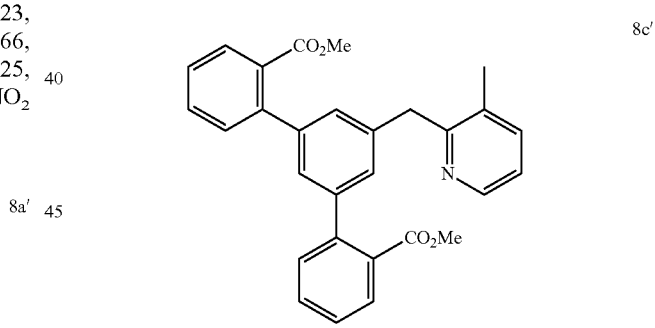

Dimethyl 5'-((3-methylpyridin-2-yl)methyl)-[1,1':3',1''-terphenyl]-2,2''-dicarboxylate (8c')

Substrate 4c was arylated following the general meta-arylation procedure using 2-norbornene. After purification by preparative thin-layer chromatography, Compound 8c' was obtained in 55% total yield as a sole product.

$^1$H NMR (400 MHz, CDCl₃) δ 8.42 (d, J=4.5 Hz, 1H), 7.77 (d, J=7.5 Hz, 2H), 7.49 (t, J=7.5 Hz, 2H), 7.43 (d, J=7.3 Hz, 1H), 7.41-7.34 (m, 4H), 7.14-7.06 (m, 4H), 4.26 (s, 2H), 3.57 (s, 6H), 2.29 (s, 3H); $^{13}$C NMR (150 MHz, CDCl₃) δ 169.11, 158.50, 146.81, 142.01, 141.26, 138.57, 138.06, 131.84, 131.12, 131.03, 130.69, 129.66, 127.59, 127.14, 126.23, 121.85, 51.85, 42.24, 19.06; HRMS (ESI-TOF) m/z Calcd for C₂₉H₂₆NO₄ [M+H]⁺: 452.1856, found: 452.1856.

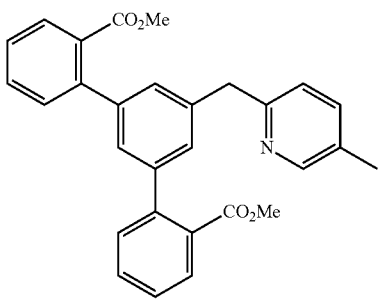

Dimethyl 5'-((5-methylpyridin-2-yl)methyl)-[1,1':3',1''-terphenyl]-2,2''-dicarboxylate (8d')

Substrate 4d was arylated following the general meta-arylation procedure using 2-norbornene. After purification by preparative thin-layer chromatography, Compound 8d' was obtained in 60% yield as a sole product. $^1$H NMR (400 MHz, CDCl$_3$) δ 8.37 (d, J=2.2 Hz, 1H), 7.82-7.76 (m, 2H), 7.50 (td, J=7.5, 1.4 Hz, 2H), 7.43-7.35 (m, 5H), 7.18 (d, J=1.6 Hz, 2H), 7.14 (t, J=1.6 Hz, 1H), 7.05 (d, J=7.9 Hz, 1H), 4.18 (s, 2H), 3.59 (s, 6H), 2.29 (s, 3H); $^{13}$C NMR (100 MHz, CDCl$_3$) δ 169.13, 157.76, 149.61, 141.99, 141.38, 139.18, 137.13, 131.13, 131.02, 130.69, 130.55, 129.69, 128.07, 127.17, 126.38, 122.61, 51.87, 44.07, 18.01; HRMS (ESI-TOF) m/z Calcd for C$_{29}$H$_{26}$NO$_4$ [M+H]$^+$: 452.1856, found: 452.1855.

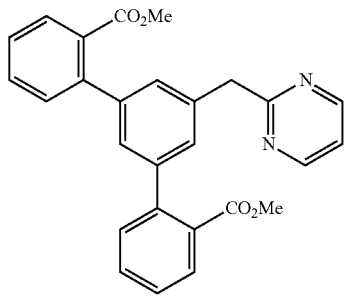

Dimethyl 5'-(pyrimidin-2-ylmethyl)-[1,1':3',1''-terphenyl]-2,2''-dicarboxylate (8e')

$^1$H NMR (400 MHz, CDCl$_3$) δ 8.69 (d, J=4.9 Hz, 2H), 7.79 (d, J=7.5 Hz, 2H), 7.50 (t, J=7.5 Hz, 2H), 7.42-7.36 (m, 4H), 7.28 (s, 2H), 7.26 (s, 1H), 7.17-7.12 (m, 1H), 4.36 (s, 2H), 3.59 (s, 6H); $^{13}$C NMR (150 MHz, CDCl$_3$) δ 169.75, 169.22, 157.29, 141.93, 141.28, 137.74, 131.14, 131.05, 130.72, 129.69, 128.06, 127.17, 126.63, 118.77, 51.89, 45.86; HRMS (ESI-TOF) m/z Calcd for C$_{27}$H$_{23}$N$_2$O$_4$ [M+H]$^+$: 439.1652, found: 439.1652.

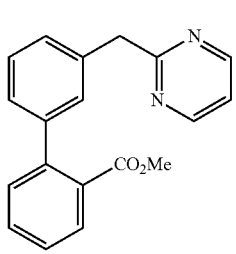

Methyl 3'-(pyrimidin-2-ylmethyl)-[1,1'-biphenyl]-2-carboxylate (8e)

Substrate 4e was arylated following the general meta-arylation procedure using 2-norbornene. Analysis of crude reaction mixture by $^1$H NMR showed the selectivity of mono- and di-products (mono:di=4:1). After purification by preparative thin-layer chromatography, Compounds 8e and 8e' were obtained in 64% total yield. $^1$H NMR (600 MHz, CDCl$_3$) δ 8.68 (d, J=4.9 Hz, 2H), 7.78 (ddd, J=7.7, 1.4, 0.6 Hz, 1H), 7.50 (td, J=7.6, 1.4 Hz, 1H); 7.41-7.32 (m, 4H), 7.31-7.29 (m, 1H), 7.18 (dt, J=6.9, 1.8 Hz, 1H), 7.13 (t, J=4.9 Hz, 1H), 4.33 (s, 2H), 3.57 (s, 3H); $^{13}$C NMR (150 MHz, CDCl$_3$) δ 169.89, 169.20, 157.29, 142.20, 141.40, 137.99, 131.13, 130.93, 130.69, 129.65, 129.10, 128.20, 128.05, 127.08, 126.59, 118.69, 51.87, 45.99; HRMS (ESI-TOF) m/z Calcd for C$_{19}$H$_{17}$N$_2$O$_2$ [M+H]$^+$: 305.1285, found: 305.1284.

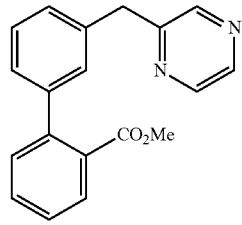

Methyl 3'-(pyrazin-2-ylmethyl)-[1,1'-biphenyl]-2-carboxylate (8f)

Substrate 4f was arylated following the general meta-arylation procedure using 2-norbornene. Analysis of crude reaction mixture by $^1$H NMR showed the selectivity of mono- and di-products (mono:di=2:1). After purification by preparative thin-layer chromatography, Compounds 8f and 8f' were obtained in 84% total yield.

$^1$H NMR (400 MHz, CDCl$_3$) δ 8.51 (d, J=2.0 Hz, 1H), 8.48 (s, 1H), 8.42 (d, J=2.5 Hz, 1H), 7.81 (d, J=7.9 Hz, 1H), 7.51 (t, J=7.4 Hz, 1H), 7.40 (t, J=8.0 Hz, 1H), 7.35 (d, J=7.6 Hz, 2H), 7.24-7.18 (m, 1H), 7.21 (d, J=8.0 Hz, 2H), 4.21 (s, 2H), 3.59 (s, 3H); $^{13}$C NMR (150 MHz, CDCl$_3$) δ 168.97, 156.41, 144.78, 144.08, 142.41, 142.09, 141.83, 137.81, 131.23, 130.79, 130.66, 129.76, 129.02, 128.48, 127.92, 127.23, 126.83, 51.92, 41.96; HRMS (ESI-TOF) m/z Calcd for C$_{19}$H$_{17}$N$_2$O$_2$ [M+H]$^+$: 305.1285, found: 305.1285.

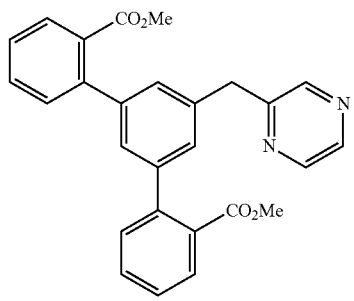

8f'

Dimethyl 5'-(pyrazin-2-ylmethyl)-[1,1':3',1''-terphenyl]-2,2''-dicarboxylate (8f')

$^1$H NMR (400 MHz, CDCl$_3$) δ 8.52 (d, J=1.6 Hz, 1H), 8.49 (s, 1H), 8.43 (d, J=2.6 Hz, 1H), 7.81 (d, J=7.7 Hz, 2H), 7.54-7.48 (m, 2H), 7.44-7.36 (m, 4H), 7.20 (s, 2H), 7.17 (s, 1H), 4.25 (s, 2H), 3.61 (s, 6H); $^{13}$C NMR (150 MHz, CDCl$_3$) δ 168.97, 156.39, 144.81, 144.07, 142.45, 141.82, 141.76, 137.46, 131.24, 130.94, 130.70, 129.82, 128.01, 127.34, 126.91, 51.97, 41.95; HRMS (ESI-TOF) m/z Calcd for C$_{27}$H$_{23}$N$_2$O$_4$ [M+H]$^+$: 439.1652, found: 439.1652.

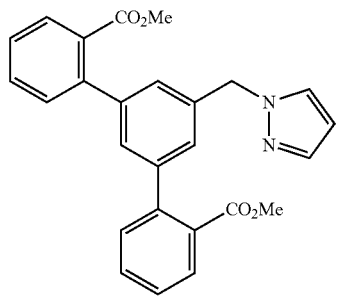

8g'

Dimethyl 5'-((1H-pyrazol-1-yl)methyl)-[1,1':3',1''-terphenyl]-2,2''-dicarboxylate (8g')

$^1$H NMR (400 MHz, CDCl$_3$) δ 7.82 (d, J=7.7 Hz, 2H), 7.57-7.48 (m, 3H), 7.45-7.35 (m, 5H), 7.22 (s, 1H), 7.15 (s, 2H), 6.29 (t, J=2.2 Hz, 1H), 5.39 (s, 2H), 3.62 (s, 6H); $^{13}$C NMR (150 MHz, CDCl$_3$) δ 168.80, 141.77, 141.64, 139.57, 136.00, 131.30, 130.82, 130.72, 129.88, 129.26, 128.10, 127.43, 126.71, 106.00, 55.79, 51.99; HRMS (ESI-TOF) m/z Calcd for C$_{26}$H$_{23}$N$_2$O$_4$ [M+H]$^+$: 427.1652, found: 427.1652.

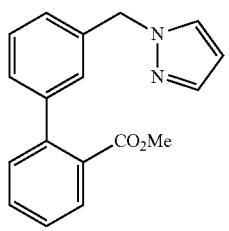

8g

Methyl 3'-((1H-pyrazol-1-yl)methyl)-[1,1'-biphenyl]-2-carboxylate (8g)

Substrate 4g was arylated following the general meta-arylation procedure using 2-norbornene. Analysis of crude reaction mixture by $^1$H NMR showed the selectivity of mono- and di-products (mono:di=1:2). After purification by preparative thin-layer chromatography, Compounds 8g and 8g' were obtained in 84% total yield.

$^1$H NMR (400 MHz, CDCl$_3$) δ 8.69 (d, J=4.9 Hz, 2H), 7.78 (d, J=7.7 Hz, 1H), 7.54-7.47 (m, 1H), 7.42-7.28 (m, 5H), 7.22-7.16 (m, 1H), 7.14 (t, J=4.9 Hz, 1H), 4.33 (s, 2H), 3.57 (s, 3H); $^{13}$C NMR (150 MHz, CDCl$_3$) δ 169.89, 169.22, 157.30, 142.20, 141.41, 137.99, 131.14, 130.92, 130.70, 129.66, 129.10, 128.21, 128.05, 127.08, 126.60, 118.70, 51.88, 45.98; HRMS (ESI-TOF) m/z Calcd for C$_{18}$H$_{17}$N$_2$O$_2$ [M+H]$^+$: 293.1285, found: 293.1285.

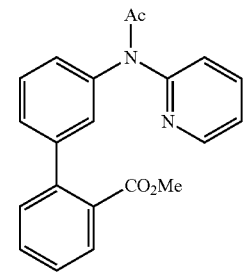

8h

Methyl 3'-(N-(pyridin-2-yl)acetamido)-[1,1'-biphenyl]-2-carboxylate (8h)

Substrate 4h was arylated following the general meta-arylation procedure using 2-norbornene. After purification by preparative thin-layer chromatography, Compound 8h was obtained in 60% yield as a sole product. $^1$H NMR (400 MHz, CDCl$_3$) δ 8.47-8.40 (m, 1H), 7.83 (dd, J=7.7, 1.4 Hz, 1H), 7.72 (td, J=7.8, 2.0 Hz, 1H), 7.57-7.35 (m, 5H), 7.35-7.28 (m, 2H), 7.22 (t, J=2.0 Hz, 1H), 7.17-7.10 (m, 1H), 3.59 (s, 3H), 2.15 (s, 3H); $^{13}$C NMR (150 MHz, CDCl$_3$) δ 171.03, 168.60, 155.16, 148.74, 142.68, 141.62, 141.37, 137.92, 131.38, 130.72, 130.60, 129.95, 129.14, 128.61, 127.52, 127.23, 121.43, 121.16, 51.97, 24.29; HRMS (ESI-TOF) m/z Calcd for C$_{21}$H$_{19}$N$_2$O$_3$ [M+H]$^+$: 347.1390, found: 347.1389.

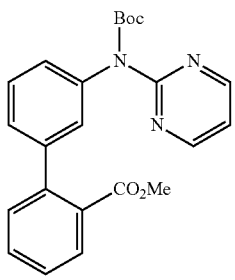

Methyl 3'-((tert-butoxycarbonyl)(pyrimidin-2-yl)amino)-[1,1'-biphenyl]-2-carboxylate (8i)

Substrate 4i was arylated following the general meta-arylation procedure using 2-norbornene. After purification by preparative thin-layer chromatography, 8i was obtained in 50% yield as a sole product. $^1$H NMR (400 MHz, CDCl$_3$) δ 8.66 (d, J=4.8 Hz, 2H), 7.82-7.77 (m, 1H), 7.51 (td, J=7.6, 1.4 Hz, 1H), 7.45-7.34 (m, 3H), 7.26-7.21 (m, 2H), 7.15 (t, J=2.0 Hz, 1H), 7.05 (t, J=4.8 Hz, 1H), 3.61 (s, 3H), 1.46 (s, 9H); $^{13}$C NMR (150 MHz, CDCl$_3$) δ 169.03, 161.28, 158.23, 153.14, 142.15, 141.49, 141.01, 131.21, 130.97, 130.62, 130.05, 129.77, 128.53, 127.61, 127.34, 126.79, 126.56, 117.27, 82.07, 51.95, 28.07; HRMS (ESI-TOF) m/z Calcd for C$_{23}$H$_{24}$N$_3$O$_4$ [M+H]$^+$: 406.1761, found: 406.1761.

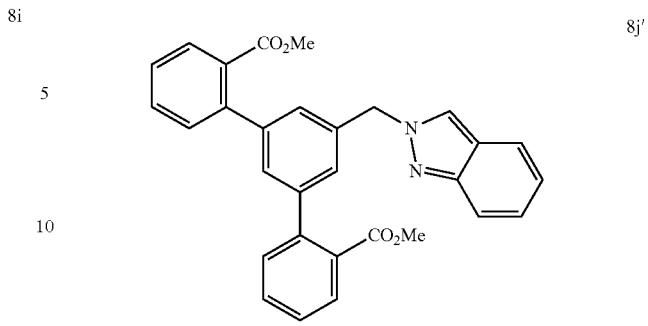

Dimethyl 5'-((2H-indazol-2-yl)methyl)-[1,1':3',1''-terphenyl]-2,2''-dicarboxylate (8j')

$^1$H NMR (400 MHz, CDCl$_3$) δ 8.04 (s, 1H), 7.79 (d, J=7.5 Hz, 2H), 7.74 (d, J=8.0 Hz, 1H), 7.49 (t, J=7.3 Hz, 2H), 7.43-7.31 (m, 6H), 7.15 (d, J=11.4 Hz, 4H), 5.66 (s, 2H), 3.49 (s, 6H); $^{13}$C NMR (150 MHz, CDCl$_3$) δ 168.82, 141.73, 141.66, 139.49, 136.42, 133.40, 131.23, 130.88, 130.72, 129.83, 127.90, 127.37, 126.38, 126.25, 124.42, 121.16, 120.67, 109.33, 52.97, 51.82; HRMS (ESI-TOF) m/z Calcd for C$_{30}$H$_{25}$N$_2$O$_4$ [M+H]$^+$: 477.1809, found: 477.1810.

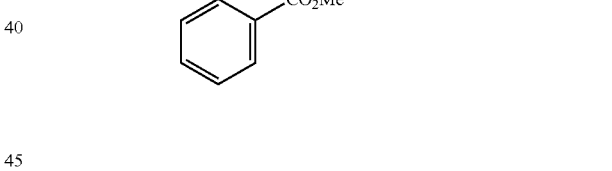

Methyl 3'-((2H-indazol-2-yl)methyl)-[1,1'-biphenyl]-2-carboxylate (8j)

Substrate 4j was arylated following the general meta-arylation procedure using 2-norbornene. Analysis of crude reaction mixture by $^1$H NMR showed the selectivity of mono- and di-products (mono:di=3:1). After purification by preparative thin-layer chromatography, Compounds 8j and 8j' were obtained in 74% total yield. $^1$H NMR (400 MHz, CDCl$_3$) δ 8.05 (d, J=0.9 Hz, 1H), 7.82-7.76 (m, 1H), 7.78-7.70 (m, 1H), 7.49 (td, J=7.5, 1.4 Hz, 1H), 7.43-7.27 (m, 5H), 7.24-7.10 (m, 4H), 5.64 (s, 2H), 3.47 (d, J=0.5 Hz, 3H); $^{13}$C NMR (100 MHz, CDCl$_3$) δ 168.82, 141.96, 141.83, 139.52, 136.68, 133.39, 131.24, 130.75, 130.68, 129.79, 128.43, 127.80, 127.28, 127.22, 126.38, 126.12, 124.38, 121.14, 120.64, 109.29, 52.96, 51.80; HRMS (ESI-TOF) m/z Calcd for C$_{22}$H$_{19}$N$_2$O$_2$ [M+H]$^+$: 343.1441, found: 343.1442.

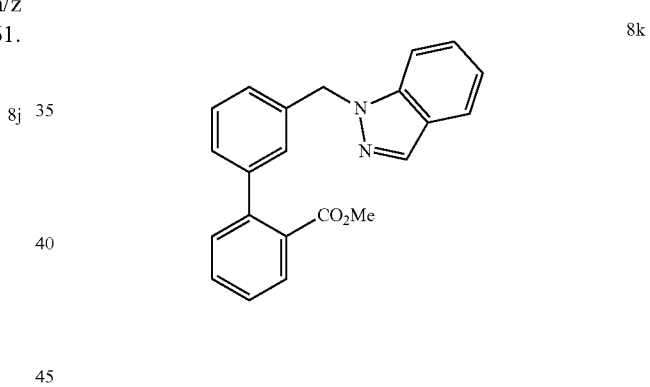

Methyl 3'-((1H-indazol-1-yl)methyl)-[1,1'-biphenyl]-2-carboxylate (8k)

Substrate 4k was arylated following the general meta-arylation procedure using 2-norbornene. Analysis of crude reaction mixture by $^1$H NMR showed the selectivity of mono- and di-products (mono:di=3:1). After purification by preparative thin-layer chromatography, 8k and 8k' was obtained in 50% total yield.

$^1$H NMR (400 MHz, CDCl$_3$) δ 8.04 (s, 1H), 7.79 (d, J=7.5 Hz, 1H), 7.74 (d, J=8.1 Hz, 1H), 7.48 (td, J=7.6, 1.4 Hz, 1H), 7.41-7.26 (m, 5H), 7.24-7.10 (m, 4H), 5.63 (s, 2H), 3.47 (s, 3H); $^{13}$C NMR (100 MHz, CDCl$_3$) δ 168.81, 141.94, 141.81, 139.51, 136.68, 133.38, 131.23, 130.74, 130.67, 129.78, 128.43, 127.79, 127.26, 127.21, 126.37, 126.11, 124.37, 121.13, 120.63, 109.28, 52.94, 51.79; HRMS (ESI-TOF) m/z Calcd for C$_{22}$H$_{19}$N$_2$O$_2$ [M+H]$^+$: 343.1441, found: 343.1440.

Scope of Aryl Iodides

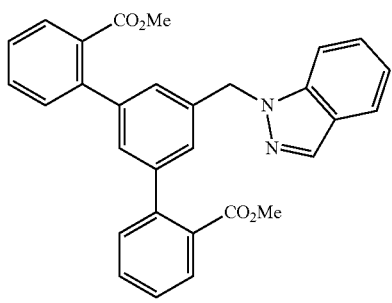

8k'

Dimethyl 5'-((1H-indazol-1-yl)methyl)-[1,1':3'1"-terphenyl]-2,2"-dicarboxylate (8k')

¹H NMR (400 MHz, CDCl₃) δ 8.04 (s, 1H), 7.79 (d, J=7.9 Hz, 2H), 7.74 (d, J=8.1 Hz, 1H), 7.49 (t, J=7.4 Hz, 2H), 7.44-7.31 (m, 6H), 7.20-7.10 (m, 4H), 5.66 (s, 2H), 3.49 (s, 6H); ¹³C NMR (150 MHz, CDCl₃) δ 168.81, 141.73, 141.66, 139.49, 136.42, 133.40, 131.23, 130.88, 130.72, 129.83, 127.90, 127.37, 126.38, 126.25, 124.42, 121.16, 120.67, 109.33, 52.97, 51.82; HRMS (ESI-TOF) m/z Calcd for $C_{30}H_{25}N_2O_4$ [M+H]⁺: 477.1809, found: 477.1808.

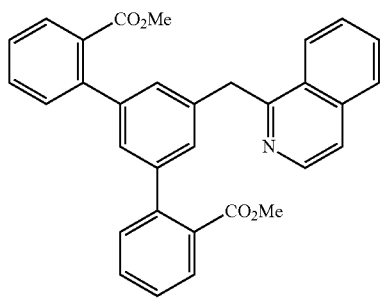

8l'

Dimethyl 5'-(isoquinolin-1-ylmethyl)-[1,1':3',1"-terphenyl]-2,2"-dicarboxylate (8l')

Substrate 4l was arylated following the general meta-arylation procedure using 2-norbornene. After purification by preparative thin-layer chromatography, Compound 8l' was obtained in 78% yield as a sole product. ¹H NMR (400 MHz, CDCl₃) δ 8.49 (d, J=5.7 Hz, 1H), 8.21 (d, J=8.4 Hz, 1H), 7.82 (d, J=8.1 Hz, 1H), 7.76 (d, J=7.7 Hz, 2H), 7.64 (t, J=7.5 Hz, 1H), 7.60-7.53 (m, 2H), 7.48 (t, J=7.9 Hz, 2H), 7.41-7.32 (m, 4H), 7.22 (s, 2H), 7.10 (s, 1H), 4.73 (s, 2H), 3.41 (s, 6H); ¹³C NMR (150 MHz, CDCl₃) δ 169.07, 159.85, 142.02, 141.89, 141.41, 139.00, 136.61, 131.11, 131.03, 130.67, 129.86, 129.66, 127.57, 127.36, 127.23, 127.17, 127.14, 126.37, 125.90, 119.90, 51.70, 42.12; HRMS (ESI-TOF) m/z Calcd for $C_{32}H_{26}NO_4$ [M+H]⁺: 488.1856, found: 488.1857.

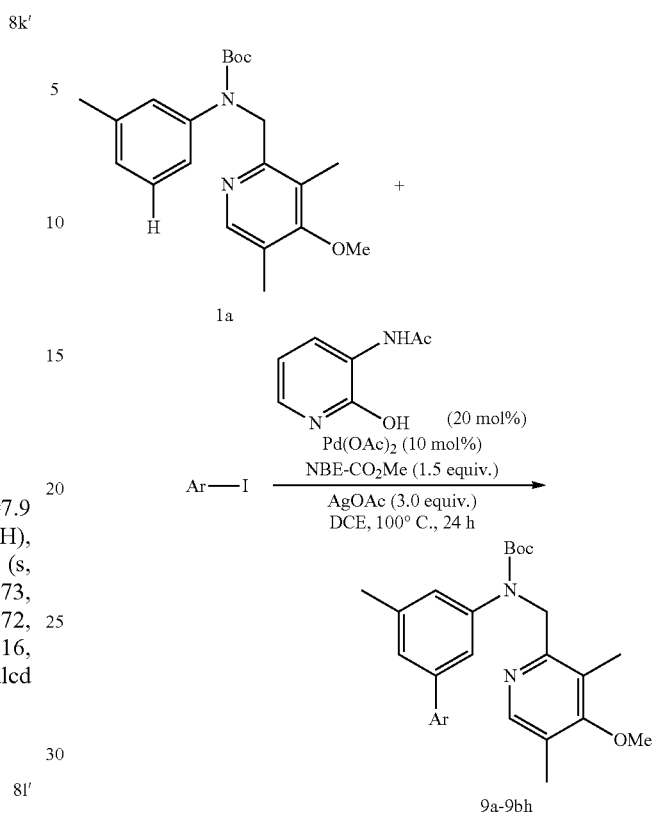

General Procedure for Meta-Arylation of Anilines:

Substrate 1a (0.1 mmol), Ar—I (0.2 mmol), Pd(OAc)₂ (2.2 mg, 10 mol %), Ligand (3.0 mg, 20 mol %), AgOAc (50.1 mg, 0.3 mmol), NBE-CO₂Me (21.6 mg, 0.15 mmol) and DCE (0.5 mL) were added to a 2-dram vial. The vial was capped and closed tightly. The reaction mixture was then stirred at 100° C. for 24 hours. After cooling to room temperature, the mixture was passed through a pad of Celite® with DCM as the eluent to remove the insoluble precipitate. The resulting solution was concentrated and purified by preparative TLC plate to afford the desired arylated product.

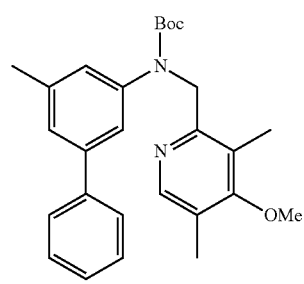

9a tert-Butyl ((4-methoxy-3,5-dimethylpyridin-2-yl)methyl)(5-methyl-[1,1'-biphenyl]-3-yl)carbamate (9a)

Following the general meta-arylation procedure using NEE-CO₂Me, Compound 9a was obtained in 87% yield as a colorless liquid. ¹H NMR (400 MHz, CDCl₃) δ 8.17 (s, 1H), 7.47 (d, J=7.5 Hz, 2H), 7.38 (t, J=7.5 Hz, 2H), 7.29 (t, J=7.3 Hz, 1H), 7.23 (s, 1H), 7.14 (s, 1H), 7.07 (s, 1H), 4.94 (s, 2H), 3.71 (s, 3H), 2.22 (s, 3H), 2.21 (s, 3H), 1.41 (s, 9H); $^{13}$C NMR (150 MHz, CDCl$_3$) δ 163.64, 155.20, 154.75, 148.96, 143.04, 141.14, 141.05, 138.35, 128.55, 127.08, 125.85, 125.23, 124.64, 123.74, 122.61, 80.25, 59.82, 53.55, 28.30, 21.46, 13.19, 10.44; HRMS (ESI-TOF) m/z Calcd for C$_{27}$H$_{33}$N$_2$O$_3$ [M+H]$^+$: 433.2486, found: 433.2487.

7.04 (s, 1H), 4.93 (s, 2H), 3.71 (s, 3H), 2.36 (s, 3H), 2.32 (s, 3H), 2.21 (s, 6H), 1.41 (s, 9H); $^{13}$C NMR (150 MHz, CDCl$_3$) δ 163.63, 155.21, 154.77, 148.94, 142.99, 141.04, 138.26, 138.15, 136.82, 129.26, 129.24, 126.89, 125.60, 125.04, 124.61, 123.73, 122.40, 80.20, 59.81, 53.55, 28.29, 28.26, 21.45, 21.05, 13.17, 10.42; HRMS (ESI-TOF) m/z Calcd for C$_{28}$H$_{35}$N$_2$O$_3$ [M+H]$^+$: 447.2642, found: 447.2643.

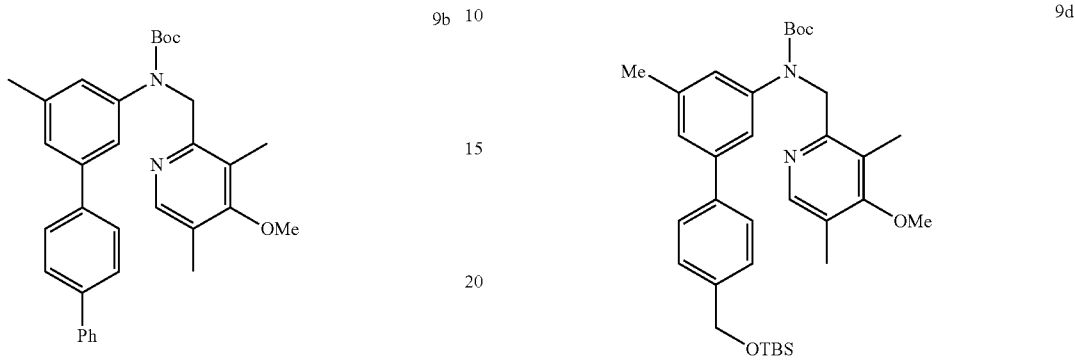

tert-Butyl ((4-methoxy-3,5-dimethylpyridin-2-yl)methyl)(5-methyl-[1,1':4',1''-terphenyl]-3-yl)carbamate (9b)

Following the general meta-arylation procedure using NBE-CO$_2$Me, Compound 9b was obtained in 79% yield as a colorless solid. $^1$H NMR (400 MHz, CDCl$_3$) δ 8.19 (s, 1H), 7.62 (d, J=8.0 Hz, 4H), 7.56 (d, J=8.1 Hz, 2H), 7.44 (t, J=7.6 Hz, 2H), 7.34 (t, J=7.3 Hz, 1H), 7.29 (s, 1H), 7.19 (s, 1H), 7.09 (s, 1H), 4.95 (s, 2H), 3.72 (s, 3H), 2.35 (s, 3H), 2.23 (s, 3H), 2.21 (s, 3H), 1.42 (s, 9H); $^{13}$C NMR (150 MHz, CDCl$_3$) δ 163.65, 155.20, 154.75, 148.97, 143.13, 140.67, 140.60, 139.94, 138.41, 137.83, 128.74, 127.41, 127.29, 127.25, 126.97, 125.97, 125.09, 124.65, 123.73, 122.48, 80.26, 59.82, 53.54, 28.30, 21.48, 13.19, 10.44; HRMS (ESI-TOF) m/z Calcd for C$_{33}$H$_{37}$N$_2$O$_3$ [M+H]$^+$: 509.2799, found: 509.2799.

tert-Butyl (4'-(((tert-butyldimethylsilyl)oxy)methyl)-5-methyl-[1,1'-biphenyl]-3-yl)((4-methoxy-3,5-dimethylpyridin-2-yl)methyl)carbamate (9d)

Following the general meta-arylation procedure using NBE-CO$_2$Me, Compound 9d was obtained in 83% yield as a light yellow liquid. $^1$H NMR (400 MHz, CDCl$_3$) δ 8.17 (s, 1H), 7.44 (d, J=8.1 Hz, 2H), 7.33 (d, J=8.1 Hz, 2H), 7.21 (s, 1H), 7.14 (s, 1H), 7.05 (s, 1H), 4.94 (s, 2H), 4.76 (s, 2H), 3.71 (s, 3H), 2.33 (s, 3H), 2.21 (s, 3H), 2.21 (s, 3H), 1.41 (s, 9H), 0.95 (s, 9H), 0.11 (s, 6H); $^{13}$C NMR (150 MHz, CDCl$_3$) δ 163.65, 155.19, 154.76, 148.95, 142.98, 140.98, 140.34, 139.66, 138.30, 126.89, 126.29, 125.75, 125.15, 124.64, 123.77, 122.51, 80.23, 64.73, 59.81, 53.54, 28.29, 25.95, 21.46, 18.42, 13.18, 10.44, −5.24; HRMS (ESI-TOF) m/z Calcd for C$_{34}$H$_{49}$N$_2$O$_4$Si [M+H]$^+$: 577.3456, found: 577.3456.

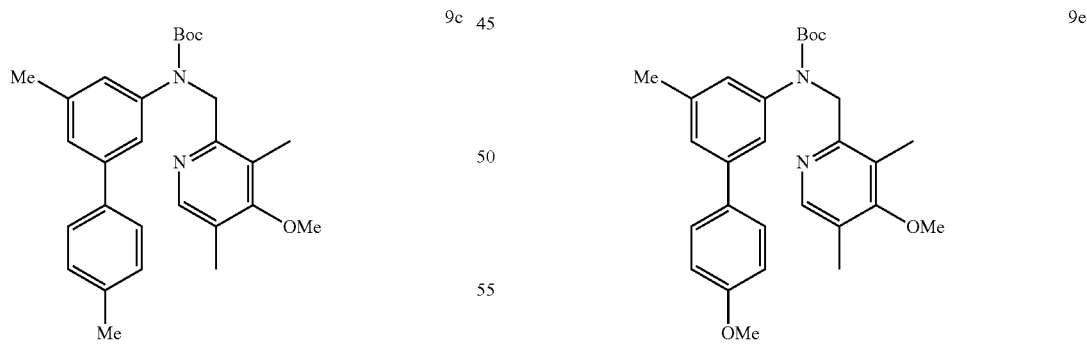

tert-Butyl (4',5-dimethyl-[1,1'-biphenyl]-3-yl)((4-methoxy-3,5-dimethylpyridin-2-yl)methyl)carbamate (9c)

Following the general meta-arylation procedure using NBE-CO$_2$Me, Compound 9c was obtained in 82% yield as a colorless liquid. $^1$H NMR (400 MHz, CDCl$_3$) δ 8.17 (s, 1H), 7.37 (d, J=7.9 Hz, 2H), 7.23-7.21 (m, 3H), 7.13 (s, 1H), tert-Butyl ((4-methoxy-3,5-dimethylpyridin-2-yl)methyl)-(4'-methoxy-5-methyl-[1,1'-biphenyl]-3-yl)carbamate (9e)

Following the general meta-arylation procedure using NBE-CO$_2$Me, Compound 9e was obtained in 81% yield as a colorless liquid. $^1$H NMR (400 MHz, CDCl$_3$) δ 8.17 (s, 1H), 7.41 (d, J=8.5 Hz, 2H), 7.19 (s, 1H), 7.10 (s, 1H), 7.02

(s, 1H), 6.92 (d, J=8.5 Hz, 2H), 4.93 (s, 2H), 3.83 (s, 3H), 3.71 (s, 3H), 2.32 (s, 3H), 2.21 (s, 6H), 1.41 (s, 9H); $^{13}$C NMR (150 MHz, CDCl$_3$) δ 163.63, 158.98, 155.22, 154.77, 148.94, 143.01, 140.72, 138.27, 133.59, 128.06, 125.28, 124.82, 124.62, 123.74, 122.17, 113.98, 80.20, 59.82, 55.29, 53.55, 28.30, 21.46, 13.19, 10.43; HRMS (ESI-TOF) m/z Calcd for C$_{28}$H$_{35}$N$_2$O$_4$ [M+H]$^+$: 463.2591, found: 463.2591.

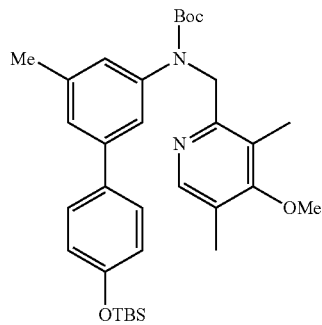

9f tert-Butyl (4'-((tert-butyldimethylsilyl)oxy)-5-methyl-[1,1'-biphenyl]-3-yl)((4-methoxy-3,5-dimethyl-pyridin-2-yl)methyl)carbamate (9f)

Following the general meta-arylation procedure using NBE-CO$_2$Me, Compound 9f was obtained in 65% yield as a colorless liquid. $^1$H NMR (400 MHz, CDCl$_3$) δ 8.17 (s, 1H), 7.34 (d, J=8.3 Hz, 2H), 7.18 (s, 1H), 7.10 (s, 1H), 7.01 (s, 1H), 6.84 (d, J=8.2 Hz, 2H), 4.94 (s, 2H), 3.71 (s, 3H), 2.31 (s, 3H), 2.22 (s, 3H), 2.21 (s, 3H), 1.41 (s, 9H), 0.99 (s, 9H), 0.21 (s, 6H); $^{13}$C NMR (150 MHz, CDCl$_3$) δ 163.66, 155.23, 155.11, 154.77, 148.92, 142.91, 140.82, 138.24, 134.12, 128.00, 125.30, 124.88, 124.64, 123.82, 122.24, 120.14, 80.19, 59.81, 53.55, 28.30, 25.68, 21.45, 18.21, 13.18, 10.45, −4.40; HRMS (ESI-TOF) m/z Calcd for C$_{33}$H$_{47}$N$_2$O$_4$Si [M+H]$^+$: 563.3300, found: 563.3300.

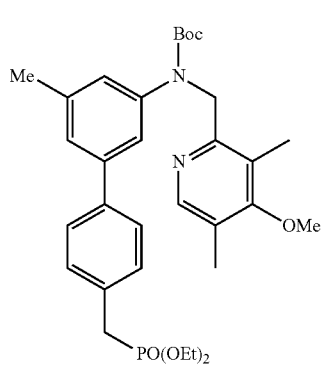

9g tert-Butyl (4'-((diethoxyphosphoryl)methyl)-5-methyl-[1,1'-biphenyl]-3-yl)((4-methoxy-3,5-dimethyl-pyridin-2-yl)methyl)carbamate (9g)

Following the general meta-arylation procedure using NBE-CO$_2$Me, Compound 9g was obtained in 92% yield as a colorless liquid. $^1$H NMR (400 MHz, CDCl$_3$) δ 8.17 (s, 1H), 7.43 (d, J=7.9 Hz, 2H), 7.31 (dd, J=8.3, 2.5 Hz, 2H), 7.23 (s, 1H), 7.13 (s, 1H), 7.06 (s, 1H), 4.94 (s, 2H), 4.12-3.94 (m, 4H), 3.72 (s, 3H), 3.17 (d, J=21.6 Hz, 2H), 2.33 (s, 3H), 2.24-2.19 (m, 6H), 1.41 (s, 9H), 1.26 (t, J=7.0 Hz, 6H); $^{13}$C NMR (150 MHz, CDCl$_3$) δ 163.63, 155.14, 154.72, 148.92, 143.06, 140.62, 139.56 (d, J=4.1 Hz), 138.35, 130.43 (d, J=9.0 Hz), 129.95 (d, J=6.6 Hz), 127.15 (d, J=3.3 Hz), 125.84, 125.03, 124.63, 123.71, 122.39, 80.25, 62.12 (d, J=7.1 Hz), 59.81, 53.50, 33.36 (d, J=138.4 Hz), 28.26, 21.43, 16.35 (d, J=6.2 Hz), 13.17, 10.41; HRMS (ESI-TOF) m/z Calcd for C$_{32}$H$_{44}$N$_2$O$_6$P [M+H]$^+$: 583.2932, found: 583.2931.

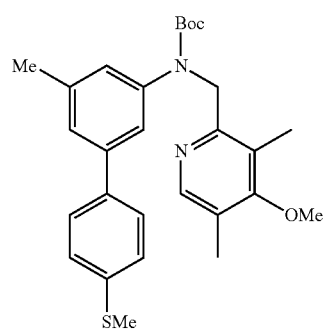

9h tert-Butyl ((4-methoxy-3,5-dimethylpyridin-2-yl)methyl)(5-methyl-4'-(methylthio)-[1,1'-biphenyl]-3-yl)carbamate (9h)

Following the general meta-arylation procedure using NBE-CO$_2$Me, Compound 9h was obtained in 70% yield as a colorless liquid. $^1$H NMR (400 MHz, CDCl$_3$) δ 8.17 (s, 1H), 7.40 (d, J=8.2 Hz, 2H), 7.27 (d, J=9.0 Hz, 2H), 7.22 (s, 1H), 7.12 (s, 1H), 7.06 (s, 1H), 4.93 (s, 2H), 3.72 (s, 3H), 2.50 (s, 3H), 2.33 (s, 3H), 2.21 (s, 6H), 1.41 (s, 9H); $^{13}$C NMR (150 MHz, CDCl$_3$) δ 163.65, 155.18, 154.74, 148.96, 143.14, 140.44, 138.42, 137.90, 137.33, 127.41, 126.80, 125.81, 124.87, 124.64, 123.72, 122.26, 80.27, 59.84, 53.54, 28.30, 21.47, 15.92, 13.20, 10.43; HRMS (ESI-TOF) m/z Calcd for C$_{28}$H$_{35}$N$_2$O$_3$S [M+H]$^+$: 479.2363, found: 479.2362.

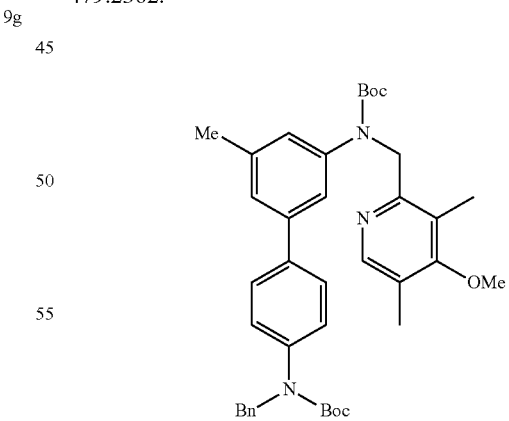

9i tert-Butyl (4'-(benzyl(tert-butoxycarbonyl)amino)-5-methyl-[1,1'-biphenyl]-3-yl)((4-methoxy-3,5-dimethylpyridin-2-yl)methyl)carbamate (9i)

Following the general meta-arylation procedure using NBE-CO$_2$Me, Compound 9i was obtained in 80% yield as a colorless solid. $^1$H NMR (400 MHz, CDCl$_3$) δ 8.16 (s, 1H), 7.38 (d, J=8.4 Hz, 2H), 7.33-7.27 (m, 2H), 7.27-7.14 (m, 6H), 7.10 (s, 1H), 7.05 (s, 1H), 4.92 (s, 2H), 4.85 (s, 2H), 3.70 (s, 3H), 2.31 (s, 3H), 2.24-2.16 m, 6H), 1.43 (s, 9H), 1.40 (s, 9H); $^{13}$C NMR (150 MHz, CDCl$_3$) δ 163.63, 155.14, 154.74, 154.71, 148.94, 143.06, 141.90, 140.43, 138.61, 138.38, 138.33, 128.36, 127.29, 127.21, 127.02, 126.38, 125.79, 125.00, 124.61, 123.68, 122.39, 80.61, 80.24, 59.81, 53.89, 53.50, 28.26, 21.43, 13.17, 10.41; HRMS (ESI-TOF) m/z Calcd for C$_{39}$H$_{48}$N$_3$O$_5$ [M+H]$^+$: 638.3588, found: 638.3588.

a colorless liquid. $^1$H NMR (400 MHz, CDCl$_3$) δ 8.17 (s, 1H), 7.40 (d, J=8.6 Hz, 2H), 7.34 (d, J=8.5 Hz, 2H), 7.22 (s, 1H), 7.10 (s, 1H), 7.08 (s, 1H), 4.93 (s, 2H), 3.72 (s, 3H), 2.33 (s, 3H), 2.22 (s, 3H), 2.21 (s, 3H), 1.41 (s, 9H); $^{13}$C NMR (150 MHz, CDCl$_3$) δ 163.66, 155.13, 154.67, 148.94, 143.20, 139.89, 139.48, 138.55, 133.14, 128.69, 128.30, 126.14, 124.98, 124.68, 123.71, 122.39, 80.33, 59.83, 53.49, 28.27, 21.44, 13.19, 10.42. HRMS (ESI-TOF) m/z Calcd for C$_{27}$H$_{32}$ClN$_2$O$_3$ [M+H]$^+$: 467.2096, found: 467.2096.

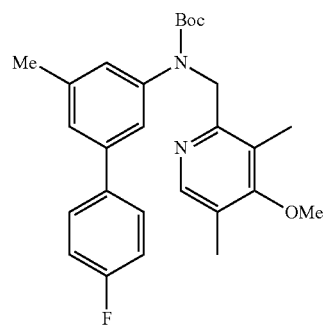

tert-Butyl (4'-fluoro-5-methyl-[1,1'-biphenyl]-3-yl)((4-methoxy-3,5-dimethylpyridin-2-yl)methyl)carbamate (9j)

Following the general meta-arylation procedure using NBE-CO$_2$Me, Compound 9j was obtained in 92% yield as a colorless liquid. $^1$H NMR (400 MHz, CDCl$_3$) δ 8.17 (s, 1H), 7.47-7.39 (m, 2H), 7.21 (s, 1H), 7.12-7.02 (m, 4H), 4.93 (s, 2H), 3.72 (s, 3H), 2.33 (s, 3H), 2.22 (s, 3H), 2.21 (s, 3H), 1.41 (s, 9H); $^{13}$C NMR (150 MHz, CDCl$_3$) δ 163.65, 162.31 (d, J=246.4 Hz), 155.17, 154.69, 148.93, 143.13, 140.15, 138.45, 137.13, 128.59 (d, J=8.3 Hz), 125.82, 125.05, 124.65, 123.71, 122.45, 115.38 (d, J=21.1 Hz), 80.29, 59.82, 53.51, 28.27, 21.43, 13.18, 10.42; $^{19}$F NMR (376 MHz, CDCl$_3$) δ -116.22; HRMS (ESI-TOF) m/z Calcd for C$_{27}$H$_{32}$FN$_2$O$_3$ [M+H]$^+$: 451.2391, found: 451.2391.

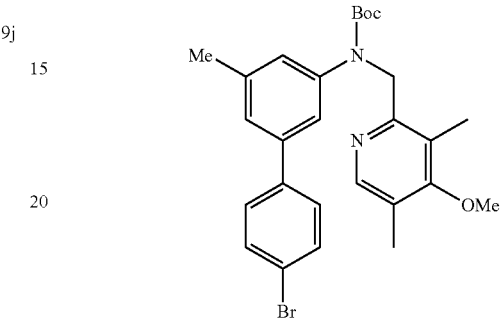

tert-Butyl (4'-bromo-5-methyl-[1,1'-biphenyl]-3-yl)((4-methoxy-3,5-dimethylpyridin-2-yl)methyl)carbamate (9l)

Following the general meta-arylation procedure using NBE-CO$_2$Me, Compound 9l was obtained in 82% yield as a colorless solid. $^1$H NMR (400 MHz, CDCl$_3$) δ 8.17 (s, 1H), 7.50 (d, J=8.3 Hz, 2H), 7.34 (d, J=8.2 Hz, 2H), 7.22 (s, 1H), 7.12-7.05 (m, 2H), 4.93 (s, 2H), 3.72 (s, 3H), 2.33 (s, 3H), 2.25-2.18 (m, 6H), 1.40 (s, 9H); $^{13}$C NMR (150 MHz, CDCl$_3$) δ 163.66, 155.13, 154.67, 148.94, 143.24, 139.95, 139.90, 138.57, 131.64, 128.66, 126.20, 124.92, 124.67, 123.69, 122.35, 121.31, 80.33, 59.83, 53.49, 28.27, 21.43, 13.20, 10.42; HRMS (ESI-TOF) m/z Calcd for C$_{27}$H$_{32}$BrN$_2$O$_3$ [M+H]$^+$: 511.1591, found: 511.1592.

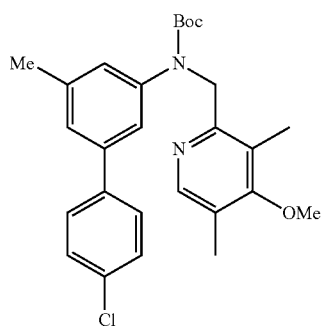

tert-Butyl (4'-chloro-5-methyl-[1,1'-biphenyl]-3-yl)((4-methoxy-3,5-dimethylpyridin-2-yl)methyl)carbamate (9k)

Following the general meta-arylation procedure using NBE-CO$_2$Me, Compound 9k was obtained in 83% yield as

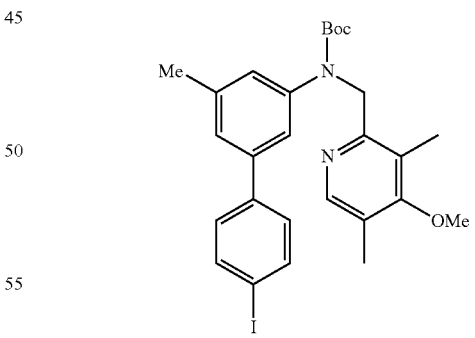

tert-Butyl (4'-iodo-5-methyl-[1,1'-biphenyl]-3-yl)((4-methoxy-3,5-dimethylpyridin-2-yl)methyl)carbamate (9m)

Following the general meta-arylation procedure using NBE-CO$_2$Me, Compound 9m was obtained in 67% yield as a colorless solid. $^1$H NMR (400 MHz, CDCl$_3$) δ 8.16 (s, 1H), 7.70 (d, J=8.1 Hz, 2H), 7.25-7.17 (m, 3H), 7.09 (s, 2H), 4.93

(s, 2H), 3.72 (s, 3H), 2.33 (s, 3H), 2.21 (s, 6H), 1.40 (s, 9H); ¹³C NMR (150 MHz, CDCl₃) δ 163.66, 155.12, 154.67, 148.95, 143.25, 140.56, 139.96, 138.59, 137.63, 128.94, 126.26, 124.87, 124.68, 123.71, 122.30, 92.81, 80.34, 59.84, 53.49, 28.27, 21.44, 13.20, 10.43; HRMS (ESI-TOF) m/z Calcd for C₂₇H₃₂IN₂O₃ [M+H]⁺: 559.1452, found: 559.1451.

2.62 (s, 3H), 2.35 (s, 3H), 2.23 (s, 3H), 2.22 (s, 3H), 1.41 (s, 9H); ¹³C NMR (150 MHz, CDCl₃) δ 197.71, 163.67, 155.08, 154.65, 148.95, 145.64, 143.31, 139.79, 138.66, 135.69, 128.72, 127.14, 126.79, 125.22, 124.70, 123.69, 122.68, 80.39, 59.83, 53.47, 28.26, 26.61, 21.44, 13.19, 10.42; HRMS (ESI-TOF) m/z Calcd for C₂₉H₃₅N₂O₄ [M+H]⁺: 475.2591, found: 475.2591.

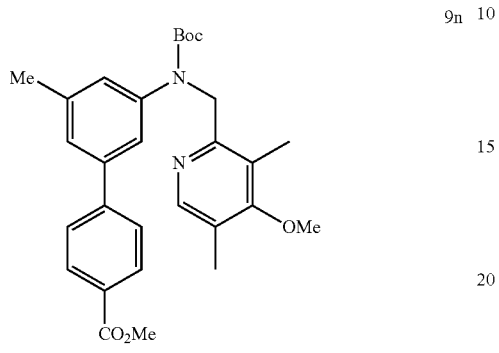

Methyl 3'-((tert-butoxycarbonyl)((4-methoxy-3,5-dimethylpyridin-2-yl)methyl)amino)-5'-methyl-[1,1'-biphenyl]-4-carboxylate (9n)

Following the general meta-arylation procedure using NBE-CO₂Me, Compound 9n was obtained in 92% yield as a colorless liquid. ¹H NMR (400 MHz, CDCl₃) δ 8.17 (s, 1H), 8.05 (d, J=8.2 Hz, 2H), 7.54 (d, J=8.2 Hz, 2H), 7.29 (s, 1H), 7.18 (s, 1H), 7.12 (s, 1H), 4.94 (s, 2H), 3.93 (s, 3H), 3.72 (s, 3H), 2.35 (s, 3H), 2.23 (s, 3H), 2.22 (s, 3H), 1.41 (s, 9H); ¹³C NMR (150 MHz, CDCl₃) δ 166.96, 163.70, 155.08, 154.65, 148.92, 145.47, 143.22, 139.92, 138.63, 129.90, 128.69, 126.96, 126.73, 125.26, 124.73, 123.76, 122.71, 80.38, 59.83, 53.45, 52.06, 28.26, 21.43, 13.19, 10.43; HRMS (ESI-TOF) m/z Calcd for C₂₉H₃₅N₂O₅ [M+H]⁺: 491.2540, found: 491.2541.

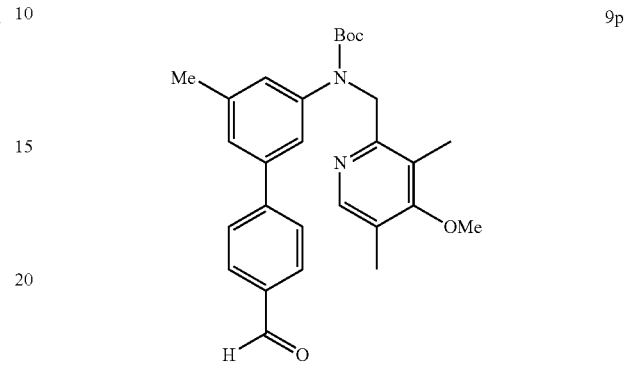

tert-Butyl (4'-formyl-5-methyl-[1,1'-biphenyl]-3-yl)((4-methoxy-3,5-dimethylpyridin-2-yl)methyl)carbamate (9p)

Following the general meta-arylation procedure using NBE-CO₂Me, Compound 9p was obtained in 96% yield as a colorless liquid. ¹H NMR (400 MHz, CDCl₃) δ 10.03 (s, 1H), 8.18 (s, 1H), 7.90 (d, J=8.1 Hz, 2H), 7.64 (d, J=8.1 Hz, 2H), 7.33 (s, 1H), 7.19 (s, 1H), 7.15 (s, 1H), 4.94 (s, 2H), 3.73 (s, 3H), 2.36 (s, 3H), 2.23 (s, 3H), 2.22 (s, 3H), 1.41 (s, 9H); ¹³C NMR (150 MHz, CDCl₃) δ 191.90, 163.69, 155.08, 154.63, 148.96, 147.08, 143.38, 139.65, 138.77, 135.05, 130.10, 127.62, 127.02, 125.31, 124.74, 123.71, 122.79, 80.44, 59.85, 53.47, 28.26, 21.45, 13.21, 10.44; HRMS (ESI-TOF) m/z Calcd for C₂₈H₃₃N₂O₄ [M+H]⁺: 461.2435, found: 461.2436.

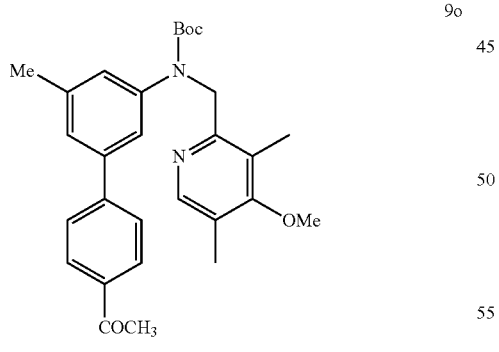

tert-Butyl (4'-acetyl-5-methyl-[1,1'-biphenyl]-3-yl)((4-methoxy-3,5-dimethylpyridin-2-yl)methyl)carbamate (9o)

Following the general meta-arylation procedure using NBE-CO₂Me, Compound 9o was obtained in 87% yield as a colorless liquid. ¹H NMR (400 MHz, CDCl₃) δ 8.18 (s, 1H), 7.98 (d, J=8.2 Hz, 2H), 7.57 (d, J=8.2 Hz, 2H), 7.31 (s, 1H), 7.18 (s, 1H), 7.13 (s, 1H), 4.94 (s, 2H), 3.72 (s, 3H),

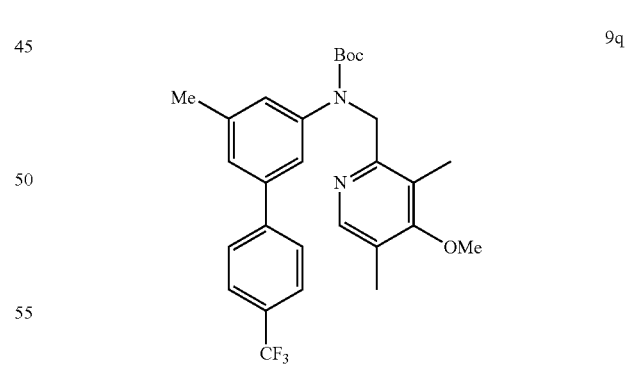

tert-Butyl ((4-methoxy-3,5-dimethylpyridin-2-yl)methyl)(5-methyl-4'-(trifluoromethyl)-[1,1'-biphenyl]-3-yl)carbamate (9q)

Following the general meta-arylation procedure using NBE-CO₂Me, Compound 9q was obtained in 97% yield as a colorless liquid. ¹H NMR (400 MHz, CDCl₃) δ 8.18 (s, 1H), 7.64 (d, J=8.2 Hz, 2H), 7.58 (d, J=8.2 Hz, 2H), 7.29 (s, 1H), 7.19-7.09 (m, 2H), 4.94 (s, 2H), 3.72 (s, 3H), 2.35 (s, 3H), 2.23 (s, 3H), 2.22 (s, 3H), 1.41 (s, 9H); $^{13}$C NMR (150 MHz, CDCl$_3$) δ 163.68, 155.10, 154.65, 148.96, 144.57, 143.36, 139.68, 138.71, 129.14 (q, J=32.6 Hz), 127.34, 126.70, 125.50 (q, J=3.4 Hz), 125.22, 124.71, 124.21 (q, J=271.8 Hz); 123.69, 122.69, 80.41, 59.84, 53.47, 28.26, 21.43, 13.20, 10.42; $^{19}$F NMR (376 MHz, CDCl$_3$) δ −62.62; HRMS (ESI-TOF) m/z Calcd for C$_{28}$H$_{32}$F$_3$N$_2$O$_3$ [M+H]$^+$: 501.2360, found: 501.2360.

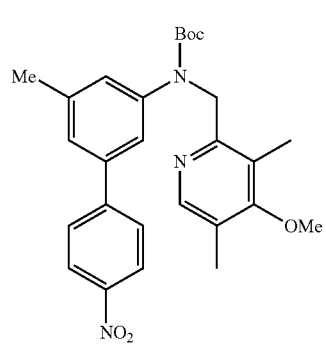

tert-Butyl ((4-methoxy-3,5-dimethylpyridin-2-yl)methyl)(5-methyl-4'-nitro-[1,1'-biphenyl]-3-yl)carbamate (9r)

Following the general meta-arylation procedure using NEE-CO$_2$Me, Compound 9r was obtained in 88% yield as a light yellow solid. $^1$H NMR (400 MHz, CDCl$_3$) δ 8.24 (d, J=8.6 Hz, 2H), 8.18 (s, 1H), 7.63 (d, J=8.6 Hz, 2H), 7.36 (s, 1H), 7.22-7.15 (m, 2H), 4.94 (s, 2H), 3.74 (s, 3H), 2.36 (s, 3H), 2.23 (s, 3H), 2.23 (s, 3H), 1.41 (s, 9H); $^{13}$C NMR (150 MHz, CDCl$_3$) δ 163.70, 155.02, 154.57, 148.96, 147.50, 146.91, 143.57, 138.96, 138.69, 127.72, 127.37, 125.24, 124.77, 123.92, 123.67, 122.76, 80.53, 59.87, 53.41, 28.24, 21.44, 13.22, 10.42; HRMS (ESI-TOF) m/z Calcd for C$_{27}$H$_{32}$N$_3$O$_5$ [M+H]$^+$: 478.2336, found: 478.2336.

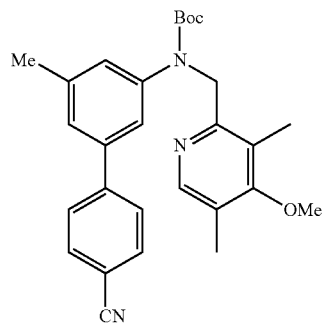

tert-Butyl (4'-cyano-5-methyl-[1,1'-biphenyl]-3-yl)((4-methoxy-3,5-dimethylpyridin-2-yl)methyl)carbamate (9s)

Following the general meta-arylation procedure using NBE-CO$_2$Me, Compound 9s was obtained in 89% yield as a colorless solid. $^1$H NMR (400 MHz, CDCl$_3$) δ 8.17 (s, 1H), 7.67 (d, J=8.2 Hz, 2H), 7.58 (d, J=8.3 Hz, 2H), 7.31 (s, 1H), 7.19-7.12 (m, 2H), 4.93 (s, 2H), 3.73 (s, 3H), 2.35 (s, 3H), 2.23 (s, 3H), 2.22 (s, 3H), 1.40 (s, 9H); $^{13}$C NMR (150 MHz, CDCl$_3$) δ 163.70, 155.02, 154.57, 148.93, 145.53, 143.47, 139.11, 138.89, 132.41, 127.67, 127.12, 125.12, 124.76, 123.70, 122.61, 118.94, 110.68, 80.49, 59.86, 53.39, 28.24, 21.43, 13.21, 10.42; HRMS (ESI-TOF) m/z Calcd for C$_{28}$H$_{32}$N$_3$O$_3$ [M+H]$^+$: 458.2438, found: 458.2438.

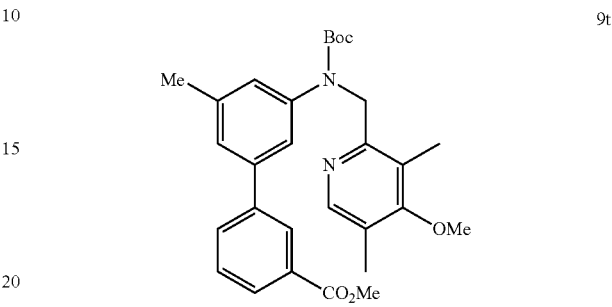

Methyl 3'-((tert-butoxycarbonyl)((4-methoxy-3,5-dimethylpyridin-2-yl)methyl)amino)-5'-methyl-[1,1'-biphenyl]-3-carboxylate (9t)

Following the general meta-arylation procedure using NEE-CO$_2$Me, Compound 9t was obtained in 88% yield as a colorless liquid. $^1$H NMR (400 MHz, CDCl$_3$) δ 8.18 (s, 2H), 7.98 (d, J=7.7 Hz, 1H), 7.67 (d, J=7.7 Hz, 1H), 7.46 (t, J=7.7 Hz, 1H), 7.29 (s, 1H), 7.17 (s, 1H), 7.10 (s, 1H), 4.95 (s, 2H), 3.94 (s, 3H), 3.72 (s, 3H), 2.35 (s, 3H), 2.23 (s, 3H), 2.21 (s, 3H), 1.42 (s, 9H); $^{13}$C NMR (150 MHz, CDCl$_3$) δ 167.01, 163.68, 155.10, 154.69, 148.95, 143.19, 141.30, 140.03, 138.60, 131.50, 130.48, 128.66, 128.20, 126.24, 125.18, 124.69, 123.75, 122.64, 80.37, 59.83, 53.47, 52.13, 28.28, 21.44, 13.19, 10.44; HRMS (ESI-TOF) m/z Calcd for C$_{29}$H$_{35}$N$_2$O$_5$ [M+H]$^+$: 491.2540, found: 491.2541.

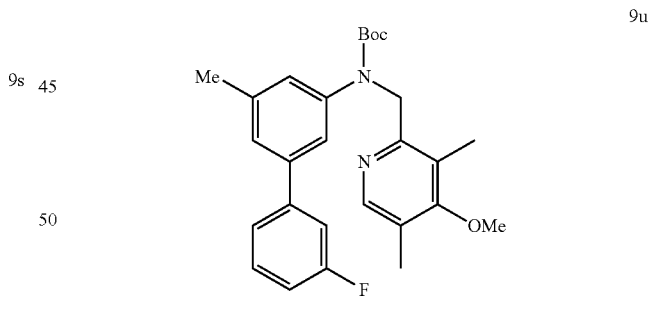

tert-Butyl (3'-fluoro-5-methyl-[1,1'-biphenyl]-3-yl)((4-methoxy-3,5-dimethylpyridin-2-yl)methyl)carbamate (9u)

Following the general meta-arylation procedure using NBE-CO$_2$Me, Compound 9u was obtained in 86% yield as a colorless liquid. $^1$H NMR (400 MHz, CDCl$_3$) δ 8.17 (s, 1H), 7.38-7.28 (m, 1H), 7.25 (d, J=6.2 Hz, 1H), 7.20 (s, 1H), 7.18-7.07 (m, 3H), 6.98 (td, J=7.7, 2.1 Hz, 1H), 4.94 (s, 2H), 3.72 (s, 3H), 2.34 (s, 3H), 2.23 (s, 3H), 2.22 (s, 3H), 1.41 (s, 9H); $^{13}$C NMR (150 MHz, CDCl$_3$) δ 163.69, 163.01 (d, J=245.4 Hz), 155.15, 154.68, 148.97, 143.33 (d, J=7.6 Hz), 143.15, 139.86, 138.57, 129.98 (d, J=8.6 Hz), 126.47, 125.14, 124.73, 123.79, 122.68 (d, J=2.6 Hz), 122.60, 113.95 (d, J=10.8 Hz), 113.81 (d, J=9.9 Hz), 80.34, 59.82, 53.52, 28.27, 21.43, 13.18, 10.44; $^{19}$F NMR (376 MHz, CDCl$_3$) δ −113.61; HRMS (ESI-TOF) m/z Calcd for C$_{27}$H$_{32}$FN$_2$O$_3$ [M+H]$^+$: 451.2391, found: 451.2391.

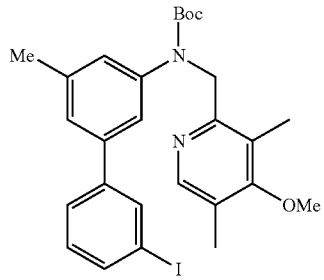

tert-Butyl (3'-iodo-5-methyl-[1,1'-biphenyl]-3-yl)((4-methoxy-3,5-dimethylpyridin-2-yl)methyl)carbamate (9v)

Following the general meta-arylation procedure using NEE-CO$_2$Me, Compound 9v was obtained in 74% yield as a light yellow solid. $^1$H NMR (400 MHz, CDCl$_3$) δ 8.18 (s, 1H), 7.80 (d, J=1.7 Hz, 1H), 7.62 (d, J=7.8 Hz, 1H), 7.43 (d, J=7.8 Hz, 1H), 7.17 (s, 1H), 7.14-7.06 (m, 3H), 4.93 (s, 2H), 3.73 (s, 3H), 2.33 (s, 3H), 2.22 (s, 6H), 1.41 (s, 9H); $^{13}$C NMR (150 MHz, CDCl$_3$) δ 163.70, 155.11, 154.67, 148.97, 143.29, 143.12, 139.53, 138.60, 136.08, 135.97, 130.22, 126.44, 126.34, 125.14, 124.73, 123.81, 122.59, 94.57, 80.37, 77.21, 59.88, 53.51, 28.29, 21.43, 13.25, 10.46; HRMS (ESI-TOF) m/z Calcd for C$_{27}$H$_{32}$IN$_2$O$_3$ [M+H]$^+$: 559.1452, found: 559.1453.

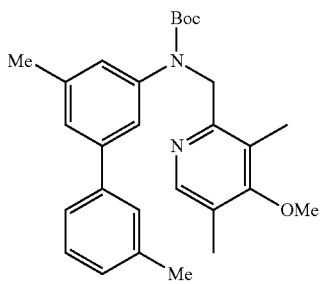

tert-Butyl (3',5-dimethyl-[1,1'-biphenyl]-3-yl)((4-methoxy-3,5-dimethylpyridin-2-yl)methyl)carbamate (9w)

Following the general meta-arylation procedure using NBE-CO$_2$Me, Compound 9w was obtained in 82% yield as a colorless liquid. $^1$H NMR (400 MHz, CDCl$_3$) δ 8.17 (s, 1H), 7.31-7.23 (m, 3H), 7.20 (s, 1H), 7.16-7.09 (m, 2H), 7.05 (s, 1H), 4.94 (s, 2H), 3.71 (s, 3H), 2.38 (s, 3H), 2.33 (s, 3H), 2.25-2.19 (m, 6H), 1.42 (s, 9H); $^{13}$C NMR (150 MHz, CDCl$_3$) δ 163.66, 155.23, 154.77, 148.94, 142.95, 141.26, 141.02, 138.28, 138.06, 128.44, 127.88, 127.83, 125.79, 125.27, 124.62, 124.17, 123.79, 122.67, 80.21, 59.81, 53.56, 28.30, 21.49, 21.45, 13.18, 10.44; HRMS (ESI-TOF) m/z Calcd for C$_{28}$H$_{35}$N$_2$O$_3$ [M+H]$^+$: 447.2642, found: 447.2643.

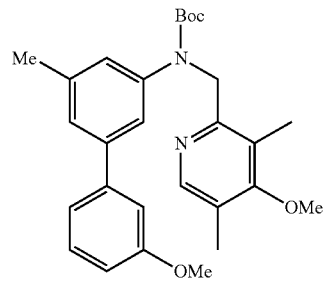

tert-Butyl ((4-methoxy-3,5-dimethylpyridin-2-yl)methyl)(3'-methoxy-5-methyl-[1,1'-biphenyl]-3-yl)-carbamate (9x)

Following the general meta-acylation procedure using NEE-CO$_2$Me, Compound 9x was obtained in 85% yield as a colorless liquid. $^1$H NMR (400 MHz, CDCl$_3$) δ 8.17 (s, 1H), 7.29 (t, J=7.9 Hz, 1H), 7.21 (s, 1H), 7.14 (s, 1H), 7.11-7.02 (m, 2H), 6.99 (t, J=2.1 Hz, 1H), 6.85 (dd, J=8.2, 2.5 Hz, 1H), 4.94 (s, 2H), 3.83 (s, 3H), 3.71 (s, 3H), 2.33 (s, 3H), 2.22 (s, 3H), 2.21 (s, 3H), 1.41 (s, 9H); $^{13}$C NMR (150 MHz, CDCl$_3$) δ 163.66, 159.76, 155.18, 154.75, 148.95, 143.01, 142.59, 141.01, 138.34, 129.52, 126.05, 125.26, 124.66, 123.77, 122.67, 119.61, 112.80, 112.54, 80.25, 59.82, 55.24, 53.54, 28.30, 21.45, 13.18, 10.43; HRMS (ESI-TOF) m/z Calcd for C$_{28}$H$_{35}$N$_2$O$_4$ [M+H]$^+$: 463.2591, found: 463.2591.

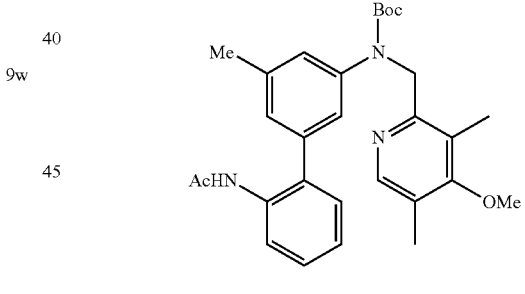

tert-Butyl (2'-acetamido-5-methyl-[1,1'-biphenyl]-3-yl)((4-methoxy-3,5-dimethylpyridin-2-yl)methyl) carbamate (9y)

Following the general meta-arylation procedure using NEE-CO$_2$Me, Compound 9y was obtained in 91% yield as a colorless solid. $^1$H NMR (400 MHz, CDCl$_3$) δ 8.32 (d, J=8.3 Hz, 1H), 8.16 (s, 1H), 7.64 (s, 1H), 7.32 (t, J=7.8 Hz, 1H), 7.25-7.17 (m, 2H), 7.14-7.07 (m, 2H), 6.94 (s, 1H), 4.89 (s, 2H), 3.74 (s, 3H), 2.33 (s, 3H), 2.23 (s, 6H), 2.11 (s, 3H), 1.35 (s, 9H); $^{13}$C NMR (150 MHz, CDCl$_3$) δ 169.01, 163.66, 155.11, 154.76, 148.93, 143.31, 139.42, 137.74, 135.06, 131.34, 129.69, 128.20, 127.12, 125.19, 124.70, 124.64, 123.33, 121.30, 80.44, 59.88, 53.27, 28.12, 24.53, 21.43, 13.20, 10.38; HRMS (ESI-TOF) m/z Calcd for C$_{29}$H$_{36}$N$_3$O$_4$ [M+H]$^+$: 490.2700, found: 490.2700.

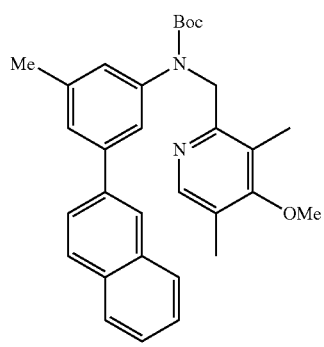

9z tert-Butyl ((4-methoxy-3,5-dimethylpyridin-2-yl)methyl)(3-methyl-5-(naphthalen-2-yl)phenyl)carbamate (9z)

Following the general meta-arylation procedure using NBE-CO$_2$Me, Compound 9z was obtained in 76% yield as a colorless liquid. $^1$H NMR (400 MHz, CDCl$_3$) δ 8.19 (s, 1H), 7.92 (s, 1H), 7.89-7.81 (m, 3H), 7.63 (dd, J=8.6, 1.8 Hz, 1H), 7.52-7.42 (m, 2H), 7.36 (s, 1H), 7.28 (s, 1H), 7.10 (s, 1H), 4.97 (s, 2H), 3.71 (s, 3H), 2.37 (s, 3H), 2.23 (s, 3H), 2.22 (s, 3H), 1.43 (s, 9H); $^{13}$C NMR (150 MHz, CDCl$_3$) δ 163.68, 155.22, 154.77, 148.98, 143.14, 141.03, 138.48, 138.38, 133.54, 132.52, 128.17, 128.10, 127.56, 126.16, 125.98, 125.78, 125.67, 125.58, 125.48, 124.67, 123.79, 122.90, 80.29, 59.83, 53.57, 28.31, 21.50, 13.21, 10.47; HRMS (ESI-TOF) m/z Calcd for C$_{31}$H$_{35}$N$_2$O$_3$ [M+H]$^+$: 483.2642, found: 483.2642.

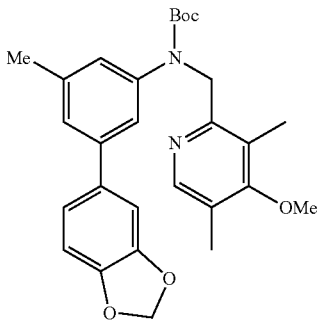

9aa tert-Butyl (3-(benzo[d][1,3]dioxol-5-yl)-5-methylphenyl)((4-methoxy-3,5-dimethylpyridin-2-yl)methyl)-carbamate (9aa)

Following the general meta-arylation procedure using NBE-CO$_2$Me, Compound 9aa was obtained in 72% yield as a colorless solid. $^1$H NMR (400 MHz, CDCl$_3$) δ 8.17 (s, 1H), 7.13 (s, 1H), 7.06 (s, 1H), 7.03 (s, 1H), 6.97-6.90 (m, 2H), 6.82 (d, J=7.8 Hz, 1H), 5.97 (s, 2H), 4.93 (s, 2H), 3.72 (s, 3H), 2.32 (s, 3H), 2.22 (s, 6H), 1.41 (s, 9H); $^{13}$C NMR (150 MHz, CDCl$_3$) δ 163.66, 155.21, 154.72, 148.95, 147.88, 146.88, 142.98, 140.83, 138.33, 135.44, 125.59, 124.99, 124.68, 123.79, 122.37, 120.51, 108.37, 107.62, 101.03, 80.24, 59.82, 53.54, 28.29, 21.44, 13.18, 10.43; HRMS (ESI-TOF) m/z Calcd for C$_{28}$H$_{33}$N$_2$O$_5$ [M+H]$^+$: 477.2384, found: 477.2384.

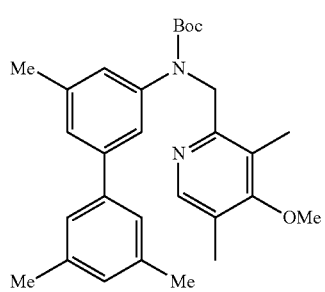

9ab tert-Butyl ((4-methoxy-3,5-dimethylpyridin-2-yl)methyl)(3',5,5'-trimethyl-[1,1'-biphenyl]-3-yl)-carbamate (9ab)

Following the general meta-arylation procedure using NBE-CO$_2$Me, Compound 9ab was obtained in 85% yield as a colorless liquid. $^1$H NMR (400 MHz, CDCl$_3$) δ 8.17 (s, 1H), 7.17 (s, 1H), 7.12 (s, 1H), 7.08 (s, 2H), 7.04 (s, 1H), 6.94 (s, 1H), 4.94 (s, 2H), 3.71 (s, 3H), 2.34 (s, 6H), 2.32 (s, 3H), 2.21 (s, 6H), 1.42 (s, 9H); $^{13}$C NMR (150 MHz, CDCl$_3$) δ 163.66, 155.26, 154.79, 148.94, 142.85, 141.36, 141.04, 138.22, 137.98, 128.72, 125.74, 125.32, 125.01, 124.61, 123.83, 122.72, 80.19, 59.82, 53.58, 28.30, 21.44, 21.35, 13.19, 10.46; HRMS (ESI-TOF) m/z Calcd for C$_{29}$H$_{37}$N$_2$O$_3$ [M+H]$^+$: 461.2799, found: 461.2799.

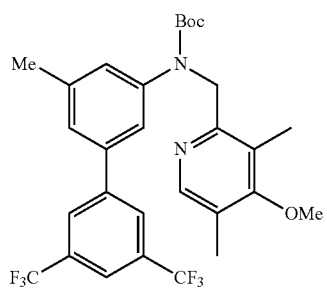

9ac tert-Butyl ((4-methoxy-3,5-dimethylpyridin-2-yl)methyl)(5-methyl-3',5'-bis(trifluoromethyl)-[1,1'-biphenyl]-3-yl)carbamate (9ac)

Following the general meta-arylation procedure using NBE-CO$_2$Me, Compound 9ac was obtained in 94% yield as a light yellow liquid. $^1$H NMR (400 MHz, CDCl$_3$) δ 8.18 (s, 1H), 7.89 (s, 2H), 7.81 (s, 1H), 7.28 (s, 1H), 7.19 (s, 1H), 7.15 (s, 1H), 4.95 (s, 2H), 3.73 (s, 3H), 2.37 (s, 3H), 2.24 (s, 3H), 2.22 (s, 3H), 1.42 (s, 9H); $^{13}$C NMR (150 MHz, CDCl$_3$) δ 163.80, 154.97, 154.60, 148.96, 143.61, 143.15, 139.22, 138.13, 131.87 (q, J=33.3 Hz), 127.42, 127.18, 125.12, 124.92, 123.84, 123.29 (q, J=273.3 Hz), 122.81, 120.72, 80.64, 59.85, 53.43, 28.26, 21.43, 13.17, 10.46; $^{19}$F NMR (376 MHz, CDCl$_3$) δ −63.09; HRMS (ESI-TOF) m/z Calcd for C$_{29}$H$_{31}$F$_6$N$_2$O$_3$ [M+H]$^+$: 569.2233, found: 569.2233.

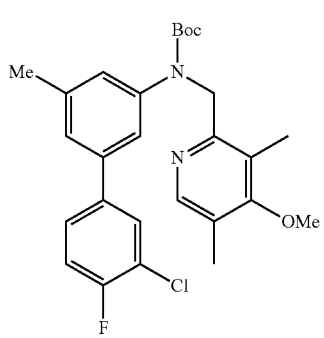

9ad tert-Butyl (3'-chloro-4'-fluoro-5-methyl-[1,1'-biphenyl]-3-yl)((4-methoxy-3,5-dimethylpyridin-2-yl)methyl)-carbamate (9ad)

Following the general meta-arylation procedure using NBE-CO$_2$Me, Compound 9ad was obtained in 82% yield as a colorless liquid. $^1$H NMR (400 MHz, CDCl$_3$) δ 8.18 (s, 1H), 7.46 (dd, J=7.0, 2.3 Hz, 1H), 7.32 (ddd, J=8.6, 4.6, 2.3 Hz, 1H), 7.20-7.11 (m, 2H), 7.10 (s, 1H), 7.07 (s, 1H), 4.93 (s, 2H), 3.73 (s, 3H), 2.33 (s, 3H), 2.26-2.19 (m, 6H), 1.41 (s, 9H); $^{13}$C NMR (150 MHz, CDCl$_3$) δ 163.72, 157.48 (d, J=248.7 Hz), 155.12, 154.63, 148.96, 143.22, 138.91, 138.71, 138.32 (d, J=4.1 Hz), 129.14, 126.70 (d, J=6.9 Hz), 126.40, 125.01, 124.77, 123.80, 122.47, 120.97 (d, J=17.8 Hz), 116.60 (d, J=21.2 Hz), 80.41, 59.86, 53.49, 28.27, 21.42, 13.21, 10.45; $^{19}$F NMR (376 MHz, CDCl$_3$) δ −118.58; HRMS (ESI-TOF) m/z Calcd for C$_{27}$H$_{31}$ClFN$_2$O$_3$ [M+H]$^+$: 485.2002, found: 485.2002.

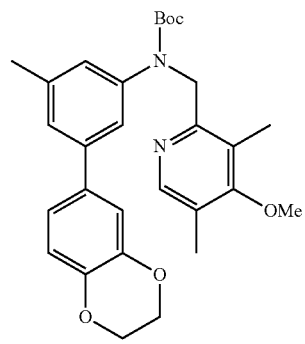

9ae tert-Butyl (3-(2,3-dihydrobenzo[b][1,4]dioxin-6-yl)-5-methylphenyl)((4-methoxy-3,5-dimethylpyridin-2-yl)methyl)carbamate (9ae)

Following the general meta-arylation procedure using NBE-CO$_2$Me, Compound 9ae was obtained in 82% yield as a colorless solid. $^1$H NMR (400 MHz, CDCl$_3$) δ 8.17 (s, 1H), 7.12 (s, 1H), 7.08 (s, 1H), 7.01 (s, 1H), 6.98-6.93 (m, 2H), 6.86 (d, J=8.7 Hz, 1H), 4.93 (s, 2H), 4.26 (s, 4H), 3.72 (s, 3H), 2.31 (s, 3H), 2.21 (s, 6H), 1.41 (s, 9H); $^{13}$C NMR (100 MHz, CDCl$_3$) δ 163.69, 155.18, 154.74, 148.91, 143.48, 142.99, 142.88, 140.49, 138.26, 134.63, 125.54, 124.90, 124.69, 123.85, 122.27, 120.07, 117.30, 115.77, 80.20, 64.40, 64.36, 59.80, 53.49, 28.29, 21.43, 13.16, 10.43; HRMS (ESI-TOF) m/z Calcd for C$_{29}$H$_{35}$N$_2$O$_5$ [M+H]$^+$: 491.2540, found: 491.2540.

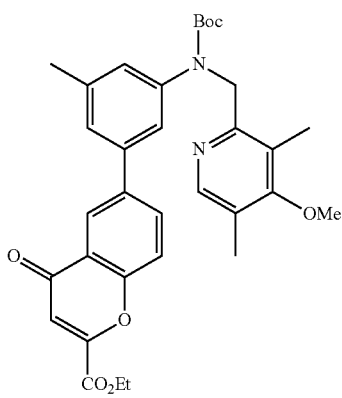

9af

Ethyl 6-(3-((tert-butoxycarbonyl)((4-methoxy-3,5-dimethylpyridin-2-yl)methyl)amino)-5-methylphenyl)-4-oxo-4H-chromene-2-carboxylate (9af)

Following the general meta-arylation procedure using NBE-CO$_2$Me, Compound 9af was obtained in 80% yield as a light yellow solid. $^1$H NMR (400 MHz, CDCl$_3$) δ 8.29 (d, J=2.3 Hz, 1H), 8.19 (s, 1H), 7.89 (dd, J=8.8, 2.3 Hz, 1H), 7.64 (d, J=8.8 Hz, 1H), 7.34 (s, 1H), 7.23 (s, 1H), 7.17-7.10 (m, 2H), 4.95 (s, 2H), 4.48 (q, J=7.1 Hz, 2H), 3.73 (s, 3H), 2.35 (s, 3H), 2.24 (s, 3H), 2.23 (s, 3H), 1.45 (t, J=7.1 Hz, 3H), 1.42 (s, 9H); $^{13}$C NMR (150 MHz, CDCl$_3$) δ 178.40, 163.69, 160.49, 155.23, 155.07, 154.62, 152.12, 148.96, 143.36, 138.95, 138.88, 138.83, 133.64, 126.70, 125.27, 124.76, 124.40, 123.75, 123.30, 122.62, 119.08, 114.64, 80.41, 62.98, 59.85, 53.44, 28.25, 21.40, 14.06, 13.19, 10.45; HRMS (ESI-TOF) m/z Calcd for C$_{33}$H$_{37}$N$_2$O$_7$ [M+H]$^+$: 573.2595, found: 573.2593.

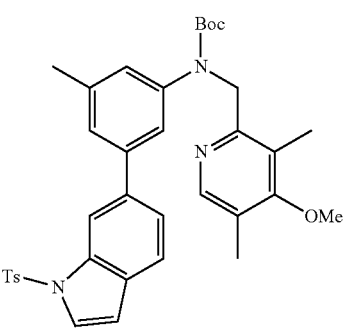

9ag tert-Butyl ((4-methoxy-3,5-dimethylpyridin-2-yl)methyl)(3-methyl-5-(1-tosyl-1H-indol-6-yl)phenyl)carbamate (9ag)

Following the general meta-arylation procedure using NBE-CO$_2$Me, Compound 9ag was obtained in 72% yield as a colorless solid. mp=100° C., $^1$H NMR (400 MHz, CDCl$_3$) δ 8.24 (s, 1H), 8.12 (s, 1H), 7.76 (d, J=8.2 Hz, 2H), 7.55 (d, J=3.7 Hz, 1H), 7.50 (d, J=8.2 Hz, 1H), 7.35 (dd, J=8.2, 1.5 Hz, 1H), 7.32 (s, 1H), 7.22-7.16 (m, 3H), 7.11 (s, 1H), 6.63 (d, J=3.6 Hz, 1H), 4.98 (s, 2H), 3.71 (s, 3H), 2.37 (s, 3H), 2.32 (s, 3H), 2.24 (s, 3H), 2.20 (s, 3H), 1.44 (s, 9H); $^{13}$C NMR (150 MHz, CDCl$_3$) δ 163.66, 155.08, 154.79, 149.03, 144.88, 143.13, 141.30, 138.39, 138.00, 135.32, 135.21, 129.86, 129.81, 126.76, 126.69, 125.78, 125.46, 124.70, 123.64, 122.98, 122.80, 121.26, 111.92, 108.82, 80.33, 59.83, 53.48, 28.30, 21.51, 13.20, 10.42; HRMS (ESI-TOF) m/z Calcd for C$_{36}$H$_{40}$N$_3$O$_5$S [M+H]$^+$: 626.2683, found: 626.2683.

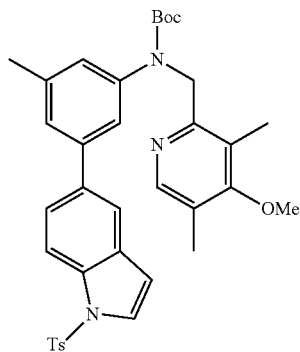

9ah tert-Butyl ((4-methoxy-3,5-dimethylpyridin-2-yl)methyl)(3-methyl-5-(1-tosyl-1H-indol-5-yl)phenyl)carbamate (9ah)

Following the general meta-arylation procedure using NBE-CO$_2$Me, Compound 9ah was obtained in 83% yield as a colorless solid. mp=92° C., $^1$H NMR (400 MHz, CDCl$_3$) δ 8.17 (s, 1H), 7.98 (d, J=8.6 Hz, 1H), 7.76 (d, J=8.1 Hz, 2H), 7.60 (s, 1H), 7.55 (d, J=3.7 Hz, 1H), 7.43 (d, J=8.2 Hz, 1H), 7.27-7.19 (m, 3H), 7.13 (s, 1H), 7.05 (s, 1H), 6.65 (d, J=3.7 Hz, 1H), 4.94 (s, 2H), 3.71 (s, 3H), 2.33 (s, 3H), 2.32 (s, 3H), 2.25-2.17 (m, 6H), 1.41 (s, 9H); $^{13}$C NMR (150 MHz, CDCl$_3$) δ 163.64, 155.20, 154.71, 148.92, 144.92, 143.02, 141.16, 138.35, 136.63, 135.21, 134.11, 131.12, 129.86, 126.80, 126.74, 125.59, 125.39, 124.62, 124.14, 123.74, 122.76, 119.72, 113.51, 109.27, 80.23, 59.81, 53.53, 28.27, 21.52, 21.44, 13.18, 10.43; HRMS (ESI-TOF) m/z Calcd for C$_{36}$H$_{40}$N$_3$O$_5$S [M+H]$^+$: 626.2683, found: 626.2684.

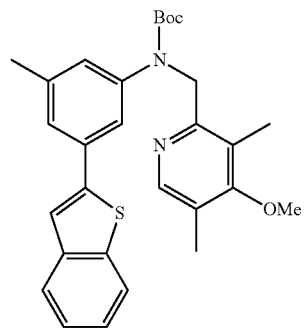

9ai tert-Butyl (3-(benzo[b]thiophen-2-yl)-5-methylphenyl)((4-methoxy-3,5-dimethylpyridin-2-yl)methyl)carbamate (9ai)

Following the general meta-arylation procedure using NBE-CO$_2$Me, Compound 9ai was obtained in 84% yield as a colorless liquid. $^1$H NMR (400 MHz, CDCl$_3$) δ 8.19 (s, 1H), 7.79 (d, J=7.7 Hz, 1H), 7.73 (d, J=7.6 Hz, 1H), 7.43 (s, 1H), 7.39 (s, 1H), 7.36-7.25 (m, 3H), 7.07 (s, 1H), 4.94 (s, 2H), 3.72 (s, 3H), 2.33 (s, 3H), 2.23 (s, 3H), 2.21 (s, 3H), 1.43 (s, 9H); $^{13}$C NMR (150 MHz, CDCl$_3$) δ 163.69, 154.99, 154.63, 149.01, 144.10, 143.25, 140.57, 139.35, 138.68, 134.09, 126.83, 124.71, 124.39, 124.38, 124.17, 123.73, 123.44, 122.15, 122.08, 119.34, 80.46, 59.84, 53.35, 28.29, 21.38, 13.20, 10.44; HRMS (ESI-TOF) m/z Calcd for C$_{29}$H$_{33}$N$_2$O$_3$S [M+H]$^+$: 489.2206, found: 489.2206.

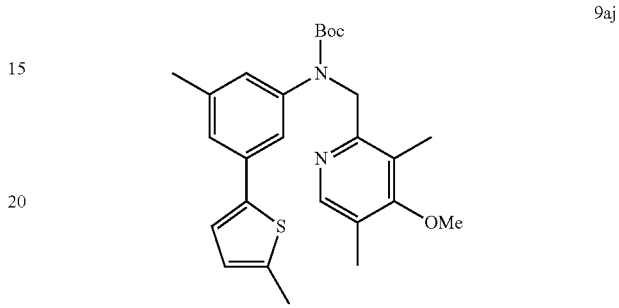

9aj tert-Butyl ((4-methoxy-3,5-dimethylpyridin-2-yl)methyl)(3-methyl-5-(5-methylthiophen-2-yl)phenyl)carbamate (9aj)

Following the general meta-arylation procedure using NBE-CO$_2$Me, Compound 9aj was obtained in 76% yield as a colorless liquid. $^1$H NMR (400 MHz, CDCl$_3$) δ 8.17 (s, 1H), 7.20 (s, 1H), 7.10 (s, 1H), 6.98 (d, J=3.5 Hz, 1H), 6.96 (s, 1H), 6.67 (d, J=3.5 Hz, 1H), 4.91 (s, 2H), 3.71 (s, 3H), 2.47 (s, 3H), 2.28 (s, 3H), 2.21 (s, 6H), 1.42 (s, 9H); $^{13}$C NMR (150 MHz, CDCl$_3$) δ 163.64, 155.06, 154.68, 148.97, 143.09, 141.82, 139.17, 138.44, 134.49, 125.98, 125.57, 124.62, 123.71, 123.48, 122.74, 121.10, 80.29, 59.82, 53.38, 28.28, 21.36, 15.40, 13.18, 10.42; HRMS (ESI-TOF) m/z Calcd for C$_{26}$H$_{33}$N$_2$O$_3$S [M+H]$^+$: 453.2206, found: 453.2206.

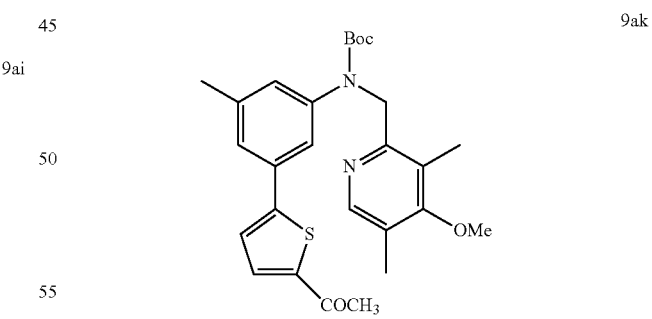

9ak tert-Butyl (3-(5-acetylthiophen-2-yl)-5-methylphenyl)((4-methoxy-3,5-dimethylpyridin-2-yl)methyl)carbamate (9ak)

Following the general meta-arylation procedure using NEE-CO$_2$Me, Compound 9ak was obtained in 98% yield as a colorless liquid. $^1$H NMR (400 MHz, CDCl$_3$) δ 8.17 (s, 1H), 7.61 (d, J=3.9 Hz, 1H), 7.34 (s, 1H), 7.25-7.18 (m, 2H), 7.12 (s, 1H), 4.91 (s, 2H), 3.74 (s, 3H), 2.54 (s, 3H), 2.32 (s, 3H), 2.23 (s, 3H), 2.22 (s, 3H), 1.41 (s, 9H); $^{13}$C NMR (150 MHz, CDCl$_3$) δ 190.49, 163.69, 154.88, 154.50, 152.73, 148.99, 143.48, 142.79, 138.92, 133.32, 133.15, 127.62, 124.78, 124.08, 123.80, 123.65, 121.75, 80.52, 59.85, 53.30, 28.22, 26.47, 21.32, 13.19, 10.40; HRMS (ESI-TOF) m/z Calcd for C$_{27}$H$_{33}$N$_2$O$_4$S [M+H]$^+$: 481.2156, found: 481.2156.

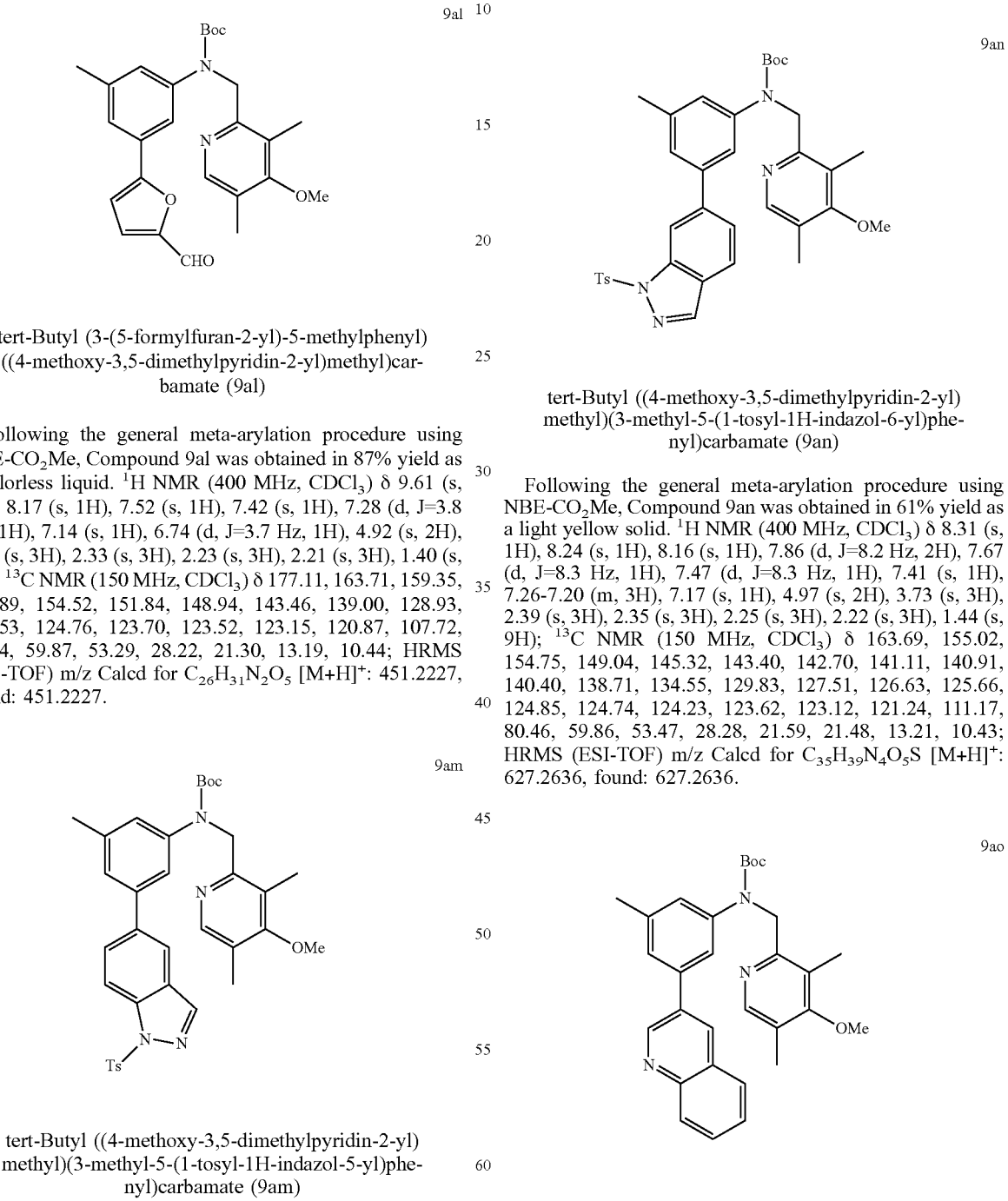

tert-Butyl (3-(5-formylfuran-2-yl)-5-methylphenyl) ((4-methoxy-3,5-dimethylpyridin-2-yl)methyl)carbamate (9al)

Following the general meta-arylation procedure using NBE-CO$_2$Me, Compound 9al was obtained in 87% yield as a colorless liquid. $^1$H NMR (400 MHz, CDCl$_3$) δ 9.61 (s, 1H), 8.17 (s, 1H), 7.52 (s, 1H), 7.42 (s, 1H), 7.28 (d, J=3.8 Hz, 1H), 7.14 (s, 1H), 6.74 (d, J=3.7 Hz, 1H), 4.92 (s, 2H), 3.74 (s, 3H), 2.33 (s, 3H), 2.23 (s, 3H), 2.21 (s, 3H), 1.40 (s, 9H); $^{13}$C NMR (150 MHz, CDCl$_3$) δ 177.11, 163.71, 159.35, 154.89, 154.52, 151.84, 148.94, 143.46, 139.00, 128.93, 128.53, 124.76, 123.70, 123.52, 123.15, 120.87, 107.72, 80.54, 59.87, 53.29, 28.22, 21.30, 13.19, 10.44; HRMS (ESI-TOF) m/z Calcd for C$_{26}$H$_{31}$N$_2$O$_5$ [M+H]$^+$: 451.2227, found: 451.2227.

tert-Butyl ((4-methoxy-3,5-dimethylpyridin-2-yl) methyl)(3-methyl-5-(1-tosyl-1H-indazol-5-yl)phenyl)carbamate (9am)

Following the general meta-arylation procedure using NBE-CO$_2$Me, Compound 9am was obtained in 63% yield as a light yellow solid. mp=137° C., $^1$H NMR (400 MHz, CDCl$_3$) δ 8.24-8.15 (m, 3H), 7.87 (d, J=8.2 Hz, 2H), 7.75 (s, 1H), 7.69 (dd, J=8.7, 1.7 Hz, 1H), 7.29 (s, 1H), 7.25 (d, J=7.9 Hz, 2H), 7.14 (s, 1H), 7.10 (s, 1H), 4.94 (s, 2H), 3.72 (s, 3H), 2.36 (s, 3H), 2.34 (s, 3H), 2.23 (s, 3H), 2.22 (s, 3H), 1.41 (s, 9H); $^{13}$C NMR (100 MHz, CDCl$_3$) δ 163.67, 155.15, 154.65, 148.93, 145.37, 143.29, 141.55, 140.24, 139.58, 138.64, 137.76, 134.50, 129.83, 129.12, 127.50, 126.43, 126.02, 125.35, 124.68, 123.69, 122.78, 119.28, 113.20, 80.36, 59.84, 53.49, 28.26, 21.60, 21.45, 13.21, 10.43; HRMS (ESI-TOF) m/z Calcd for C$_{35}$H$_{39}$N$_4$O$_5$S [M+H]$^+$: 627.2636, found: 627.2635.

tert-Butyl ((4-methoxy-3,5-dimethylpyridin-2-yl) methyl)(3-methyl-5-(1-tosyl-1H-indazol-6-yl)phenyl)carbamate (9an)

Following the general meta-arylation procedure using NBE-CO$_2$Me, Compound 9an was obtained in 61% yield as a light yellow solid. $^1$H NMR (400 MHz, CDCl$_3$) δ 8.31 (s, 1H), 8.24 (s, 1H), 8.16 (s, 1H), 7.86 (d, J=8.2 Hz, 2H), 7.67 (d, J=8.3 Hz, 1H), 7.47 (d, J=8.3 Hz, 1H), 7.41 (s, 1H), 7.26-7.20 (m, 3H), 7.17 (s, 1H), 4.97 (s, 2H), 3.73 (s, 3H), 2.39 (s, 3H), 2.35 (s, 3H), 2.25 (s, 3H), 2.22 (s, 3H), 1.44 (s, 9H); $^{13}$C NMR (150 MHz, CDCl$_3$) δ 163.69, 155.02, 154.75, 149.04, 145.32, 143.40, 142.70, 141.11, 140.91, 140.40, 138.71, 134.55, 129.83, 127.51, 126.63, 125.66, 124.85, 124.74, 124.23, 123.62, 123.12, 121.24, 111.17, 80.46, 59.86, 53.47, 28.28, 21.59, 21.48, 13.21, 10.43; HRMS (ESI-TOF) m/z Calcd for C$_{35}$H$_{39}$N$_4$O$_5$S [M+H]$^+$: 627.2636, found: 627.2636.

tert-Butyl ((4-methoxy-3,5-dimethylpyridin-2-yl) methyl)(3-methyl-5-(quinolin-3-yl)phenyl)carbamate (9ao)

Following the general meta-arylation procedure using NBE-CO$_2$Me, Compound 9ao was obtained in 54% yield as a colorless solid. ¹H NMR (400 MHz, CDCl₃) δ 9.07 (d, J=2.2 Hz, 1H), 8.21 (d, J=2.2 Hz, 1H), 8.20 (s, 1H), 8.11 (d, J=8.5 Hz, 1H), 7.85 (d, J=8.1 Hz, 1H), 7.70 (t, J=7.7 Hz, 1H), 7.56 (t, J=7.5 Hz, 1H), 7.43 (s, 1H), 7.27 (s, 1H), 7.19 (s, 1H), 4.96 (s, 2H), 3.73 (s, 3H), 2.40 (s, 3H), 2.24 (s, 3H), 2.22 (s, 3H), 1.42 (s, 9H); ¹³C NMR (150 MHz, CDCl₃) δ 163.69, 155.04, 154.67, 149.94, 149.02, 147.26, 143.64, 138.96, 137.79, 133.70, 133.14, 129.25, 129.16, 127.94, 126.89, 126.62, 125.32, 124.74, 123.63, 122.75, 80.48, 59.86, 53.49, 28.29, 21.50, 13.22, 10.43; HRMS (ESI-TOF) m/z Calcd for C₃₀H₃₄N₃O₃ [M+H]⁺: 484.2595, found: 484.2593.

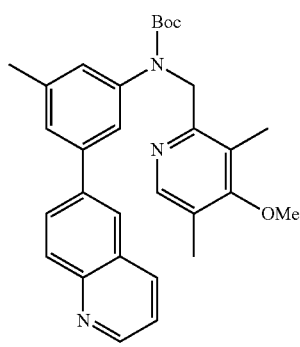

9ap tert-Butyl ((4-methoxy-3,5-dimethylpyridin-2-yl)methyl)(3-methyl-5-(quinolin-6-yl)phenyl)carbamate (9ap)

Following the general meta-arylation procedure using 20 mol % of Pd(OAc)₂ and 40 mol % of L12, Compound 9ap was obtained in 41% yield as a light yellow liquid. ¹H NMR (400 MHz, CDCl₃) δ 8.90 (dd, J=4.3, 1.7 Hz, 1H), 8.22-8.16 (m, 2H), 8.12 (d, J=8.7 Hz, 1H), 7.91 (d, J=2.0 Hz, 1H), 7.87 (dd, J=8.7, 2.1 Hz, 1H), 7.41 (dd, J=8.3, 4.2 Hz, 1H), 7.39 (s, 1H), 7.28 (s, 1H), 7.13 (s, 1H), 4.97 (s, 2H), 3.73 (s, 3H), 2.38 (s, 3H), 2.24 (s, 3H), 2.22 (s, 3H), 1.43 (s, 9H); ¹³C NMR (150 MHz, CDCl₃) δ 163.72, 155.18, 154.72, 150.25, 148.98, 147.60, 143.29, 140.25, 139.18, 138.68, 136.20, 129.65, 129.25, 128.36, 126.37, 125.51, 125.39, 124.73, 123.81, 122.94, 121.39, 80.40, 59.86, 53.54, 28.31, 21.50, 13.22, 10.47; HRMS (ESI-TOF) m/z Calcd for C₃₀H₃₄N₃O₃ [M+H]⁺: 484.2595, found: 484.2592.

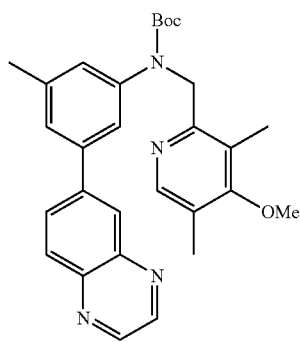

9aq tert-Butyl ((4-methoxy-3,5-dimethylpyridin-2-yl)methyl)(3-methyl-5-(quinoxalin-6-yl)phenyl)carbamate (9aq)

Following the general meta-arylation procedure using NBE-CO₂Me, Compound 9aq was obtained in 63% yield as a yellow liquid. ¹H NMR (400 MHz, CDCl₃) δ 8.85 (d, J=1.8 Hz, 1H), 8.82 (d, J=1.8 Hz, 1H), 8.19 (s, 2H), 8.13 (d, J=8.7 Hz, 1H), 7.96 (dd, J=8.8, 2.0 Hz, 1H), 7.44 (s, 1H), 7.32 (s, 1H), 7.19 (s, 1H), 4.97 (s, 2H), 3.74 (s, 3H), 2.39 (s, 3H), 2.25 (s, 3H), 2.23 (s, 3H), 1.42 (s, 9H); ¹³C NMR (150 MHz, CDCl₃) δ 163.71, 155.09, 154.66, 149.01, 145.30, 144.62, 143.47, 143.17, 142.77, 142.29, 139.51, 138.86, 129.87, 129.58, 126.94, 126.75, 125.58, 124.78, 123.75, 122.97, 80.44, 59.86, 53.49, 28.28, 21.49; HRMS (ESI-TOF) m/z Calcd for C₂₉H₃₃N₄O₃ [M+H]⁺: 485.2547, found: 485.2547.

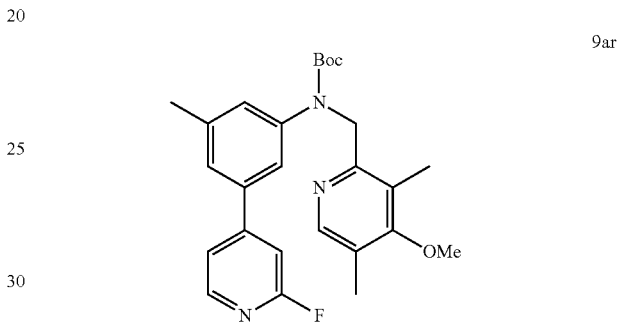

9ar tert-Butyl (3-(2-fluoropyridin-4-yl)-5-methylphenyl)((4-methoxy-3,5-dimethylpyridin-2-yl)methyl)carbamate (9ar)

Following the general meta-arylation procedure using NBE-CO₂Me, Compound 9ar was obtained in 90% yield as a light yellow liquid. ¹H NMR (400 MHz, CDCl₃) δ 8.20 (d, J=5.3 Hz, 1H), 8.18 (s, 1H), 7.33 (s, 1H), 7.30 (d, J=5.2 Hz, 1H), 7.21 (s, 1H), 7.18 (s, 1H), 7.00 (s, 1H), 4.93 (s, 2H), 3.74 (s, 3H), 2.36 (s, 3H), 2.24 (s, 3H), 2.23 (s, 3H), 1.41 (s, 9H); ¹³C NMR (150 MHz, CDCl₃) δ 164.36 (d, J=237.8 Hz), 163.74, 154.94, 154.52, 153.98, 153.93, 148.96, 147.74 (d, J=15.4 Hz), 143.61, 139.11, 136.99, 128.18, 124.87, 123.74, 122.46, 119.49 (d, J=3.9 Hz), 107.00 (d, J=38.3 Hz), 80.59, 59.86, 53.35, 28.23, 21.40, 13.20, 10.42; ¹⁹F NMR (376 MHz, CDCl₃) δ −68.68; HRMS (ESI-TOF) m/z Calcd for C₂₆H₃₁FN₃O₃ [M+H]⁺: 452.2344, found: 452.2344.

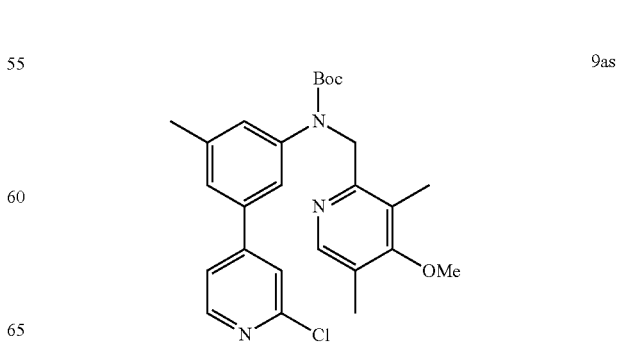

9as tert-Butyl (3-(2-chloropyridin-4-yl)-5-methylphenyl) ((4-methoxy-3,5-dimethylpyridin-2-yl)methyl)carbamate (9as)

Following the general meta-arylation procedure using NBE-CO$_2$Me, Compound 9as was obtained in 96% yield as a colorless liquid. Only 9% NMR yield was obtained in the absence of L12. $^1$H NMR (400 MHz, CDCl$_3$) δ 8.37 (d, J=5.2 Hz, 1H), 8.18 (s, 1H), 7.41 (s, 1H), 7.33 (dd, J=5.2, 1.5 Hz, 1H), 7.30 (s, 1H), 7.21 (s, 1H), 7.16 (s, 1H), 4.93 (s, 2H), 3.74 (s, 3H), 2.36 (s, 3H), 2.24 (s, 6H), 1.41 (s, 9H); $^{13}$C NMR (150 MHz, CDCl$_3$) δ 163.74, 154.94, 154.50, 151.97, 151.44, 149.79, 148.96, 143.62, 139.16, 136.76, 128.20, 124.87, 124.84, 123.74, 122.47, 121.97, 120.46, 80.59, 59.87, 53.36, 28.22, 21.39, 13.21, 10.42; HRMS (ESI-TOF) m/z Calcd for C$_{26}$H$_{31}$ClN$_3$O$_3$ [M+H]$^+$: 468.2048, found: 468.2048.

tert-Butyl ((4-methoxy-3,5-dimethylpyridin-2-yl)methyl)(3-methyl-5-(2-(trifluoromethyl)pyridin-4-yl)-phenyl)-carbamate (9au)

Following the general meta-arylation procedure using NBE-CO$_2$Me, Compound 9au was obtained in 93% yield as a light yellow liquid. $^1$H NMR (400 MHz, CDCl$_3$) δ 8.72 (d, J=5.1 Hz, 1H), 8.18 (s, 1H), 7.77 (s, 1H), 7.60 (d, J=3.5 Hz, 1H), 7.39 (s, 1H), 7.24 (s, 1H), 7.21 (s, 1H), 4.94 (s, 2H), 3.74 (s, 3H), 2.38 (s, 3H), 2.24 (s, 3H), 2.23 (s, 3H), 1.41 (s, 9H); $^{13}$C NMR (150 MHz, CDCl$_3$) δ 163.76, 154.90, 154.52, 150.27, 150.10, 148.96, 149.49 (q, J=33.2 Hz), 143.80, 139.32, 136.79, 128.33, 124.88, 124.86, 124.10, 123.73, 122.54, 121.61 (q, J=274.4 Hz), 118.40 (q, J=3.0 Hz), 80.67, 59.86, 53.34, 28.23, 21.41, 13.18, 10.42; $^{19}$F NMR (376 MHz, CDCl$_3$) δ −68.23; HRMS (ESI-TOF) m/z Calcd for C$_{27}$H$_{31}$F$_3$N$_3$O$_3$ [M+H]$^+$: 502.2312, found: 502.2312.

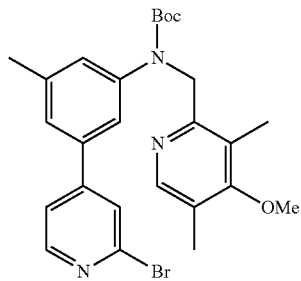

9at

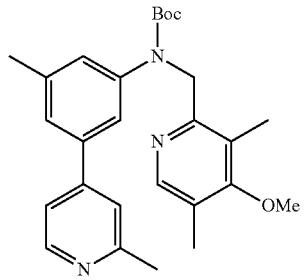

9av tert-Butyl (3-(2-bromopyridin-4-yl)-5-methylphenyl) ((4-methoxy-3,5-dimethylpyridin-2-yl)methyl)carbamate (9at)

Following the general meta-arylation procedure using NBE-CO$_2$Me, Compound 9at was obtained in 56% yield as a light yellow liquid. $^1$H NMR (400 MHz, CDCl$_3$) δ 8.35 (d, J=5.2 Hz, 1H), 8.18 (s, 1H), 7.57 (s, 1H), 7.36 (dd, J=5.2, 1.5 Hz, 1H), 7.29 (s, 1H), 7.20 (s, 1H), 7.15 (s, 1H), 4.93 (s, 2H), 3.74 (s, 3H), 2.36 (s, 3H), 2.23 (s, 6H), 1.41 (s, 9H); $^{13}$C NMR (150 MHz, CDCl$_3$) δ 163.77, 154.92, 154.51, 151.18, 150.19, 148.95, 143.60, 142.70, 139.17, 136.64, 128.22, 125.78, 124.90, 124.88, 123.78, 122.49, 120.84, 80.62, 59.89, 53.34, 28.24, 21.40, 13.24, 10.44; HRMS (ESI-TOF) m/z Calcd for C$_{26}$H$_{31}$BrN$_3$O$_3$ [M+H]$^+$: 512.1543, found: 512.1540.

tert-Butyl ((4-methoxy-3,5-dimethylpyridin-2-yl)methyl)(3-methyl-5-(2-methylpyridin-4-yl)phenyl)carbamate (9av)

Following the general meta-arylation procedure using 20 mol % of Pd(OAc)$_2$ and 40 mol % of L12, Compound 9av was obtained in 42% yield as a colorless, liquid. $^1$H NMR (400 MHz, CDCl$_3$) δ 8.48 (d, J=5.2 Hz, 1H), 8.18 (s, 1H), 7.31 (s, 1H), 7.26 (s, 1H), 7.20 (d, J=5.2 Hz, 1H), 7.17 (s, 1H), 7.16 (s, 1H), 4.93 (s, 2H), 3.73 (s, 3H), 2.59 (s, 3H), 2.35 (s, 3H), 2.23 (s, 3H), 2.22 (s, 3H), 1.41 (s, 9H); $^{13}$C NMR (150 MHz, CDCl$_3$) δ 163.69, 158.62, 155.06, 154.60, 149.38, 148.95, 148.54, 143.40, 138.81, 138.38, 127.42, 124.93, 124.73, 123.72, 122.47, 121.15, 118.82, 80.44, 59.84, 53.44, 28.26, 24.52, 21.42, 13.20, 10.43; HRMS (ESI-TOF) m/z Calcd for C$_{27}$H$_{34}$N$_3$O$_3$ [M+H]$^+$: 448.2595, found: 448.2596.

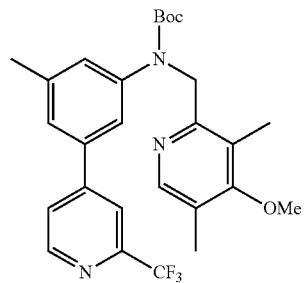

9au

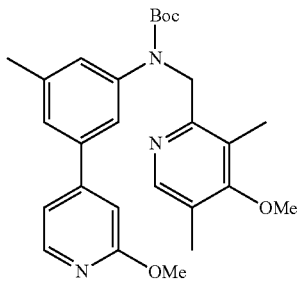

9aw tert-Butyl ((4-methoxy-3,5-dimethylpyridin-2-yl)methyl)(3-(2-methoxypyridin-4-yl)-5-methylphenyl)carbamate (9aw)

Following the general meta-acylation procedure using NBE-CO$_2$Me, Compound 9aw was obtained in 55% yield as a colorless liquid. $^1$H NMR (400 MHz, CDCl$_3$) δ 8.17 (s, 1H), 8.15 (d, J=5.4 Hz, 1H), 7.26 (s, 1H), 7.16 (s, 2H), 7.00 (dd, J=5.4, 1.5 Hz, 1H), 6.81 (s, 1H), 4.93 (s, 2H), 3.96 (s, 3H), 3.73 (s, 3H), 2.34 (s, 3H), 2.22 (s, 6H), 1.41 (s, 9H); $^{13}$C NMR (150 MHz, CDCl$_3$) δ 164.75, 163.73, 155.03, 154.61, 151.08, 148.97, 147.00, 143.32, 138.77, 138.21, 127.54, 124.94, 124.80, 123.77, 122.46, 115.38, 108.37, 80.46, 59.84, 53.46, 53.43, 28.26, 21.42, 13.20, 10.43; HRMS (ESI-TOF) m/z Calcd for C$_{27}$H$_{34}$N$_3$O$_4$ [M+H]$^+$: 464.2544, found: 464.2544.

tert-Butyl (3-(6-fluoropyridin-3-yl)-5-methylphenyl)((4-methoxy-3,5-dimethylpyridin-2-yl)methyl)carbamate (9ay)

Following the general meta-arylation procedure using NBE-CO$_2$Me, Compound 9ay was obtained in 52% yield as a colorless liquid. $^1$H NMR (400 MHz, CDCl$_3$) δ 8.30 (d, J=2.6 Hz, 1H), 8.17 (s, 1H), 7.88 (td, J=8.0, 2.6 Hz, 1H), 7.26 (s, 1H), 7.15 (s, 1H), 7.08 (s, 1H), 6.95 (dd, J=8.5, 3.0 Hz, 1H), 4.93 (s, 2H), 3.73 (s, 3H), 2.35 (s, 3H), 2.26-2.20 (m, 6H), 1.40 (s, 9H); $^{13}$C NMR (126 MHz, CDCl$_3$) δ 163.70, 162.98 (d, J=238.4 Hz), 155.02, 154.60, 148.97, 145.74 (d, J=14.9 Hz), 143.59, 139.68 (d, J=7.8 Hz), 138.95, 136.60, 134.70 (d, J=4.6 Hz), 126.67, 124.93, 124.75, 123.64, 122.41, 109.22 (d, J=37.5 Hz), 80.48, 59.85, 53.44, 28.25, 21.42, 13.20, 10.41; $^{19}$F NMR (376 MHz, CDCl$_3$) δ −71.02; HRMS (ESI-TOF) m/z Calcd for C$_{26}$H$_{31}$FN$_3$O$_3$ [M+H]$^+$: 452.2344, found: 452.2344.

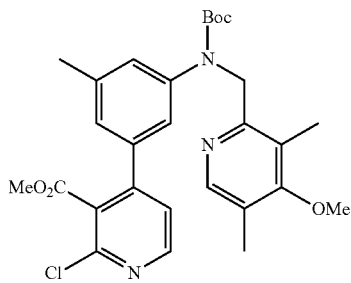

9ax

Methyl 4-(3-((tert-butoxycarbonyl)((4-methoxy-3,5-dimethylpyridin-2-yl)methyl)amino)-5-methyl-phenyl)-2-chloronicotinate (9ax)

Following the general meta-arylation procedure using NBE-CO$_2$Me, Compound 9ax was obtained in 51% yield as a colorless liquid. $^1$H NMR (400 MHz, CDCl$_3$) δ 8.41 (d, J=5.1 Hz, 1H), 8.18 (s, 1H), 7.24-7.19 (m, 2H), 7.17 (s, 1H), 6.96 (s, 1H), 4.88 (s, 2H), 3.74 (s, 3H), 3.70 (s, 3H), 2.32 (s, 3H), 2.225 (s, 3H), 2.217 (s, 3H), 1.37 (s, 9H); $^{13}$C NMR (150 MHz, CDCl$_3$) δ 166.19, 163.68, 154.86, 154.45, 150.21, 149.72, 148.97, 147.93, 143.57, 138.86, 136.58, 128.83, 127.89, 125.55, 124.74, 123.48, 123.09, 123.05, 80.52, 59.88, 53.32, 52.70, 28.18, 21.36, 13.22, 10.37; HRMS (ESI-TOF) m/z Calcd for C$_{28}$H$_{33}$ClN$_3$O$_5$ [M+H]$^+$: 526.2103, found: 526.2103.

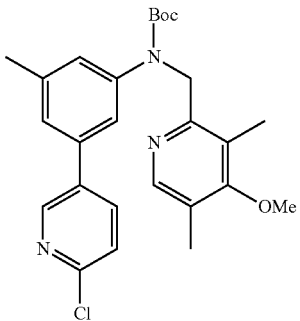

9az tert-Butyl (3-(6-chloropyridin-3-yl)-5-methylphenyl)((4-methoxy-3,5-dimethylpyridin-2-yl)methyl)carbamate (9az)

Following the general meta-arylation procedure using NEE-CO$_2$Me, Compound 9az was obtained in 52% yield as a colorless solid. $^1$H NMR (400 MHz, CDCl$_3$) δ 8.49 (d, J=2.5 Hz, 1H), 8.17 (s, 1H), 7.75 (dd, J=8.2, 2.6 Hz, 1H), 7.34 (d, J=8.3 Hz, 1H), 7.28 (s, 1H), 7.16 (s, 1H), 7.09 (s, 1H), 4.92 (s, 2H), 3.73 (s, 3H), 2.35 (s, 3H), 2.22 (s, 6H), 1.40 (s, 9H); $^{13}$C NMR (150 MHz, CDCl$_3$) δ 163.70, 154.96, 154.59, 150.12, 148.98, 147.93, 143.68, 139.05, 137.15, 136.39, 135.51, 126.93, 124.87, 124.77, 124.04, 123.64, 122.34, 80.54, 59.87, 53.41, 28.24, 21.43, 13.21, 10.40; HRMS (ESI-TOF) m/z Calcd for C$_{26}$H$_{31}$ClN$_3$O$_3$ [M+H]$^+$: 468.2048, found: 468.2048.

9ay

9ba

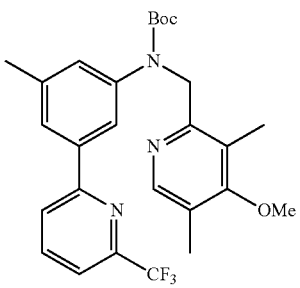

tert-Butyl ((4-methoxy-3,5-dimethylpyridin-2-yl)methyl)-(3-methyl-5-(6-(trifluoromethyl)pyridin-2-yl)-phenyl)carbamate (9ba)

Following the general meta-arylation procedure using 20 mol % of Pd(OAc)$_2$ and 40 mol % of L12, Compound 9ba was obtained in 84% yield as a red liquid. $^1$H NMR (400 MHz, CDCl$_3$) δ 8.16 (s, 1H), 7.86 (t, J=7.8 Hz, 1H), 7.80 (d, J=8.0 Hz, 1H), 7.74 (s, 1H), 7.62 (s, 1H), 7.56 (d, J=7.5 Hz, 1H), 7.18 (s, 1H), 4.97 (s, 2H), 3.71 (s, 3H), 2.36 (s, 3H), 2.24 (s, 3H), 2.20 (s, 3H), 1.43 (s, 9H); $^{13}$C NMR (150 MHz, CDCl$_3$) δ 163.77, 157.56, 154.95, 154.71, 148.86, 147.93 (q, J=34.2 Hz), 143.17, 138.72, 137.86, 137.73, 128.28, 124.93, 124.76, 123.89, 122.84, 122.68, 121.51 (q, J=274.5 Hz), 118.35 (q, J=2.8 Hz), 80.50, 59.82, 53.25, 28.23, 21.45, 13.16, 10.44; HRMS (ESI-TOF) m/z Calcd for C$_{27}$H$_{31}$F$_3$N$_3$O$_3$ [M+H]$^+$: 502.2312, found: 502.2312.

tert-Butyl 4-((tert-butoxycarbonyl)((4-methoxy-3,5-dimethylpyridin-2-yl)methyl)amino)-6-(2-chloropyridin-4-yl)-1H-indole-1-carboxylate (9bc)

Substrate 2i was arylated following the general meta-arylation procedure using 20 mol % of Pd(OAc)$_2$ and 40 mol % of L12. After purification by preparative thin-layer chromatography, Compound 9bc was obtained in 48% yield as a colorless solid. $^1$H NMR (400 MHz, CDCl$_3$) δ 8.41-8.31 (m, 2H), 8.13 (s, 1H), 7.61 (d, J=3.7 Hz, 1H), 7.42 (s, 1H), 7.39 (d, J=5.2 Hz, 1H), 7.21 (s, 1H), 6.58 (d, J=3.7 Hz, 1H), 5.02 (s, 2H), 3.71 (s, 3H), 2.23 (s, 3H), 2.22 (s, 3H), 1.68 (s, 9H), 1.37 (s, 9H); $^{13}$C NMR (150 MHz, CDCl$_3$) δ 163.83, 154.94, 154.56, 152.00, 151.86, 149.75, 149.35, 148.90, 136.46, 135.52, 132.83, 129.57, 127.15, 125.08, 124.60, 121.95, 120.53, 112.49, 105.52, 84.22, 80.54, 59.82, 53.19, 28.18, 28.12, 13.21, 10.62; HRMS (ESI-TOF) m/z Calcd for C$_{32}$H$_{38}$ClN$_4$O$_5$ [M+H]$^+$: 593.2525, found: 593.2522.

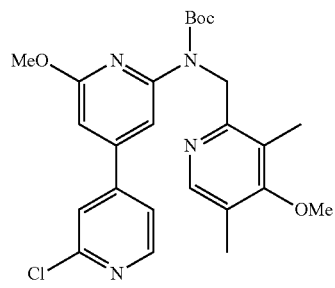

tert-Butyl (2'-chloro-6-methoxy-[4,4'-bipyridin]-2-yl)((4-methoxy-3,5-dimethylpyridin-2-yl)methyl)carbamate (9bb)

Substrate 2b was arylated following the general meta-arylation procedure using 20 mol % of Pd(OAc)$_2$ and 40 mol % of L12. After purification by preparative thin-layer chromatography, Compound 9bb was obtained in 40% yield as a colorless solid. $^1$H NMR (400 MHz, CDCl$_3$) δ 8.44 (d, J=5.2 Hz, 1H), 8.12 (s, 1H), 7.78 (s, 1H), 7.55 (s, 1H), 7.44 (dd, J=5.2, 1.5 Hz, 1H), 6.55 (s, 1H), 5.26 (s, 2H), 3.74 (s, 3H), 3.65 (s, 3H), 2.27 (s, 3H), 2.21 (s, 3H), 1.45 (s, 9H); $^{13}$C NMR (150 MHz, CDCl$_3$) δ 163.38, 162.79, 155.60, 154.34, 153.17, 152.24, 150.12, 149.73, 148.92, 148.15, 123.97, 122.26, 122.23, 120.60, 108.40, 102.43, 81.45, 59.88, 53.22, 48.92, 28.16, 13.17, 10.34; HRMS (ESI-TOF) m/z Calcd for C$_{25}$H$_{30}$ClN$_4$O$_4$ [M+H]$^+$: 485.1950, found: 485.1950.

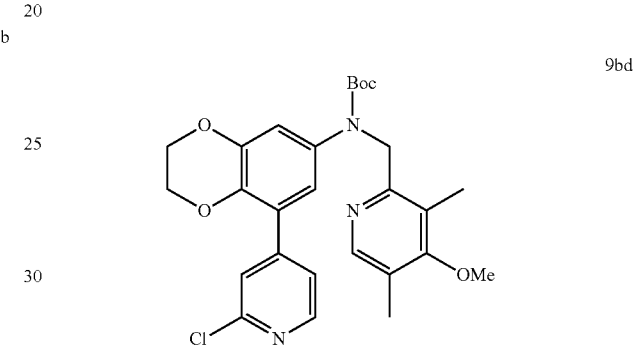

tert-Butyl (8-(2-chloropyridin-4-yl)-2,3-dihydrobenzo[b]-[1,4]dioxin-6-yl)((4-methoxy-3,5-dimethyl-pyridin-2-yl)methyl)carbamate (9bd)

Substrate 2l was arylated following the general meta-arylation procedure. After purification by preparative thin-layer chromatography, Compound 9bd was obtained in 52% yield as a colorless solid. $^1$H NMR (400 MHz, CDCl$_3$) δ 8.35 (d, J=5.2 Hz, 1H), 8.17 (s, 1H), 7.39 (s, 1H), 7.32 (d, J=5.2 Hz, 1H), 6.92 (s, 1H), 6.78 (s, 1H), 4.86 (s, 2H), 4.24 (s, 4H), 3.74 (s, 3H), 2.23 (s, 3H), 2.22 (s, 3H), 1.40 (s, 9H); $^{13}$C NMR (150 MHz, CDCl$_3$) δ 163.78, 154.92, 154.72, 151.27, 149.10, 148.92, 148.27, 143.53, 138.83, 136.28, 125.60, 124.89, 124.36, 123.90, 122.86, 121.00, 117.09, 80.50, 64.34, 63.99, 59.88, 53.56, 28.25, 13.23, 10.43; HRMS (ESI-TOF) m/z Calcd for C$_{27}$H$_{31}$ClN$_3$O$_5$ [M+H]$^+$: 512.1947, found: 512.1948.

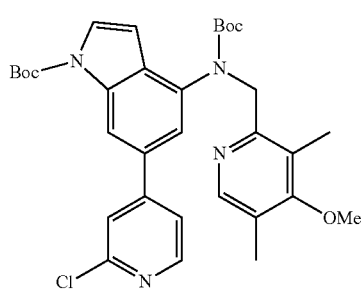

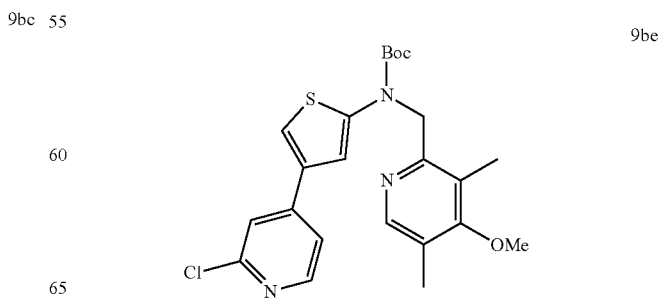

tert-Butyl (4-(2-chloropyridin-4-yl)thiophen-2-yl)((4-methoxy-3,5-dimethylpyridin-2-yl)methyl)carbamate (9be)

Substrate 2c was arylated following the general meta-arylation procedure. After purification by preparative thin-layer chromatography, Compound 9be was obtained in 93% yield as a yellow solid. $^1$H NMR (400 MHz, CDCl$_3$) δ 8.30 (d, J=5.2 Hz, 1H), 8.20 (s, 1H), 7.36 (s, 1H), 7.29-7.22 (m, 2H), 6.92 (s, 1H), 5.03 (s, 2H), 3.75 (s, 3H), 2.23 (s, 6H), 1.48 (s, 9H); $^{13}$C NMR (150 MHz, CDCl$_3$) δ 163.86, 153.64, 153.46, 152.08, 149.83, 149.05, 146.81, 145.94, 134.60, 125.14, 123.73, 120.55, 119.14, 118.02, 112.98, 82.30, 59.91, 53.42, 28.12, 13.23, 10.29; HRMS (ESI-TOF) m/z Calcd for C$_{23}$H$_{27}$ClN$_3$O$_3$S [M+H]$^+$: 460.1456, found: 460.1456.

tert-Butyl (5-acetyl-[2,3'-bithiophen]-5'-yl)((4-methoxy-3,5-dimethylpyridin-2-yl)methyl)carbamate (9bg)

Substrate 2c was arylated following the general meta-arylation procedure. After purification by preparative thin-layer chromatography, Compound 9bg was obtained in 47% yield as a yellow solid. $^1$H NMR (400 MHz, CDCl$_3$) δ 8.19 (s, 1H), 7.56 (d, J=3.9 Hz, 1H), 7.11 (s, 1H), 7.07 (d, J=3.9 Hz, 1H), 6.83 (s, 1H), 5.00 (s, 2H), 3.75 (s, 3H), 2.52 (s, 3H), 2.23 (s, 6H), 1.48 (s, 9H); $^{13}$C NMR (150 MHz, CDCl$_3$) δ 190.47, 163.83, 153.61, 153.55, 149.12, 148.08, 146.41, 141.70, 133.34, 131.48, 125.08, 123.66, 123.36, 116.57, 113.35, 82.24, 59.94, 53.39, 28.15, 26.45, 13.24, 10.29; HRMS (ESI-TOF) m/z Calcd for C$_{24}$H$_{29}$N$_2$O$_4$S$_2$ [M+H]$^+$: 473.1563, found: 473.1564.

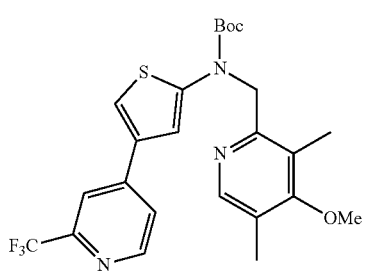

tert-Butyl ((4-methoxy-3,5-dimethylpyridin-2-yl)methyl)(4-(2-(trifluoromethyl)pyridin-4-yl)thiophen-2-yl)carbamate (9bf)

Substrate 2c was arylated following the general meta-arylation procedure. After purification by preparative thin-layer chromatography, Compound 9bf was obtained in 80% yield as a yellow solid. $^1$H NMR (400 MHz, CDCl$_3$) δ 8.64 (d, J=5.2 Hz, 1H), 8.21 (s, 1H), 7.70 (s, 1H), 7.52 (d, J=5.0 Hz, 1H), 7.31 (s, 1H), 6.99 (s, 1H), 5.05 (s, 2H), 3.75 (s, 3H), 2.27-2.20 (m, 6H), 1.49 (s, 9H); $^{19}$C NMR (150 MHz, CDCl$_3$) δ 163.92, 153.69, 153.46, 150.38, 149.08, 148.72 (q, J=34.7 Hz), 147.03, 144.65, 134.71, 125.22, 123.81, 122.65, 121.60 (q, J=274.3 Hz), 118.52, 117.08 (d, J=3.4 Hz), 112.86, 82.42, 59.93, 53.44, 28.15, 13.24, 10.32; $^{19}$F NMR (376 MHz, CDCl$_3$) δ −68.37; HRMS (ESI-TOF) m/z Calcd for C$_{24}$H$_{27}$F$_3$N$_3$O$_3$S [M+H]$^+$: 494.1720, found: 494.1718.

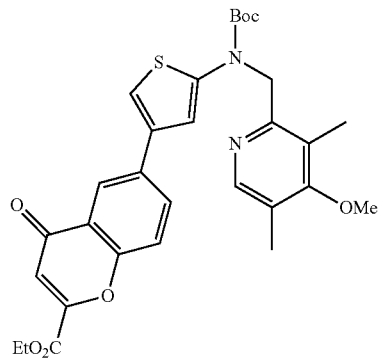

Ethyl 6-(5-((tert-butoxycarbonyl)((4-methoxy-3,5-dimethylpyridin-2-yl)methyl)amino)thiophen-3-yl)-4-oxo-4H-chromene-2-carboxylate (9bh)

Substrate 2c was arylated following the general meta-arylation procedure. After purification by preparative thin-layer chromatography, Compound 9bh was obtained in 41% yield as a yellow solid. $^1$H NMR (400 MHz, CDCl$_3$) δ 8.25-8.18 (m, 2H), 7.87 (dd, J=8.8, 2.3 Hz, 1H), 7.59 (d, J=8.8 Hz, 1H), 7.14 (s, 1H), 7.10 (s, 1H), 6.98 (s, 1H), 5.03 (s, 2H), 4.47 (q, J=7.2 Hz, 2H), 3.76 (s, 3H), 2.25 (s, 3H), 2.23 (s, 3H), 1.47 (s, 9H), 1.44 (t, J=7.2 Hz, 3H); $^{13}$C NMR (150 MHz, CDCl$_3$) δ 178.43, 163.81, 160.49, 154.87, 153.82, 153.65, 152.09, 149.13, 146.50, 136.66, 134.12, 132.60, 125.02, 124.46, 123.63, 121.85, 119.12, 115.84, 114.55, 113.82, 82.02, 62.98, 59.93, 53.55, 28.16, 14.07, 13.23, 10.33; HRMS (ESI-TOF) m/z Calcd for C$_{30}$H$_{33}$N$_2$O$_7$S [M+H]$^+$: 565.2003, found: 565.2002.

Meta-Arylation of Lenalidomide Derivative

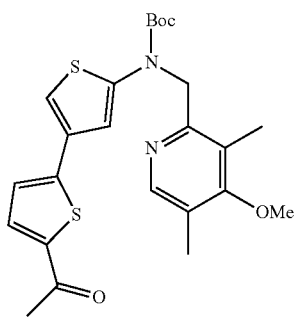

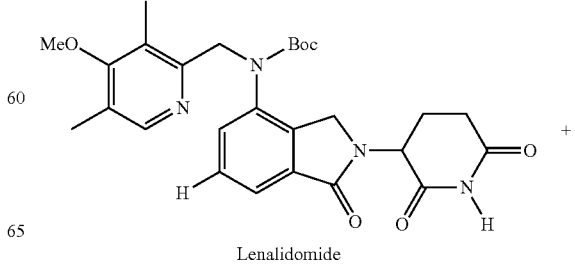

Lenalidomide

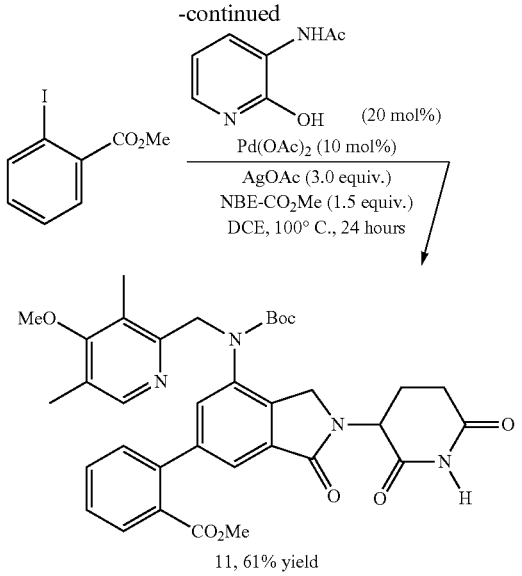

General Procedures for Meta-Arylation of Lenalidomide:

Substrate (0.05 mmol), Ar—I (0.1 mmol), Pd(OAc)$_2$ (1.1 mg, 10 mol %), L12 (1.5 mg, 20 mol %), AgOAc (25.0 mg, 0.15 mmol), NBE-CO$_2$Me (11.4 mg, 0.075 mmol) and DCE (0.5 mL) were added to a 2-dram vial. The vial was capped and closed tightly. The reaction mixture was then stirred at 100° C. for 24 hours. After cooling to room temperature, the mixture was passed through a pad of Celite® with DCM as the eluent to remove the insoluble precipitate. The resulting solution was concentrated and purified by preparative TLC plate to afford the desired arylated product in 61% yield as a colorless solid.

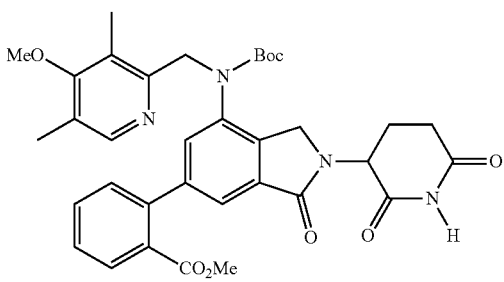

11

Colorless solid, $^1$H NMR (400 MHz, CDCl$_3$) δ 8.20 (s, 1H), 8.15 (s, 1H), 7.85 (d, J=7.7 Hz, 1H), 7.71 (s, 1H), 7.53 (t, J=7.5 Hz, 1H), 7.43 (t, J=7.6 Hz, 1H), 7.33 (d, J=5.7 Hz, 1H), 5.25 (dd, J=13.3, 5.1 Hz, 1H), 4.89 (s, 2H), 4.66 (d, J=16.5 Hz, 1H), 4.51 (d, J=16.5 Hz, 1H), 3.71 (s, 3H), 3.58 (s, 3H), 3.00-2.78 (m, 2H), 2.38 (qd, J=13.6, 13.0, 4.7 Hz, 1H), 2.29-2.14 (m, 7H), 1.36 (s, 9H); $^{13}$C NMR (150 MHz, CDCl$_3$) δ 170.70, 168.99, 168.46, 168.02, 163.38, 153.82, 153.25, 148.36, 142.11, 140.57, 138.02, 137.33, 131.90, 131.07, 130.42, 130.15, 130.07, 129.73, 127.24, 124.61, 121.49, 80.50, 59.45, 52.42, 51.43, 51.35, 45.99, 31.15, 27.72, 23.05, 12.80, 9.95; HRMS (ESI-TOF) m/z Calcd for C$_{35}$H$_{39}$N$_4$O$_8$ [M+H]$^+$: 643.2762, found: 643.2762.

3.15 Meta-Arylation of Anilines without Sliver

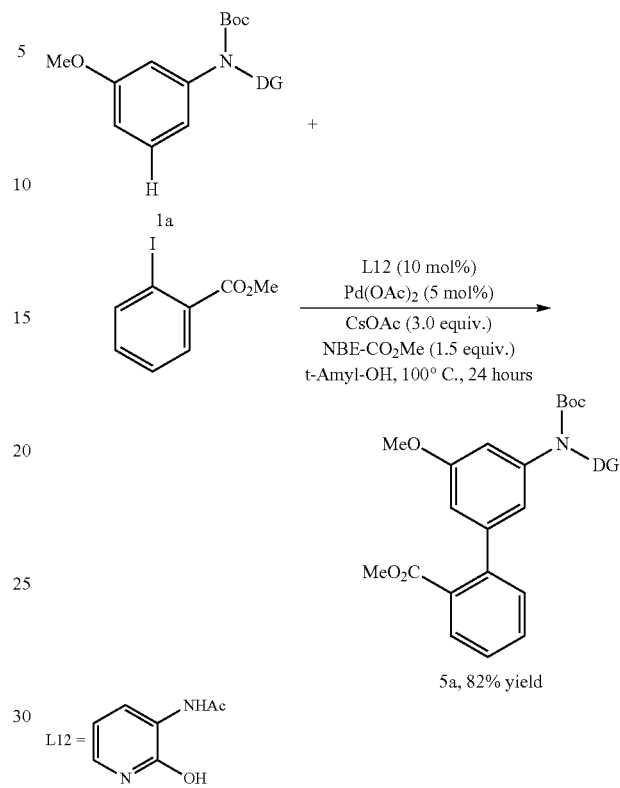

General Procedure for Arylation of 1a without Sliver Using Methyl 2-iodobenzoate as Coupling Partner on Gram Scale:

Substrate 1a (35.6 mg, 0.1 mmol), methyl 2-iodobenzoate (30 μL, 0.2 mmol), Pd(OAc)$_2$ (1.2 mg, 5 mol %), L12 (1.5 mg, 10 mol %), CsOAc (57.6 mg, 0.3 mmol), NBE-CO$_2$Me (21.6 mg, 0.15 mmol), and t-Amyl-OH (0.2 mL) were added to a 2-dram vial. The vial was capped and closed tightly. Then the reaction mixture was stirred at 100° C. for 24 hours. After cooling to room temperature, the mixture was passed through a pad of Celite® with DCM as the eluent to remove the insoluble precipitate. The resulting solution was concentrated and purified by preparative TLC to afford the desired product Compound 5a in 82% yield.

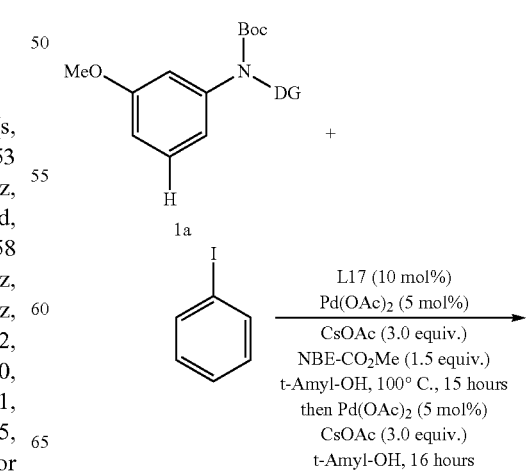

-continued

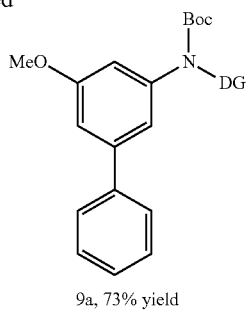

9a, 73% yield

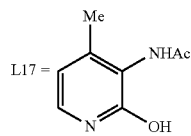

L17 =

General Procedure for Arylation of 1a without Sliver Using Iodobenzene as Coupling Partner:

Substrate 1a (35.6 mg, 0.1 mmol), iodobenzene (23 μL, 0.2 mmol), Pd(OAc)₂ (1.2 mg, 5 mol %), L17 (1.5 mg, 10 mol %), CsOAc (57.6 mg, 0.3 mmol), NBE-CO₂Me (21.6 mg, 0.15 mmol), and t-Amyl-OH (0.2 mL) were added to a 2-dram vial. The vial was capped and closed tightly. Then the reaction mixture was stirred at 100° C. for 15 hours. After cooling to room temperature, the mixture was diluted by DCM (5.0 mL) and stirred for 10 minutes. The mixture was passed through a pad of Celite® with DCM as the eluent to remove the insoluble precipitate. After concentration, CsOAc (57.6 mg, 0.3 mmol), Pd(OAc)₂ (1.2 mg, 5 mol %) and t-Amyl-OH (0.2 mL) were added into a 2-dram vial with the residue. The vial was capped and closed tightly, the reaction mixture was then stirred at 100° C. for another 16 hours. After cooling to room temperature, the mixture was passed through a pad of Celite® with DCM as the eluent to remove the insoluble precipitate. The resulting solution was concentrated and purified by preparative TLC to afford the desired product Compound 9a in 73% yield.

Meta-Amination of Anilines

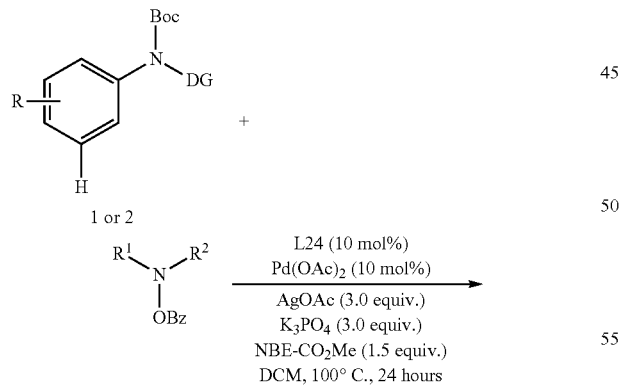

-continued

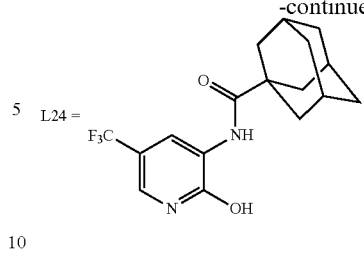

L24 =

General Procedure for Amination of Anilines:

Substrate 1 or 2 (0.1 mmol), aminating reagent (0.15 mmol), Pd(OAc)₂ (2.2 mg, 10 mol %), L24 (3.4 mg, 10 mol %), AgOAc (33.4 mg, 0.2 mmol), NBE-CO₂Me (21.6 mg, 0.15 mmol), K₃PO₄ (62.8 mg, 0.3 mmol) and DCM (1.0 mL) were added to a 2-dram vial. The vial was capped and closed tightly. Then the reaction mixture was then stirred at 100° C. for 24 hours. After cooling to room temperature, the mixture was passed through a pad of Celite® with DCM as the eluent to remove the insoluble precipitate. The resulting solution was concentrated and purified by preparative TLC to afford the desired product Compound 10.

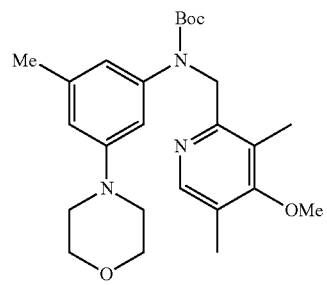

10a tert-Butyl ((4-methoxy-3,5-dimethylpyridin-2-yl)methyl)(3-methyl-5-morpholinophenyl)carbamate (10a)

Substrate 1a was aminated following the general meta-amination procedure. After purification by preparative thin-layer chromatography, Compound 10a was obtained in 77% yield as a colorless liquid, $^1$H NMR (400 MHz, CDCl₃) δ 8.16 (s, 1H), 6.63 (s, 1H), 6.60 (s, 1H), 6.49 (s, 1H), 4.87 (s, 2H), 3.80 (t, J=4.8 Hz, 4H), 3.72 (s, 3H), 3.04 (t, J=4.8 Hz, 4H), 2.23 (s, 3H), 2.21 (s, 3H), 2.20 (s, 3H), 1.39 (s, 9H); $^{13}$C NMR (150 MHz, CDCl₃) δ 163.59, 155.36, 154.75, 151.28, 148.87, 143.53, 138.55, 124.54, 123.72, 119.03, 114.16, 111.84, 80.06, 66.90, 59.81, 53.60, 49.52, 28.29, 21.72, 13.19, 10.42; HRMS (ESI-TOF) m/z Calcd for C₂₅H₃₆N₃O₄ [M+H]⁺: 442.2700, found: 442.2700.

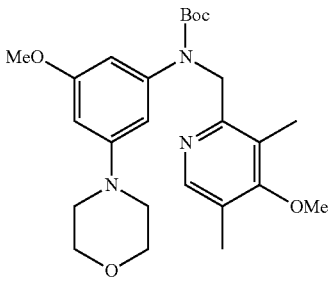

10b

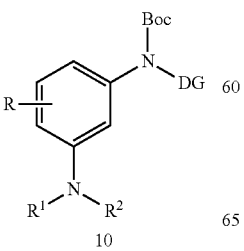

10 tert-Butyl ((4-methoxy-3,5-dimethylpyridin-2-yl)methyl)(3-methoxy-5-morpholinophenyl)carbamate (10b)

Substrate 1b was aminated following the general meta-amination procedure. After purification by preparative thin-layer chromatography, Compound 10b was obtained in 65% yield as a colorless liquid, $^1$H NMR (400 MHz, CDCl$_3$) δ 8.16 (s, 1H), 6.46 (s, 1H), 6.37 (s, 1H), 6.22 (t, J=2.2 Hz, 1H), 4.88 (s, 2H), 3.80 (t, J=4.7 Hz, 4H), 3.72 (s, 3H), 3.70 (s, 3H), 3.05 (t, J=4.6 Hz, 4H), 2.21 (s, 3H), 2.20 (s, 3H), 1.40 (s, 9H); $^{13}$C NMR (150 MHz, CDCl$_3$) δ 163.57, 160.15, 155.20, 154.64, 152.11, 148.88, 144.47, 124.57, 123.70, 107.47, 103.88, 99.79, 80.17, 66.81, 59.82, 55.20, 53.57, 49.31, 28.29, 13.19, 10.41; HRMS (ESI-TOF) m/z Calcd for C$_{25}$H$_{36}$N$_3$O$_5$ [M+H]$^+$: 458.2649, found: 458.2650.

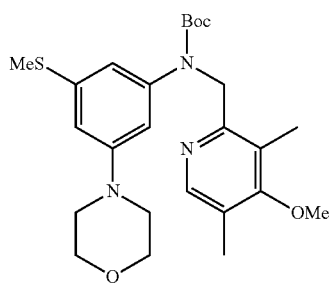

10c tert-Butyl ((4-methoxy-3,5-dimethylpyridin-2-yl)methyl)(3-(methylthio)-5-morpholinophenyl)-carbamate (10c)

Substrate 1c was aminated following the general meta-amination procedure. After purification by preparative thin-layer chromatography, Compound 10c was obtained in 57% yield as a colorless solid, $^1$H NMR (400 MHz, CDCl$_3$) δ 8.16 (s, 1H), 6.67 (s, 1H), 6.65 (s, 1H), 6.57 (t, J=2.0 Hz, 1H), 4.87 (s, 2H), 3.84-3.76 (m, 4H), 3.72 (s, 3H), 3.10-3.01 (m, 4H), 2.38 (s, 3H), 2.21 (s, 3H), 2.19 (s, 3H), 1.40 (s, 9H); $^{13}$C NMR (150 MHz, CDCl$_3$) δ 163.63, 155.09, 154.59, 151.51, 148.89, 144.05, 138.70, 124.67, 123.76, 116.61, 111.87, 111.62, 80.31, 66.79, 59.85, 53.43, 49.24, 28.29, 16.01, 13.20, 10.43; HRMS (ESI-TOF) m/z Calcd for C$_{25}$H$_{36}$N$_3$O$_4$S [M+H]$^+$: 474.2421, found: 474.2421.

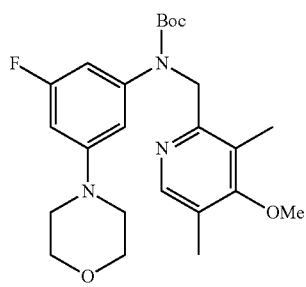

10d tert-Butyl (3-fluoro-5-morpholinophenyl)((4-methoxy-3,5-dimethylpyridin-2-yl)methyl)carbamate (10d)

Substrate 1e was aminated following the general meta-amination procedure. After purification by preparative thin-layer chromatography, Compound 10d was obtained in 63% yield as a colorless liquid, $^1$H NMR (400 MHz, CDCl$_3$) δ 8.16 (s, 1H), 6.65 (s, 1H), 6.51 (dt, J=10.0, 2.1 Hz, 1H), 6.35 (dt, J=11.7, 2.3 Hz, 1H), 4.86 (s, 2H), 3.84-3.77 (m, 4H), 3.73 (s, 3H), 3.10-3.03 (m, 4H), 2.22 (s, 3H), 2.20 (s, 3H), 1.39 (s, 9H); $^{13}$C NMR (150 MHz, CDCl$_3$) δ 164.00, 163.65, 162.40, 154.84, 152.24, 152.16, 148.93, 144.78, 144.69, 124.72, 123.61, 109.47, 105.05, 104.89, 99.91, 99.74, 80.54, 66.64, 59.85, 53.35, 28.21, 13.20, 10.37; HRMS (ESI-TOF) m/z Calcd for C$_{24}$H$_{33}$FN$_3$O$_4$ [M+H]$^+$: 446.2450, found: 446.2452.

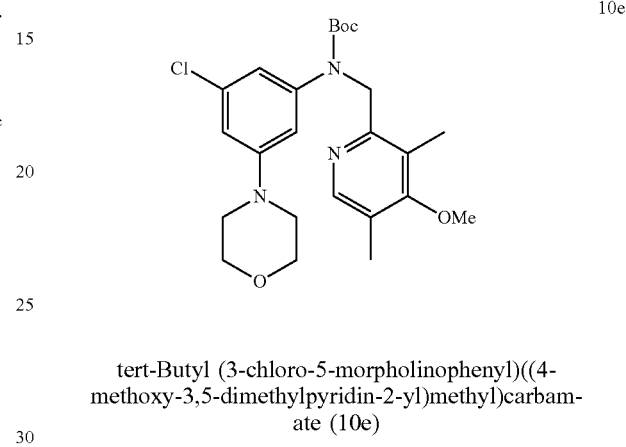

tert-Butyl (3-chloro-5-morpholinophenyl)((4-methoxy-3,5-dimethylpyridin-2-yl)methyl)carbamate (10e)

Substrate 1f was aminated following the general meta-amination procedure. After purification by preparative thin-layer chromatography, Compound 10e was obtained in 63% yield as a colorless liquid, $^1$H NMR (400 MHz, CDCl$_3$) δ 8.17 (s, 1H), 6.77 (s, 2H), 6.63 (t, J=2.1 Hz, 1H), 4.85 (s, 2H), 3.84-3.77 (m, 4H), 3.73 (s, 3H), 3.10-3.02 (m, 4H), 2.22 (s, 3H), 2.20 (s, 3H), 1.39 (s, 9H); $^{13}$C NMR (150 MHz, CDCl$_3$) δ 163.66, 154.80, 154.35, 151.92, 148.94, 144.54, 134.17, 124.75, 123.62, 117.94, 112.84, 112.50, 80.58, 66.66, 59.86, 53.30, 48.87, 28.22, 13.21, 10.39; HRMS (ESI-TOF) m/z Calcd for C$_{24}$H$_{33}$ClN$_3$O$_4$ [M+H]$^+$: 462.2154, found: 462.2155.

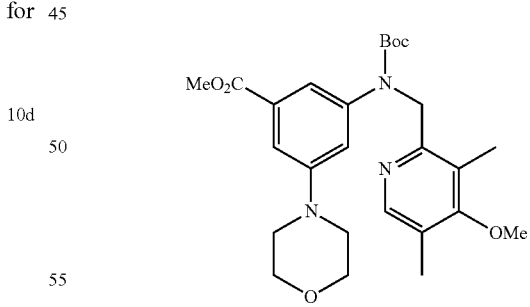

Methyl 3-((tert-butoxycarbonyl)((4-methoxy-3,5-dimethylpyridin-2-yl)methyl)amino)-5-morpholinobenzoate (10f)

Substrate 1h was aminated following the general meta-amination procedure using Pd(OAc)$_2$ (3.4 mg, 15 mol %), L24 (5.1 mg, 15 mol %), AgOAc (50.1 mg, 0.3 mmol) and NBE-CO$_2$Me (45.7 mg, 0.3 mmol). After purification by preparative thin-layer chromatography, Compound 10f was obtained in 60% yield as a colorless solid, $^1$H NMR (400 MHz, CDCl$_3$) δ 8.14 (s, 1H), 7.42 (s, 1H), 7.36-7.32 (m, 1H), 7.08 (s, 1H), 4.91 (s, 2H), 3.86 (s, 3H), 3.84-3.80 (m, 4H), 3.72 (s, 3H), 3.15-3.08 (m, 4H), 2.23-2.19 (m, 6H), 1.39 (s, 9H); $^{13}$C NMR (150 MHz, CDCl$_3$) δ 166.97, 163.71, 154.89, 154.48, 151.26, 148.90, 143.71, 130.80, 124.78, 123.86, 119.26, 118.86, 113.76, 80.55, 66.74, 59.85, 53.24, 52.09, 49.06, 28.23, 13.21, 10.46; HRMS (ESI-TOF) m/z Calcd for C$_{26}$H$_{36}$N$_3$O$_6$ [M+H]$^+$: 486.2599, found: 486.2600.

layer chromatography, Compound 10h was obtained in 62% yield as a colorless solid, $^1$H NMR (400 MHz, CDCl$_3$) δ 8.16 (s, 1H), 7.86-7.79 (m, 2H), 6.93 (s, 1H), 6.44 (s, 1H), 4.95 (s, 2H), 3.94 (s, 3H), 3.92-3.88 (m, 4H), 3.73 (s, 3H), 3.25-3.16 (m, 4H), 2.23 (s, 3H), 2.22 (s, 3H), 1.41 (s, 9H); $^{13}$C NMR (150 MHz, CDCl$_3$) δ 163.67, 155.14, 154.75, 148.88, 145.25, 142.42, 141.34, 130.99, 124.73, 123.82, 115.44, 106.64, 100.31, 80.40, 66.89, 59.83, 53.94, 51.40, 35.64, 28.29, 13.21, 10.48; HRMS (ESI-TOF) m/z Calcd for C$_{26}$H$_{36}$N$_5$O$_4$ [M+H]$^+$: 482.2762, found: 482.2766.

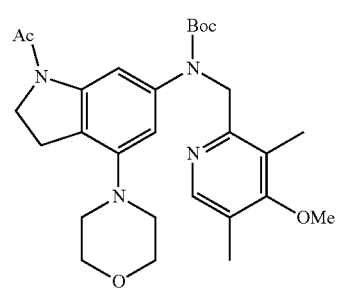

10g tert-Butyl (1-acetyl-4-morpholinoindolin-6-yl)((4-methoxy-3,5-dimethylpyridin-2-yl)methyl)carbamate (10g)

Substrate 2g was aminated following the general meta-amination procedure. After purification by preparative thin-layer chromatography, Compound 10g was obtained in 76% yield as a light yellow solid, Rotameric mixture, ratio of the rotamers=74/26; $^1$H NMR (500 MHz, CDCl$_3$) δ 8.14 (s, 1H), 7.87 (s, 0.74H), 6.86 (s, 0.26H), 6.68-6.52 (m, 1H), 4.97-4.81 (m, 2H), 4.09 (t, J=8.4 Hz, 0.52H), 4.01 (t, J=8.2 Hz, 1.48H), 3.84-3.76 (m, 4H), 3.76-3.69 (m, 3H), 3.02 (t, J=8.3 Hz, 1.42H), 2.97-2.82 (m, 4.52H), 2.28-2.13 (m, 9H), 1.41 (s, 9H); $^{13}$C NMR (150 MHz, CDCl$_3$) resonances for the minor rotamer are enclosed in parenthesis ( ): δ 168.21, 163.64 (163.71), 155.27 (155.13), 154.74, 148.77 (148.88), 147.80, 143.81, 143.21 (142.78), 124.56 (124.83), 123.96 (123.43), 120.93, 112.74 (111.75), 110.80 (108.80), 80.22 (80.41), 67.15 (67.10), 59.82, 53.53 (53.68), 50.91 (50.71), 49.41 (48.60), 28.29, 26.61 (25.61), 24.21 (24.00), 13.18, 10.48 (10.45); HRMS (ESI-TOF) m/z Calcd for C$_{28}$H$_{39}$N$_4$O$_5$ [M+H]$^+$: 511.2915, found: 511.2914.

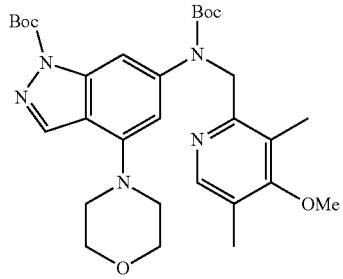

10i tert-Butyl 6-((tert-butoxycarbonyl)((4-methoxy-3,5-dimethylpyridin-2-yl)methyl)amino)-4-morpholino-1H-indole-1-carboxylate (10i)

Substrate 2h was aminated following the general meta-amination procedure. After purification by preparative thin-layer chromatography, Compound 10i was obtained in 53% yield as a colorless solid, $^1$H NMR (400 MHz, CDCl$_3$) δ 8.12 (s, 1H), 7.67 (s, 1H), 7.49 (d, J=3.7 Hz, 1H), 6.66 (s, 1H), 6.48 (d, J=3.7 Hz, 1H), 4.97 (s, 2H), 3.89 (t, J=4.5 Hz, 4H), 3.72 (s, 3H), 3.06 (t, J=4.6 Hz, 4H), 2.23 (s, 3H), 2.20 (s, 3H), 1.57 (s, 9H), 1.41 (s, 9H); $^{13}$C NMR (150 MHz, CDCl$_3$) δ 163.67, 155.32, 154.97, 149.52, 148.85, 144.70, 140.07, 135.82, 124.76, 124.63, 124.02, 121.87, 110.77, 108.56, 105.03, 83.54, 80.10, 67.12, 59.78, 54.13, 52.06, 28.34, 28.02, 28.01, 13.15, 10.50; HRMS (ESI-TOF) m/z Calcd for C$_{31}$H$_{43}$N$_4$O$_6$ [M+H]$^+$: 567.3177, found: 567.3179.

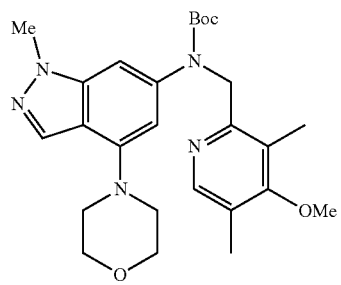

10h tert-Butyl ((4-methoxy-3,5-dimethylpyridin-2-yl)methyl)(1-methyl-4-morpholino-1H-indazol-6-yl)-carbamate (10h)

Substrate 2j was aminated following the general meta-amination procedure. After purification by preparative thin-

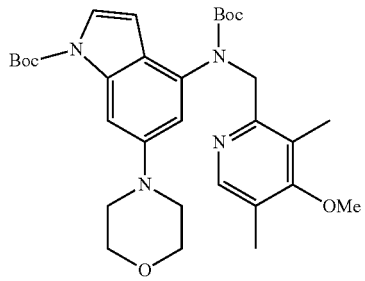

10j tert-Butyl 4-((tert-butoxycarbonyl)((4-methoxy-3,5-dimethylpyridin-2-yl)methyl)amino)-6-morpholino-1H-indole-1-carboxylate (10j)

Substrate 2i was aminated following the general meta-amination procedure. After purification by preparative thin-layer chromatography, Compound 10j was obtained in 44% yield as a colorless solid, $^1$H NMR (400 MHz, CDCl$_3$) δ 8.11 (s, 1H), 7.60 (s, 1H), 7.38 (d, J=3.7 Hz, 1H), 6.69 (s, 1H), 6.41 (d, J=3.8 Hz, 1H), 4.95 (s, 2H), 3.86-3.78 (m, 4H), 3.68 (s, 3H), 3.12-3.01 (m, 4H), 2.23-2.13 (m, 6H), 1.64 (s, 9H), 1.35 (s, 9H); $^{13}$C NMR (150 MHz, CDCl$_3$) δ 163.63, 155.23, 154.80, 149.81, 149.28, 148.83, 136.84, 135.05, 124.71, 124.42, 124.05, 122.23, 112.58, 105.50, 101.10, 83.29, 80.10, 66.95, 59.75, 53.28, 50.54, 28.22, 28.17, 13.16, 10.57; HRMS (ESI-TOF) m/z Calcd for C$_{31}$H$_{43}$N$_4$O$_6$ [M+H]$^+$: 567.3177, found: 567.3174.

4H), 2.23 (s, 3H), 2.21 (s, 3H), 2.20 (s, 3H), 1.48 (s, 9H), 1.39 (s, 9H); $^{13}$C NMR (150 MHz, CDCl$_3$) δ 163.56, 155.30, 154.67, 151.23, 148.85, 143.46, 138.54, 124.54, 123.68, 119.20, 115.09, 112.60, 80.06, 79.78, 59.80, 53.57, 49.53, 44.01, 42.98, 28.38, 28.26, 21.68, 13.18, 10.40; HRMS (ESI-TOF) m/z Calcd for C$_{30}$H$_{45}$N$_4$O$_5$ [M+H]$^+$: 541.3384, found: 541.3387.

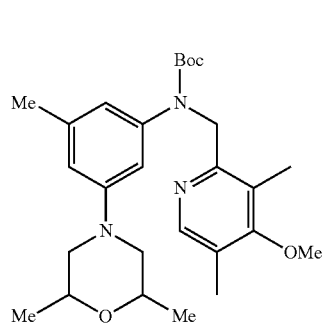

tert-Butyl (3-(2,6-dimethylmorpholino)-5-methyl-phenyl)((4-methoxy-3,5-dimethylpyridin-2-yl)methyl)-carbamate (10k)

Substrate 1a was aminated following the general meta-amination procedure. After purification by preparative thin-layer chromatography, Compound 10k was obtained in 81% yield as a colorless liquid, $^1$H NMR (400 MHz, CDCl$_3$) δ 8.15 (s, 1H), 6.57 (s, 2H), 6.48 (s, 1H), 4.87 (s, 2H), 3.80-3.67 (m, 5H), 3.30 (d, J=10.4 Hz, 2H), 2.31 (t, J=11.1 Hz, 2H), 2.25-2.18 (m, 9H), 1.39 (s, 9H), 1.23 (s, 3H), 1.21 (s, 3H); $^{13}$C NMR (150 MHz, CDCl$_3$) δ 163.58, 155.40, 154.76, 150.94, 148.83, 143.42, 138.55, 124.52, 123.79, 118.79, 114.24, 112.01, 80.02, 71.55, 59.81, 54.99, 53.62, 28.28, 21.71, 19.01, 13.18, 10.43; HRMS (ESI-TOF) m/z Calcd for C$_{27}$H$_{40}$N$_3$O$_4$ [M+H]$^+$: 470.3013, found: 470.3014.

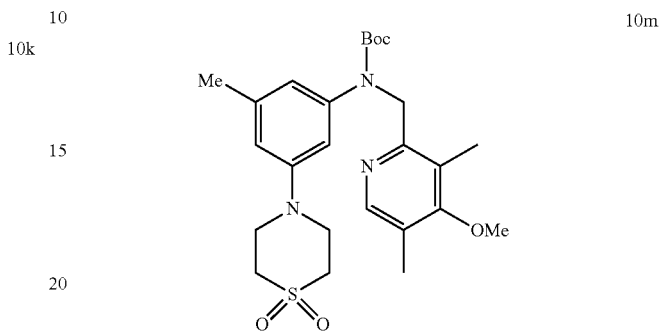

tert-Butyl (3-(1,1-dioxidothiomorpholino)-5-methyl-phenyl)-((4-methoxy-3,5-dimethylpyridin-2-yl)methyl)-carbamate (10m)

Substrate 1a was aminated following the general meta-amination procedure. After purification by preparative thin-layer chromatography, Compound 10m was obtained in 70% yield as a light yellow solid, $^1$H NMR (400 MHz, CDCl$_3$) δ 8.15 (s, 1H), 6.71 (s, 1H), 6.66 (s, 1H), 6.48 (s, 1H), 4.87 (s, 2H), 3.81-3.69 (m, 7H), 3.07-2.98 (m, 4H), 2.24 (s, 3H), 2.23-2.19 (m, 6H), 1.39 (s, 9H); $^{13}$C NMR (150 MHz, CDCl$_3$) δ 163.64, 155.16, 154.51, 148.83, 147.34, 143.93, 139.30, 124.76, 123.78, 119.61, 114.42, 112.37, 80.32, 59.85, 53.40, 50.33, 47.62, 28.24, 21.74, 13.21, 10.42; HRMS (ESI-TOF) m/z Calcd for C$_{25}$H$_{36}$N$_3$O$_5$S [M+H]$^+$: 490.2370, found: 490.2368.

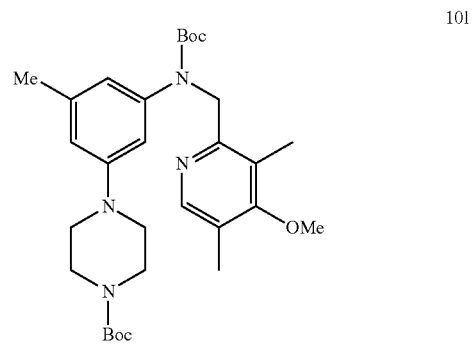 [SMILES: COc1c(C)cnc(CN(C(=O)OC(C)(C)C)c2cc(C)cc(N3CCN(C(=O)OC(C)(C)C)CC3)c2)c1C]

tert-Butyl 4-(3-((tert-butoxycarbonyl)((4-methoxy-3,5-dimethylpyridin-2-yl)methyl)amino)-5-methylphenyl)piperazine-1-carboxylate (10l)

Substrate 1a was aminated following the general meta-amination procedure. After purification by preparative thin-layer chromatography, Compound 10l was obtained in 84% yield as a colorless solid, $^1$H NMR (400 MHz, CDCl$_3$) δ 8.15 (s, 1H), 6.63 (s, 1H), 6.61 (s, 1H), 6.50 (s, 1H), 4.87 (s, 2H), 3.72 (s, 3H), 3.52 (t, J=5.1 Hz, 4H), 3.01 (t, J=5.2 Hz,

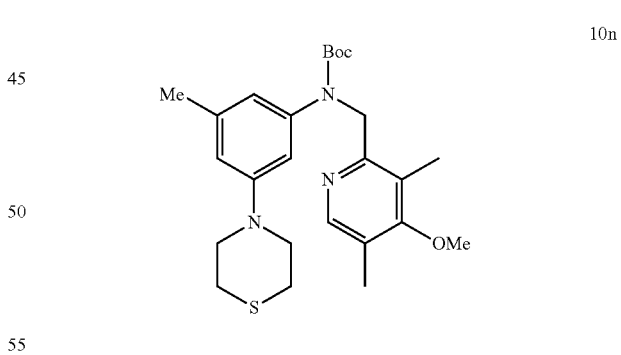

tert-Butyl ((4-methoxy-3,5-dimethylpyridin-2-yl)methyl)(3-methyl-5-thiomorpholinophenyl)carbamate (10n)

Substrate 1a was aminated following the general meta-amination procedure using Pd(OAc)$_2$ (3.4 mg, 15 mol %), L24 (5.1 mg, 15 mol %), AgOAc (50.1 mg, 0.3 mmol) and NBE-CO$_2$Me (45.7 mg, 0.3 mmol). After purification by preparative thin-layer chromatography, Compound 10n was obtained in 62% yield as a colorless solid, $^1$H NMR (400 MHz, CDCl$_3$) δ 8.15 (s, 1H), 6.58 (s, 2H), 6.47 (s, 1H), 4.87

(s, 2H), 3.72 (s, 3H), 3.45-3.38 (m, 4H), 2.71-2.64 (m, 4H), 2.24-2.18 (m, 9H), 1.39 (s, 9H); $^{13}$C NMR (150 MHz, CDCl$_3$) δ 163.61, 155.34, 154.74, 151.33, 148.85, 143.49, 138.66, 124.60, 123.78, 118.82, 115.65, 113.26, 80.10, 59.84, 53.59, 52.27, 28.30, 26.79, 21.71, 13.21, 10.44; HRMS (ESI-TOF) m/z Calcd for C$_{25}$H$_{36}$N$_3$O$_3$S [M+H]$^+$: 458.2472, found: 458.2469.

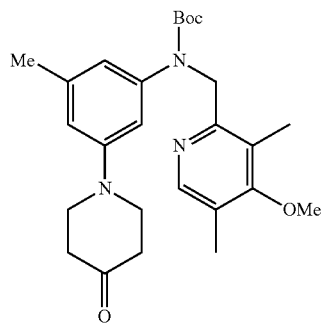

10o tert-Butyl ((4-methoxy-3,5-dimethylpyridin-2-yl)methyl)(3-methyl-5-(4-oxopiperidin-1-yl)phenyl)-carbamate (10o)

Substrate 1a was aminated following the general meta-amination procedure using Pd(OAc)$_2$ (3.4 mg, 15 mol %), L24 (5.1 mg, 15 mol %), AgOAc (50.1 mg, 0.3 mmol) and NBE-CO$_2$Me (45.7 mg, 0.3 mmol). After purification by preparative thin-layer chromatography, Compound 10o was obtained in 53% yield as a colorless liquid, $^1$H NMR (400 MHz, CDCl$_3$) δ 8.14 (s, 1H), 6.71 (s, 1H), 6.61 (s, 1H), 6.56 (s, 1H), 4.88 (s, 2H), 3.73 (s, 3H), 3.50 (t, J=6.0 Hz, 4H), 2.47 (t, J=6.0 Hz, 4H), 2.25 (s, 3H), 2.21 (s, 6H), 1.39 (s, 9H); $^{13}$C NMR (150 MHz, CDCl$_3$) δ 208.41, 163.61, 155.33, 154.69, 148.97, 148.83, 143.73, 138.94, 124.63, 123.77, 118.81, 114.26, 112.10, 80.16, 59.84, 53.57, 49.00, 40.69, 28.29, 21.77, 13.20, 10.43; HRMS (ESI-TOF) m/z Calcd for C$_{26}$H$_{36}$N$_3$O$_4$ [M+H]$^+$: 454.2700, found: 454.2699.

Meta-Alkynylation of Anilines

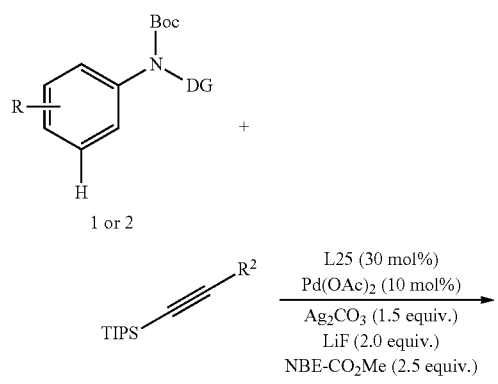

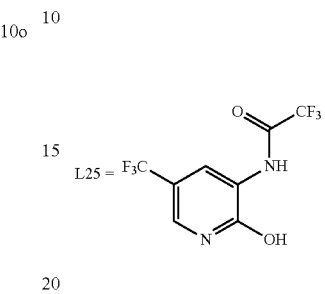

L25 =

General Procedure for Alkynylation of Anilines:

Substrate 1 or 2 (0.1 mmol), alkynylating reagent (52.2 mg, 0.2 mmol), Pd(OAc)$_2$ (2.2 mg, 10 mol %), L25 (8.2 mg, 30 mol %), Ag$_2$CO$_3$ (41.1 mg, 0.15 mmol), NBE-CO$_2$Me (38.0 mg, 0.25 mmol), LiF (5.2 mg, 0.2 mmol) and DCM (1.0 mL) were added to a 2-dram vial. The vial was capped and closed tightly. Then the reaction mixture was then stirred at 100° C. for 24 hours. After cooling to room temperature, the mixture was passed through a pad of Celite® with DCM as the eluent to remove the insoluble precipitate. The resulting solution was concentrated and purified by preparative TLC to afford the desired product Compound 14.

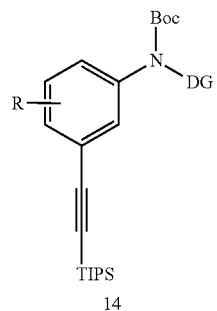

14

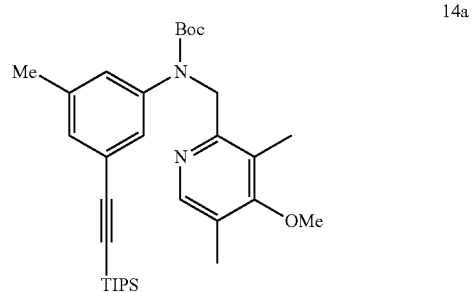

14a tert-Butyl ((4-methoxy-3,5-dimethylpyridin-2-yl)methyl)(3-methyl-5-((triisopropylsilyl)ethynyl)phenyl)-carbamate (14a)

Substrate 1a was alkynylated following the general meta-alkynylation procedure. After purification by preparative thin-layer chromatography, Compound 14a was obtained in 72% yield as a colorless liquid, $^1$H NMR (400 MHz, CDCl$_3$) δ 8.15 (s, 1H), 7.11 (s, 1H), 7.05 (s, 2H), 4.87 (s, 2H), 3.72 (s, 3H), 2.24 (s, 3H), 2.21 (s, 6H), 1.40 (s, 9H), 1.10 (s, 21H); $^{13}$C NMR (150 MHz, CDCl$_3$) δ 163.70, 154.94, 154.59, 148.95, 142.57, 138.08, 129.93, 127.64, 127.31, 124.69, 123.75, 123.25, 107.04, 89.82, 80.42, 59.83, 53.32, 28.22, 21.10, 18.63, 13.18, 11.29, 10.44; HRMS (ESI-TOF) m/z Calcd for C$_{32}$H$_{49}$N$_2$O$_3$Si [M+H]$^+$: 537.3507, found: 537.3506.

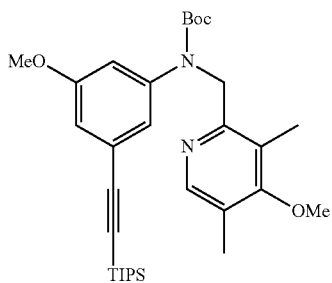

tert-Butyl ((4-methoxy-3,5-dimethylpyridin-2-yl)
methyl)(3-methoxy-5-((triisopropylsilyl)ethynyl)
phenyl)-carbamate (14b)

Substrate 1b was alkynylated following the general meta-alkynylation procedure. After purification by preparative thin-layer chromatography, Compound 14b was obtained in 62% yield as a colorless liquid, $^1$H NMR (400 MHz, CDCl$_3$) δ 8.16 (s, 1H), 6.94 (s, 1H), 6.83 (s, 1H), 6.75 (s, 1H), 4.87 (s, 2H), 3.73 (s, 3H), 3.72 (s, 3H), 2.23-2.18 (m, 6H), 1.41 (s, 9H), 1.10 (s, 21H); $^{13}$C NMR (150 MHz, CDCl$_3$) δ 163.70, 159.17, 154.78, 154.49, 148.97, 143.84, 124.70, 123.95, 123.70, 122.97, 114.24, 113.82, 106.82, 90.18, 80.56, 59.84, 55.39, 53.26, 28.23, 18.63, 13.18, 11.27, 10.41; HRMS (ESI-TOF) m/z Calcd for C$_{32}$H$_{49}$N$_2$O$_4$Si [M+H]$^+$: 553.3456, found: 553.3457.

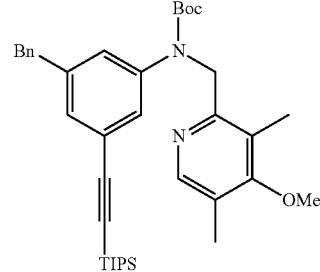

tert-Butyl (3-benzyl-5-((triisopropylsilyl)ethynyl)-
phenyl)((4-methoxy-3,5-dimethylpyridin-2-yl)
methyl)-carbamate (14d)

Substrate 1y was alkynylated following the general meta-alkynylation procedure. After purification by preparative thin-layer chromatography, Compound 14d was obtained in 50% yield as a colorless liquid, $^1$H NMR (400 MHz, CDCl$_3$) δ 8.09 (s, 1H), 7.28-7.22 (m, 2H), 7.18 (t, J=7.2 Hz, 1H), 7.14 (s, 1H), 7.11-7.05 (m, 3H), 7.00 (s, 1H), 4.86 (s, 2H), 3.86 (s, 2H), 3.69 (s, 3H), 2.19 (s, 3H), 2.17 (s, 3H), 1.36 (s, 9H), 1.09 (s, 21H); $^{13}$C NMR (150 MHz, CDCl$_3$) δ 163.72, 154.80, 154.56, 148.94, 142.65, 141.02, 140.40, 129.77, 128.85, 128.39, 128.10, 127.89, 126.10, 124.69, 123.86, 123.56, 106.87, 90.22, 80.49, 59.82, 53.22, 41.40, 28.21, 18.64, 13.20, 11.29, 10.44; HRMS (ESI-TOF) m/z Calcd for C$_{38}$H$_{53}$N$_2$O$_3$Si [M+H]$^+$: 613.3820, found: 613.3820.

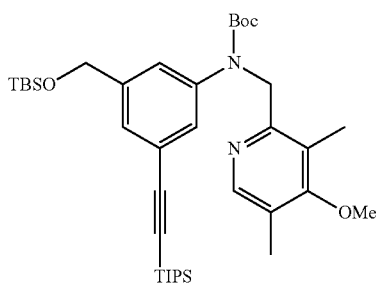

tert-Butyl (3-(((tert-Butyldimethylsilyl)oxy)methyl)-
5-((triisopropylsilyl)ethynyl)phenyl)((4-methoxy-3,
5-dimethylpyridin-2-yl)methyl)carbamate (14c)

Substrate 1x was alkynylated following the general meta-alkynylation procedure. After purification by preparative thin-layer chromatography, Compound 14c was obtained in 70% yield as a colorless liquid, $^1$H NMR (400 MHz, CDCl$_3$) δ 8.15 (s, 1H), 7.20 (s, 1H), 7.19-7.14 (m, 2H), 4.88 (s, 2H), 4.62 (s, 2H), 3.72 (s, 3H), 2.23-2.17 (m, 6H), 1.40 (s, 9H), 1.10 (s, 21H), 0.89 (s, 9H), 0.04 (s, 6H); $^{13}$C NMR (150 MHz, CDCl$_3$) δ 163.67, 154.81, 154.61, 149.02, 142.77, 141.83, 128.46, 126.71, 124.63, 124.27, 123.63, 123.26, 107.06, 90.03, 80.45, 64.15, 59.82, 53.28, 28.23, 25.86, 18.63, 18.31, 13.17, 11.29, 10.39, −5.35; HRMS (ESI-TOF) m/z Calcd for C$_{38}$H$_{63}$N$_2$O$_4$Si$_2$ [M+H]$^+$: 667.4321, found: 667.4322.

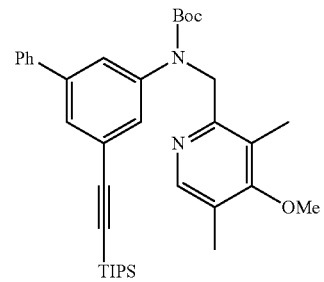

tert-Butyl ((4-methoxy-3,5-dimethylpyridin-2-yl)
methyl)(5-((triisopropylsilyl)ethynyl)-[1,1'-biphe-
nyl]-3-yl)carbamate (14e)

Substrate 1z was alkynylated following the general meta-alkynylation procedure. After purification by preparative thin-layer chromatography, Compound 14e was obtained in 61% yield as a colorless liquid, $^1$H NMR (400 MHz, CDCl$_3$) δ 8.17 (s, 1H), 7.48 (d, J=7.6 Hz, 2H), 7.45-7.36 (m, 4H), 7.33 (d, J=7.2 Hz, 1H), 7.31 (s, 1H), 4.94 (s, 2H), 3.71 (s, 3H), 2.22 (s, 3H), 2.21 (s, 3H), 1.43 (s, 9H), 1.12 (s, 21H); $^{13}$C NMR (150 MHz, CDCl$_3$) δ 163.76, 154.86, 154.55, 149.02, 143.01, 141.45, 140.14, 128.90, 128.68, 127.99, 127.53, 127.10, 126.01, 124.81, 123.89, 106.78, 90.51, 80.62, 59.83, 53.28, 28.29, 28.26, 18.65, 13.19, 11.30, 10.48; HRMS (ESI-TOF) m/z Calcd for C$_{37}$H$_{51}$N$_2$O$_3$Si [M+H]$^+$: 599.3663, found: 599.3662.

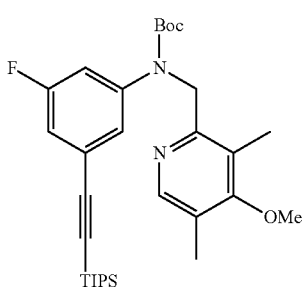

14f tert-Butyl (3-fluoro-5-((triisopropylsilyl)ethynyl)-phenyl)((4-methoxy-3,5-dimethylpyridin-2-yl)methyl)-carbamate (14f)

Substrate 1e was alkynylated following the general meta-alkynylation procedure. After purification by preparative thin-layer chromatography, Compound 14f was obtained in 44% yield as a colorless liquid, $^1$H NMR (400 MHz, CDCl$_3$) δ 8.17 (s, 1H), 7.15 (s, 1H), 7.03 (d, J=10.3 Hz, 1H), 6.92 (d, J=8.1 Hz, 1H), 4.86 (s, 2H), 3.73 (s, 3H), 2.22 (s, 3H), 2.20 (s, 3H), 1.40 (s, 9H), 1.10 (s, 21H); $^{13}$C NMR (150 MHz, CDCl$_3$) δ 163.74, 161.84 (d, J=245.3 Hz), 154.42, 154.21, 149.09, 144.41 (d, J=11.1 Hz), 125.76, 124.84, 124.54 (d, J=10.9 Hz), 123.53, 115.79 (d, J=23.0 Hz), 114.50 (d, J=23.3 Hz), 105.59 (d, J=3.3 Hz), 91.74, 80.96, 59.88, 53.09, 28.18, 18.60, 13.20, 11.23, 10.38; HRMS (ESI-TOF) m/z Calcd for C$_{31}$H$_{46}$FN$_2$O$_3$Si [M+H]$^+$: 541.3256, found: 541.3257.

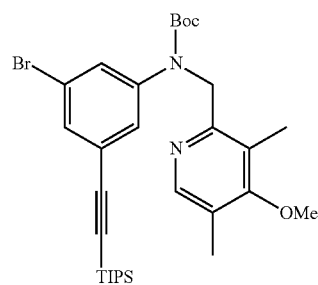

14h tert-Butyl (3-bromo-5-((triisopropylsilyl)ethynyl)-phenyl)((4-methoxy-3,5-dimethylpyridin-2-yl)methyl)-carbamate (14h)

Substrate 1aa was alkynylated following the general meta-alkynylation procedure. After purification by preparative thin-layer chromatography, Compound 14h was obtained in 56% yield as a colorless liquid, $^1$H NMR (400 MHz, CDCl$_3$) δ 8.17 (s, 1H), 7.43 (s, 1H), 7.35 (s, 1H), 7.29 (s, 1H), 4.85 (s, 2H), 3.73 (s, 3H), 2.22 (s, 3H), 2.20 (s, 3H), 1.40 (s, 9H), 1.10 (s, 21H); $^{13}$C NMR (151 MHz, CDCl$_3$) δ 163.76, 154.38, 154.16, 149.10, 144.04, 131.65, 129.88, 128.69, 125.00, 124.86, 123.55, 121.16, 105.14, 92.19, 81.00, 59.89, 53.05, 28.17, 18.61, 13.20, 11.23, 10.40; HRMS (ESI-TOF) m/z Calcd for C$_{31}$H$_{46}$BrN$_2$O$_3$Si [M+H]$^+$: 601.2456, found: 601.2456.

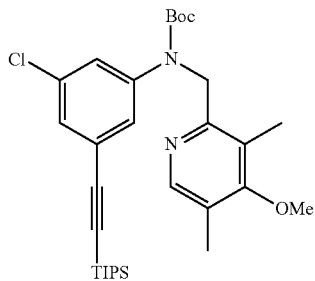

14g tert-Butyl (3-chloro-5-((triisopropylsilyl)ethynyl)phenyl)((4-methoxy-3,5-dimethylpyridin-2-yl)methyl)-carbamate (14g)

Substrate 1f was alkynylated following the general meta-alkynylation procedure. After purification by preparative thin-layer chromatography, Compound 14g was obtained in 59% yield as a colorless liquid, $^1$H NMR (400 MHz, CDCl$_3$) δ 8.17 (s, 1H), 7.28 (s, 1H), 7.27-2.24 (m, 1H), 7.20 (s, 1H), 4.85 (s, 2H), 3.73 (s, 3H), 2.22 (s, 3H), 2.20 (s, 3H), 1.40 (s, 9H), 1.10 (s, 21H); $^{13}$C NMR (150 MHz, CDCl$_3$) δ 163.75, 154.40, 154.18, 149.10, 144.00, 133.45, 128.83, 128.22, 127.03, 124.85, 124.70, 123.53, 105.31, 92.05, 80.98, 59.89, 53.06, 28.17, 18.61, 13.20, 11.23, 10.39; HRMS (ESI-TOF) m/z Calcd for C$_{31}$H$_{46}$ClN$_2$O$_3$Si [M+H]$^+$: 557.2961, found: 557.2960.

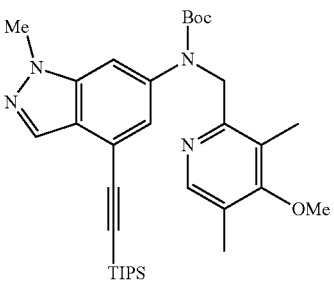

14i tert-Butyl ((4-methoxy-3,5-dimethylpyridin-2-yl)methyl)(1-methyl-4-((triisopropylsilyl)ethynyl)-1H-indazol-6-yl)carbamate (14i)

Substrate 2j was alkynylated following the general meta-alkynylation procedure. After purification by preparative thin-layer chromatography, Compound 14i was obtained in 53% yield as a colorless solid, $^1$H NMR (400 MHz, CDCl$_3$) δ 8.15 (s, 1H), 7.96 (s, 1H), 7.35 (s, 1H), 7.17 (s, 1H), 4.95 (s, 2H), 3.98 (s, 3H), 3.72 (s, 3H), 2.23 (s, 3H), 2.21 (s, 3H), 1.41 (s, 9H), 1.15 (s, 21H); $^{13}$C NMR (150 MHz, CDCl$_3$) δ 163.79, 154.81, 154.68, 148.93, 141.15, 139.74, 132.28, 125.06, 124.86, 123.91, 123.35, 115.60, 107.69, 103.86, 94.66, 80.72, 59.84, 53.70, 35.69, 28.23, 18.66, 13.18, 11.26, 10.50; HRMS (ESI-TOF) m/z Calcd for C$_{33}$H$_{49}$N$_4$O$_3$Si [M+H]$^+$: 577.3568, found: 577.3568.

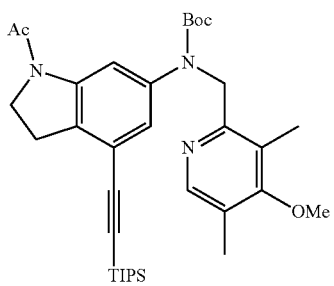

14j tert-Butyl (1-acetyl-4-((triisopropylsilyl)ethynyl)-indolin-6-yl)((4-methoxy-3,5-dimethylpyridin-2-yl)methyl)carbamate (14j)

Substrate 2g was alkynylated following the general meta-alkynylation procedure. After purification by preparative thin-layer chromatography, Compound 14j was obtained in 46% yield as a light yellow solid, Rotameric mixture, ratio of the rotamers=84/16; $^1$H NMR (400 MHz, CDCl$_3$) δ 8.15 (s, 1H), 8.11 (s, 0.84H), 7.19 (s, 0.16H), 6.97 (s, 1H), 4.93-4.82 (m, 2H), 4.18-4.96 (m, 2H), 3.72 (s, 3H), 3.17 (t, J=8.5 Hz, 1.68H), 3.05 (t, J=8.4 Hz, 0.32H), 2.33-2.14 (m, 9H), 1.40 (s, 9H), 1.10 (s, 21H); $^{13}$C NMR (150 MHz, CDCl$_3$) resonances for the minor rotamer are enclosed in parenthesis ( ): $^{13}$C NMR (150 MHz, CDCl$_3$) δ 168.55 (168.27), 163.74, 154.98 (154.84), 154.67, 148.88, 142.87 (142.36), 142.27 (141.67), 131.84 (134.48), 125.21 (124.90), 124.68 (124.64), 123.98, 119.35 (120.76), 116.60 (114.42), 104.10 (103.69), 94.27 (95.13), 80.46 (80.63), 59.82, 53.49, 48.97 (48.06), 28.24, 27.72 (26.48), 24.11 (24.34), 18.62, 13.17, 11.18, 10.52 (10.45); HRMS (ESI-TOF) m/z Calcd for C$_{35}$H$_{52}$N$_3$O$_4$Si [M+H]$^+$: 606.3722, found: 606.3722.

3.18 Meta-Arylation of Phenylacetic Acid

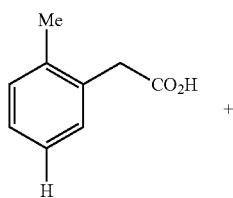

+

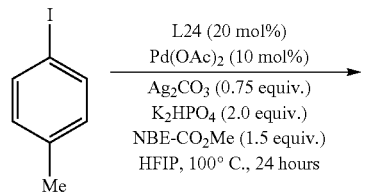

General Procedure for Arylation of Phenylacetic Acid:

2-Methyl phenylacetic acid (0.1 mmol), Ar—I (0.25 mmol), Pd(OAc)$_2$ (2.2 mg, 10 mol %), L24 (6.8 mg, 20 mol %), Ag$_2$CO$_3$ (20.7 mg, 0.075 mmol), NBE-CO$_2$Me (38.0 mg, 0.25 mmol), K$_2$HPO$_4$ (35 mg, 0.2 mmol) and HFIP (1.0 mL) were added to a 10 mL vial. The vial was capped and closed tightly. Then the reaction mixture was first stirred at room temperature for 5 minutes and then heated to 100° C. for 24 hours. After cooling to room temperature, 0.05 mL HOAc was added. Then the mixture was passed through a pad of Celite® with DCM as the eluent to remove the insoluble precipitate. The resulting solution was concentrated and purified by preparative TLC using 2:1 hexanes: EtOAc (with 1% HOAc) as the eluent to afford the desired product Compound 15.

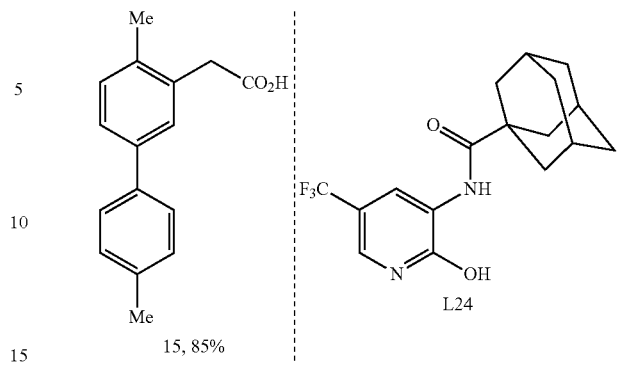

15, 85%

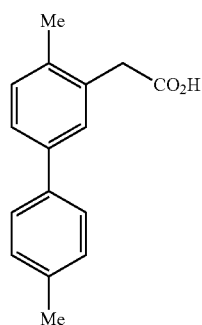

2-(4,4'-dimethyl-[1,1'-biphenyl]-3-yl)acetic Acid

Colorless solid, $^1$H NMR (400 MHz, CDCl$_3$) δ 7.46 (d, J=8.0 Hz, 2H), 7.43-7.36 (m, 2H), 7.27-7.15 (m, 3H), 3.72 (s, 2H), 2.38 (s, 3H), 2.35 (s, 3H); $^{13}$C NMR (150 MHz, CDCl$_3$) δ 177.3, 139.2, 137.8, 136.9, 135.7, 132.3, 130.8, 129.4, 128.9, 126.8, 126.2, 39.0, 21.1, 19.2; HRMS (ESI-TOF) m/z Calcd for C$_{16}$H$_{17}$O$_2$$^+$[M+H]$^+$: 241.1223, found: 241.1223.

Gram-Scale Reaction for Meta-Arylation of Anilines

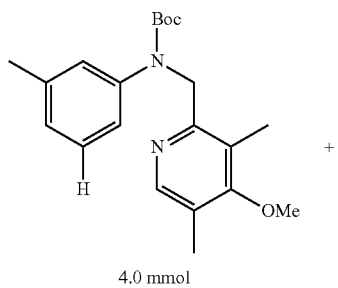

4.0 mmol

+

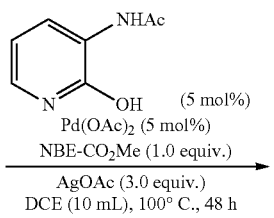

8.0 mmol

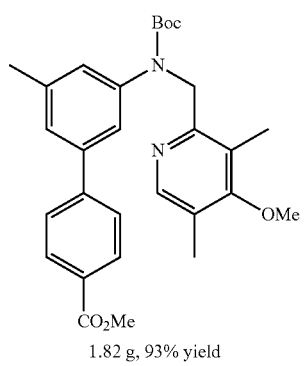

1.82 g, 93% yield

Compound 1a (1.43 g, 4.0 mmol), methyl 4-iodobenzoate (2.1 g, 8.0 mmol), Pd(OAc)$_2$ (44.8 mg, 0.2 mmol, 5 mol %), Ligand L12 (30.4 mg, 0.2 mmol, 5 mol %), AgOAc (2.0 g, 12.0 mmol), NBE-CO$_2$Me (608.8 mg, 4.0 mmol) and DCE (10.0 mL) were added to a 150 mL sealed tube. Then the reaction mixture was stirred at 100° C. for 48 hours. After cooling to room temperature, the mixture was passed through a pad of Celite® with DCM as the eluent to remove the insoluble precipitate. The resulting solution was concentrated and purified by silica gel column chromatography to afford the desired arylated product in 93% yield as a colorless liquid.

Directing Group Removal for Amines

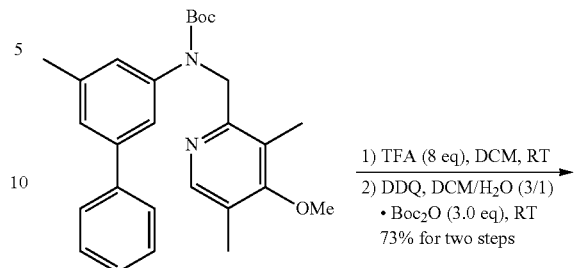

9n

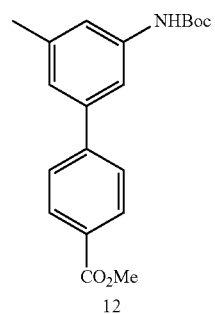

12

General Procedure for Directing Group Removal from Amines:

To a solution of 9n (981.2 mg, 2.0 mmol) in DCM (8.0 mL) was added TFA (1.2 mL, 16.0 mmol) at room temperature. The mixture was stirring at room temperature for another 24 hours. The resulting solution was diluted by DCM (50 mL), and washed by with a saturated sodium carbonate solution. The aqueous phase was extracted with DCM (3×10 mL). The combined organic phases were dried by Na$_2$SO$_4$ and concentrated to afford a solid, which was used for next step without purification.

To a mixture of the solid amine obtained in the previous step (39.0 mg, 0.1 mmol), was added DDQ (22.7 mg, 0.1 mmol), DCM/H$_2$O (0.6 mL/0.2 mL) and Boc$_2$O (69 μL, 0.3 mmol). The mixture was stirred at room temperature for another 24 hours. Next, the mixture was passed through a pad of Celite® with DCM as the eluent to remove the insoluble precipitate. The resulting solution was concentrated and purified by preparative TLC to afford the desired arylated product (Hexane/EA=3/1) as a colorless solid (25.2 mg, 74% yield).

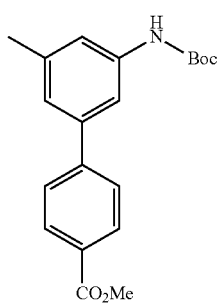

12

Methyl 3'-((tert-butoxycarbonyl)amino)-5'-methyl-[1,1'-biphenyl]-4-carboxylate (12)

$^1$H NMR (400 MHz, CDCl$_3$) δ 8.09 (d, J=8.3 Hz, 2H), 7.65 (d, J=8.4 Hz, 2H), 7.47 (s, 1H), 7.25 (s, 1H), 7.12 (s, 1H), 6.60 (s, 1H), 3.95 (s, 3H), 2.41 (s, 3H), 1.55 (s, 9H); $^{13}$C NMR (150 MHz, CDCl$_3$) δ 167.00, 152.74, 145.45, 140.75, 139.45, 138.85, 129.96, 128.88, 127.07, 127.04, 122.83, 118.79, 114.53, 80.61, 52.09, 28.33, 21.57.

Directing Group Removal for Phenols

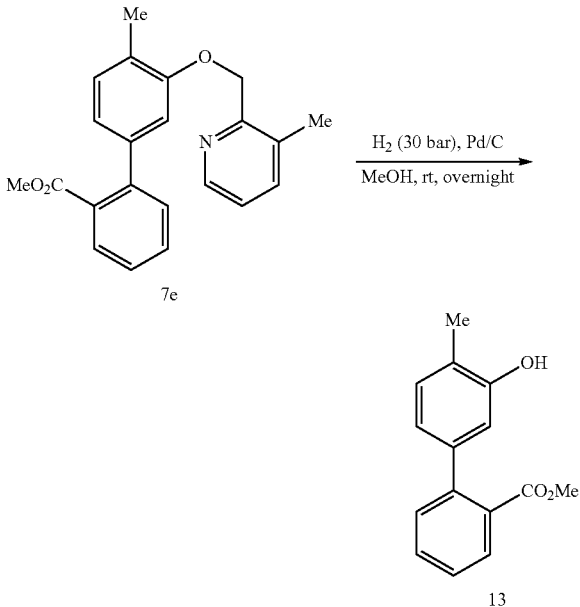

General Procedure for Directing Group Hydrogenolysis (Phenols):

Substrate 7e (0.1 mmol) and 10% Pd/C (30.0 mg), were charged to a 10 mL vial equipped with a stir bar and a rubber septa. The vial was evacuated and purged with nitrogen, followed by addition of 2.0 mL of MeOH. The vial was then placed in an autoclave with a needle piercing the septa. The autoclave was purged with hydrogen three times then filled to a pressure of 30 bar H$_2$. The autoclave was placed on a stirring plate at room temperature overnight with good stirring. The resulting solution was diluted with EtOAc (5.0 mL) and passed through a plug of Celite® with EtOAc as the eluent. The filtrate was concentrated and purified by preparative TLC to provide the desired phenol 13 in 79% yield.

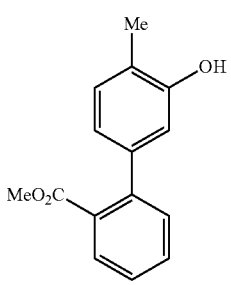

13

Methyl 4'-methyl-3'-((3-methylpyridin-2-yl)methoxy)-[1,1'-biphenyl]-2-carboxylate (13)

Colorless solid, $^1$H NMR (400 MHz, CDCl$_3$) δ 7.77 (d, J=7.7 Hz, 1H), 7.53-7.44 (t, J=7.6 Hz, 1H), 7.41-7.32 (m, 2H), 7.13 (d, J=7.6 Hz, 1H), 6.79 (dd, J=7.5, 1.7 Hz, 1H), 6.74 (d, J=1.7 Hz, 1H), 5.02 (s, 1H), 3.68 (s, 3H), 2.28 (s, 3H); $^{13}$C NMR (150 MHz, CDCl$_3$) δ 169.56, 153.56, 141.87, 140.18, 131.17, 130.84, 130.69, 130.53, 129.53, 127.02, 122.91, 120.66, 114.86, 52.12, 15.56; HRMS (ESI-TOF) m/z Calcd for C$_{15}$H$_{14}$O$_3$ [M+H]$^+$: 243.1016, found: 243.1017.

REFERENCES

1. Surry, D. S. & Buchwald, S. L. Biaryl phosphane ligands in palladium-catalyzed amination. *Angew. Chem. Int. Ed.* 47, 6338-6361 (2008).
2. Fortman, G. C. & Nolan, S. P. N-Heterocyclic carbene (NHC) ligands and palladium in homogeneous cross-coupling catalysis: a perfect union. *Chem. Soc. Rev.* 40, 5151-5169 (2011).
3. Cope, A. C. & Siekman, R. W. Formation of covalent bonds from platinum or palladium to carbon by direct substitution. *J. Am. Chem. Soc.* 87, 3272-3273 (1965).
4. Chen, X., Engle, K. M., Wang, D.-H. & Yu, J.-Q. Pd(II)-Catalyzed C—H activation/C—C cross-coupling reactions: versatility and practicality. *Angew. Chem. Int. Ed.* 48, 5094-5115 (2009).
5. Lyons, T. W. & Sanford, M. S. Palladium-catalyzed ligand-directed C—H functionalization reactions. *Chem. Rev.* 110, 1147-1169 (2010).
6. Daugulis, O., Do, H.-Q. & Shabashov, D. Palladium- and copper-catalyzed arylation of carbon-hydrogen bonds. *Acc. Chem. Res.* 42, 1074-1086 (2009).
7. Engle, K. M. & Yu, J.-Q. Developing ligands for palladium(II)-catalyzed C—H functionalization: intimate dialogue between ligand and substrate. *J. Org. Chem.* 78, 8927-8955 (2013).
8. Catellani, M., Frignani, F. & Rangoni, A. A complex catalytic cycle leading to a regioselective synthesis of o,o-disubstituted vinylarenes. *Angew. Chem. Int. Ed.* 36, 119-122 (1997).
9. Ye, J. & Lautens, M. Palladium-catalysed norbornene-mediated C—H functionalization of arenes. *Nature Chemistry* 7, 863-870 (2015).
10. Jiao, L. & Bach, T. Palladium-catalyzed direct 2-alkylation of indoles by norbornene-mediated regioselective cascade C—H activation. *J. Am. Chem. Soc.* 133, 12990-12993 (2011).
11. Jiao, L., Herdtweck, E. & Bach, T. Pd(II)-catalyzed regioselective 2-alkylation of indoles via a norbornene-mediated C—H activation: mechanism and applications. *J. Am. Chem. Soc.* 134, 14563-14572 (2012).
12. Wang, X.-C., Gong, W., Fang, L.-Z., Zhu, R.-Y., Li, S., Engle, K. M. & Yu, J.-Q. Ligand-enabled meta-C—H activation using a transient mediator. *Nature* 519, 334-338 (2015).
13. Dong, Z., Wang, J. & Dong, G. Simple amine-directed meta-selective C—H Arylation via Pd/norbornene catalysis. *J. Am. Chem. Soc.* 137, 5887-5890 (2015).
14. Shen, P.-X., Wang, X.-C., Wang, P., Zhu, R.-Y. & Yu, J.-Q. Ligand-enabled meta-C—H alkylation and acylation using a modified norbornene *J. Am. Chem. Soc.* 137, 11574-11577 (2015).

15. Leow, D., Li, G., Mei, T.-S. & Yu, J.-Q. Activation of remote meta-C—H bond assisted by an end-on template. *Nature* 486, 518-522 (2012).
16. Saidi, O. et al. Ruthenium-catalyzed meta-sulfonation of 2-phenylpyridines. *J. Am. Chem. Soc.* 133, 19298-19301 (2011).
17. Hofmann, N. & Ackermann, L. meta-Selective C—H bond alkylation with secondary alkyl halides. *J. Am. Chem. Soc.* 135, 5877-5884 (2013).
18. Mkhalid, I. A. I., Barnard, J. H., Marder, T. B., Murphy, J. M. & Hartwig, J. F. C—H activation for the construction of C—B bonds. *Chem. Rev.* 110, 890-931 (2010).
19. Maleczka, R. E., Jr., Shi, F., Holmes, D. & Smith, M. R., III C—H activation/borylation/oxidation: A one-pot unified route to meta-substituted phenols bearing ortho-/para-directing groups *J. Am. Chem. Soc.* 125, 7792-7793 (2003).
20. Phipps, R. J. & Gaunt, M. J. A meta-selective copper-catalyzed C—H bond arylation. *Science* 323, 1593-1597 (2009).
21. Duong, H. A., Gilligan, R. E., Cooke, M. L., Phipps, R. J. & Gaunt, M. J. Copper(II)-catalyzed meta-selective direct arylation of α-aryl carbonyl compounds. *Angew. Chem. Int. Ed.* 50, 463-466 (2010).
22. Li, J., Warratz, S., Zell, D., De Sarkar, S., Ishikawa, E. E. & Ackermann, L. N-acyl amino acid ligands for ruthenium(II)-catalyzed meta-C—H tert-alkylation with removable auxiliaries. *J. Am. Chem. Soc.* 13894-13901 (2015).
23. Martinez-Martinez, A. J., Kennedy, A. R., Mulvey, R. E., O'Hara, C. T. Directed ortho-meta'- and meta-meta'-dimetalations: A template base approach to deprotonation. *Science* 346, 834-837 (2014)
24. Wang, D.-H., Engle, K. M., Shi, B.-F. & Yu, J.-Q. Ligand-enabled reactivity and selectivity in a synthetically versatile aryl C—H olefination. *Science* 327, 315-319 (2010).
25. Chan, K. S. L., Wasa, M., Chu, L., Laforteza, B. N., Miura M. & Yu, J.-Q. Ligand-enabled cross-coupling of C(sp³)-H bonds with arylboron reagents via Pd(II)/Pd(0) catalysis. *Nature Chemistry* 6, 146-150 (2014).
26. Musaev, D. G., Kaledinm, A. L., Shi, B.-F. & Yu, J.-Q. Key mechanistic features of enantioselective C—H bond activation reactions catalyzed by [(chiral mono-N-protected amino acid)-Pd(II)] complexes. *J. Am. Chem. Soc.* 134, 1690-1698 (2012).
27. Cheng, G.-J. et al. Role of N-acyl amino acid ligands on Pd(II)-catalyzed remote C—H activation of tethered arenes. *J. Am. Chem. Soc.* 136, 894-897 (2014).
28. Wan, L., Dastbaravardeh, N., Li, G. & Yu, J.-Q. Cross-coupling of remote meta-C—H bonds directed by a U-shaped template. *J. Am. Chem. Soc.* 135, 18056-18059 (2013).
29. Luo, J., Preciado, S. & Larrosa, I. Overriding ortho-para selectivity via a traceless directing group relay strategy: the meta-selective arylation of phenols. *J. Am. Chem. Soc.* 136, 4109-4112 (2013).
30. Cong, X., You, J., Gao, G. & Lan, J. 2-Pyridylmethyl ether: a readily removable and efficient directing group for amino acid ligand accelerated ortho-C—H olefination of phenols. *Chem. Commun.* 49, 662-664 (2013).
31. Chamberlain, P. P. et al. Structure of the human Cereblon-DDB1-lenalidomide complex reveals basis for responsiveness to thalidomide analogs. *Nat. Struct. Mol. Biol.* 21, 803-810 (2014).
32. Dong, Z. & Dong, G. Ortho vs ipso: site-selective Pd and norbornene-catalyzed arene C—H amination using aryl halides. *J. Am. Chem. Soc.* 135, 18350-18353 (2013).

Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art.

The invention claimed is:

1. A method for preparing a compound of Formula IA:

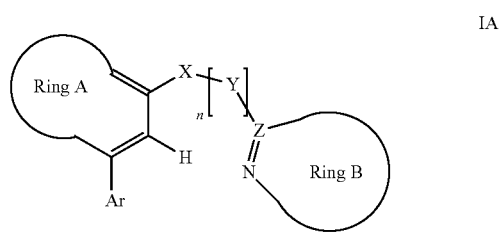

wherein:
Ar is aryl or heteroaryl;
Ring A is a carbocyclic ring selected from the group consisting of:

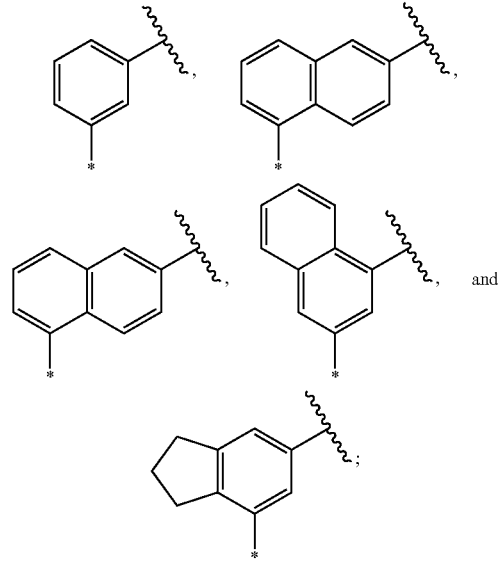

or
Ring A is a heterocyclic ring selected from the group consisting of:

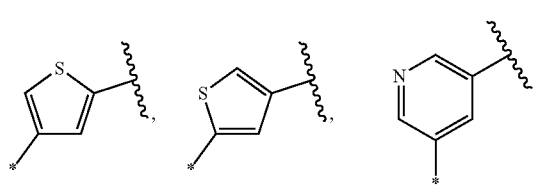

-continued

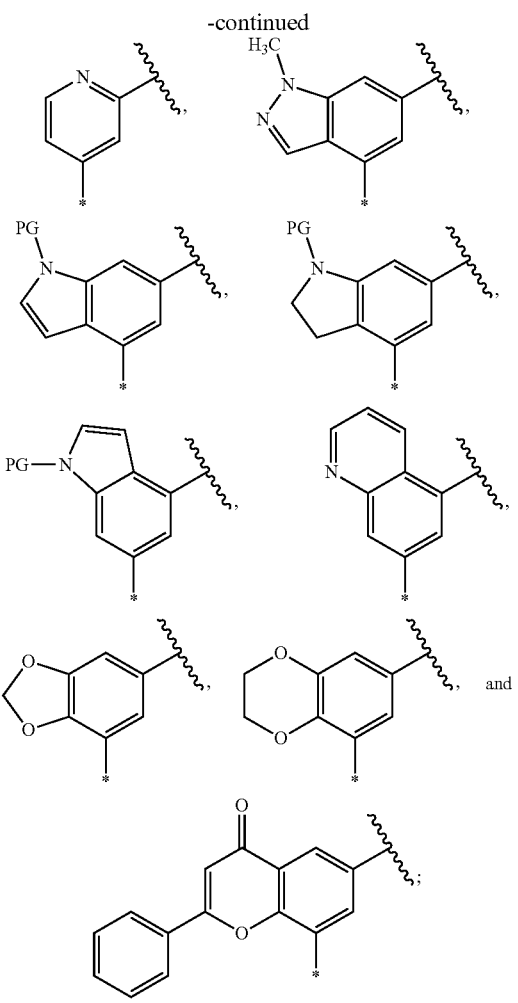

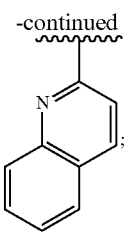

-continued wherein:
PG is selected from the group consisting of acetyl, pivaloyl, tert-butoxycarbonyl, benzyloxycarbonyl, 2,2,2-trichloroethoxycarbonyl, 9-fluorenylmethoxycarbonyl, methanesulfonyl, trifluoromethanesulfonyl, and nitrobenzenesulfonyl;

* is the point of attachment to Ar; and

∿∿ is the point of attachment to X;

Ring B is a heteroaromatic ring selected from the group consisting of:

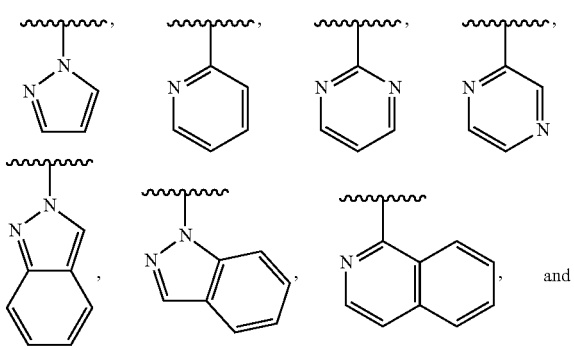

wherein:
∿∿ is the point of attachment to Y;
X is —$CH_2$—, —O—, or —N-PG-;
Y is —$CH_2$—;
PG is benzyl or tert-butoxycarbonyl; and
n is 0 or 1;
wherein aryl is optionally substituted at the meta and para positions with one or two substituents independently selected from the group consisting of fluoro, chloro, bromo, iodo, nitro, cyano, $C_1$-$C_7$-hydrocarbyl, $C_1$-$C_7$-hydrocarbyl substituted by protected hydroxy, perfluoro-$C_1$-$C_3$-hydrocarbyl, C(O)—$C_1$-$C_7$-hydrocarbyl, C(O)O—$C_1$-$C_7$-hydrocarbyl, protected amino, di-($C_1$-$C_7$-hydrocarbyl) $C_1$-$C_7$-hydrocarbylphosphonate, protected hydroxy, —O—$C_1$-$C_7$-hydrocarbyl, —S—$C_1$-$C_7$-hydrocarbyl, $C_3$-$C_7$ cyclic hydrocarbyl, $C_3$-$C_7$ cyclic hydrocarbyl substituted by protected hydroxy, and a fused ring having 3 or 4 added ring atoms; or
wherein aryl is optionally substituted at the ortho position with a substituent selected from the group consisting of C(O)O—$C_1$-$C_7$-hydrocarbyl and NHC(O)—$C_1$-$C_7$-hydrocarbyl;
wherein heteroaryl is optionally substituted with one or two substituents independently selected from the group consisting of fluoro, chloro, bromo, iodo, $C_1$-$C_7$-hydrocarbyl, perfluoro-$C_1$-$C_3$-hydrocarbyl, C(O)—$C_1$-$C_7$-hydrocarbyl, C(O)O—$C_1$-$C_7$-hydrocarbyl, —O—$C_1$-$C_7$-hydrocarbyl, —S—$C_1$-$C_7$-hydrocarbyl, $C_3$-$C_7$ cyclic hydrocarbyl, and a fused ring having 3 or 4 added ring atoms in which any nitrogen atom is free of reactive hydrogens;
wherein Ring A is optionally substituted with one, two or three substituents independently selected from the group consisting of fluoro, chloro, bromo, nitro, cyano, $C_1$-$C_7$-hydrocarbyl, perfluoro-$C_1$-$C_3$-hydrocarbyl, $C_1$-$C_7$-hydrocarbyl-4- to 6-membered ring, C(O)—$C_1$-$C_7$-hydrocarbyl, C(O)O—$C_1$-$C_7$-hydrocarbyl, protected amino, —O—$C_1$-$C_7$-hydrocarbyl, —S—$C_1$-$C_7$-hydrocarbyl, and $C_3$-$C_7$ cyclic hydrocarbyl;
wherein Ring B is optionally substituted with one, two or three substituents independently selected from the group consisting of $C_1$-$C_7$-hydrocarbyl, $C_1$-$C_3$-hydrocarbyl-$CF_3$, $C_1$-$C_7$-hydrocarbyl-4- to 6-membered ring, —O—$C_1$-$C_7$-hydrocarbyl, and —O—$C_1$-$C_7$-hydrocarbyl-$CF_3$; and
wherein the hydroxy and amino protecting groups are independently selected from the group consisting of acetyl, pivaloyl, tert-butoxycarbonyl, benzyloxycarbonyl, 2,2,2-trichloroethoxycarbonyl, 9-fluorenylmethoxycarbonyl, methanesulfonyl, trifluoromethanesulfonyl, and nitrobenzenesulfonyl;
provided that:
(a) when n is 0, X is —$CH_2$— or —N-PG-; and
(b) when n is 1, X is —O— or —N-PG-;

wherein the method comprises the following steps:

(A) reacting a compound of Formula I:

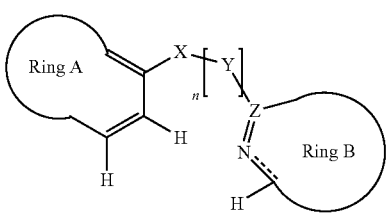

wherein:

Ring A is a carbocyclic ring selected from the group consisting of:

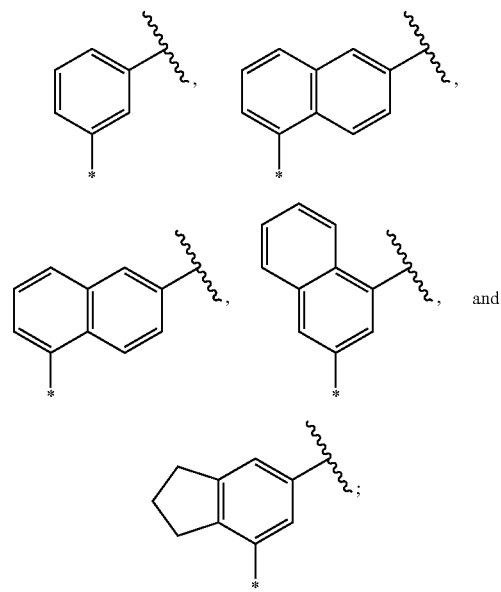

or

Ring A is a heterocyclic ring selected from the group consisting of:

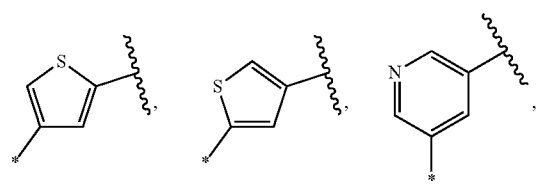

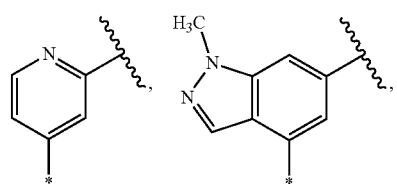

-continued

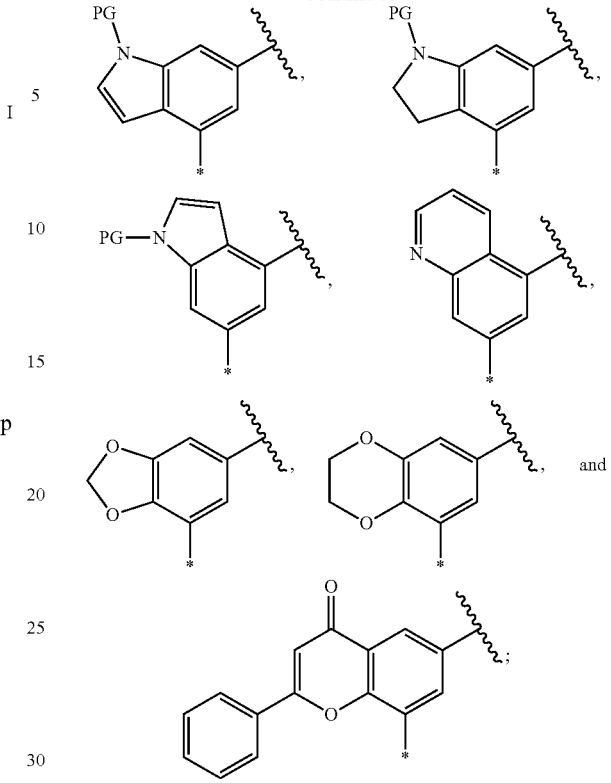

wherein:

PG is selected from the group consisting of acetyl, pivaloyl, tert-butoxycarbonyl, benzyloxycarbonyl, 2,2,2-trichloroethoxycarbonyl, 9-fluorenylmethoxycarbonyl, methanesulfonyl, trifluoromethanesulfonyl, and nitrobenzenesulfonyl;

* is the point of attachment to Ar; and

⁓ is the point of attachment to X;

Ring B is a heteroaromatic ring selected from the group consisting of:

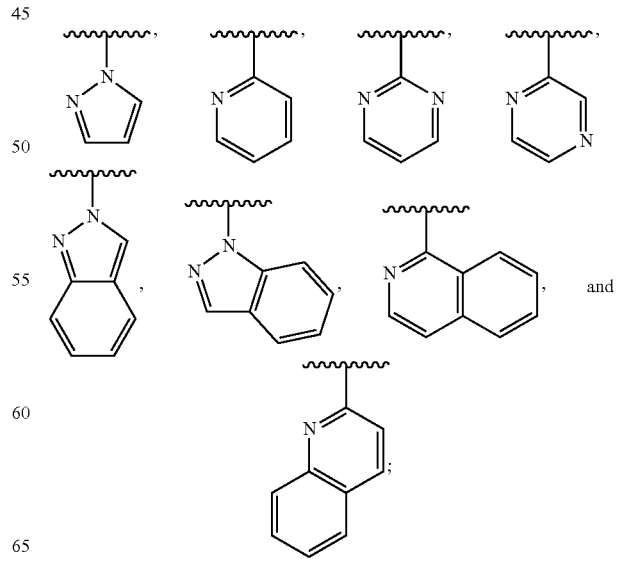

wherein:

∼ is the point of attachment to Y;

X is —CH$_2$—, —O—, or —N-PG-;

Y is —CH$_2$—;

PG is benzyl or tert-butoxycarbonyl; and n is 0 or 1;

wherein aryl is optionally substituted at the meta and para positions with one or two substituents independently selected from the group consisting of fluoro, chloro, bromo, iodo, nitro, cyano, $C_1$-$C_7$-hydrocarbyl, $C_1$-$C_7$-hydrocarbyl substituted by protected hydroxy, perfluoro-$C_1$-$C_3$-hydrocarbyl, C(O)—$C_1$-$C_7$-hydrocarbyl, C(O)O—$C_1$-$C_7$-hydrocarbyl, protected amino, di-($C_1$-$C_7$-hydrocarbyl) $C_1$-$C_7$-hydrocarbylphosphonate, protected hydroxy, —O—$C_1$-$C_7$-hydrocarbyl, —S—$C_1$-$C_7$-hydrocarbyl, $C_3$-$C_7$ cyclic hydrocarbyl, $C_3$-$C_7$ cyclic hydrocarbyl substituted by protected hydroxy, and a fused ring having 3 or 4 added ring atoms; or wherein aryl is optionally substituted at the ortho position with a substituent selected from the group consisting of C(O)O—$C_1$-$C_7$-hydrocarbyl and NHC(O)—$C_1$-$C_7$-hydrocarbyl;

wherein heteroaryl is optionally substituted with one or two substituents independently selected from the group consisting of fluoro, chloro, bromo, iodo, $C_1$-$C_7$-hydrocarbyl, perfluoro-$C_1$-$C_3$-hydrocarbyl, C(O)—$C_1$-$C_7$-hydrocarbyl, C(O)O—$C_1$-$C_7$-hydrocarbyl, —O—$C_1$-$C_7$-hydrocarbyl, —S—$C_1$-$C_7$-hydrocarbyl, $C_3$-$C_7$ cyclic hydrocarbyl, and a fused ring having 3 or 4 added ring atoms in which any nitrogen atom is free of reactive hydrogens;

wherein Ring A is optionally substituted with one, two or three substituents independently selected from the group consisting of fluoro, chloro, bromo, nitro, cyano, $C_1$-$C_7$-hydrocarbyl, perfluoro-$C_1$-$C_3$-hydrocarbyl, $C_1$-$C_7$-hydrocarbyl-4- to 6-membered ring, C(O)—$C_1$-$C_7$-hydrocarbyl, C(O)O—$C_1$-$C_7$-hydrocarbyl, protected amino, —O—$C_1$-$C_7$-hydrocarbyl, —S—$C_1$-$C_7$-hydrocarbyl, and $C_3$-$C_7$ cyclic hydrocarbyl;

wherein Ring B is optionally substituted with one, two or three substituents independently selected from the group consisting of $C_1$-$C_7$-hydrocarbyl, $C_1$-$C_3$-hydrocarbyl-CF$_3$, $C_1$-$C_7$-hydrocarbyl-4- to 6-membered ring, —O—$C_1$-$C_7$-hydrocarbyl, and —O—$C_1$-$C_7$-hydrocarbyl-CF$_3$; and wherein the hydroxy and amino protecting groups are independently selected from the group consisting of acetyl, pivaloyl, tert-butoxycarbonyl, benzyloxycarbonyl, 2,2,2-trichloroethoxycarbonyl, 9-fluorenylmethoxycarbonyl, methanesulfonyl, trifluoromethanesulfonyl, and nitrobenzenesulfonyl;

provided that:

(a) when n is 0, X is —CH$_2$— or —N-PG-; and (b) when n is 1, X is —O— or —N-PG-;

with:

(i) Pd(OAc)$_2$; and (ii) a ligand of Formula III:

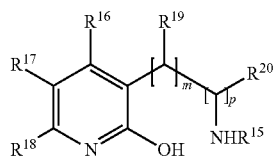

wherein:

$R^{15}$ is —C(O)—$C_1$-$C_{11}$ hydrocarbyl or perfluorinated —C(O)—$C_1$-$C_5$ hydrocarbyl;

$R^{16}$ is H or $C_1$-$C_6$-hydrocarbyl;

$R^{17}$ is H, $C_1$-$C_6$-hydrocarbyl, or CF$_3$;

$R^{18}$ is H or $C_1$-$C_6$-hydrocarbyl; or $R^{16}$ and $R^{17}$, together with the carbon atoms to which they are bonded, form a fused 6-membered ring; or $R^{17}$ and $R^{18}$, together with the carbon atoms to which they are bonded, form a fused 6-membered ring;

m is 0 or 1; and p is 0 or 1;

provided that:

(a) m and p are identical; and (b) when m is 1 and p is 1, $R^{19}$ and $R^{20}$, together with the carbon atoms to which they are bonded, form a phenyl ring;

in the presence of:

(iii) a compound of Formula II:

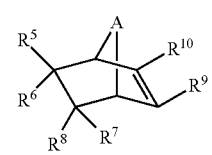

wherein:

A is —CH$_2$—;

$R^5$ is H, $C_1$-$C_6$-hydrocarbyl, —C(O)—$C_1$-$C_6$-hydrocarbyl, —C(O)O—$C_1$-$C_6$-hydrocarbyl, or —O—$C_1$-$C_6$-hydrocarbyl;

$R^6$ is H, $C_1$-$C_6$-hydrocarbyl, —C(O)—$C_1$-$C_6$-hydrocarbyl, —C(O)O—$C_1$-$C_6$-hydrocarbyl, or —O—$C_1$-$C_6$-hydrocarbyl;

$R^7$ is H, $C_1$-$C_6$-hydrocarbyl, —C(O)—$C_1$-$C_6$-hydrocarbyl, —C(O)O—$C_1$-$C_6$-hydrocarbyl, or —O—$C_1$-$C_6$-hydrocarbyl;

$R^8$ is H, $C_1$-$C_6$-hydrocarbyl, —C(O)—$C_1$-$C_6$-hydrocarbyl, —C(O)O—$C_1$-$C_6$-hydrocarbyl, or —O—$C_1$-$C_6$-hydrocarbyl;

$R^9$ is H, $C_1$-$C_6$-hydrocarbyl, —C(O)—$C_1$-$C_6$-hydrocarbyl, —C(O)O—$C_1$-$C_6$-hydrocarbyl, or —O—$C_1$-$C_6$-hydrocarbyl; and $R^{10}$ is H, $C_1$-$C_6$-hydrocarbyl, —C(O)—$C_1$-$C_6$-hydrocarbyl, —C(O)O—$C_1$-$C_6$-hydrocarbyl, or —O—$C_1$-$C_6$-hydrocarbyl;

(iv) an oxidant selected from the group consisting of: AgC(O)C(CH$_3$)$_3$, AgOC(O)CH$_3$, AgOC(O)CF$_3$, AgOS(O)$_2$CF$_3$, Ag$_2$CO$_3$, and Ag$_2$O; and (vi) a coupling agent of the formula:

Ar—I, wherein:
Ar is aryl or heteroaryl;
wherein aryl is optionally substituted at the meta and para positions with one or two substituents independently selected from the group consisting of fluoro, chloro, bromo, iodo, nitro, cyano, $C_1$-$C_7$-hydrocarbyl, $C_1$-$C_7$-hydrocarbyl substituted by protected hydroxy, perfluoro-$C_1$-$C_3$-hydrocarbyl, C(O)—$C_1$-$C_7$-hydrocarbyl, C(O)O—$C_1$-$C_7$-hydrocarbyl, protected amino, di-($C_1$-$C_7$-hydrocarbyl) $C_1$-$C_7$-hydrocarbyl-phosphonate, protected hydroxy, —O—$C_1$-$C_7$-hydrocarbyl, —S—$C_1$-$C_7$-hydrocarbyl, $C_3$-$C_7$ cyclic hydrocarbyl, $C_3$-$C_7$ cyclic hydrocarbyl substituted by protected hydroxy, and a fused ring having 3 or 4 added ring atoms; or
wherein aryl is optionally substituted at the ortho position with a substituent selected from the group consisting of C(O)O—$C_1$-$C_7$-hydrocarbyl and NHC(O)—$C_1$-$C_7$-hydrocarbyl;
wherein heteroaryl is optionally substituted with one or two substituents independently selected from the group consisting of fluoro, chloro, bromo, iodo, $C_1$-$C_7$-hydrocarbyl, perfluoro-$C_1$-$C_3$-hydrocarbyl, C(O)—$C_1$-$C_7$-hydrocarbyl, C(O)O—$C_1$-$C_7$-hydrocarbyl, —O—$C_1$-$C_7$-hydrocarbyl, —S—$C_1$-$C_7$-hydrocarbyl, $C_3$-$C_7$ cyclic hydrocarbyl, and a fused ring having 3 or 4 added ring atoms in which any nitrogen atom is free of reactive hydrogens; and
wherein the hydroxy and amino protecting groups are independently selected from the group consisting of acetyl, pivaloyl, tert-butoxycarbonyl, benzyloxycarbonyl, 2,2,2-trichloroethoxycarbonyl, 9-fluorenylmethoxycarbonyl, methanesulfonyl, trifluoromethanesulfonyl, and nitrobenzenesulfonyl;
to provide the compound of Formula IA; and
(B) optionally recovering the compound of Formula IA.

2. The method according to claim 1, wherein n is 0.
3. The method according to claim 1, wherein n is 1.
4. The method according to claim 3, wherein Ring B is an optionally substituted heteroaromatic ring selected from the group consisting of:

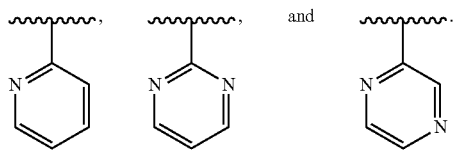 [SMILES: *c1ccccn1 ; *c1ncccn1 ; *c1cnccn1]

5. The method according to claim 4, wherein Ring B is:

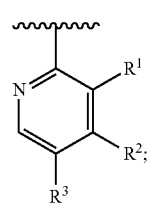

wherein:
$R^1$ is H, $C_1$-$C_6$-hydrocarbyl, —O—$C_1$-$C_6$-hydrocarbyl, or —O—$C_1$-$C_6$-hydrocarbyl-$CF_3$;
$R^2$ is H, $C_1$-$C_6$-hydrocarbyl, —O—$C_1$-$C_6$-hydrocarbyl, or —O—$C_1$-$C_6$-hydrocarbyl-$CF_3$; and
$R^3$ is H, $C_1$-$C_6$-hydrocarbyl, —O—$C_1$-$C_6$-hydrocarbyl, or —O—$C_1$-$C_6$-hydrocarbyl-$CF_3$;
provided that at least one of $R^1$, $R^2$ and $R^3$ is other than H.

6. The method according to claim 5, wherein X is —O—.
7. The method according to claim 5, wherein X is —N-PG-.
8. The method according to claim 5, wherein Ring A is selected from the group consisting of:

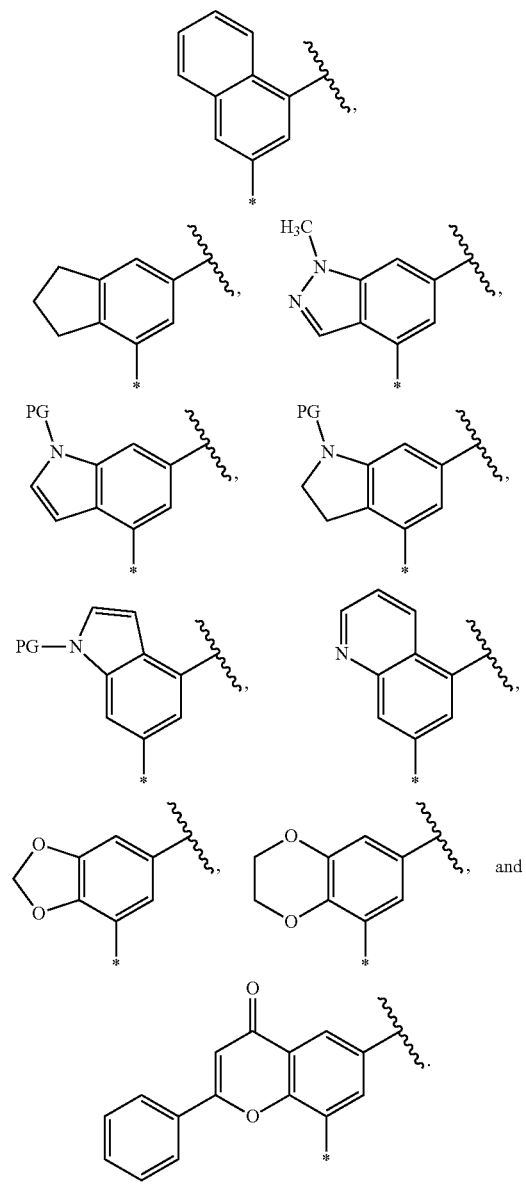

9. The method according to claim 5, wherein Ring A is selected from the group consisting of:

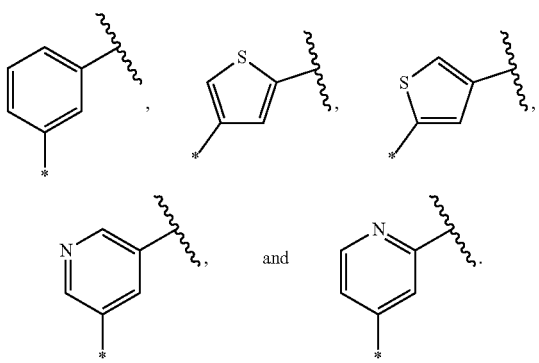

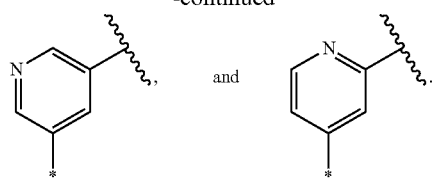

10. The method according to claim 9, wherein Ring A is:

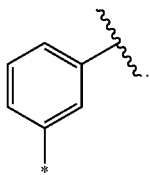

11. The method according to claim 10, wherein Ring A is substituted with at least one substituent.

12. The method according to claim 9, wherein Ring A is selected from the group consisting of:

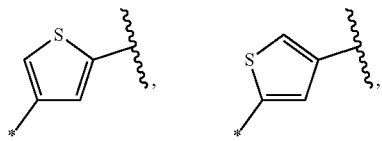

13. The method according to claim 12, wherein Ring A is selected from the group consisting of:

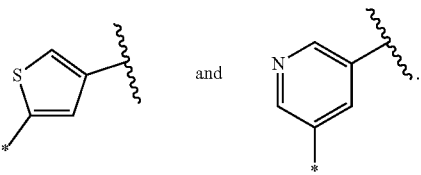

14. The method according to claim 1, wherein $R^{10}$ is —C(O)O—$C_1$-$C_6$-hydrocarbyl.

15. The method according to claim 14, wherein:
$R^5$ is H;
$R^6$ is H;
$R^7$ is H;
$R^8$ is H; and
$R^9$ is H.

16. The method according to claim 1, wherein $R^{15}$ is —C(O)—$CH_3$ or —C(O)-adamantan-1-yl.

17. The method according to claim 16, wherein:
$R^{16}$ is H;
$R^{17}$ is $C_1$-$C_6$-hydrocarbyl or $CF_3$; and
$R^{18}$ is H.

18. The method according to claim 1, wherein the method comprises recovering the compound of Formula IA.

* * * * *